United States Patent
Shue et al.

[11] Patent Number: 5,981,520
[45] Date of Patent: Nov. 9, 1999

[54] PIPERAZINO DERIVATIVES AS NEUROKININ ANTAGONISTS

[75] Inventors: Ho-Jane Shue, Pine Brook; Neng-Yang Shih; David J. Blythin, both of North Caldwell; Xiao Chen, Edison; Wing C. Tom, Cedar Grove; John J. Piwinski, Clinton Township; Kevin D. McCormick, Edison, all of N.J.

[73] Assignee: Schering Corporation, Kenilworth, N.J.

[21] Appl. No.: 09/099,221

[22] Filed: Jun. 17, 1998

Related U.S. Application Data

[60] Division of application No. 08/663,880, Jun. 14, 1996, Pat. No. 5,795,894, which is a continuation-in-part of application No. PCT/US96/05660, May 1, 1996, which is a continuation-in-part of application No. 08/432,739, May 2, 1995, Pat. No. 5,719,156
[60] Provisional application No. 60/003,084, Aug. 31, 1995.

[51] Int. Cl.⁶ .................. A61K 31/495; C07D 401/12; C07D 401/14; C07D 413/14
[52] U.S. Cl. .................. 514/212; 514/252; 514/253; 540/598; 544/295; 544/360; 544/363; 544/364; 544/366; 544/367; 544/370; 544/372; 544/373
[58] Field of Search .................. 544/360, 364, 544/363, 372, 295, 366, 367, 370, 373; 540/598; 514/212, 252, 253

[56] References Cited

U.S. PATENT DOCUMENTS

| | | | |
|---|---|---|---|
| 4,935,419 | 6/1990 | Bjork et al. | 514/231.5 |
| 5,350,852 | 9/1994 | Emonds-Alt et al. | 544/336 |
| 5,719,156 | 2/1998 | Shue et al. | 514/255 |
| 5,783,579 | 7/1998 | McCormick | 514/255 |
| 5,795,894 | 8/1998 | Shue et al. | 514/253 |

FOREIGN PATENT DOCUMENTS

| | | |
|---|---|---|
| 0 655 442 | 5/1995 | European Pat. Off. . |
| 2230262 | 10/1990 | United Kingdom . |
| WO 92/20661 | 11/1992 | WIPO . |
| WO 94/13646 | 6/1994 | WIPO . |

OTHER PUBLICATIONS

J. Med. Chem., 9 (1966), p. 181, Roderick et al.
Maggi et al, Eur. J. Pharmacol., 166, (1989), pp. 435–440.
Ellis et al, J. Pharmacol. Exp. Ther., 267, 1 (1993), pp. 95–101.
Furchgott, Pharm. Rev., 7 (1955), pp. 183–265.
Arunlakshana et al, Brit. J. Pharmacol., 14, 48 (1959), pp. 48–58.
Danko et al, Pharmacol. Comm., 1,3 (1992), pp. 203–209.
Frossard et al, Life Sciences vol. 49 pp. 1941–1953 (1991).
Stratton et al, Eur. J. Pharmacol., 250 (1993), pp. R11–R12.
Walsh et al, Psychopharmacology, 121 (1995), pp. 186–191.
Lecci et al, Neuroscience Let., 129 (1991), pp. 299–302.
Teixeira et al, Eur. J. Pharmacol., 311 (1996), pp. 7–14.
Picard et al, Eur. J. Pharmacol., 232 (1993), pp. 255–261.
Fleetwood–Walker et al, Eur. J. Pharmacol., 242 (1993), pp. 173–181.

Primary Examiner—Emily Bernhardt
Attorney, Agent, or Firm—Anita W. Magatti

[57] ABSTRACT

The invention relates to compounds of the formula

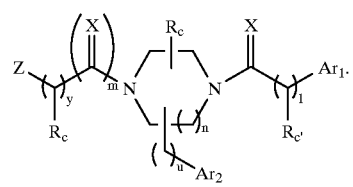

These compounds are neurokinin antagonists. These compounds are useful in the treatment of chronic airway diseases such as asthma.

7 Claims, No Drawings

PIPERAZINO DERIVATIVES AS NEUROKININ ANTAGONISTS

This application is a divisional of U.S. Ser. No. 08/663,880, filed Jun. 14, 1996, now U.S. Pat. No. 5,795,894, which is continuation-in part of International Application No. PCT/US96/05660, filed May 1, 1996, which claims the benefit of U.S. provisional application Ser. No. 60/003084, filed Aug. 31, 1995, and is a continuation-in-part of U.S. Ser. No, 08/432,739, filed May 2, 1995, now U.S. Pat. No. 5,719,156.

BACKGROUND OF THE INVENTION

The present invention relates to a genus of compounds useful as antagonists of neurokinin receptors. In particular, these can be neurokinin-1 receptor ($NK_1$) antagonists. Some can also be neurokinin-1 receptor ($NK_1$)antagonists and neurokinin-2 receptor ($NK_2$) antagonists, that is, $NK_1/NK_2$ dual receptor antagonists. Some can also be neurokinin-2 receptor ($NK_2$) antagonists. Some can also be neurokinin-3 receptor ($NK_3$) antagonists.

Neurokinin receptors are found in the nervous system and the circulatory system and peripheral tissues of mammals, and therefore are involved in a variety of biological processes. Neurokinin receptor antagonists are consequently expected to be useful in the treatment or prevention of various mammalian disease states, for example pulmonary disorders like asthma, cough, bronchospasm, chronic obstructive pulmonary diseases, and airway hyperreactivity; skin disorders and itch, for example, atopic dermatitis, and cutaneous wheal and flare; neurogenic inflammation inflammatory diseases such as arthritis, migraine, nociception; CNS diseases such as anxiety, Parkinson's disease, movement disorders and psychosis; convulsive disorders, renal disorders, urinary incontinence, ocular inflammation, inflammatory pain, and eating disorders such as food intake inhibition; allergic rhinitis, neurodegenerative disorders, psoriasis, Huntington's disease, depression, and various gastrointestinal disorders such as Crohn's disease.

In particular, $NK_1$ receptors have been reported to be involved in microvascular leakage and mucus secretion, and $NK_2$ receptors have been associated with smooth muscle contraction, making $NK_1$ and $NK_2$ receptor antagonists especially useful in the treatment and prevention of asthrma.

Moreover, $NK_3$ receptor antagonists are especially useful in the treatment and prevention of asthma, inflammatory diseases and conditions, such as ocular inflammation, allergic rhinitis, cutaneous wheal and flare, psoriasis, atopic dermatitis, CNS diseases such as anxiety and Parkinson's disease.

SUMMARY OF THE INVENTION

The invention relates to compounds of the formula:

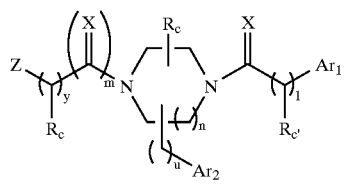

I each X is independently, O, (H,H), $NR_d$, or S;
n is 0 to 2, u is 0 to 2, l is 0 to 2, m is 1, and y is 1 to 3; or m is 2, and y is 0;
and with the further proviso that no more than one $R_c$ is other than H in the

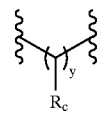

moiety;

each $R_c$ is independently H, $C_1-C_6$ alkyl, $-(CH_2)_{n1}-R4$ where $n_1$ is 1 to 6; $R_d$ is independently selected from the group consisting of H, $C_1-C_6$ alkyl, CN, $OR_a$, phenyl, substituted phenyl, benzyl, substituted benzyl, or allyl;

$R_4$ is $-OR_a$, $SR_a$,

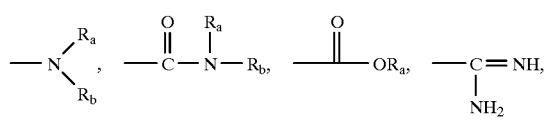

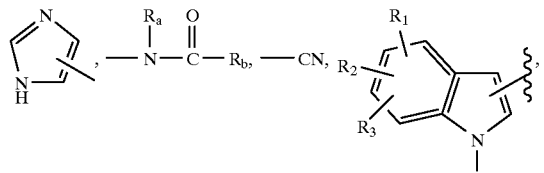

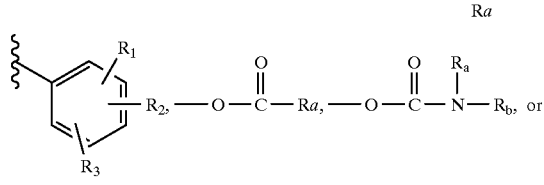

$R_{c'}$ is $C_1-C_6$ alkyl or $(CH_2)_nOR_a$, with the proviso that no more than one $R_{c'}$ is other than H;

each $R_a$ and $R_b$ is independently selected from the group consisting of H, $C_1-C_6$ alkyl, phenyl, substituted phenyl; benzyl, substituted benzyl, allyl; or when $R_a$ and $R_b$ are attached to the same nitrogen, then $R_a$ and $R_b$ together with the nitrogen to which they are attached, form a 4 to 7 member ring;

wherein each $R_1$ and $R_2$ is independently H, $C_1-C_6$ alkyl, $CF_3$, $C_2F_5$, Cl, Br, I, F, $NO_2$, $OR_a$, CN, $NR_aR_b$,

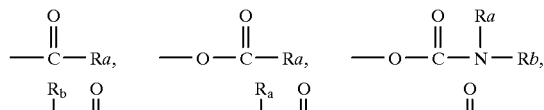

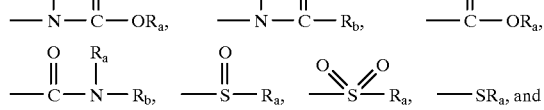

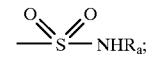

and where $R_a$ is not H in

 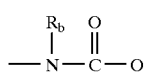

or when $R_1$ and $R_2$ are on adjacent carbons on a ring, they can form

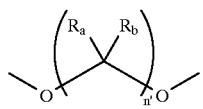

wherein n' is 1 or 2; and each $R_3$ is independently H, $C_1$–$C_6$ alkyl, $CF_3$, $C_2F_5$,

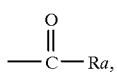 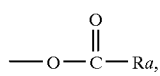 

Cl, Br, I, or F, $OR_a$, $OCF_3$, or phenyl;

$Ar_1$ is heteroaryl or substituted heteroaryl,

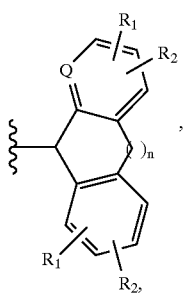 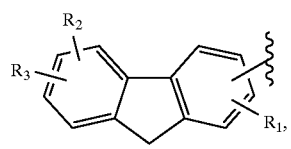

or

Q is N or CH $Ar_2$ is heteroaryl or substituted heteroaryl;

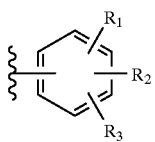 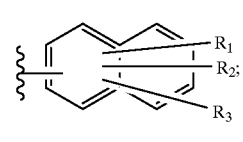

Z is

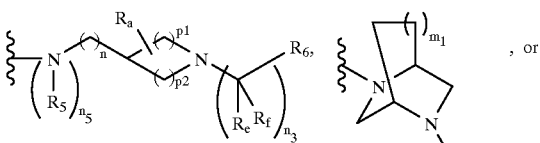

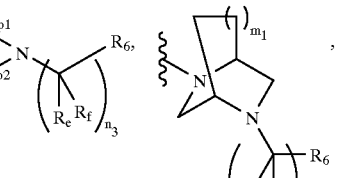

$m_1 = 0$–1;

$n_3$ is 0–4;

each $R_e$ and $R_f$ is independently selected from the group consisting of H, $C_1$–$C_6$ alkyl, phenyl, substituted phenyl; benzyl, substituted benzyl, allyl; or $R_e$ and $R_f$ taken together with the carbon to which they are attached can also form a carbonyl group with the proviso that no more than one carbonyl group is in the

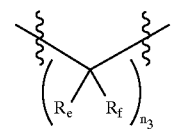

moiety.

each $R_5$ is independently selected from the group consisting of H, OH,

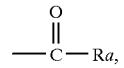

$C_1$–$C_6$ alkyl, $(CH_2)_{n_1}$-$R_4$, wherein $n_1$ is 1 to 6 with the proviso that when $n_1$ is 1, $R_4$ is not OH or $NR_aR_b$; also with the proviso that when $R_5$ is $C_1$–$C_6$ alkyl, two $R_5$ can be attached to the nitrogen to form a quaternary salt; and $n_5$ is 1, or $n_5$ is 2 with the proviso that each $R_5$ is independently $C_1$–$C_6$ alkyl;

$p_1$ and $p_2$ are each independently 1 to 4 with the proviso that $p_1$ and $p_2$ added together are 2 to 6;

$R_6$ is H, $C_1$–$C_6$ alkyl, $C_3$–$C_6$ cycloalkyl,

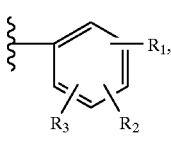 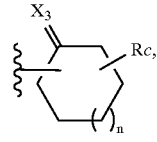

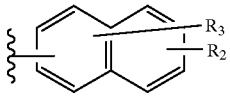 or 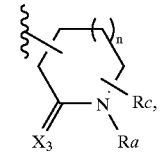

wherein $X_3$ is O, $NR_d$, or S, wherein $R_d$ is independently selected from the group consisting of H, $C_1$–$C_6$ alkyl, CN, $OR_a$, phenyl, substituted phenyl, benzyl, substituted benzyl, or allyl, when $n_3$ is 0–4;

or $R_6$ is heteroaryl, substituted heteroaryl, heterocycloalkyl, substituted heterocycloalkyl, when $n_3$ is 0–4;

or $R_6$ is ORa wherein Ra is not H, —NRa,Rb, O-heteroaryl, O-substituted heteroaryl, O-heterocycloalkyl, O-substituted heterocycloalkyl, —NRa-heteroaryl, —NRa-substituted heteroaryl, —NRa-heterocycloalkyl, —NRa-substituted heterocycloalkyl, provided that Re,Rf taken together with the carbon atom to which they are attached form a carbonyl group and $n_3$ is 1.

or a pharmaceutically acceptable salt thereof.

All of the variables in the above formulas such as Z, $R_1$, $R_2$, and $R_3$, have the same meaning throughout the specification unless otherwise specified.

Preferred compounds of the invention are compounds of formula I, wherein each X is O or (H,H) and at least one X is O.

Also preferred are compounds of formula I wherein both X's are O.

Also preferred are compounds of formula I wherein I is 0, m is 1, and y is 1.

Also preferred are compounds of formula I wherein n is 1 and u is 0.

Also preferred are compounds of formula I wherein $Ar_1$ is wherein Q is N or CH;
each $X_1$ is independently O, S or $NR_a$;
each $X_2$ is independently CH or N; and
$n_4$ is 0 or 1.

Also preferred are compounds of formula I wherein $Ar_2$ is

Also preferred are compounds of formula I wherein Z is

Also preferred are compounds of formula I wherein Z is

Also preferred are compounds of formula I wherein Z is

Also preferred are compounds of formula I wherein both X's are O, I is 0, m is 1, y is 1, n is 1, u is 0, and $Ar_1$ is

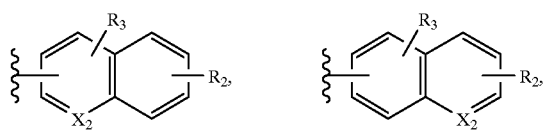

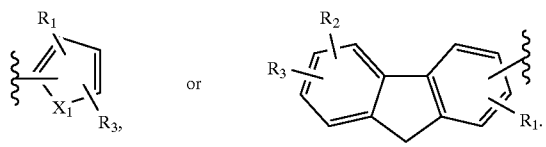

Also preferred are compounds of formula I wherein Ar$_2$ is

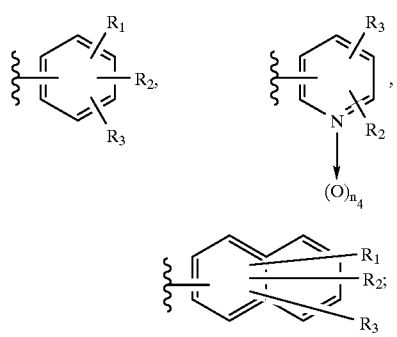

wherein n$_4$ is 0 or 1.

Also preferred are compounds of formula I wherein Z is

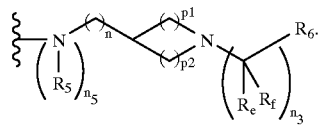

Also preferred are compounds of formula I wherein Z is

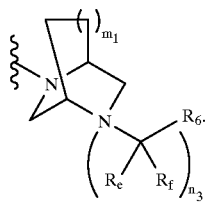

Also preferred are compounds of formula I wherein Z is

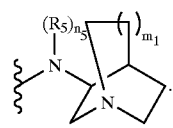

Also preferred are compounds of formula I, wherein R$_6$ is

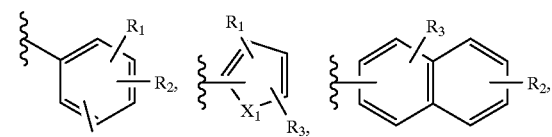

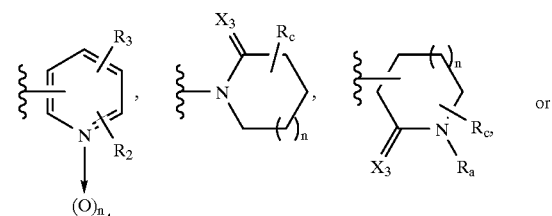

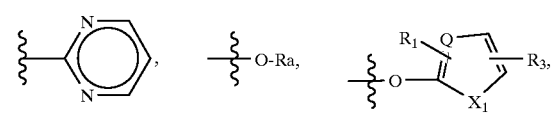

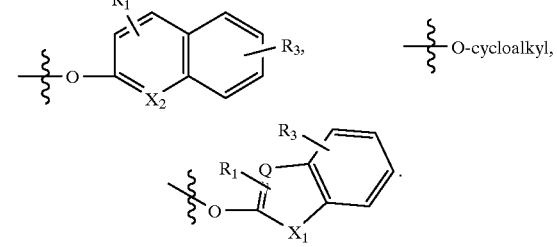

Also preferred are compounds of formula I wherein

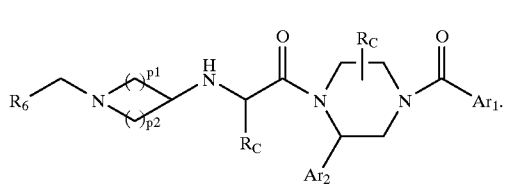

Also preferred are compounds of formula I' where in R$_c$ is H, p$_1$ and p$_2$ are 2, Ar$_1$ and Ar$_2$ are both

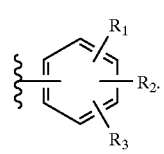

Also preferred are compounds of formula I' wherein R$_6$ is

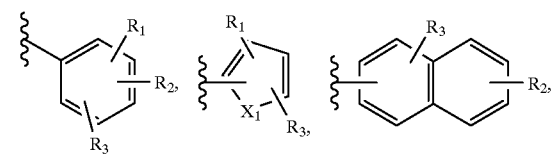

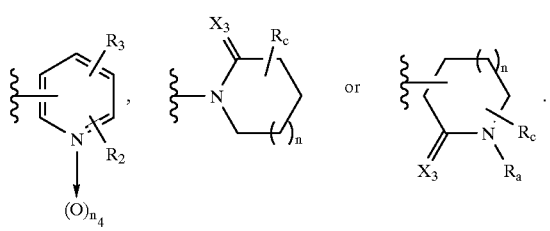
Also preferred are compounds of formula I' wherein $R_6$ is
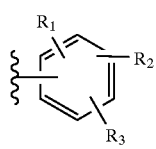
Also preferred are compounds of formula I wherein Z is
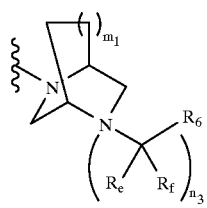
and $R_6$ is
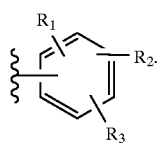
Exemplary compounds of the invention are compounds of the formulas:
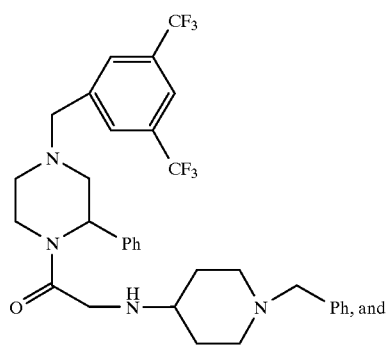
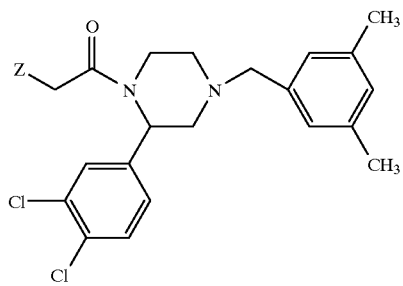
or a compound selected from the group consisting of
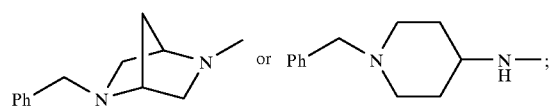
or a compound selected from the group consisting of

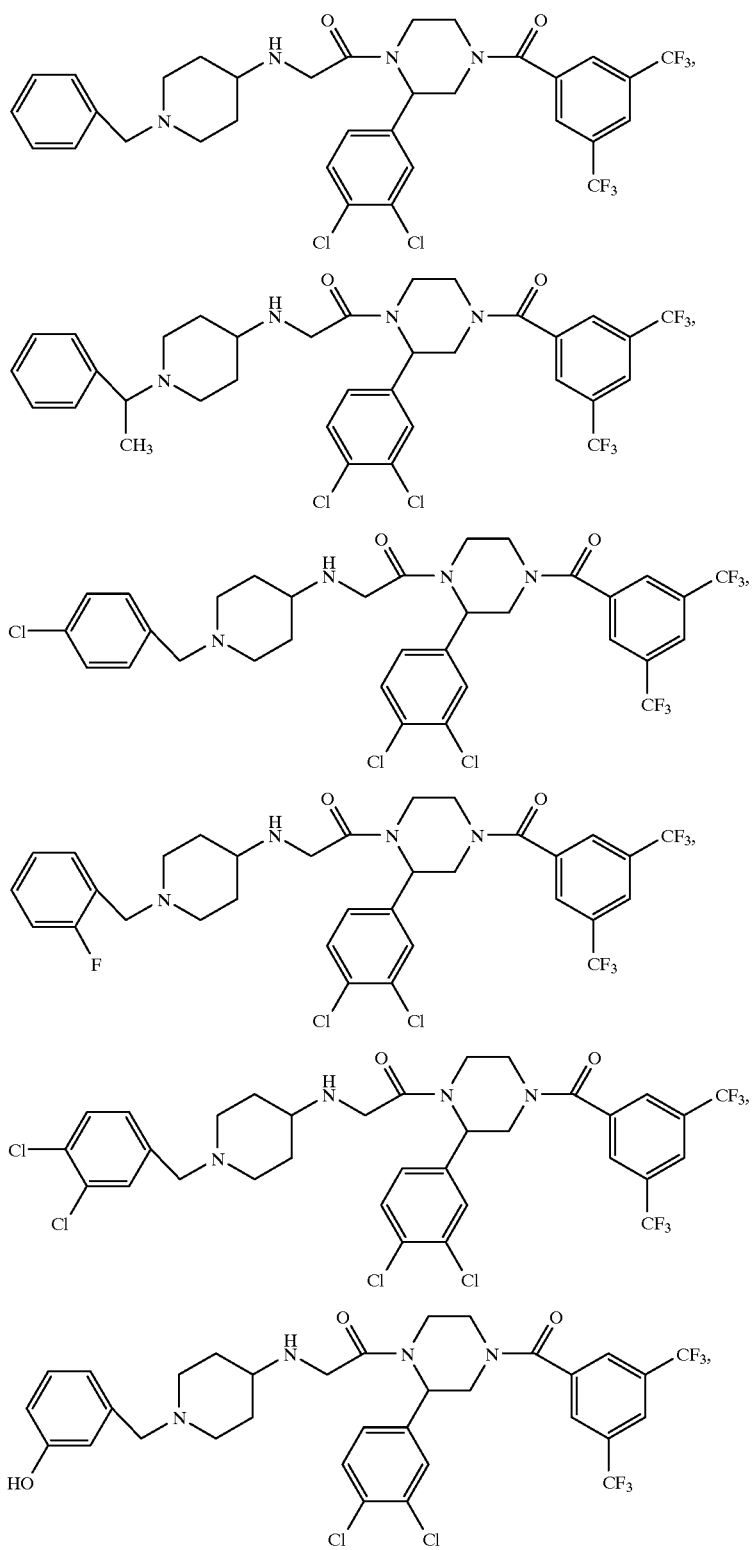

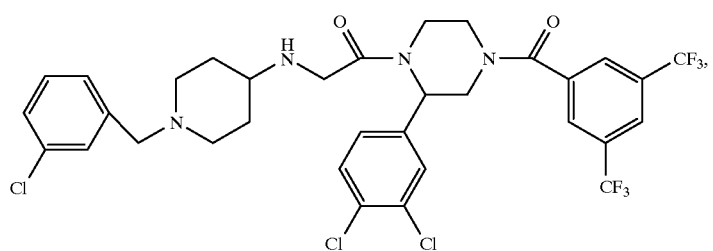
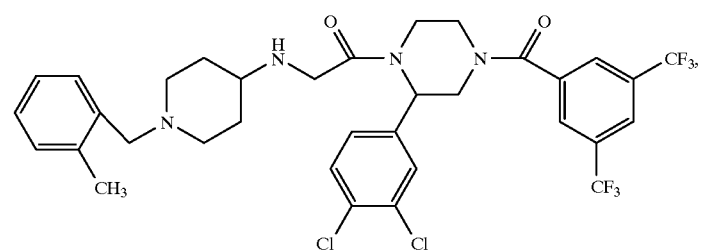
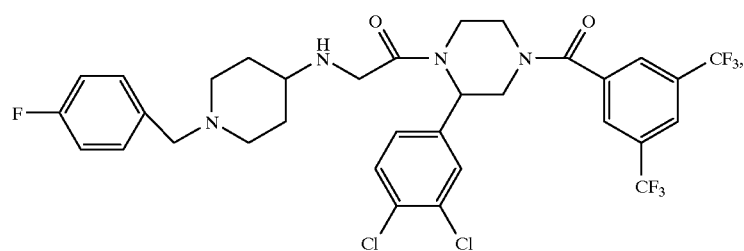
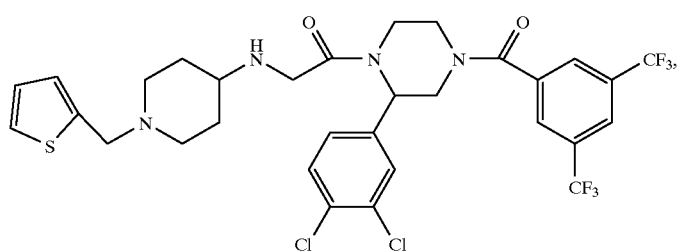
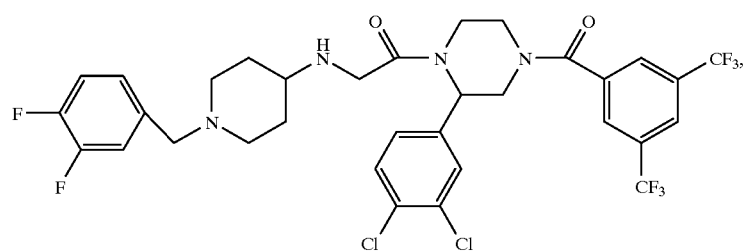
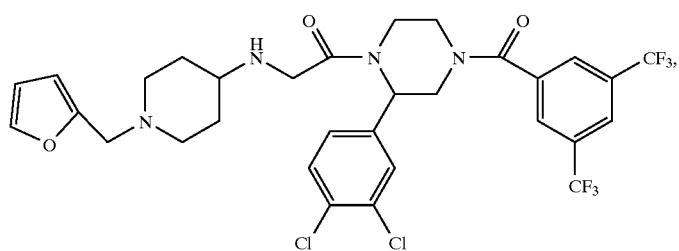

-continued
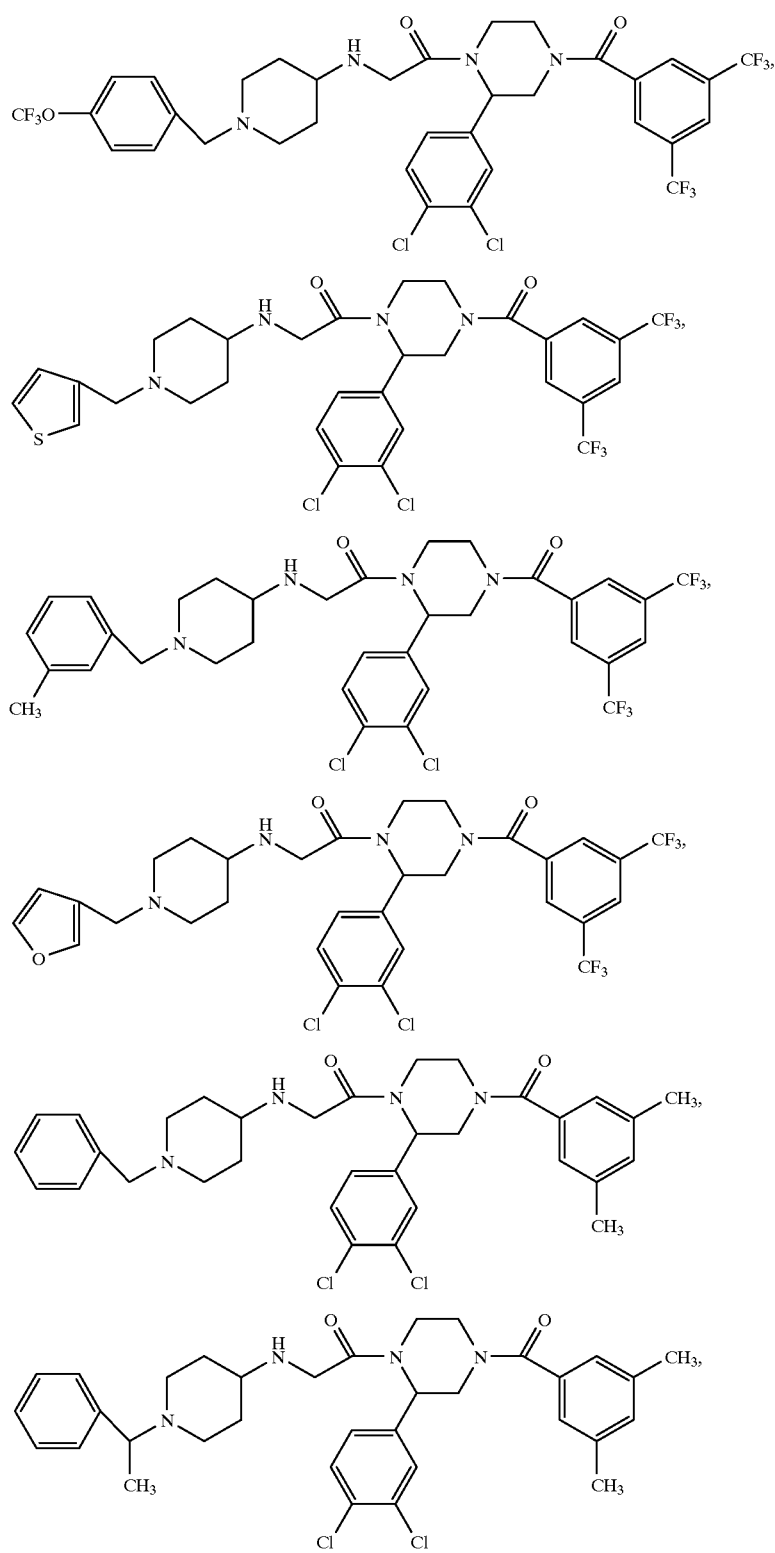

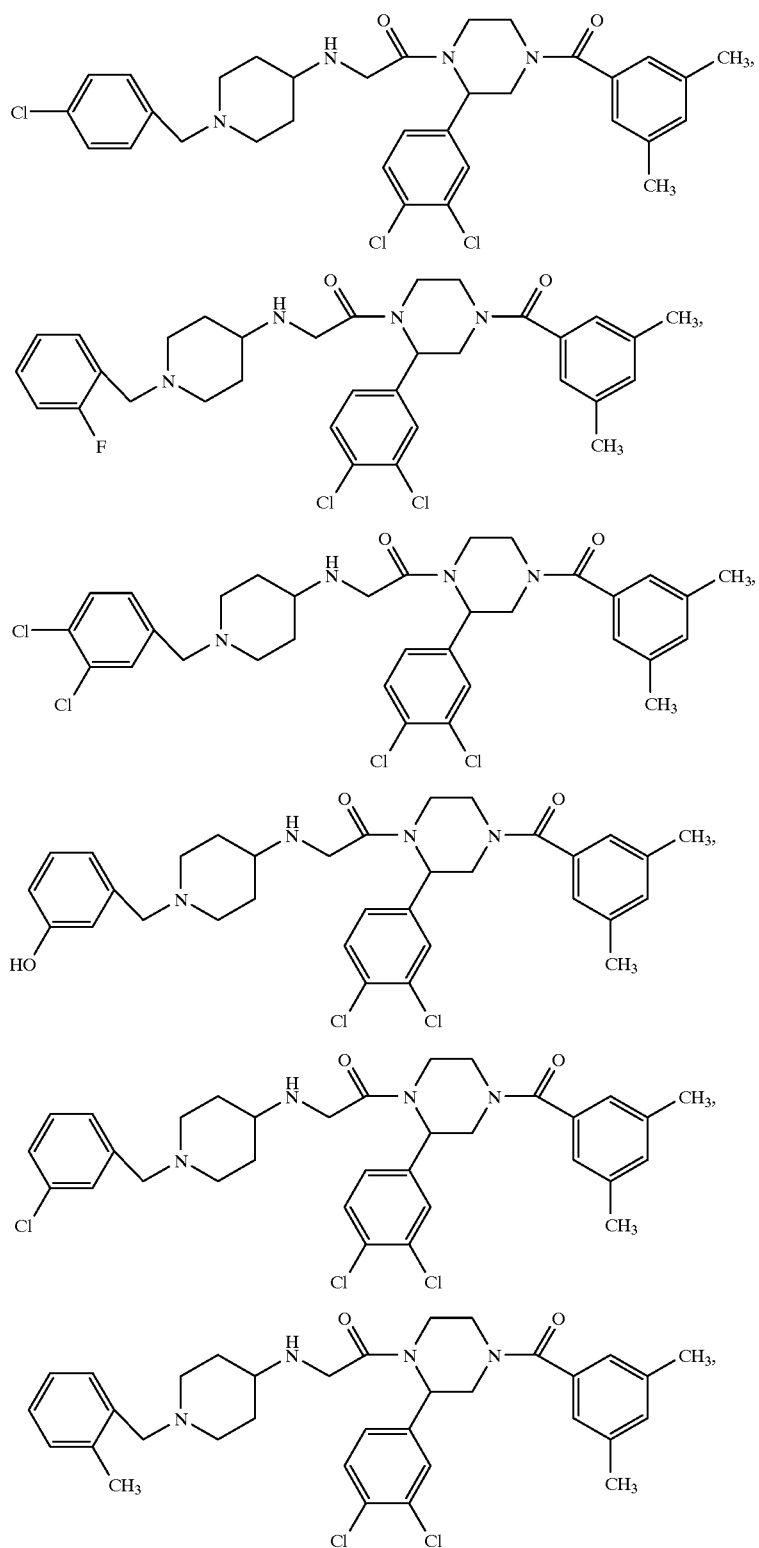

-continued
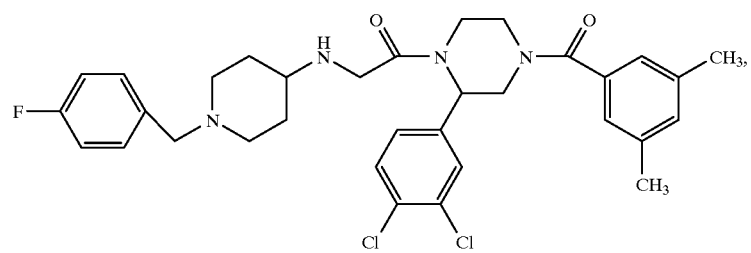
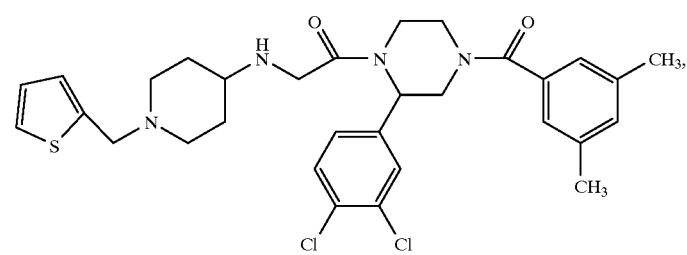
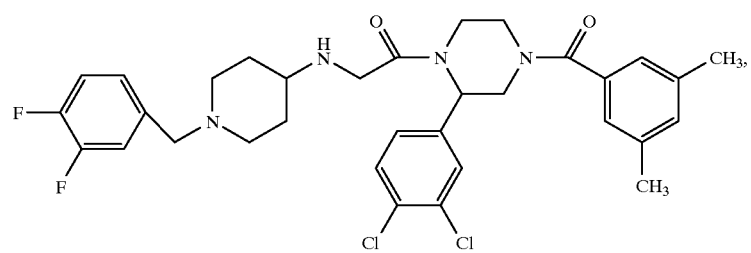
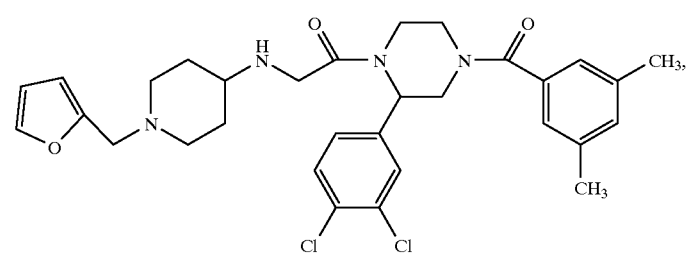
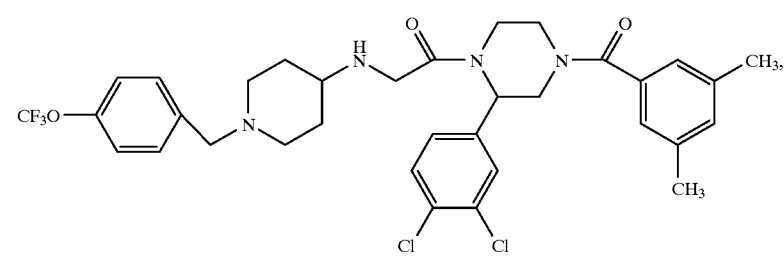
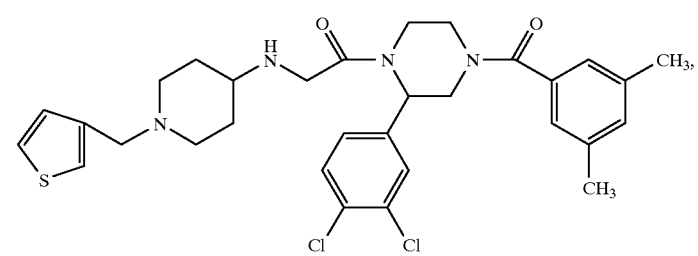

-continued
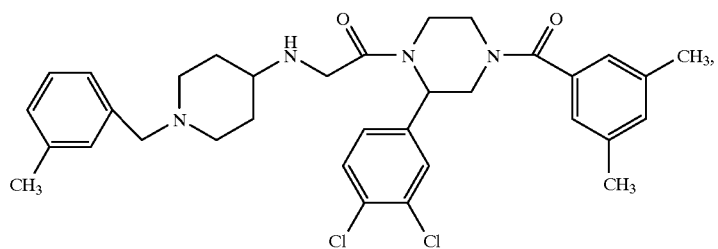
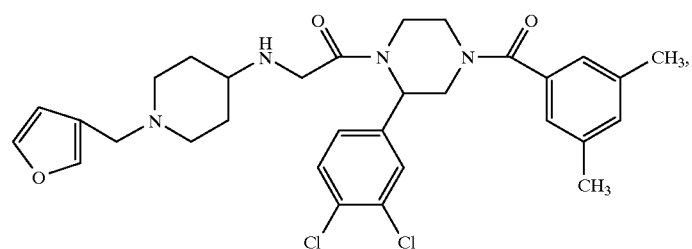
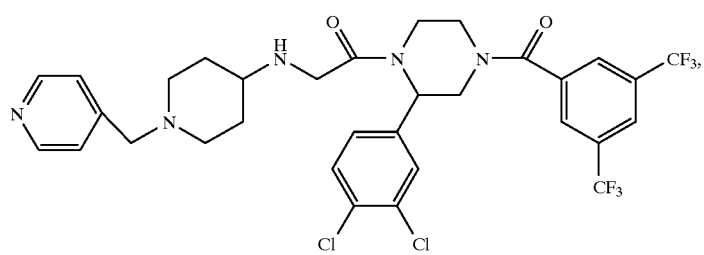
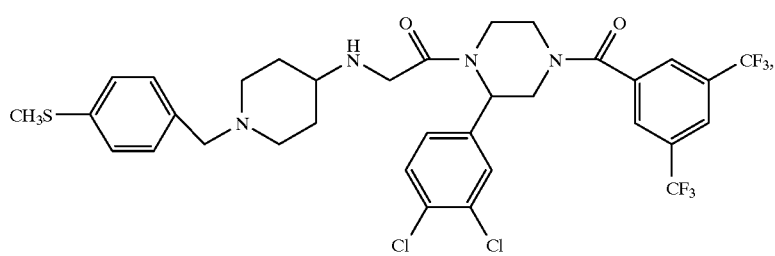
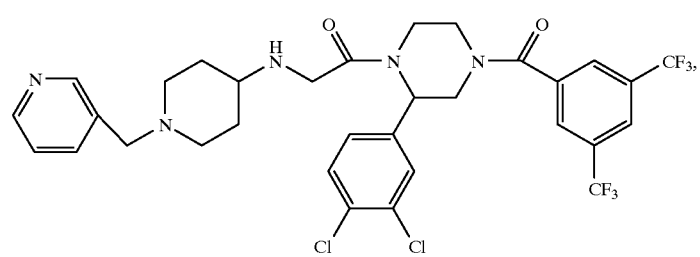
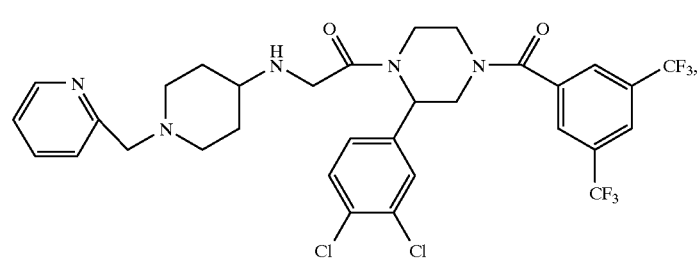

-continued
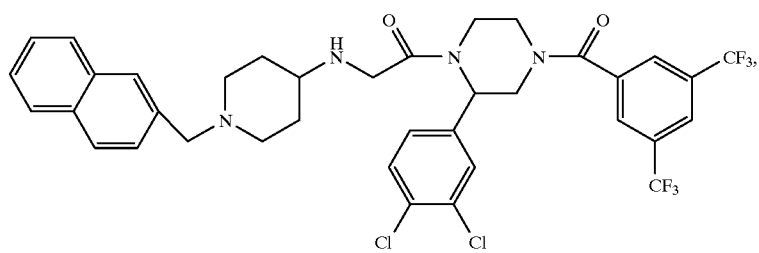
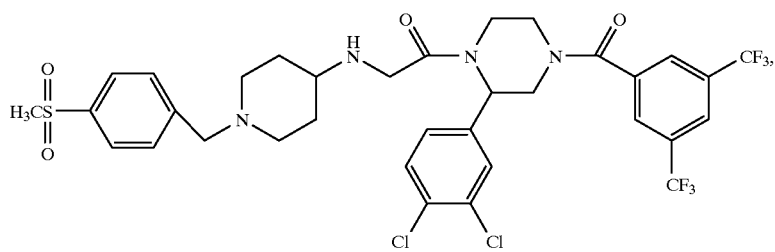
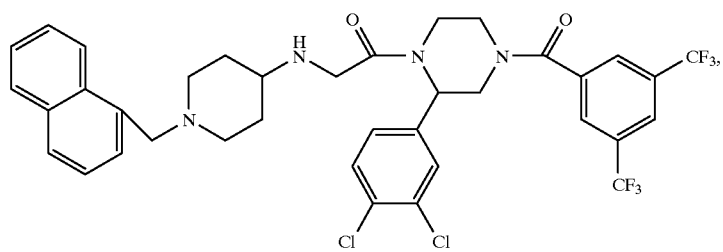
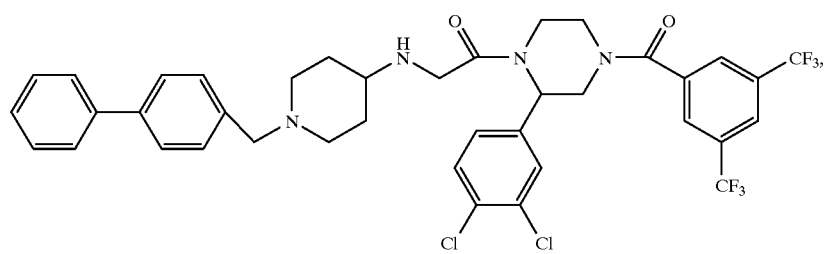
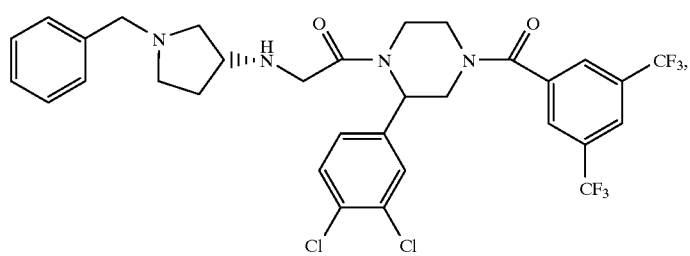
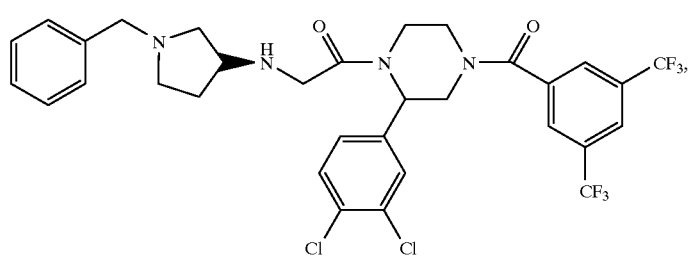

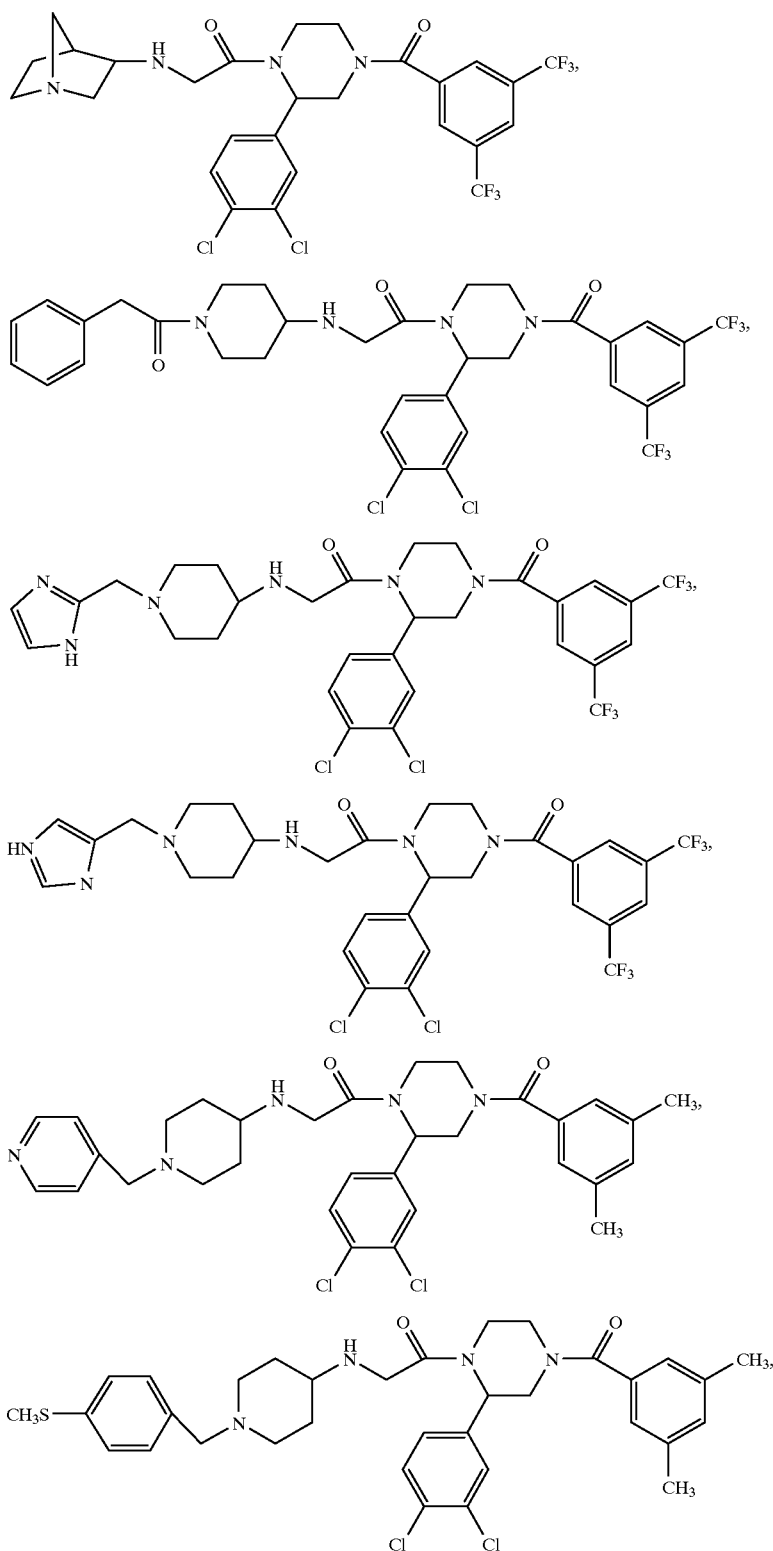

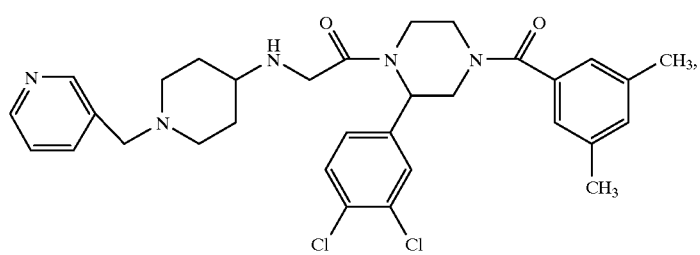
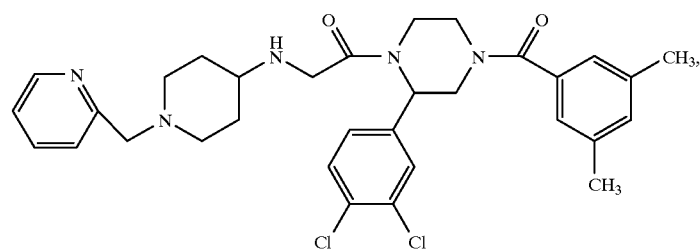
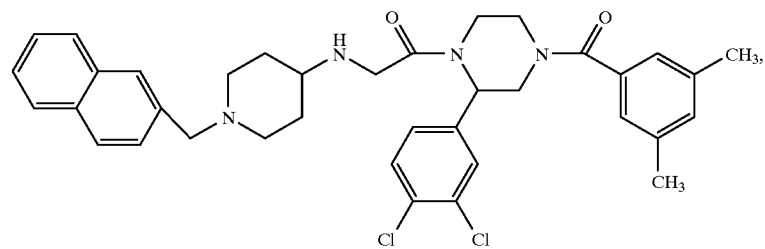
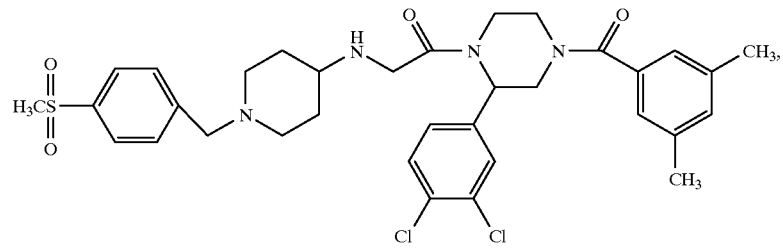
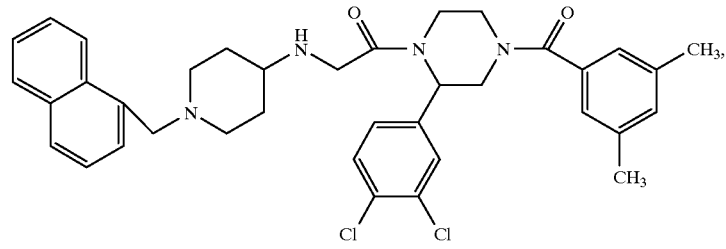
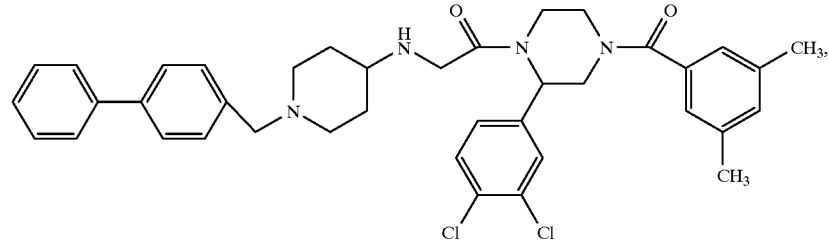

-continued
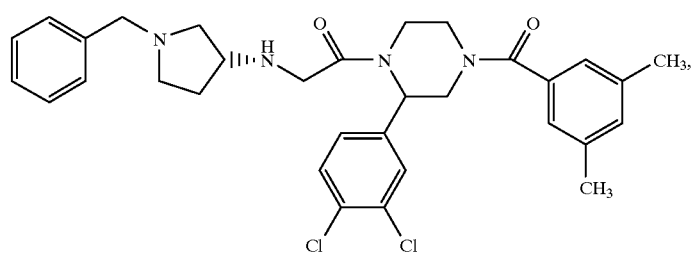
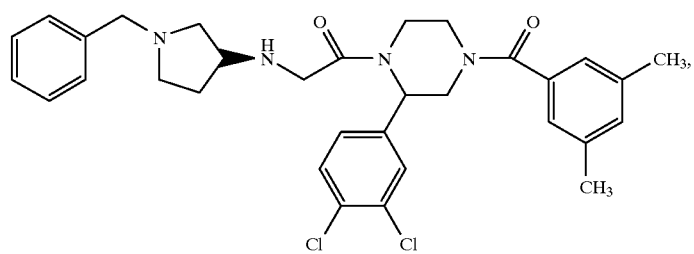
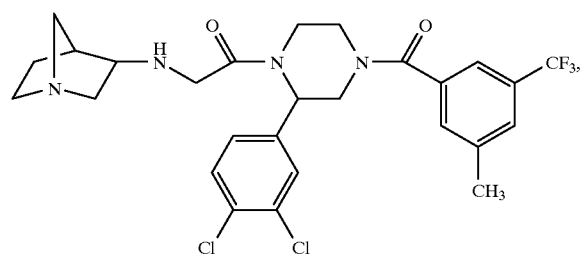
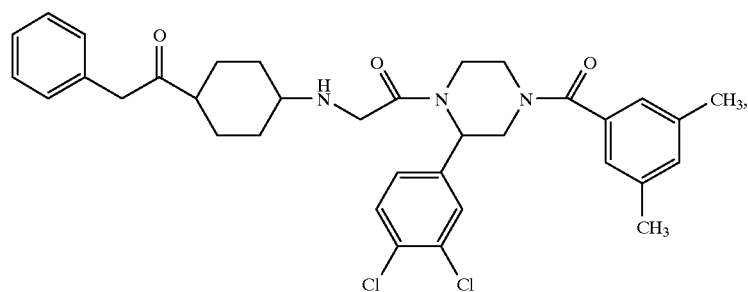
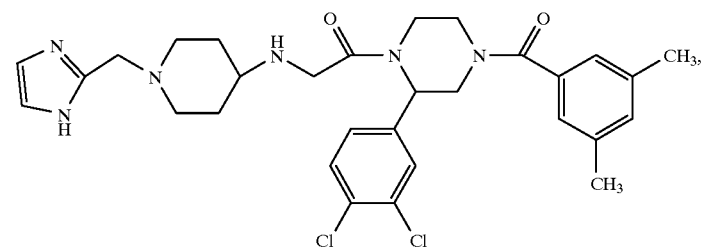
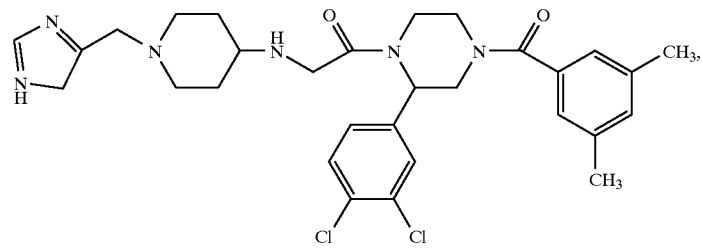

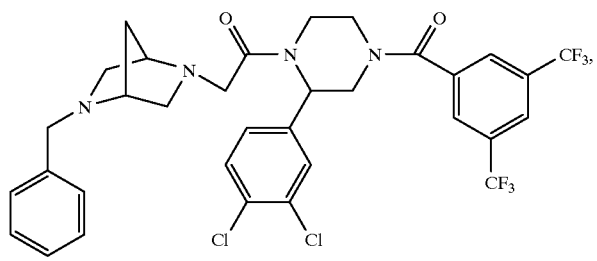
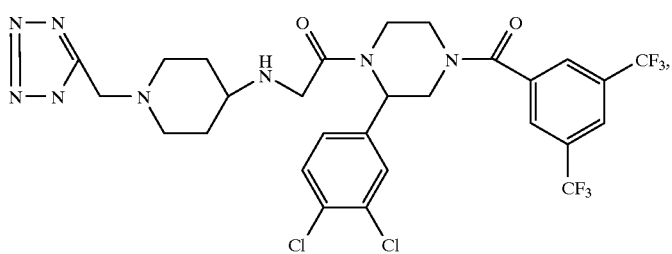
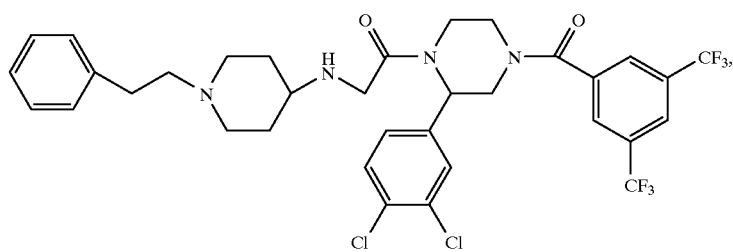
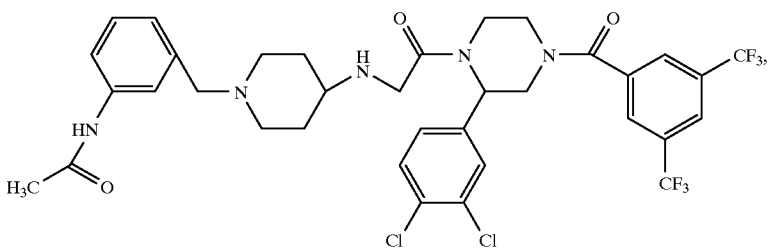
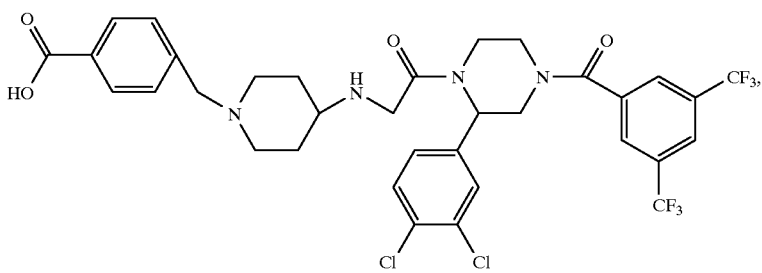
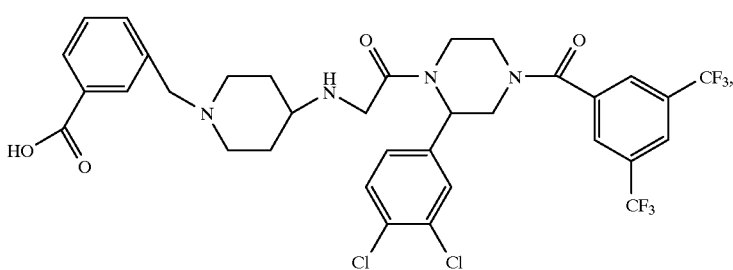

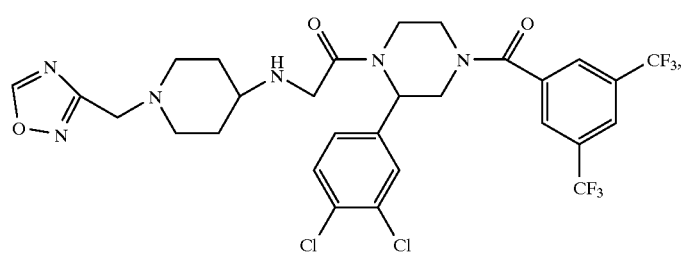
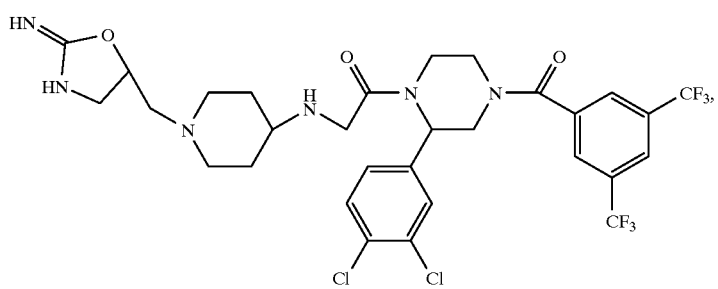
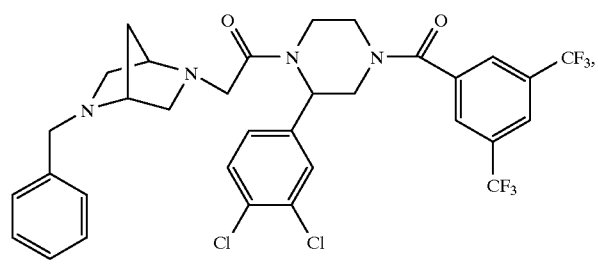
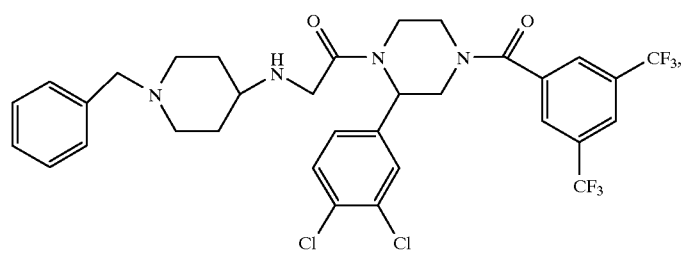
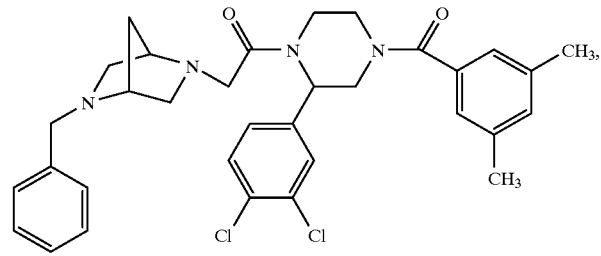
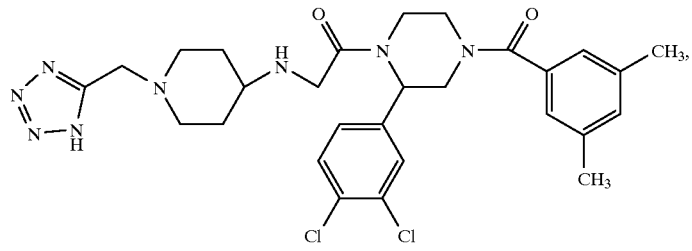

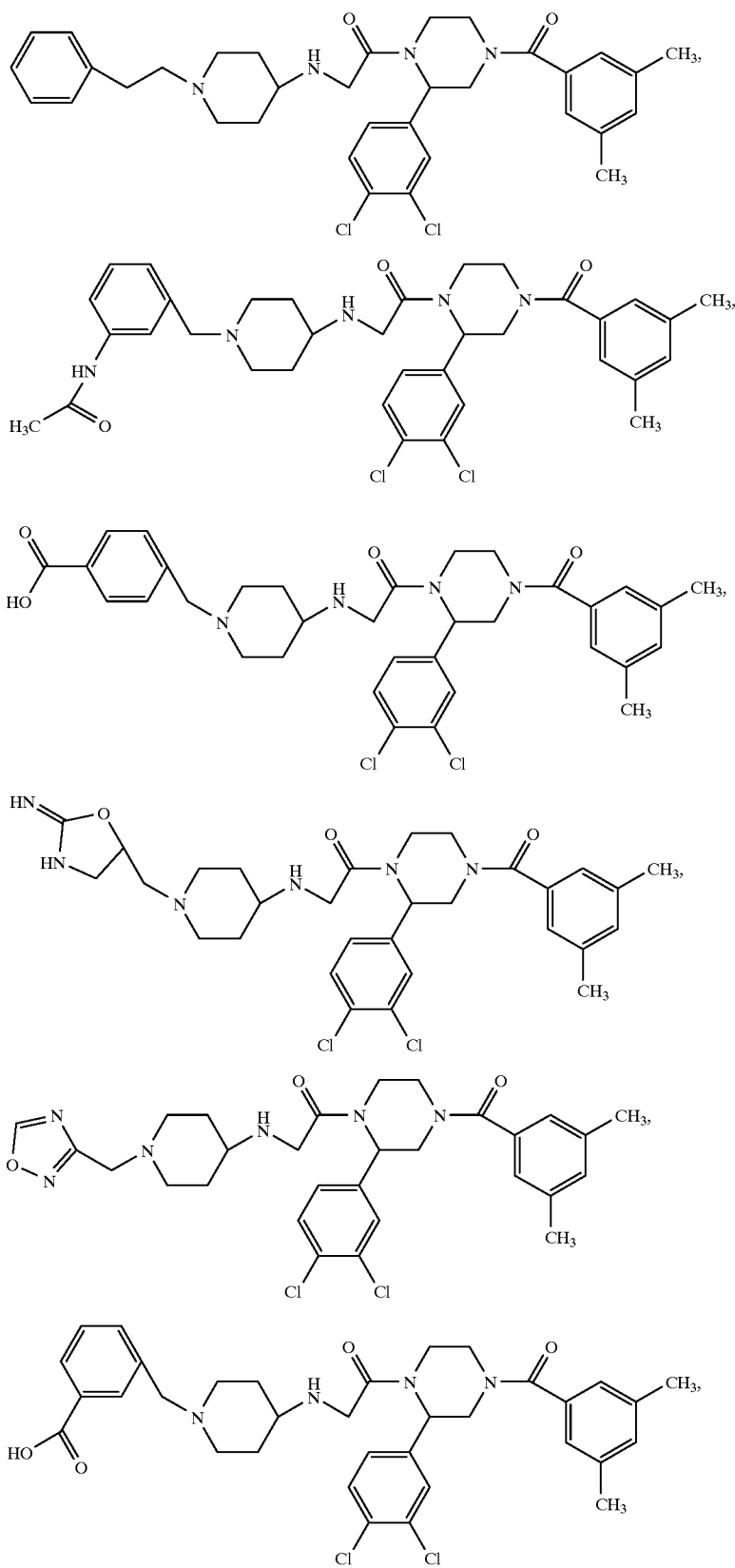

-continued
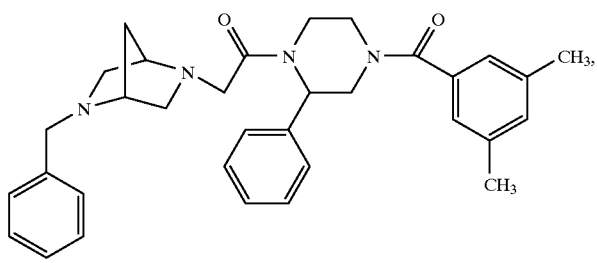
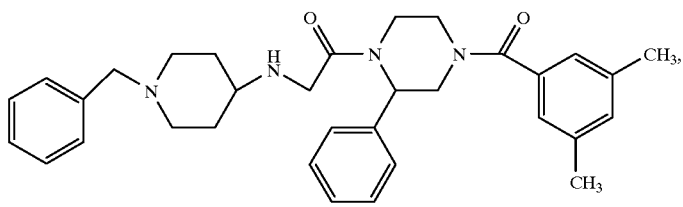
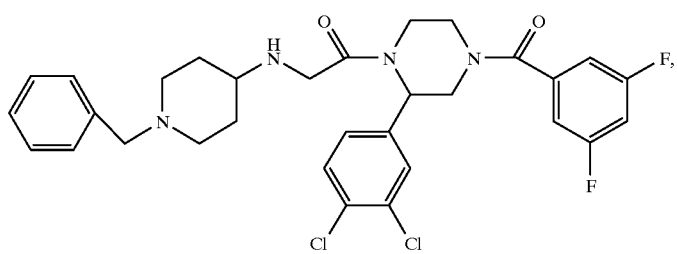
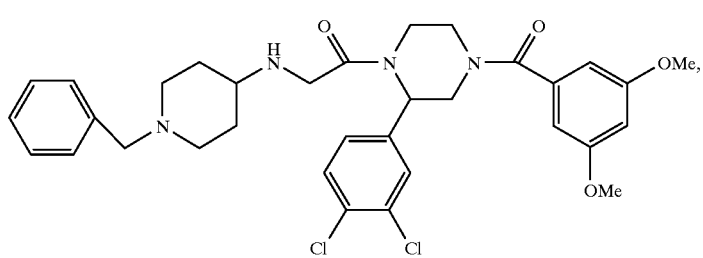
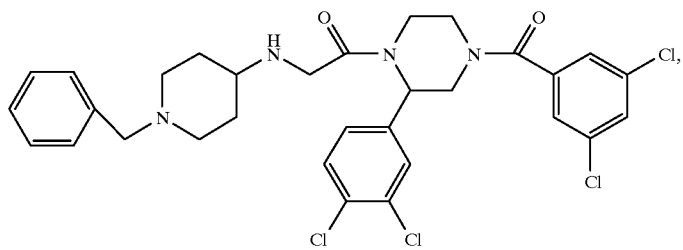
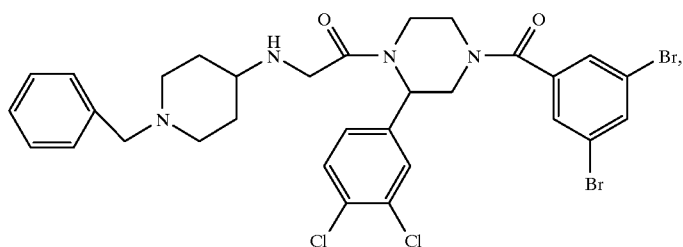

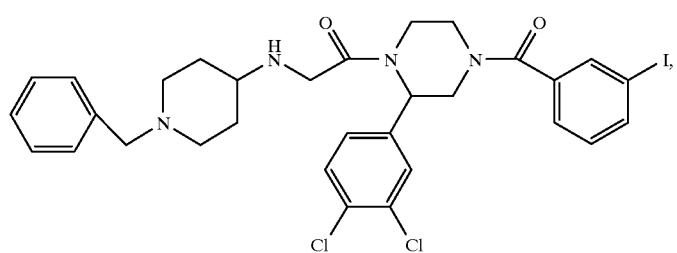
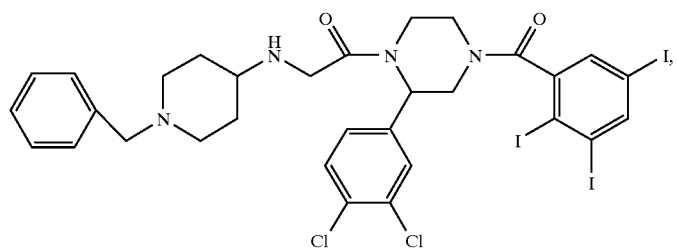
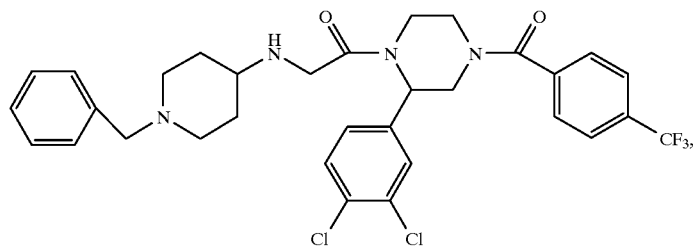
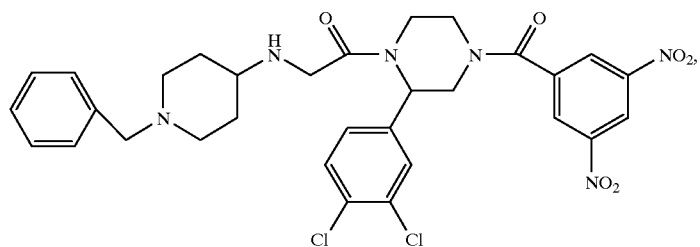
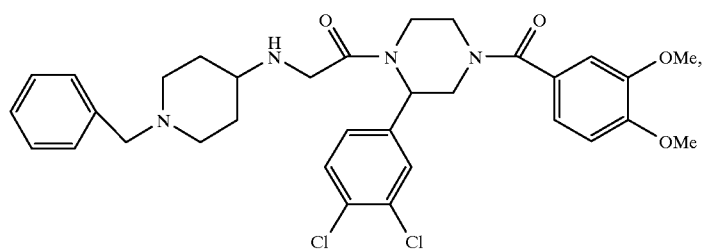
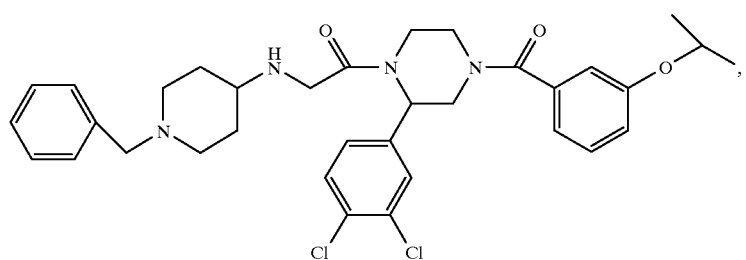

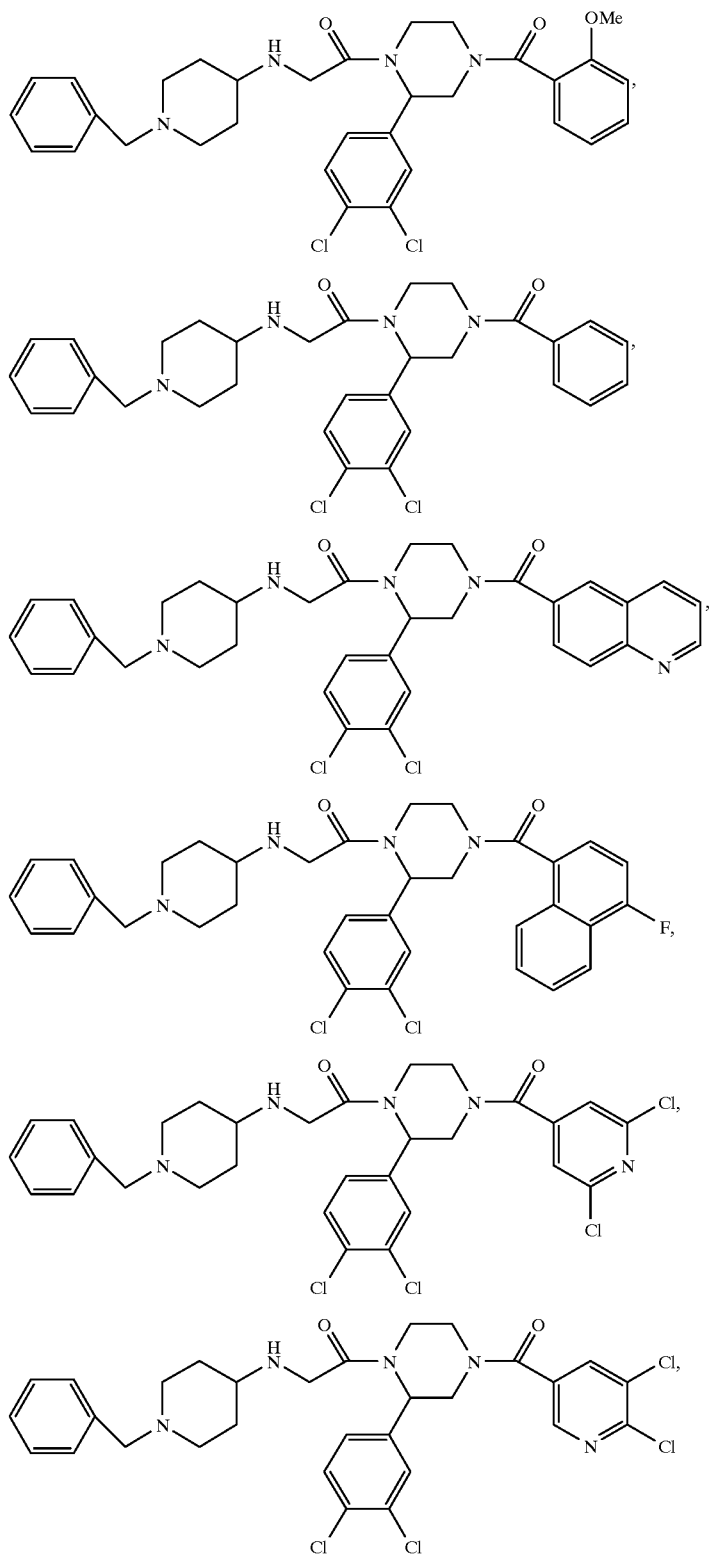

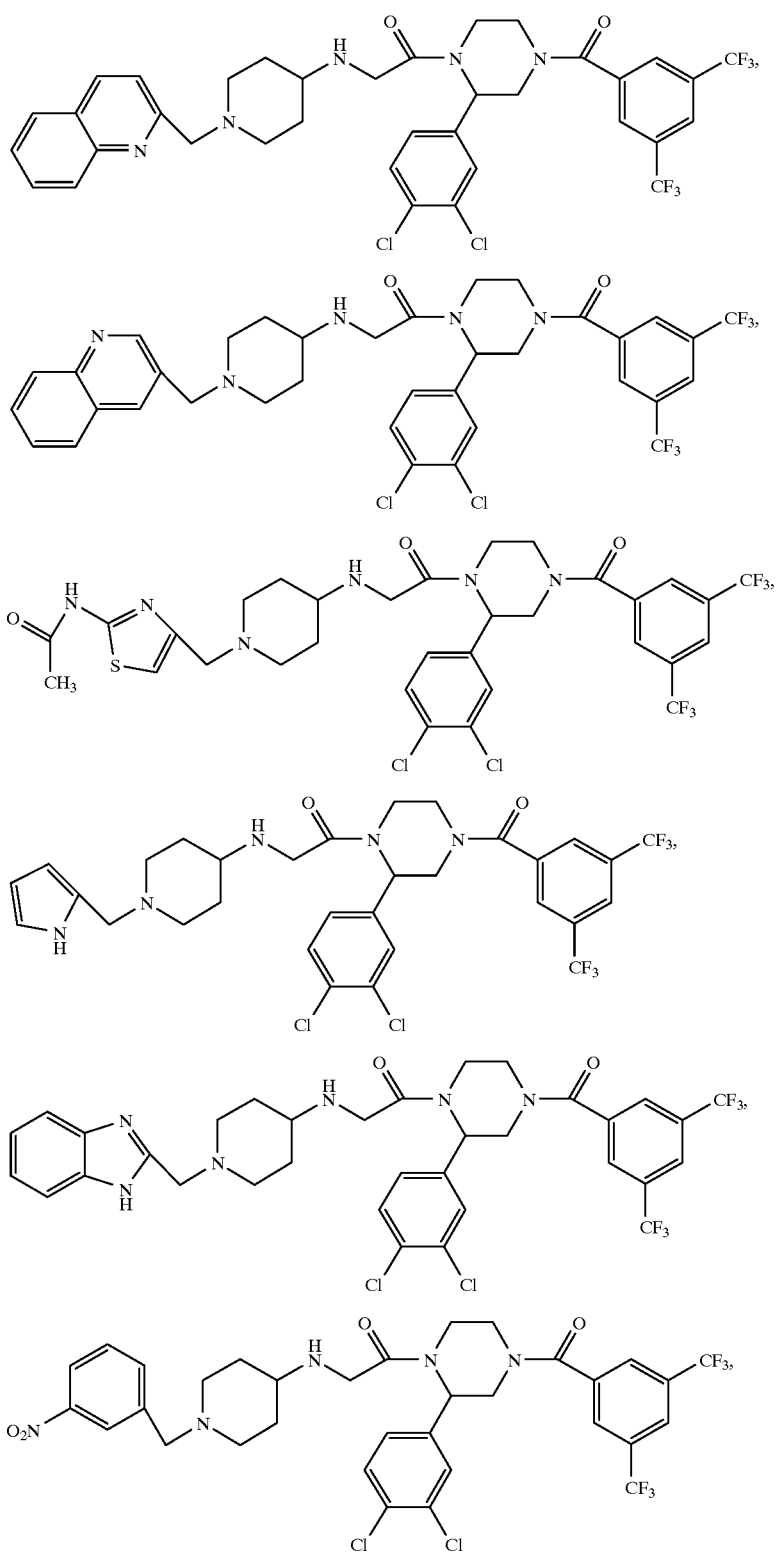

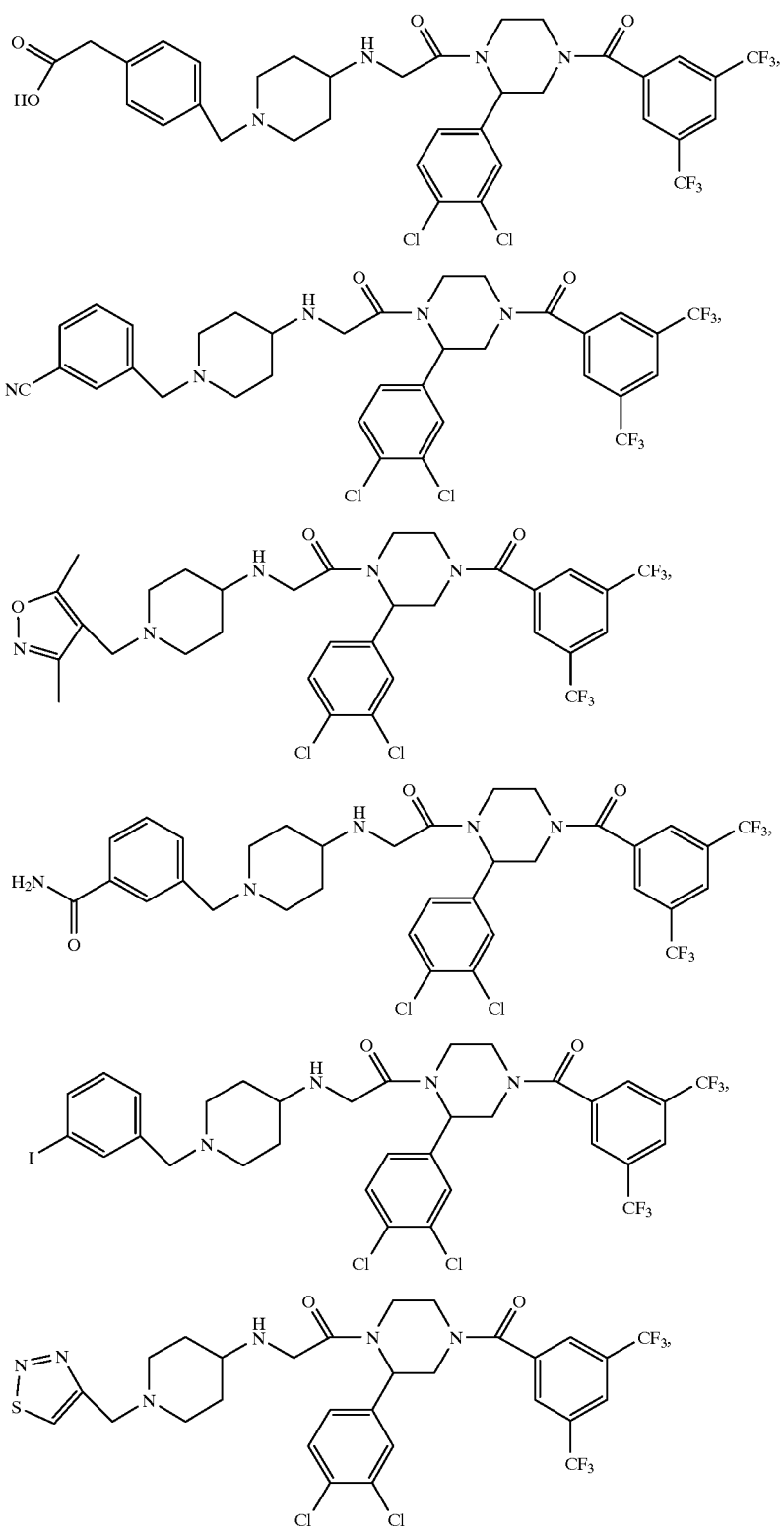

-continued
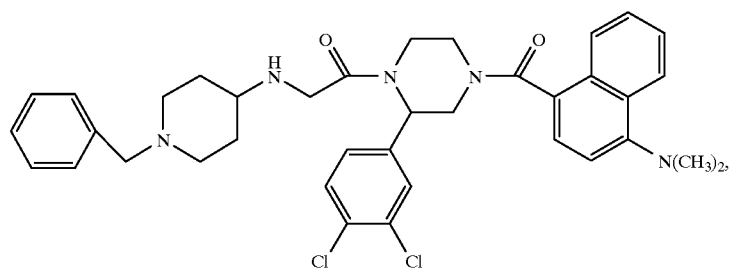
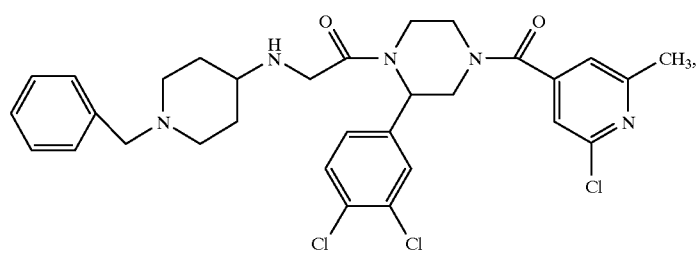
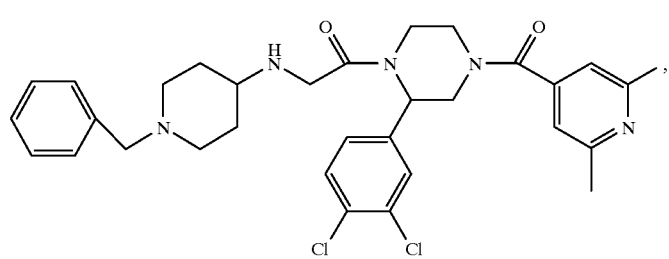
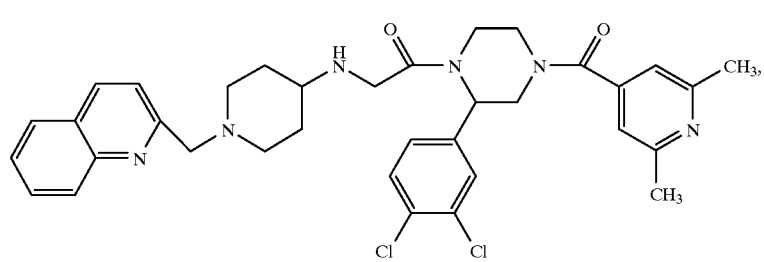
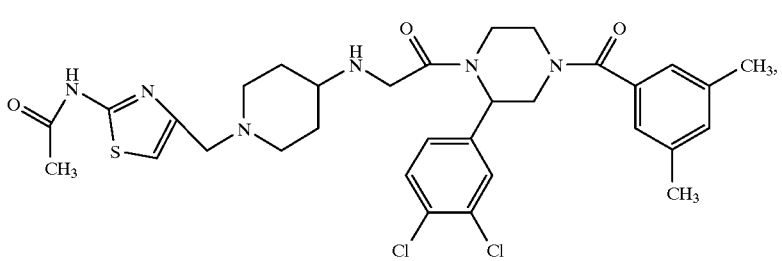
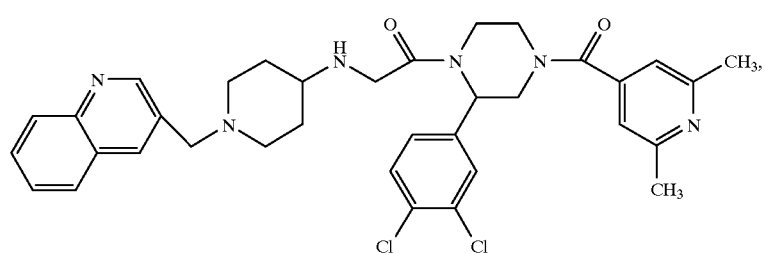

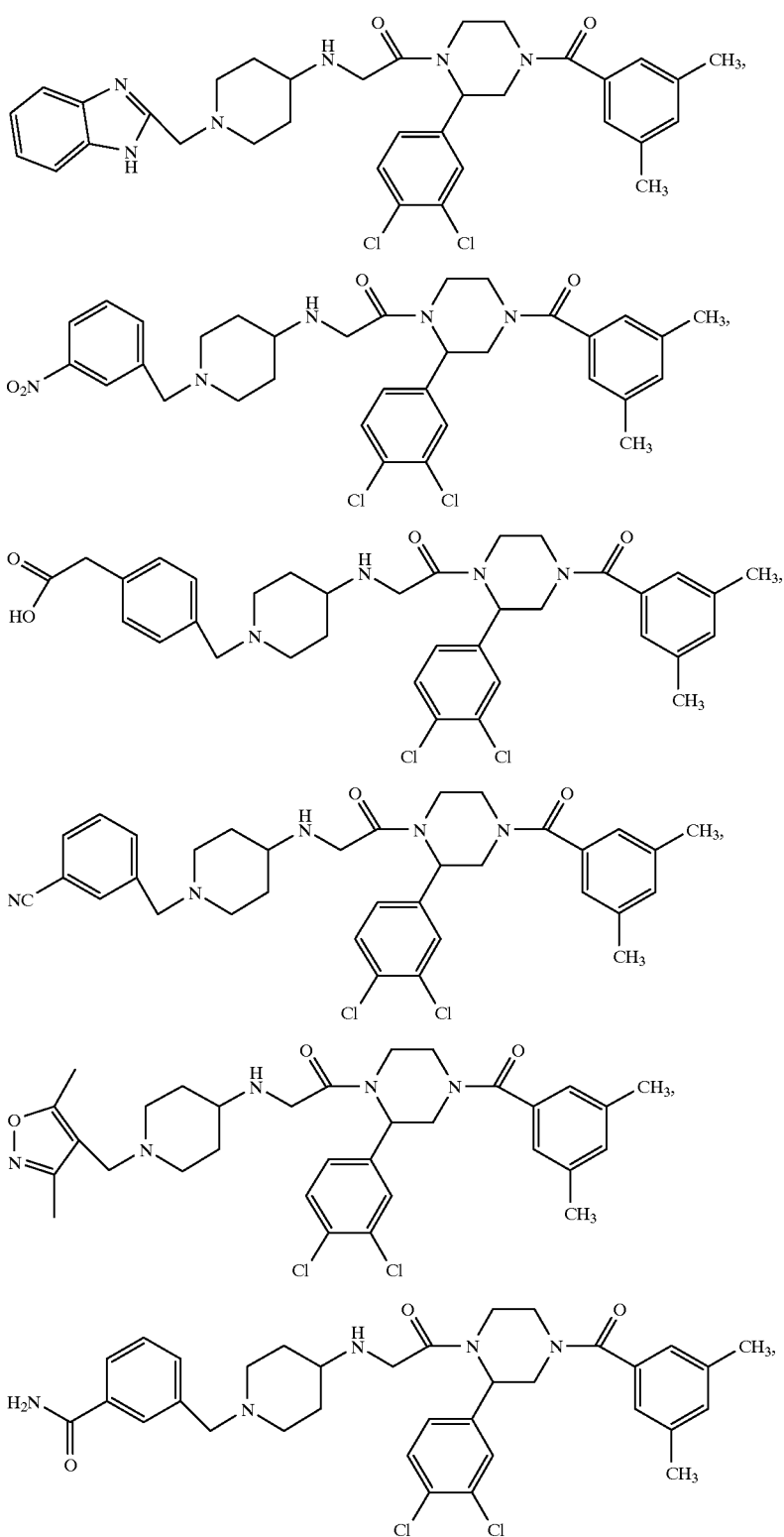

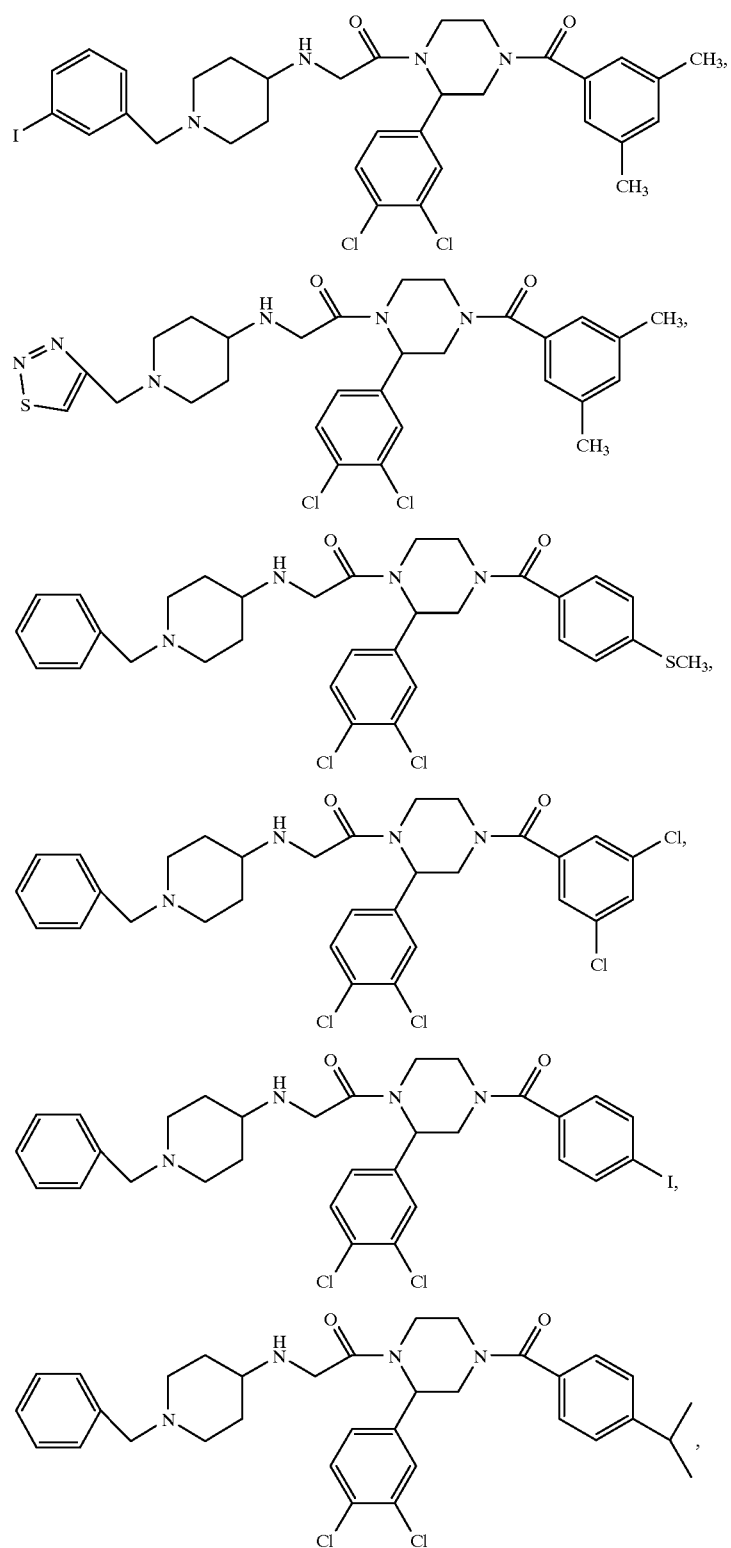

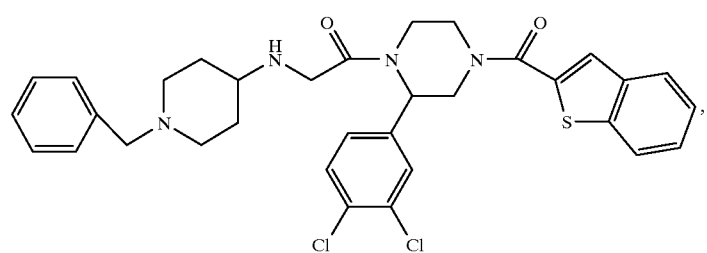
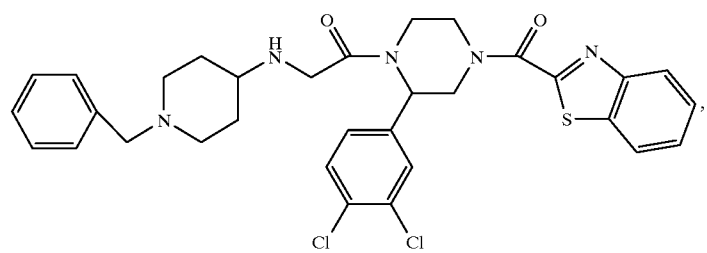
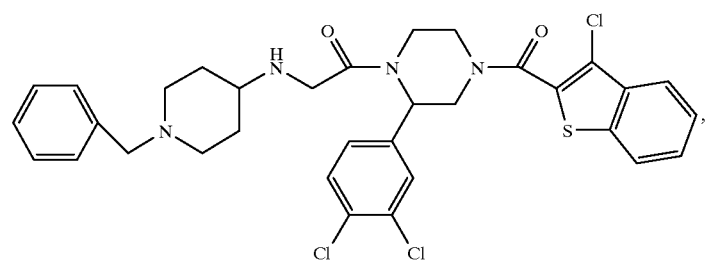
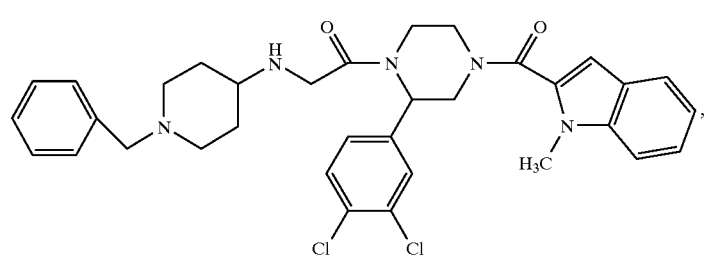
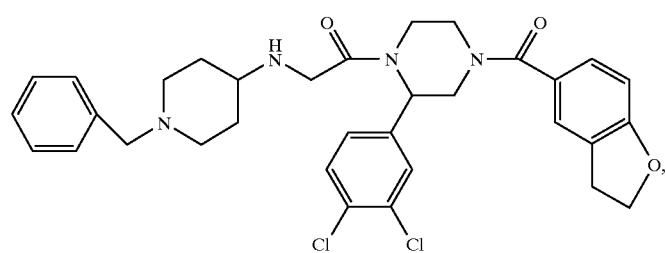
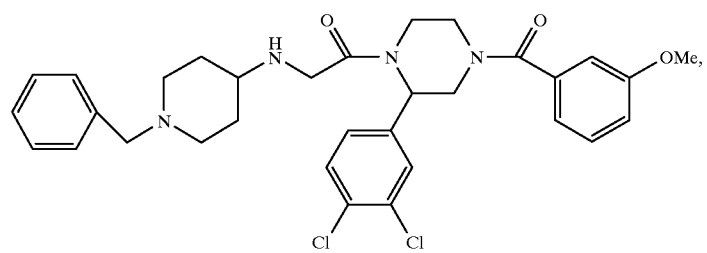

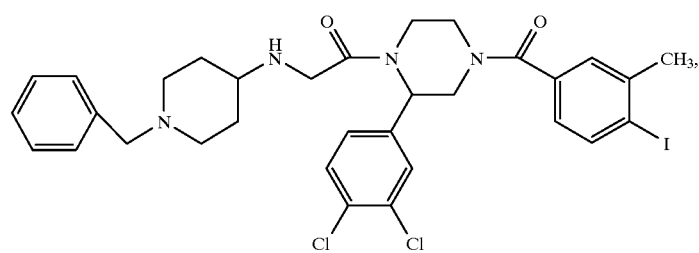
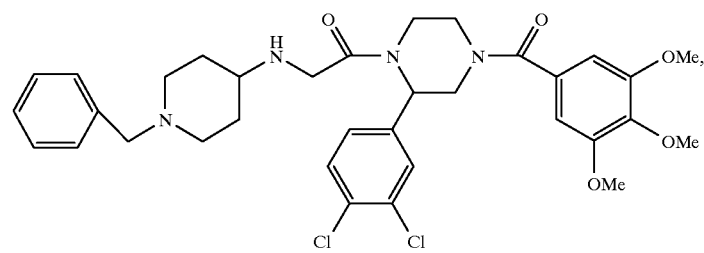
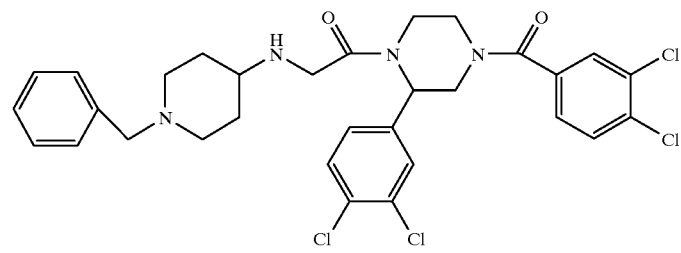
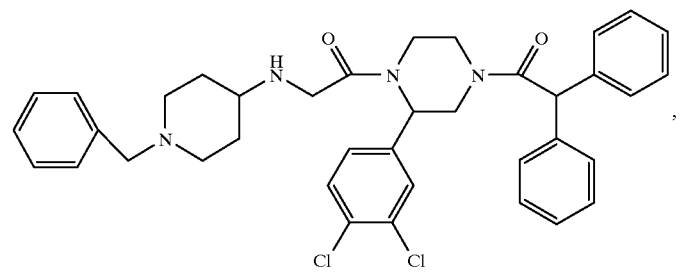
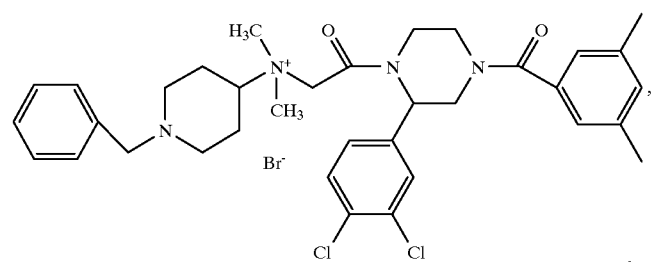
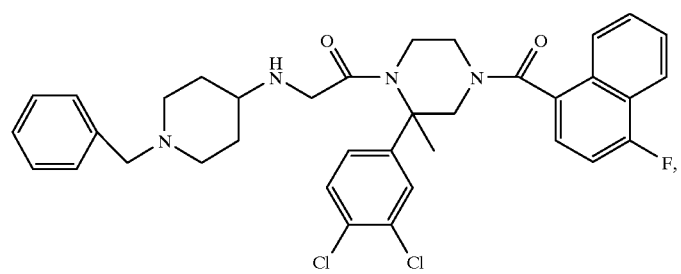

-continued
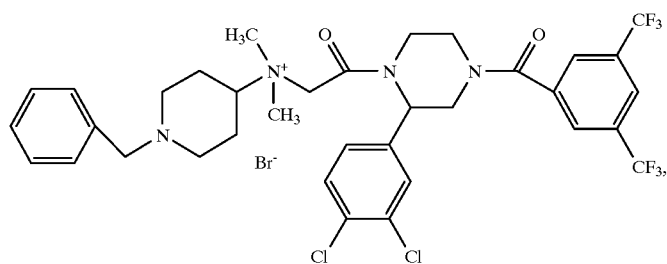
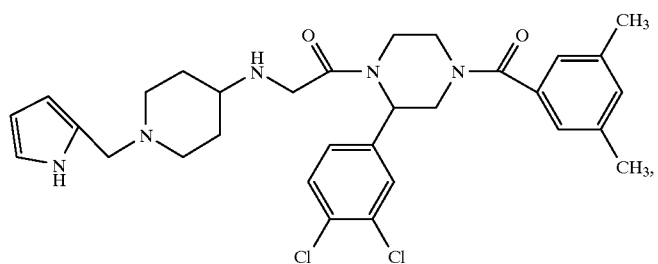
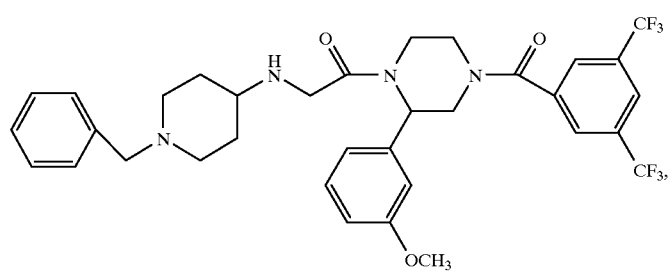
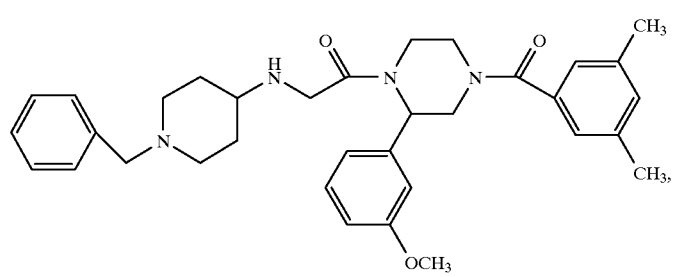
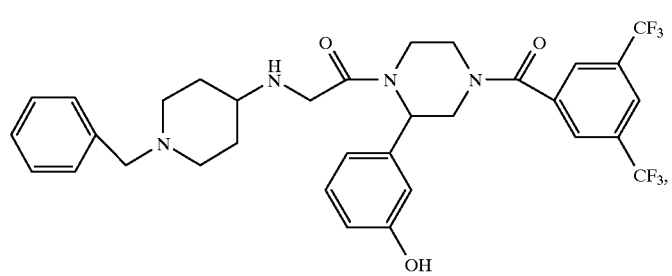
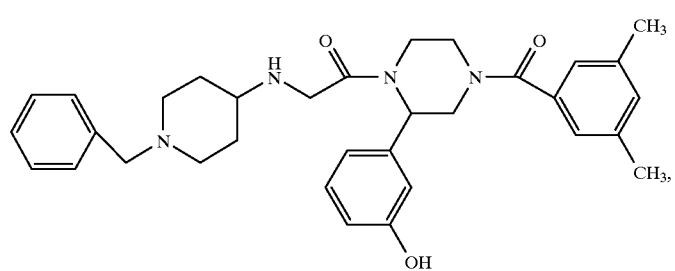

-continued
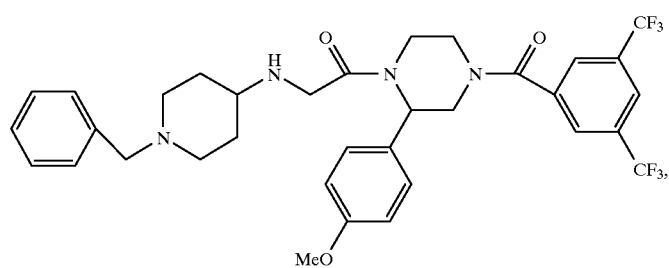
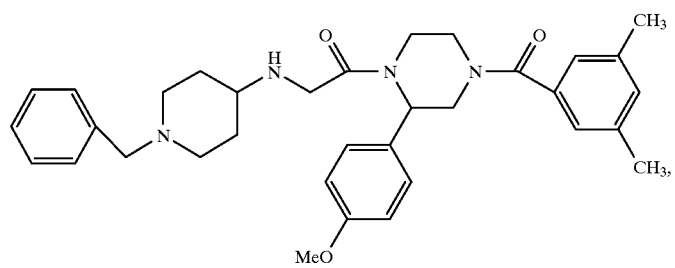
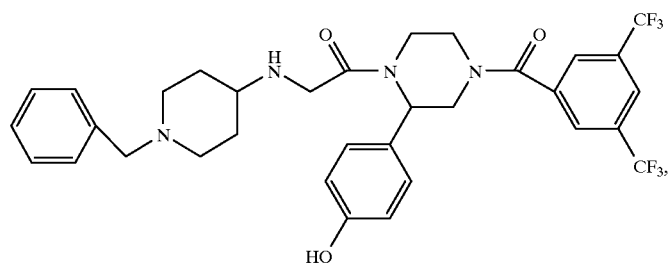
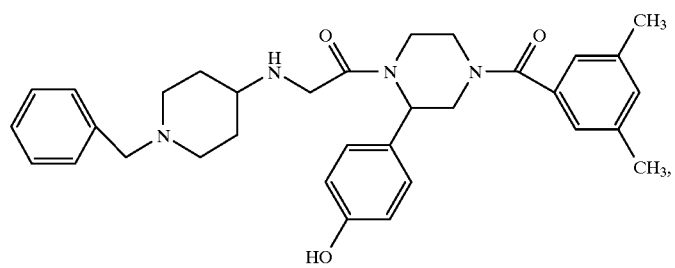
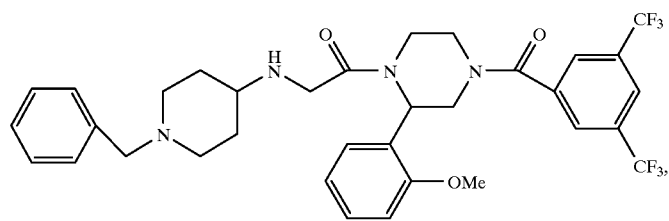
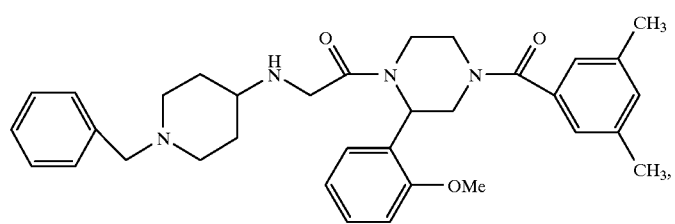

-continued
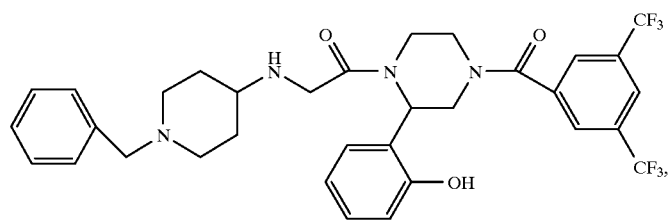
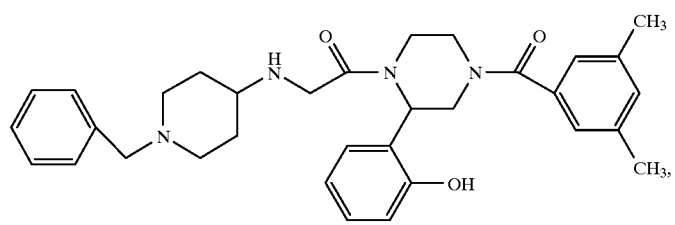
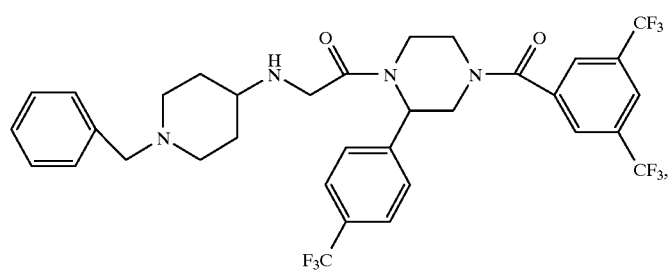
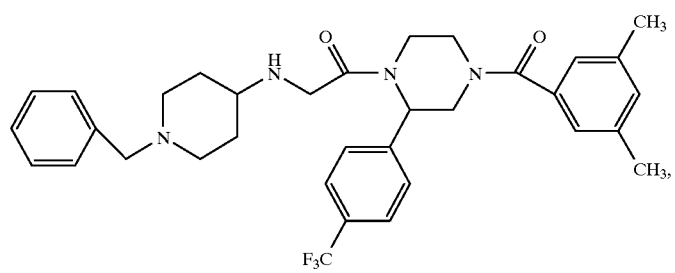
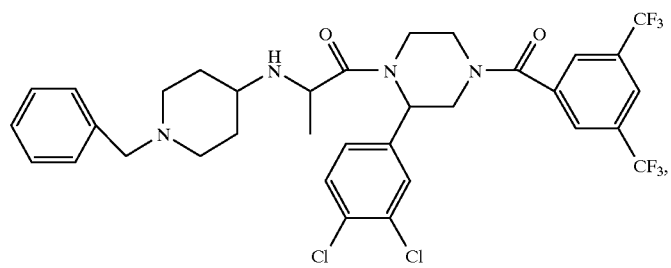
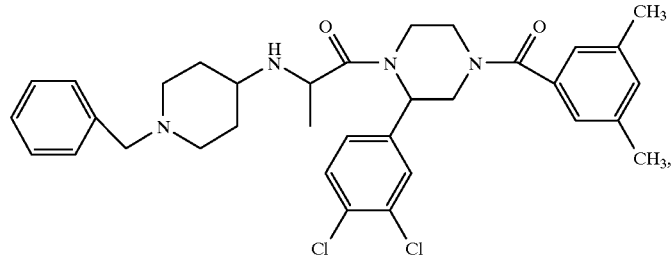

-continued
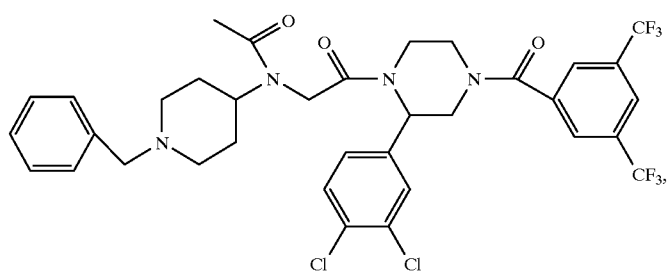
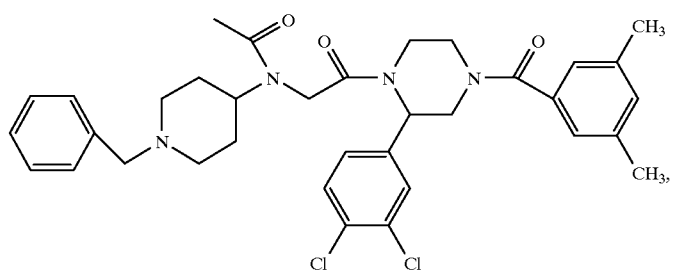
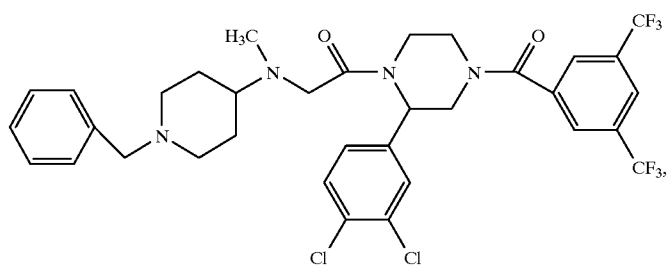
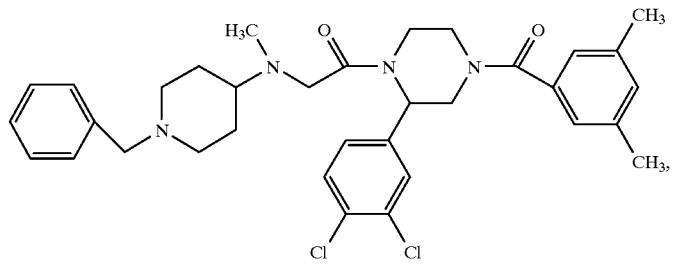
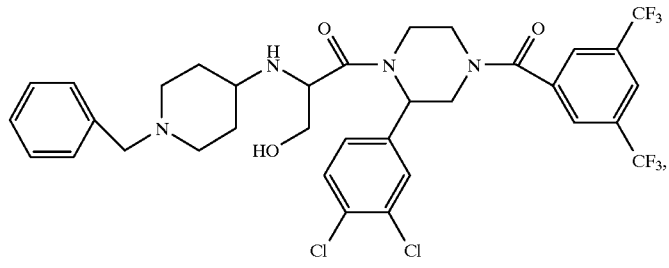
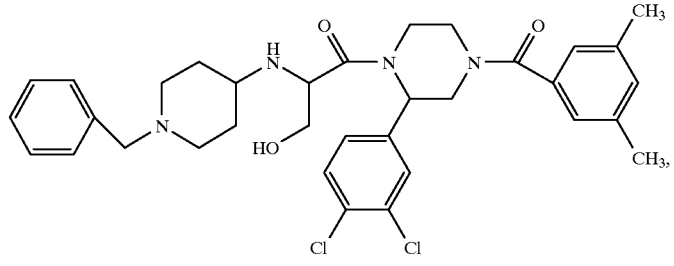

-continued
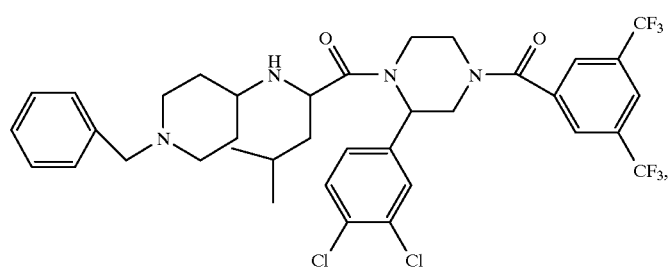
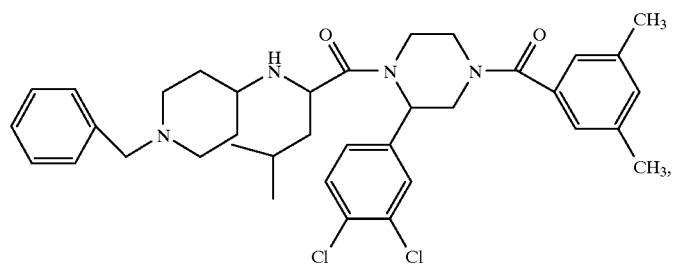
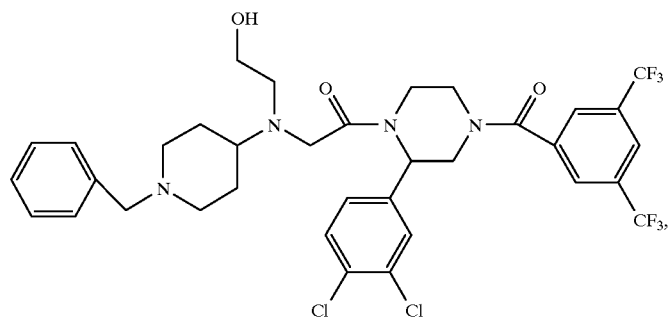
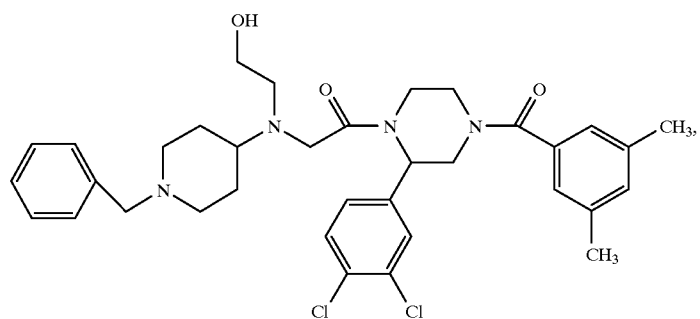
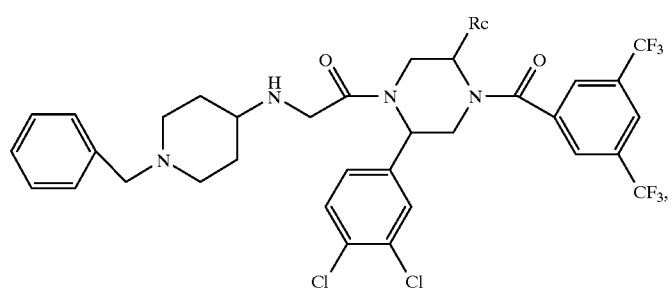
Rc = CH₃, isobutyl, —(CH₂)ₙ₁—COOH, —(CH₂)ₙ₁—OH, —(CH₂)ₙ₁—CONH₂,
$n_1 = 1-6$ -continued
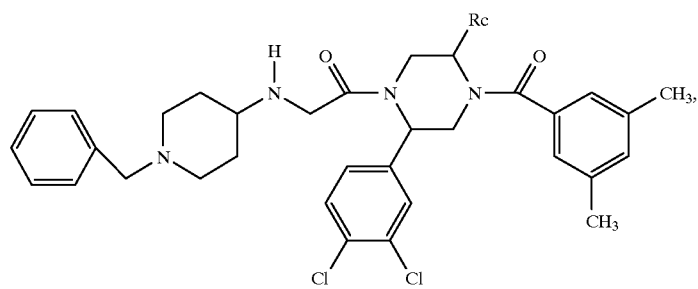
Rc = CH₃, isobutyl, —(CH₂)n1—COOH, —(CH₂)n1—OH, —(CH₂)n1—CONH₂,
$n_1$ = 1–6
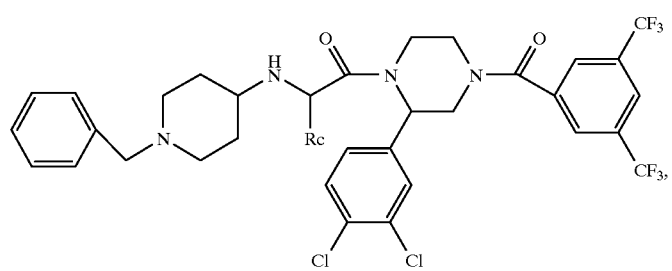
Rc = —(CH₂)n2—OH, —(CH₂)n1—COOH, —(CH₂)n1—COOH,
$n_1$ = 1–6  $n_2$ = 2–6
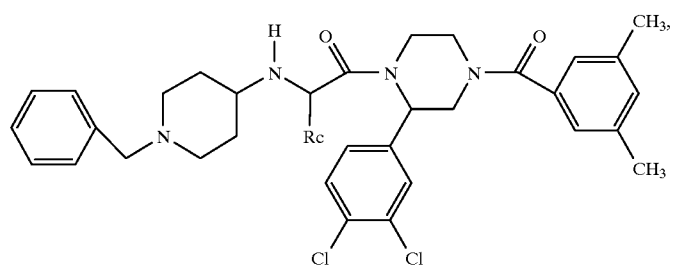
Rc = —(CH₂)n2—OH, —(CH₂)n1—COOH, —(CH₂)n1—COOH,
$n_1$ = 1–6  $n_2$ = 2–6
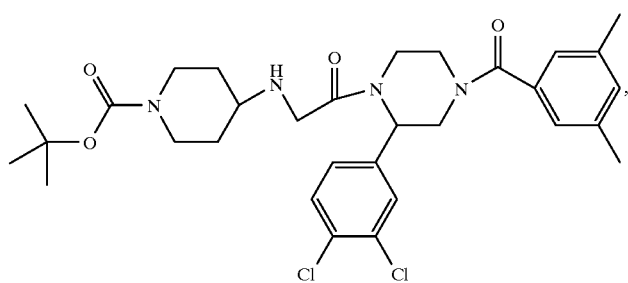
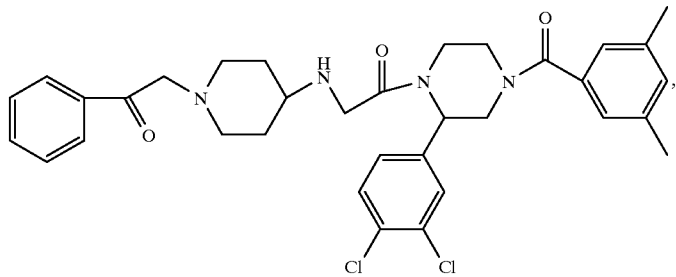

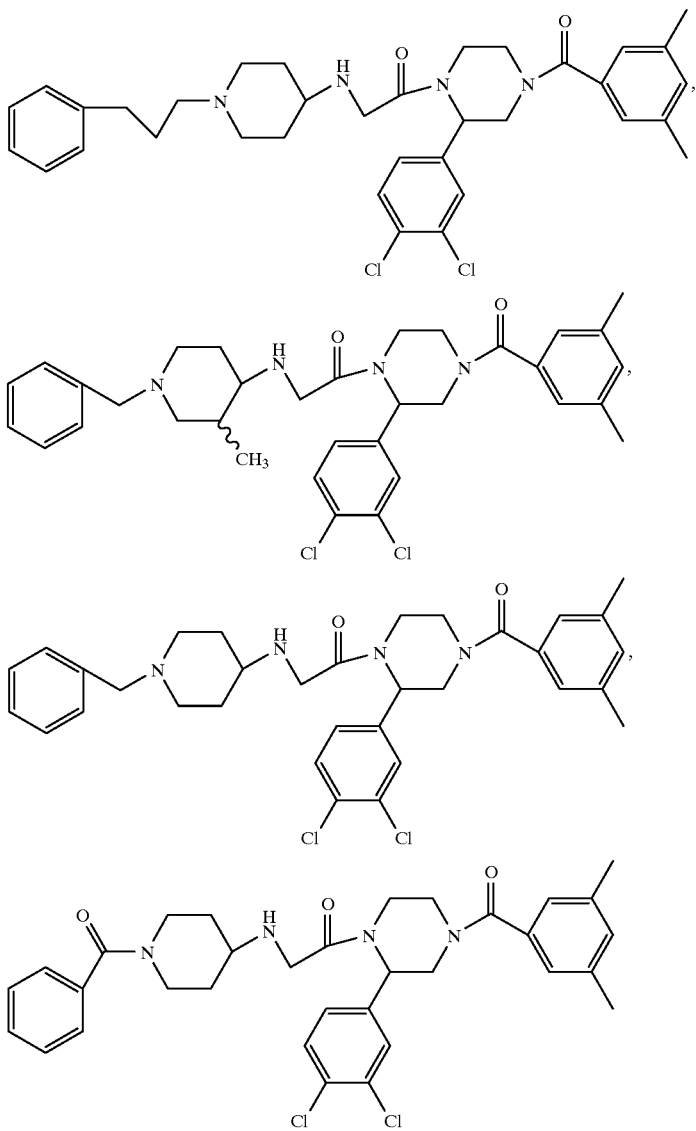

or a pharmaceutically acceptable salt thereof.

The invention also relates to a pharmaceutical composition comprising a thereapeutically effective amount of a compound of formula I in combination with a pharmaceutically acceptable carrier.

The invention also relates to a method for inducing neurokinin antagonism which comprises administering a neurokinin antagonistic effective amount of a compound of formula I to a mammal in need thereof.

The invention also relates to a method for treating chronic airway diseases such as asthma and allergies; inflammatory diseases such as inflammatory bowel disease, psoriasis, fibrositos, osteoarthritis, and rheumatoid arthritis; migraine; central nervous system disorders such as depression, psychosis, dementia, and Alzheimer's disease; Down's syndrome; neuropathy; multiple sclerosis; ophthalmic disorders; conjunctivitis; auto immune disorders; graft rejection; systemic lupus erythematosus; GI disorders such as Crohn's disease and ulcerative colitis; disorders of bladder function; circulatory disorders such as angina; Raynaud's disease; coughing and pain. In particular, the invention also relates to a method of treating asthma which comprises administering to a mammal in need of such treatment an anti-asthma effective amount of a compound of formula I for such purpose.

DETAILED DESCRIPTION OF THE INVENTION

As used herein the term alkyl means a straight or branched, saturated hydrocarbon chain having from 1 to 6 carbon atoms. The number of carbon atoms may be designated. For example, "$C_1$–$C_6$ alkyl" represents a straight or branched, saturated hydrocarbon having from 1 to 6 carbon atoms.

The term $C_3$–$C_6$ cycloalkyl means a cycloalkyl having from 3 to 6 carbon atoms, that is cyclopropyl, cyclobutyl, cyclopentyl and cyclohexyl.

The term alkenyl means means a straight or branched, saturated alkenyl having from 2 to 6 carbon atoms. The number of carbon atoms may be designated. For example, "$C_2$–$C_6$ alkenyl" represents a straight or branched alkenyl having from 1 to 6 carbon atoms.

The term alkynyl means a straight or branched alkynyl having from 2 to 6 carbon atoms. The number of carbon atoms may be designated. For example, "$C_2$–$C_6$ alkynyl" represents a straight or branched chain alkynyl having from 2 to 6 carbon atoms.

As used herein, a heavy dark line (◀) denotes a chemical bond coming above the plane of the page. A dashed line (⋯⋯) denotes a chemical bond coming below the plane of the page.

As used herein,

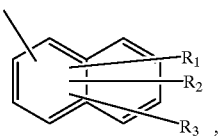

for example, means that $R_1$, $R_2$, and $R_3$ can be in either of the rings of the above naphthyl moiety.

Asymmetric centers exist in compounds of formula I of the invention. Accordingly, compounds of formula I include stereoisomers.

All such isomeric forms and mixtures thereof are within the scope of the present invention. Unless otherwise indicated, the methods of preparation disclosed herein may result in product distributions which include all possible structural isomers, although it is understood that physiological response may vary according to stereochemical structure. The isomers may be separated by conventional means such as fractional crystallization, preparative plate or column chromatography on silica, alumina, or reversed phase supports or HPLC (high performance liquid chromatography).

Enantiomers may be separated, where appropriate, by derivatization or salt formation with an optically pure reagent, followed by separation by one of the aforementioned methods. Alternatively, enantiomers may be separated by chromatography on a chiral support.

The compounds of formula I can exist in unsolvated as well as solvated forms, including hydrated forms, e.g. the hemihydrate. In general, the solvated forms, with pharmaceutically acceptable solvents such as water, ethanol, and the like are equivalent to the unsolvated forms for the purposes of the invention.

Those compounds of formula I which contain a basic group such as —$CH_2NH_2$, form pharmaceutically acceptable salts. The preferred pharmaceutically acceptable salts are nontoxic acid addition salts formed by adding to a suitable compound of the invention about a stoichiometric amount of a mineral acid, such as HCl, HBr, $H_2SO_4$ or $H_3PO_4$ or of an organic acid such as acetic, propionic, valeric, oleic, palmitic, stearic, lauric, benzoic, lactic, para-toluenesulfonic, methanesulfonic, citric, maleic, fumaric, succinic and the like, respectively.

General Methods of Preparation

The compounds of this invention may be prepared by one of the following general methods. As used herein RT means room temperature. Unless otherwise indicated, variables in the structural formulas below are as defined above. Starting materials and reagents used in the methods and examples below, are known or may be prepared according to known methods.

As used herein the term "substituted phenyl" means

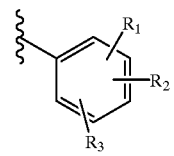

wherein $R_1$, $R_2$, and $R_3$ are as described herein.

"substituted" means substituted by $R_1$, $R_2$, and/or $R_3$ as described herein.

"Aryl" means phenyl, naphthyl, indenyl, tetrahydronaphthyl, indanyl, anthracenyl or fluorenyl.

"Halogeno" refers to fluoro, chloro, bromo or iodo atoms.

"Heterocycloalkyl" refers to 4- to 6-membered rings comprising 1 to 3 heteroatoms independently selected from the group consisting of —O—, —S— and —N($R^6$)—, with the remaining ring members being carbon. Examples of heterocycloalkyl rings are tetrahydrofuranyl, pyrrolidinyl, piperidinyl, morpholinyl, thiomorpholinyl and piperazinyl.

"Heteroaryl" refers to 5- to 10-membered single or benzofused aromatic rings comprising 1 to 3 heteroatoms independently selected from the group consisting of —O—, —S— and —N=. Examples of single-ring heteroaryl groups are pyridyl, isoxazolyl, oxadiazolyl, furanyl, pyrrolyl, thienyl, imidazolyl, pyrazolyl, tetrazolyl, thiazolyl, thiadiazolyl, pyrazinyl, pyrimidinyl, pyridazinyl and triazolyl. Examples of benzofused heteroaryl groups are quinolinyl, thianaphthenyl and benzofurazanyl. N-oxides of nitrogen-containing heteroaryl groups are also included. All positional isomers are contemplated, e.g., 1-pyridyl, 2-pyridyl, 3-pyridyl and 4-pyridyl.

Where $R^2$ and $R^3$ substituents form a ring and additional heteroatoms are present, the rings do not include adjacent oxygen and/or sulfur atoms or three adjacent heteroatoms. Typical rings so formed are morpholinyl, piperazinyl and piperidinyl.

As used herein, the term "BOC" means t-butoxycarbonyl.

As used herein, the term "Ph" means phenyl.

As used herein, the term "RT" means room temperature.

As used herein, the term "parallel synthesis" means the preparation of individual chemical compounds as one of a batch of, for instance, 20, 30, or even 100 identical reactions on usually a single substrate but using a different reagent in each vessel. Such reagents are always of the same general class—in this case, either carboxylic acids or organic amines in any set of parallel reactions. The conditions used for each reaction are identical to those described in the examples, except that a simplified work-up is employed, generally a simple wash either with acid or base if appropriate, then water. The presence of the product is detected by thin layer chromatography (TLC) using known products as representative standards. Further characterization by combination HPLC/MS is generally performed. No further purification is performed on these materials before they are submitted to biological assays.

As used herein, each $R_c$ and $R_c'$ is independently selected from the group consisting of H, $C_1$–$C_6$ alkyl, $C_2$–$C_6$ alkenyl, $C_2$–$C_6$ alkynyl, unsubstituted or substituted phenyl, and unsubstituted or substituted benzyl.

The starting materials in the methods below are either known or can be prepared in accordance with known methods. In particular, the following compounds are either known or can be prepared in accordance with known methods: the diamine A, the compounds of formulas A, VI, VIII, X, XI, XIV, XVIII, XIX, XXa, A', XXV, and Z-H, as well as esters of formula XI, and compounds of formula

Method 1

If the group Ar$_2$ is an aromatic group with no I or Br substituents, then the following method may be used to prepare the useful intermediates (IV):

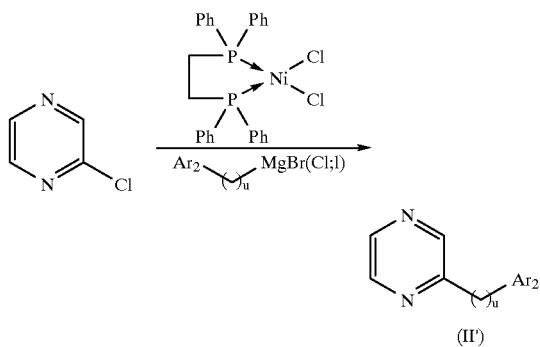

Transition metal catalyzed coupling of 2-chloropyrazine with an aromatic Grignard reagent in a dry, ether solvent, such as THF, yields the aryl-substituted pyrazine of formula II'. The catalyst shown, [1,2-bis-(diphenylphosphino) ethane]nickel$^{II}$ chloride, is a preferred reagent for this transformation. Where Ar$_2$ has no halo substituents, reduction of a compound of formula II' by catalytic hydrogenation, using, for instance, palladium acetate, preferably in acetic acid solvent, results in preferential reduction of the pyrazine ring, leaving the aromatic ring unreduced, that is, it results in a compound of formula II. Similarly, 10% Pd on charcoal (Pd-C) can be used in an alcohol solvent, preferably methanol, with or without the addition of a small quantity (1 to 5 equivalents) of acetic acid. Reaction times of from 1 to 24 hours generally suffice for this reaction, which is preferentially run at room temperature or slightly above (up to about 50° C.) and using from 1 to about 6 atmospheres pressure of hydrogen.

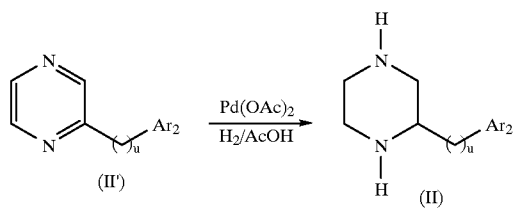

The intermediate of formula II may also be prepared from a compound of formula II', even if the group Ar$_2$ contains halogen atoms, by reduction using a strong hydride ion donor, preferably lithium aluminum hydride (LAH) or diisobutyl aluminum hydride (DIBAL-H) in an ether solvent, such as ether, THF or dimethoxyethane (DME).

Selective alkylation of a compound of formula II is possible using low temperature conditions. Thus, reacting a compound of formula II with a substituted aryl-alkyl halide of formula III where I is 0 to 2, results in the formation of the 4-substituted derivative of formula IV. Suitable conditions include use of a halogenated solvent, such as CH$_2$Cl$_2$, at low temperature. Suitable temperatures are from −78° C.

initially, allowing the reaction mixture to warm gradually to RT if the reaction is not completed after several hours. The reaction is catalyzed by the addition of an equivalent amount of an organic base, such as triethylamine and diisopropylethylamine (Hünig's base).

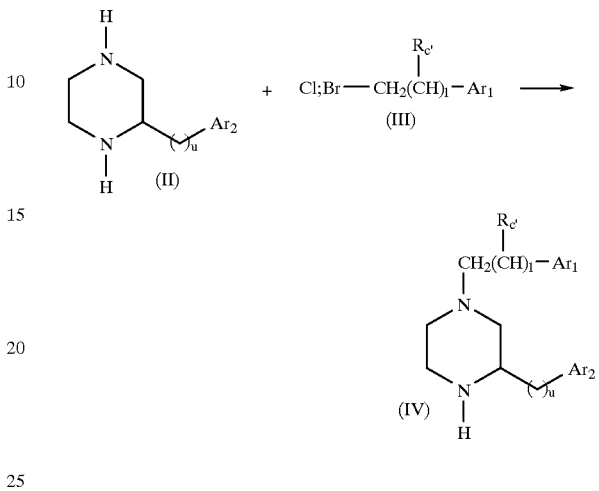

Method 2

If the group Ar$_2$ contains one or more halogen atoms on an aromatic ring and the other groups are as in Method 1, then an alternate route to a compound of formula IV is preferred. In addition, this method can be used to prepare compounds in which I is from 0 to 2. Mono-protection of the diamine of formula (A), preferably with BOC anhydride, or other agents known to introduce the t-butyloxycarbonyl protecting group, in an alcohol solvent, such as methanol, preferably at about −10° C., produces a compound of formula V.

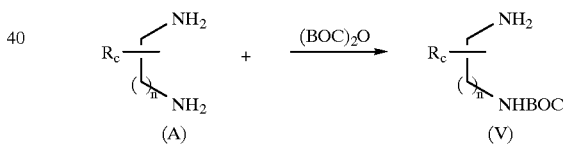

These compounds are used to perform a reductive amination reaction with the aldehyde of formula VI to produce an amine of formula VII. (In structures (A), (V), (VII), and (IX) herein, Rc can be bound to any position between the two nitrogens. In cyclic structures like (IVA) below, R$_c$ can be bound to any available cyclic position that is occupied by carbon, and that is between the two nitrogens.)

Suitable conditions for this type of reaction include the use of an alcohol solvent, preferably methanol, or 2,2,2-trifluoroethanol, made slightly acidic with a weak organic acid, such as acetic acid, and a reducing agent known to favor reductive amination reactions, preferably sodium cyanoborohydride, NaBH$_3$CN.

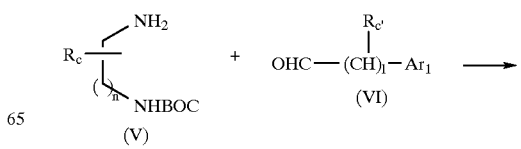

-continued

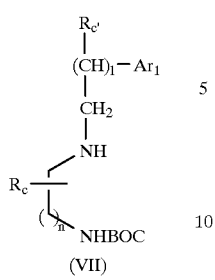

(VII)

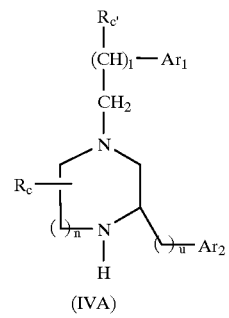

(IVA)

Reaction of a compound of formula VII with an α-haloketone of formula VIII, in which $Ar_2$ preferably represents a halogenated aromatic ring, but may be any of the claimed aromatic rings, in the presence of an organic base, such as di-isopropylethylamine, also known as Hünig's Base, in an ether solvent, such as THF, results in the formation of the intermediates of formula IX.

Method 3

An alternate route to compounds of the invention in which I is 0 to 2 is as follows. Standard coupling of an N-protected amino acid of formula X, wherein $Ar_2$ is as described above, with an amino acid ester derivative

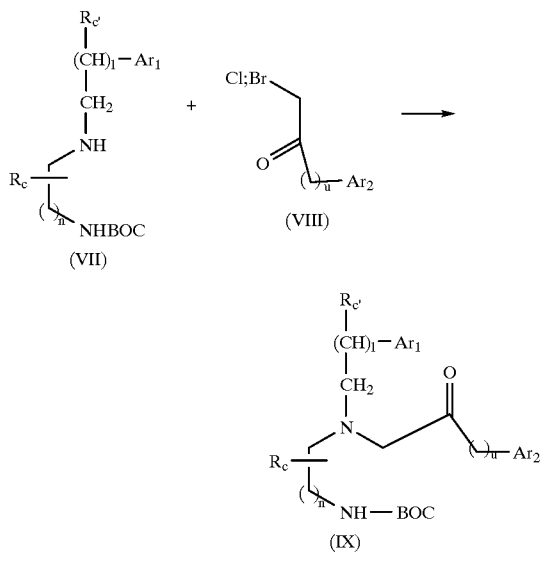

(R' is $C_2-C_4$ alkyl, preferably, the ethyl ester of formula XI, .Et in the formulas herein means ethyl), produces a dipeptide of formula XII. A suitable protecting group is BOC, although many others may also be used. Other esters of the amino acid may also be used. Standard coupling techniques may be applied, an example being the use of N-hydroxybenztriazole (HOBT) and a water-soluble carbodiimide, such as 1-(3-dimethylaminopropyl)-3-ethylcarbodiimide (DEC), in a non-hydroxylic solvent such as $CH_2Cl_2$, DMF or a mixture of the two foregoing solvents. The reaction is run, preferably, at or below RT, and takes from 1 to 40 hours for completion, depending upon the substrates.

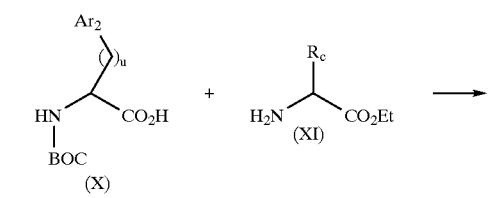

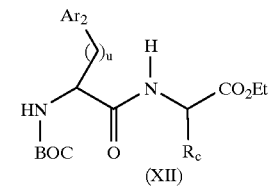

Removal of the BOC protecting group using a suitable acidic catalyst, such as trifluoroacetic acid, followed by an intramolecular reductive amination, under conditions such as those described above for the preparation of a compound of formula VII, leads to the formation of compounds of formula IVA.

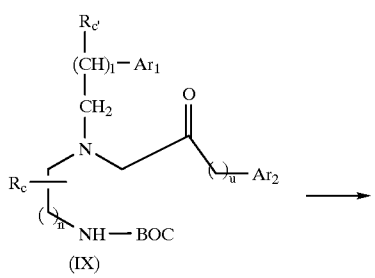

Removal of the protecting group under standard conditions, followed by treatment of the product with a base results in cyclization to the diketopiperazine of formula XIII. Suitable conditions for removal of the exemplified BOC group are well known in the art and include catalysis by trifluoroacetic acid (TFA). A suitable base for cyclization is the alkali metal salt of an alcohol in the alcohol itself used as solvent. For example, a solution of sodium ethoxide in ethanol may be used. The temperature is preferably around RT but may be slightly above or below, in the range 0° C. to about 40° C. The reaction is generally complete within a few hours. Suitable reaction times are from 1 to 24 hours.

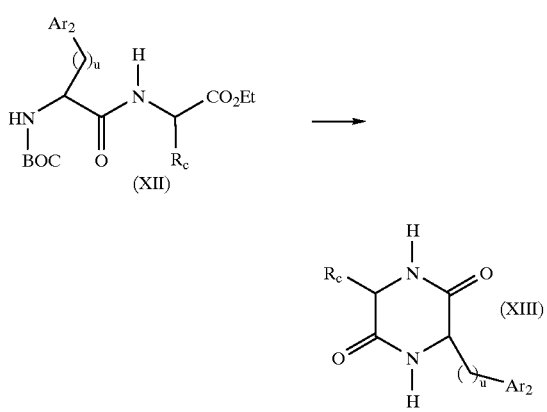

Reduction of the diketopiperazine of formula XIII to a compound of formula II may be accomplished preferentially with a strong hydride reducing agent, such as LAH or a solution of sodium bis(2-methoxyethoxy)aluminum hydride in toluene (also known as Red-Al®), or the $BH_3 \cdot S(CH_3)_2$ complex. Suitable solvents for this reaction are DME and other higher boiling ethers since the reaction is run at elevated temperatures, from about 50° C. to about 110° C., preferably at about 90° C.

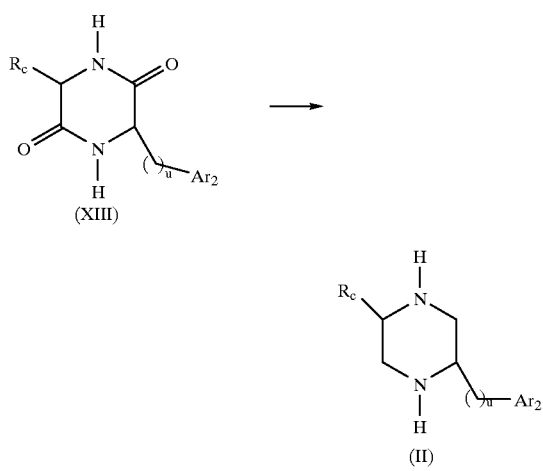

Alternatively, a compound of formula of II may be prepared by the scheme shown below (J. Med. Chem., 9, 191 (1966)). As used herein L is any readily available ester residue such as $C_1$–$C_7$ alkyl, more preferably methyl or ethyl.

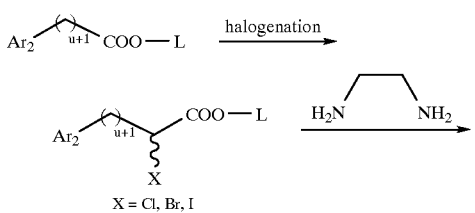

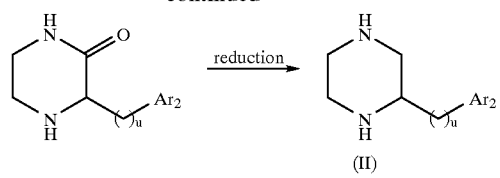

A compound of formula II may be converted to a compound of formula IV by the processes described in Method 1 above or Method 6 below.

Method 4

The intermediates of formula IV or IVA, formed via any of the previous methods, may be further processed as follows. A compound of formula IVA will be used in the Schemes. Reaction of a compound of formula IVA with an activated halo-acid, generally the acid halide of formula XIV, in which Hal represents Cl, Br, or I, yields the acylated derivative of formula XV that is, m is 1 for formula I. An organic base is used to take up the hydrogen halide formed in the reaction, suitable bases being triethylamine (TEA) and Hünig's Base. Suitable reaction media include halogenated solvents, such as methylene chloride and chloroform. The reaction is preferably run at low temperature, at least initially. Suitable temperatures are in the region of −50° C. down to −80° C. Later in the reaction it may be desirable to allow the mixture to warm up to about RT to ensure completion of the reaction.

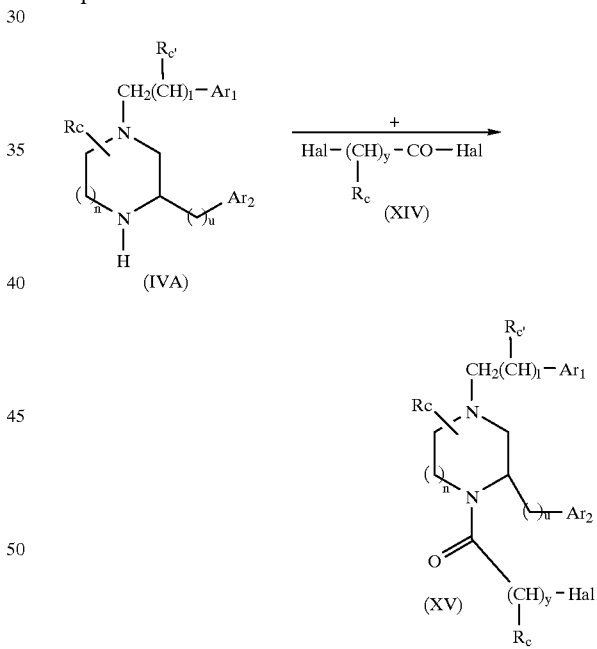

Reaction of the halogenated amides of formula XV with an amine of formula Z-H results in formation of the products of formula XVI, which are compounds of the invention in which X is O and m is 1. Compounds of formula XVI have been modified to show the fact that these products could have been prepared from compounds of formula IVA as well as from IV. Suitable solvents for this reaction are halogenated hydrocarbons, such as methylene chloride, and an organic base is present to absorb the H-Hal formed. Appropriate bases include Hünig's Base. The reaction is performed at or around RT, a suitable temperature being generally in the range of from 0° C. to 40° C. Reaction is complete within 1 to 48 hours.

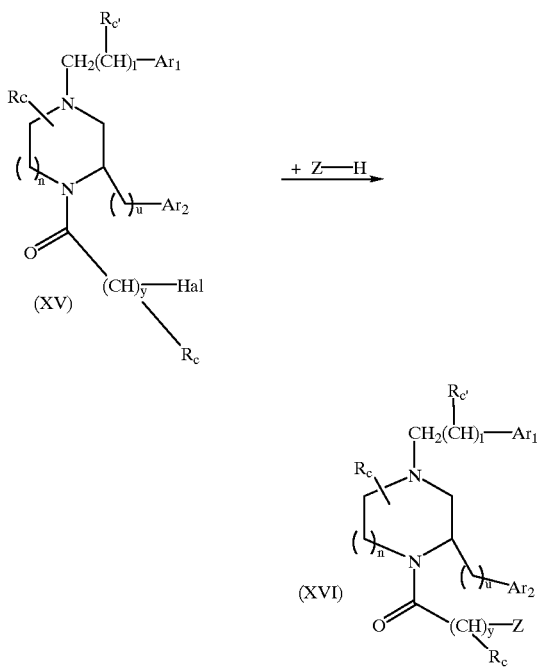

Method 5

Compounds of formula XVI where y≠0 may be converted to other compounds of the invention of formula XVII by reduction under controlled conditions.

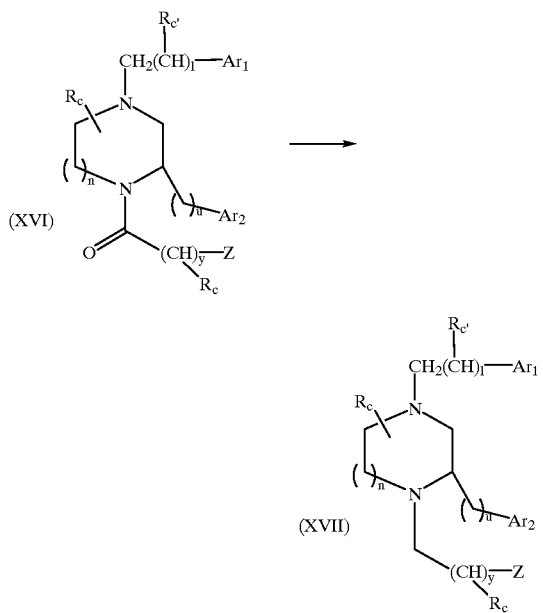

Suitable reducing agents to effect this transformation include the borane-dimethyl sulfide complex, as well as other less selective reagents, such as LAH, (assuming that no other group reactive to LAH is present), Red-Al®, and diborane in ether. Effective temperatures for the boranedimethylsulfide complex to reduce compounds of formula XVI, range from RT to the reflux temperature of the solution of the reagent in THF (about 80° C.).

Method 6

Intermediates of the formula XVIII may be selectively acylated by coupling with an acid of the formula XIX. Standard coupling techniques may be applied, an example being the use of HOBT, a water-soluble carbodiimide, such as DEC, and an organic base, such as triethylamine, in a non-hydroxylic solvent, such as $CH_2Cl_2$, at a temperature of about −20° C. initially. The mixture may be allowed to warm to RT to complete the reaction. The product of reaction is the amide of formula XX.

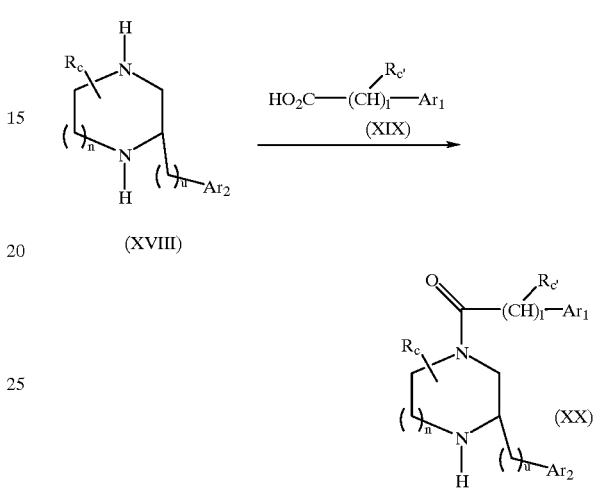

Compounds of the formula XX, may be further acylated using an acid halide of formula XXa. The reaction is run, preferably at about −78° C., over a period of 1 to 12 hours, in a halogenated solvent, such as methylene chloride or similar solvent. An organic tertiary amine is used to absorb the H-Hal produced in the reaction. Suitable amines include triethylamine and Hünig's Base. As used herein Hal means Cl, Br, or I.

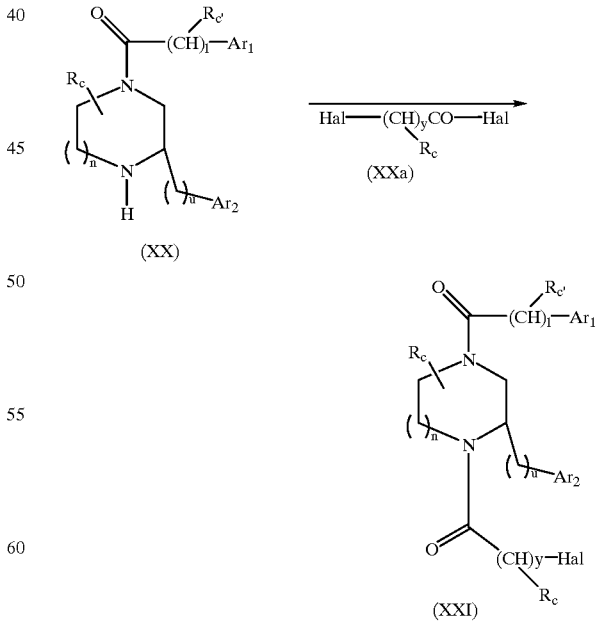

The compounds of formula XXI, that is, m is 1 in formula I, y=1–3, l=0–2 may be used for further reaction without isolation. Additional organic base, for instance, Hünig's Base, is added to the mixture followed by Z-H, at or around −78° C. The reaction is completed by allowing the mixture to warm to RT overnight yielding the compounds of formula XXII after work-up and purification by standard methods.

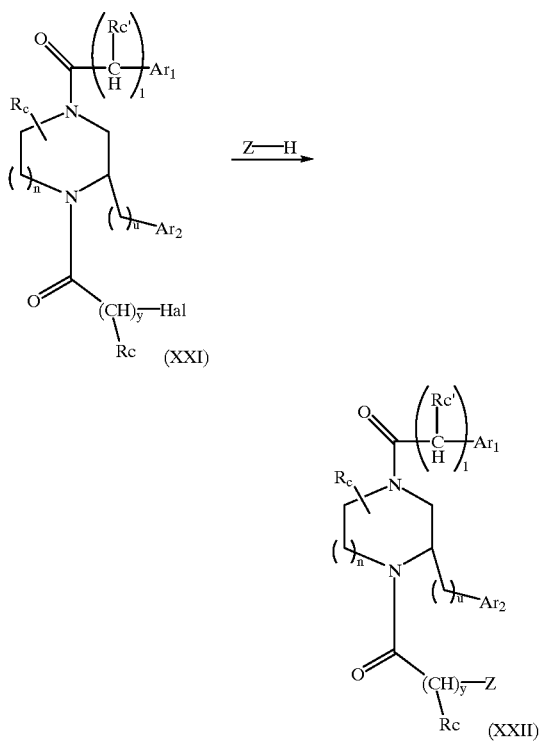

The compounds of formula XXII, in which y=1–3 may be converted to other products of formula XXIII by reduction under controlled conditions.

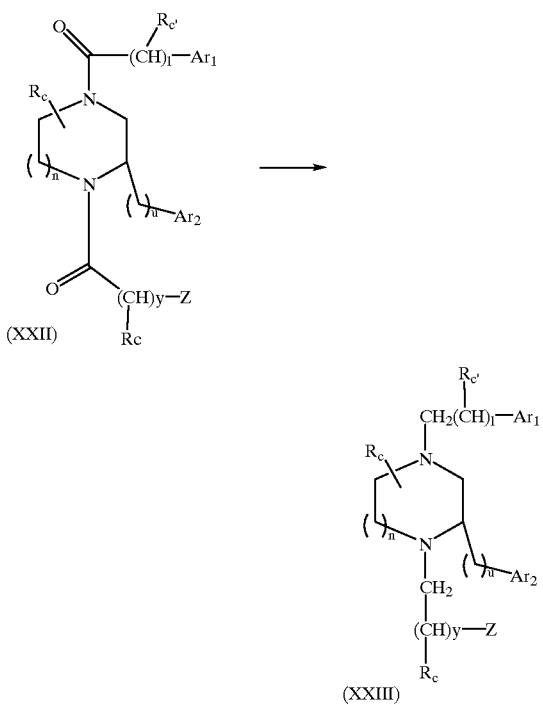

Suitable reducing agents to effect this transformation include the borane-methyl sulfide complex, as well as other less selective reagents, such as LAH, Red-Al®, and diborane in ether or other unreactive solvents, such as THF. Using the borane-methyl sulfide complex in THF, at the reflux temperature of the solution, which is about 80° C., the reaction is complete in about 2 hours to 48 hours depending on the precise substrate.

Some of the substrates Z-H for the alkylation reaction were synthesized from diamino compound (A) by initial conversion to the t-BOC protected derivative(B) followed by removal of the benzyl group by hydrogenolysis over a suitable catalyst such as $Pd(OH)_2$ to yield the t-BOC protected derivative (C). Subsequent elaboration of (C) can be accomplished by either alkylation or reductive alkylation depending on the availability of reagents for these reactions.

Reaction of the intermediate (C) with an aldehyde or ketone (D) under the conditions of reductive amination, such as in methanol and in the presence of $NaBH_3CN$ with sufficient AcOH (acetic acid) present to allow the reaction to proceed at a suitable rate, produces the amine (E) from which the t-BOC group may be removed, for instance, with 4N-HCl in dioxane followed by basification, for instance, with an aqueous solution of NaOH, to produce the compound of formula (F).

The same product, (Ea), may be prepared from (C) by alkylation with the halide derivative (G) in which "Hal" is Cl, Br, or I. Other activated leaving groups are also possible for this reagent, such as mesylates or tosylates. The reagent is preferably primary but the reaction can also often be made to work acceptably for secondary derivatives.

The product of the alkylation, (Ea), may be treated as described above to produce the reagent (Fa) which represents one of the preferred forms of Z which can be used to convert a compound of formula XXI to a compound of formula XXII.

The intermediate (C) (below) may also be modified by acylation, for instance with an acid halide of formula (H), to produce the intermediate (I), in which $n_3 \neq 0$. Removal of the BOC protecting group, as described previously, leads to the amine (J) which represents one of the preferred forms of Z. This may be used to convert a compound of formula (XXI) to a compound of the invention, as described above.

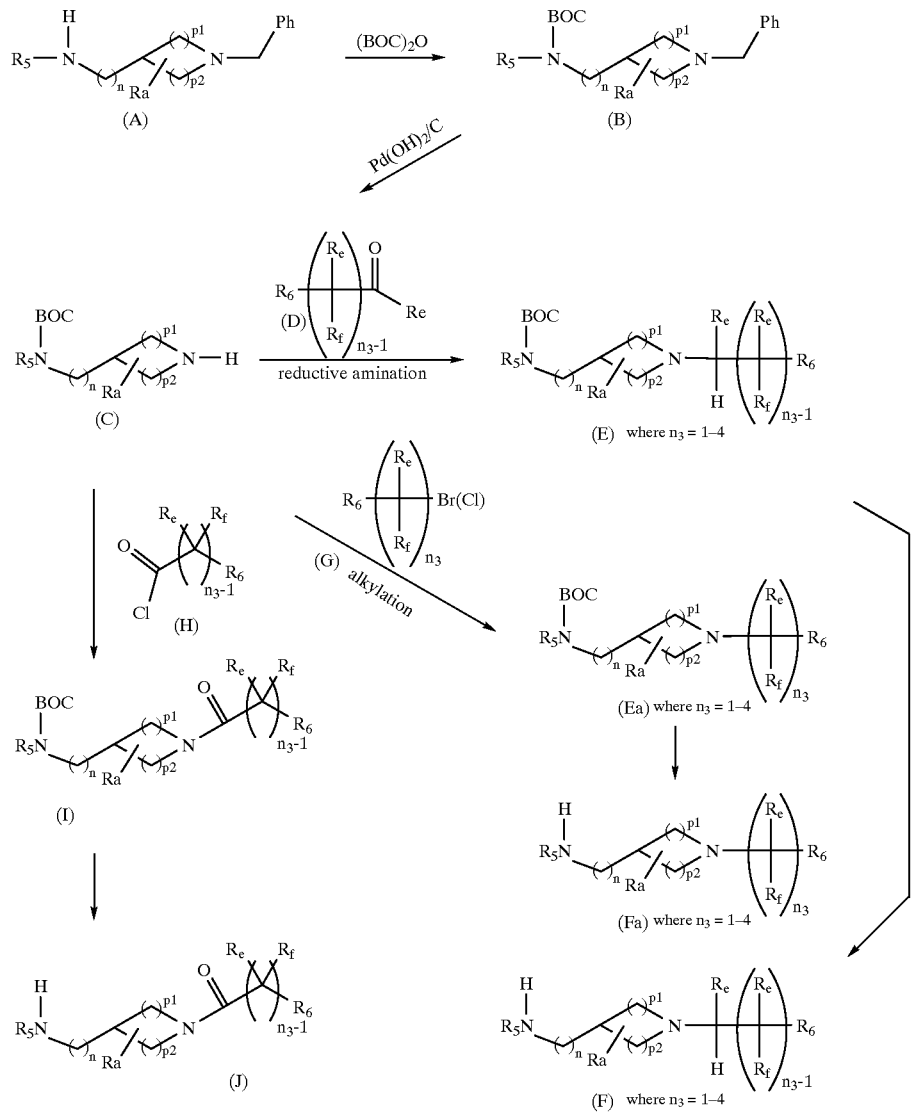

Method 6a

A useful intermediate for certain variations in the group Z is the compound (K). This may be prepared from (XXI) and the protected amine (L). The starting material for this process is the N-BOC protected amine (M) which may be converted to (L) by standard techniques involving formation of the oxime using hydroxylamine hydrochloride in pyridine followed by reduction with hydrogen over Raney nickel in ethanol solution. Removal of the protecting group from (K), under conditions described previously, results in the amine (N).

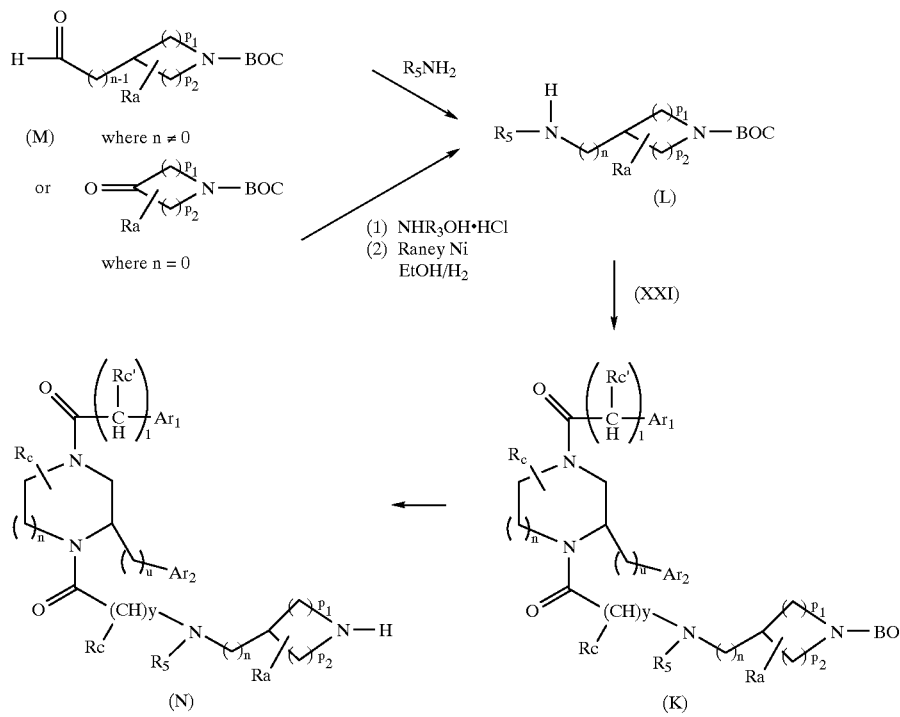

Use of this intermediate under conditions of acylation, under controlled conditions, results in reaction at the ring nitrogen atom to yield products such as (O). Either the acid halide, e.g. chloride (P), may be used, or a coupling reaction with a carboxylic acid may be used under conditions essentially similar to those described earlier using a water-soluble carbodimide reagent, for instance.

Sometimes the starting material (N) is provided as a salt, such as the HCl salt. In this case, it is necessary to add an organic tertiary base, such as Hünig's base to produce the free amine.

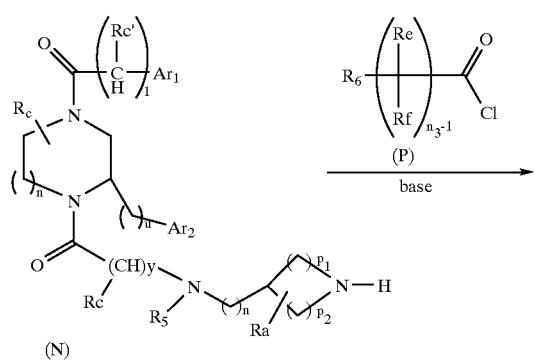

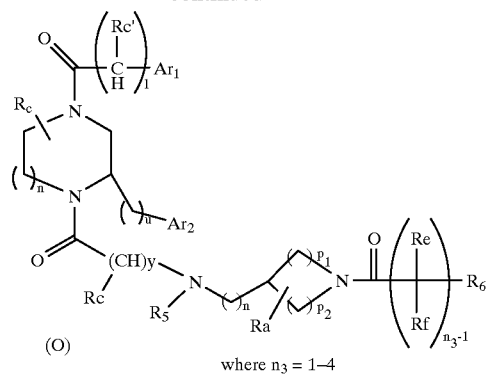

Alkylation of (N) may be accomplished with a suitable halogen-containing reagent, for instance, to produce (Q). Reagents such as (G) may be used for this conversion.

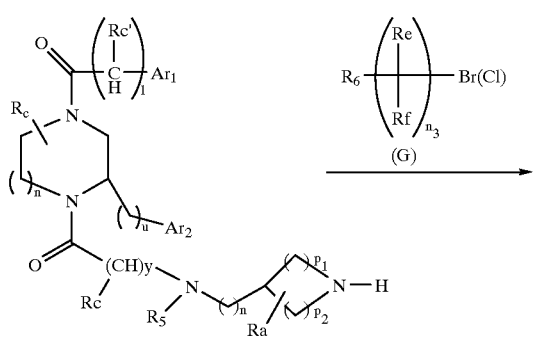

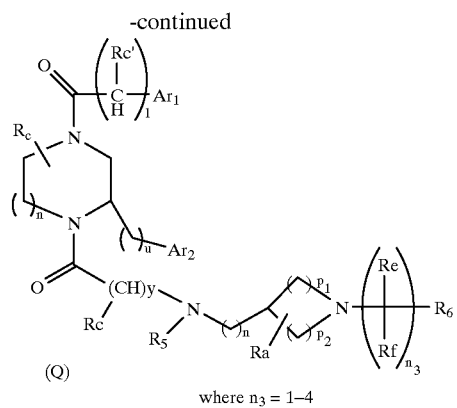

where n₃ = 1–4

In some cases, one of the —C(R$_e$)(R$_f$)— groups may be a carbonyl group with the exception that the carbon in the carbonyl can not be directly attached to the nitrogen atom since these products are amides which are described above.

Under certain circumstances, specifically where at least one of the groups R$_e$ and R$_f$ on the carbon atom to be directly attached to the ring nitrogen is H, then a reductive alkylation reaction may be performed, as described previously, to produce the compound of the invention (R). The reagent used for this conversion is (D), an aldehyde (if Re=H) or ketone.

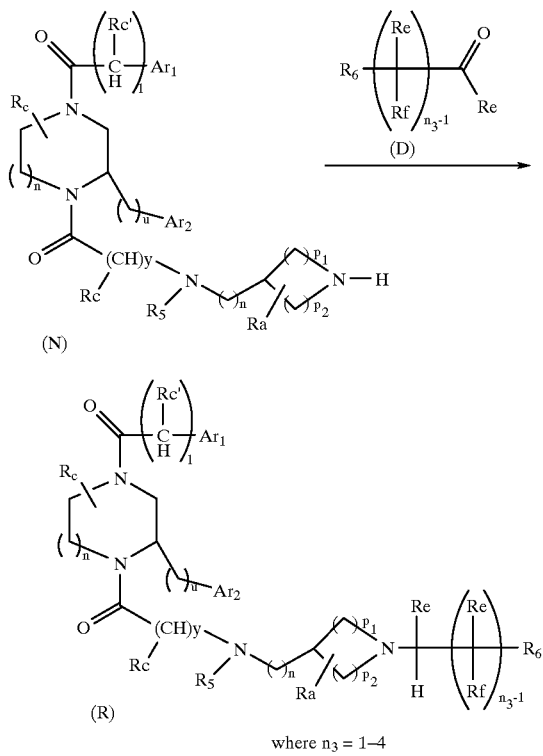

where n₃ = 1–4

Method 7

The acylated derivatives of formula XX from Method 6 may be reduced to the saturated alkyl chain derivatives of formula XXIV.

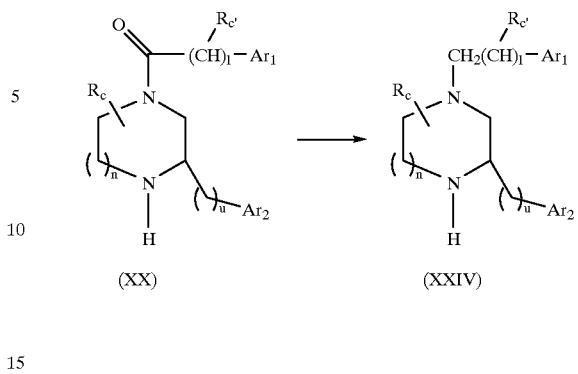

The process to conduct this conversion is the same as described in Method 6 for conversion of a compound of formula XXII to a compound of formula XXIII. The reagent of preference is the boranemethyl sulfide complex.

Reaction of the intermediate of formula XXIV with the acyl halide of formula XXV at temperatures of about −78° C. produces the amides of formula XXVI. The reaction is run preferably in a halogenated solvent, such as methylene chloride, in the presence of an organic base to take up the H-Hal formed. A suitable base is Hünig's Base. The product, a compound of formula XXVI, may be used without isolation in the subsequent step.

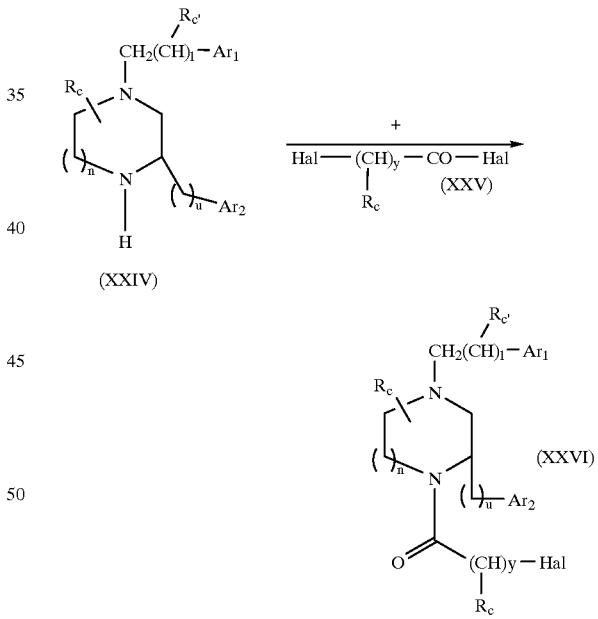

The halo-derivative of formula XXVI may be used without isolation to react with the amine compound of formula Z-H. An additional equivalent amount of a suitable organic base, such as Hünig's Base, is added to the mixture to consume H-Hal. The reaction is initially run at about −78° C. but is allowed to warm gradually to RT to complete the reaction. The product, a compound of formula XXVII, is isolated by conventional techniques and may be purified by flash chromatography.

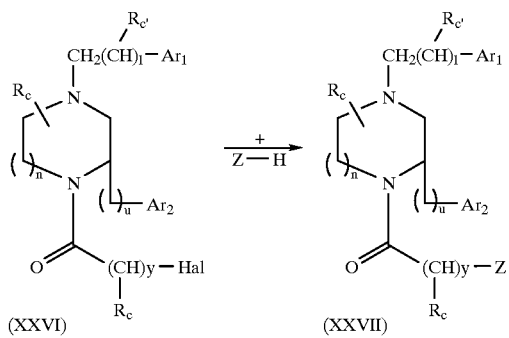

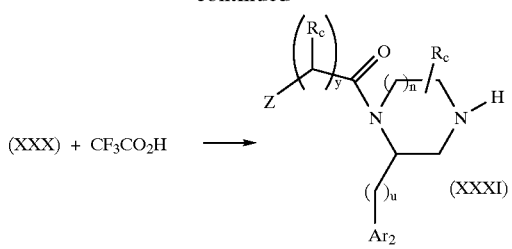

Reaction of (XXXI) with a carboxylic acid (XIX) under such coupling conditions as described above, leads to the products of formula (XXII).

Method 7a

Synthesis of the compounds of the invention wherein the pendant aromatic group $Ar_2$, or the pendant aromatic group $Ar_2$ and its sidechain, are located in the alternate ring position to the compounds of formula XXII (i.e. compounds of formula C below), may be prepared using compounds of formula XXVIII from method 7 as starting materials. Coupling of compounds of formula XXVIII with any of the acids An alternate route to compounds of structure (XXII) also starts with compound (XVIII). Initial reaction with an amine protecting group reagent, preferably BOC anhydride, produces the N-t-butyloxycarbonyl derivative of the formula XXVIII.

under standard coupling conditions, for instance using HOBT, $Et_3N$ and DEC in $CH_2Cl_2$, produces the intermediate (A). Removal of the t-BOC or other protecting group under standard conditions releases the free amine (B). Acylation of (B) and further reaction with Z-H proceeds as described in Method 6 for the conversion of (XX) via (XXI) to (XXII) to produce compound (C) of the invention.

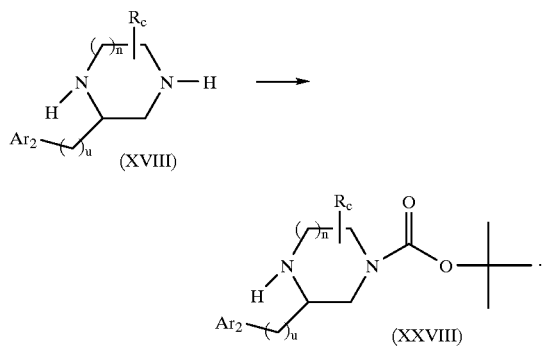

As before, reaction occurs preferentially at the nitrogen atom further away from the $Ar_2$ group. Reaction of this intermediate with a reagent of structure (XXa) as described above, leads to the halo-derivative (XXIX). Reaction of (XXIX) with Z-H, again as described above, produces the intermediate (XXX) which may be de-protected to produce (XXXI). Suitable reagents include trifluoroacetic acid and HCl.

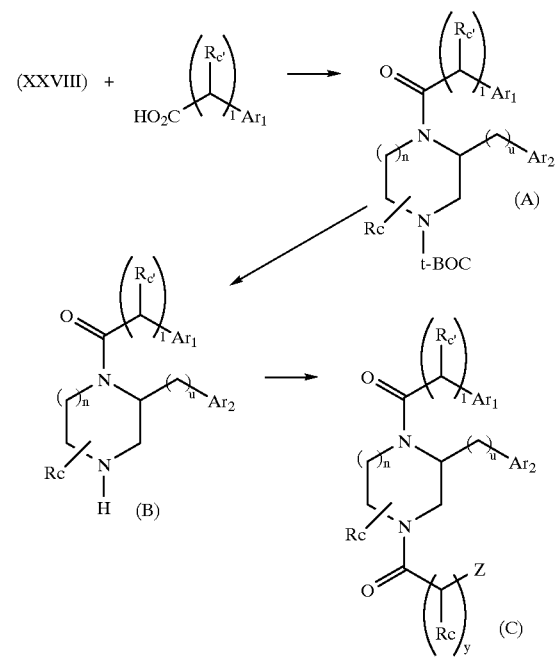

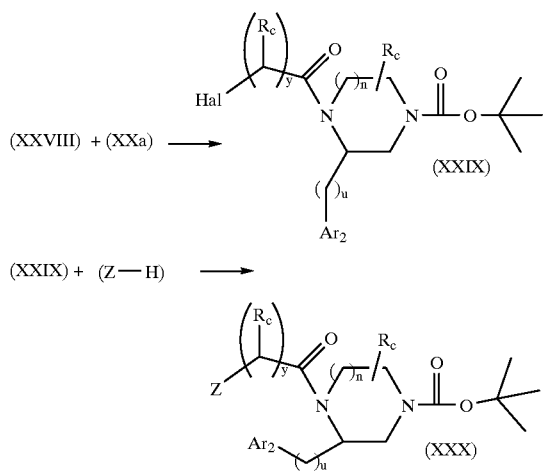

Method 8

A method for introducing a group, $R_c$, into the sidechain of a compound of the invention begins with a previously prepared compound of formula (XX). This may be coupled with a suitably protected amino-acid derivative of formula (XXXII) in which the t-BOC group is used as a representative protecting group. Use of a relatively reactive coupling agent, such as BOP-Cl of formula (XXXIII), is preferred and the reaction is run under standard coupling conditions well known to one skilled in the art. Suitable conditions include the use of $CH_2Cl_2$ and/or DMF as solvent, with triethylamine or Hünig's Base, and a temperature between 0° C. initially and RT. Usual work-up conditions yield the protected intermediate of formula (XXXIV).

In the case of (XXXIV), in which the N-protecting group is t-BOC, the usual conditions for removal of such a group may be used to free the amine function. Various concentrations of $CF_3CO_2H$ in $CH_2Cl_2$ will usually suffice. In some substrates a fairly dilute solution (e.g. 2N) will be sufficient whereas in other cases a more concentrated solution, up to neat TFA, may be necessary. In addition, other N-protecting groups may be employed and removed by methods well known in the art. An example is use of the N-Cbz which may be removed under either acidic or hydrogenolytic conditions. The result of deprotection is the amine intermediate of the formula (XXXV).

Conversion of intermediate of the formula (XXXV) to compounds of the invention is then carried out by a reductive alkylation process.

The group Z is introduced into the molecule using an aldehyde or ketone in which the aforementioned group is present at the carbon atom that is to be joined to the amino group of the formula (XXXV). An example of such an intermediate is a compound of the formula (XXXVI).

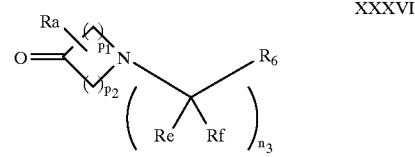

After the reaction this group becomes the Z group of the compounds of the invention, that is, the "Y-NH" group shown in compounds of the formula (XXXVII) just below

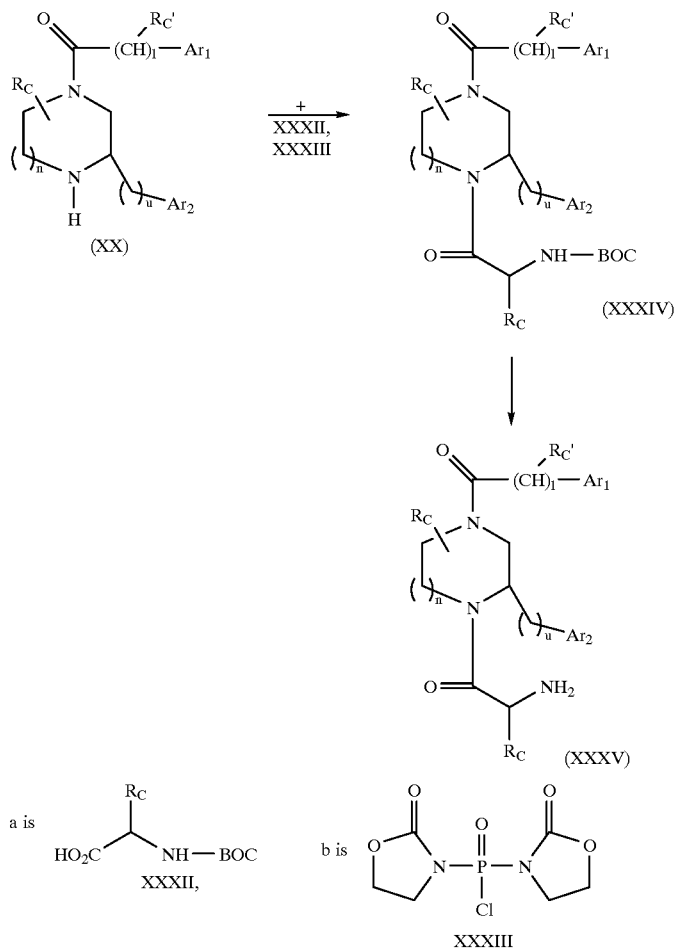

XXXVII

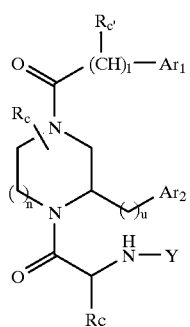

is equivalent to the "Z" group shown in the Summary of the Invention. Conditions for this reductive amination procedure are known in the art and are exemplified by the use of NaBH$_3$CN in MeOH with the addition of several equivalents of acetic acid. Generally, the reaction is performed at RT and is left to react overnight.

Product is isolated by standard means, such as decomposition of excess reagent with H$_2$O and extraction of the product into an organic solvent such as CH$_2$Cl$_2$ or a mixture of Et$_2$O and CH$_2$Cl$_2$.

Using procedures similar to those described in the above or using procedures known to those skilled in the art, one can produce all of the compounds of formula I of the invention. For example, one can obtain compounds of the invention of formula I wherein the R$_c$ moiety is on various carbons of the piperazine ring.

The in vitro and in vivo activity of the compounds of formula I can be determined by the following procedures.

In vitro Procedure to Identify NK$_1$ Activity

Test compounds are evaluated for their ability to inhibit the activity of the NK$_1$ agonist Substance P on the isolated guinea pig vas deferens. Freshly cut vas deferens are removed from male Hartley guinea pigs (230–350 g) and suspended in 25 ml tissue baths containing Kreb's Henseleit solution warmed to 37° C. and constantly aerated with 95% O$_2$ and 5% CO$_2$. Tissues are adjusted to 0.5 g and allowed to equilibrate for a period of 30 minutes. The vas deferens are exposed to an electrical field stimulation (Grass S48 Stimulator) every 60 seconds at an intensity that will cause the tissue to contract 80% of its maximum capacity. All responses are recorded isometrically by means of a Grass force displacement transducer (FT03) and Harvard electronic recorder. Substance P inhibits the electrical field stimulated-induced contractions of the guinea pig vas deferens. In unpaired studies, all tissues (control or drug treated) are exposed to cumulative concentrations of Substance P (1×10$^{-10}$ M–7×10$^{-7}$ M). Single log-concentrations of the test compounds are given to separate tissues and allowed to equilibrate for 30 minutes before a Substance P concentration-response curve is generated. At least 5 separate tissues are used for each control and individual drug-concentration for every drug assay.

Inhibition of the Substance P is demonstrated by a rightward shift of its concentration-response curve. These shifts are used to determine the pA$_2$ value, which is defined as the negative log of the molar concentration of the inhibitor which would require that twice as much agonist be used to elicit a chosen response. This value is used to determine relative antagonist potency.

Isolated Hamster Trachea NK$_2$ Assay

General methodology and characterization of hamster trachea responses to neurokinin agonists as providing an NK$_2$ monoreceptor assay is found in C. A. Maggi, et al., Eur. J. PharmacoL 166 (1989) 435 and J. L. Ellis, et al., J. Pharm. Exp. Ther. 267 (1993) 95.

Continuous isometric tension monitoring is achieved with Grass FT-03 force displacement transducers connected to Buxco Electronics preamplifiers built into a Graphtec Linearcorder Model WR 3310.

Male Charles River LAK:LVG (SYR) hamsters, 100–200 g fed weight, are stunned by a sharp blow to the head, loss of corneal reflex is assured, the hamsters are sacrificed by thoracotomy and cutting the heart. Cervical trachea segments are removed to room temperature Krebs buffer, pH 7.4, aerated with 95% O$_2$-5% CO$_2$ gas and cleaned of adhering tissue. The segments are cut into two 3–4 mm long ring segments. Tracheal rings are suspended from transducers and anchored in 15.0 ml water jacketed organ baths by means of stainless steel hooks and 6-0 silk. Baths are filled with Krebs buffer, pH 7.4, maintained at 37° C. and continuously aerated with 95% O$_2$-5% CO$_2$ gas. Tracheal rings are placed under 1.0 g initial tension and allowed a 90 min equilibration period with four 1 μM NKA challenge, wash and recovery cycles at 20 min intervals. 30 min vehicle pretreatment is followed by cumulative additions of rising doses of NKA (3 nM–1 μM final concentration, 5 min intervals between additions). The final NKA response is followed by a 15 min wash and recovery period. 30 min pretreatment with a test compound or its vehicle is followed by cumulative additions of rising doses of NKA (3 nM–10 μM final concentration if necessary, 5 minutes intervals between additions). The final NKA response is followed by a 1 mM carbachol challenge to obtain a maximal tension response in each tissue.

Tissue responses to NKA are recorded as positive pen displacements over baseline and converted to grams tension by comparison to standard weights. Responses are normalized as a % of the maximal tissue tension. ED$_{50}$'s are calculated for NKA from the control and treated NKA dose responses and compared. Test compounds resulting in an agonist dose ratio$\geq$2 at a screening concentration of 1 μM (i.e. pA$_2 \geq$=6.0) are considered actives. Further dose response data is obtained for actives so that an apparent pA$_2$ estimate can be calculated. pA$_2$ is calculated either by estimation of K$_i$ as described by Furchgott (where pA$_2$=– Log K$_i$, R. F. Furchgott, Pharm. Rev. 7[1995]183) or by Shild Plot Analysis (O. Arunlakshana & H. O. Shild, Br. J. Pharmacol. 14[1959]48) if the data is sufficient.

Effect of NK$_1$ Antagonists on Substance P-Induced Airway Microvascular Leakage In Guinea Pigs Studies are performed on male Hartley guinea pigs ranging in weight from 400–650 g. The animals are given food and water ad libitum. The animals are anesthetized by intraperitoneal injection of dialurethane (containing 0.1 g/ml diallylbarbituric acid, 0.4 g/ml ethylurea and 0.4 g/ml urethane). The trachea is cannulated just below the larynx and the animals are ventilated (V$_T$=4 ml, f=45 breaths/min) with a Harvard rodent respirator. The jugular vein is cannulated for the injection of drugs.

The Evans blue dye technique (Danko, G. et al., Pharmacol. Commun., 1, 203–209, 1992) is used to measure airway microvascular leakage (AML). Evans blue (30 mg/kg) is injected intravenously, followed 1 min later by i.v. injection of substance P (10 μg/kg). Five min later, the thorax is opended and a blunt-ended 13-guage needle passed into the aorta. An incision is made in the right atrium and blood is expelled by flushing 100 ml of saline through the aortic catheter. The lungs and trachea are removed en-bloc and the trachea and bronchi are then blotted dry with filter paper and weighed. Evans blue is extracted by incubation of the tissue at 37° C. for 18 hr in 2 ml of formamide in stoppered tubes. The absorbance of the formamide extracts of dye is measured at 620 nm. The amount of dye is calculated by interpolation from a standard curve of Evans blue in the range 0.5–10 μg/ml in formamide. The dye concentration is expressed as ng dye per mg tissue wet weight. Test compounds were suspended in cyclodextran vehicle and given i.v. 5 min before substance P.

Measurement of $NK_2$ Activity In Vivo

Male Hartley guinea pigs (400–500 gm) with ad lib. access to food and water are anesthetized with an intraperitoneal injection of 0.9 ml/kg dialurethane (containing 0.1 g/m diallylbarbituric acid, 0.4 g/ml ethylurea and 0.4 g/ml urethane). After induction of a surgical plane of anesthesia, tracheal, esophageal and jugular venous cannulae are implanted to facilitate mechanical respiration, measurement of esophageal pressure and administration of drugs, respectively.

The guinea pigs are placed inside a whole body plethysmograph and the catheters connected to outlet ports in the plethysmograph wall. Airflow is measured using a differential pressure transducer (Validyne, Northridge Calif., model MP45-1, range ±2 $cmH_2O$) which measures the pressure across a wire mesh screen that covers a 1 inch hole in the wall of the plethysmograph. The airflow signal is electrically integrated to a signal proportional to volume. Transpulmonary pressure is measured as the pressure difference between the trachea and the esophagus using a differential pressure transducer (Validyne, Northridge, Calif., model MP45-1, range ±20 cm $H_2O$). The volume, airflow and transpulmonary pressure signals are monitored by means of a pulmonary analysis computer (Buxco Electronics, Sharon, Conn., model 6) and used for the derivation of pulmonary resistance ($R_L$) and dynamic lung compliance ($C_{Dyn}$).

Bronchoconstriction Due to NKA

Increasing iv doses of NKA are administered at half log (0.01–3 μg/kg) intervals allowing recovery to baseline pulmonary mechanics between each dose. Peak bronchoconstriction occurs within 30 seconds after each dose of agonist. The dose response is stopped when $C_{Dyn}$ is reduced 80–90% from baseline. One dose-response to NKA is performed in each animal. Test compounds are suspended in cyclodextran vehicle and given i.v. 5 min before the initiation of the NKA dose response.

For each animal, dose response curves to NKA are constructed by plotting the percent increase in $R_L$ or decrease in $C_{Dyn}$ against log dose of agonist. The doses of NKA that increased $R_L$ by 100% ($R_L$100) or decreased $C_{Dyn}$ by 40% ($C_{Dyn}$40) from baseline values are obtained by log-linear interpolation of the dose response curves.

Neurokinin Receptor Binding Assay(s)

Chinese Hamster ovary (CHO) cells transfected with the coding regions for the human neurokinin 1 ($NK_1$) of the human neurokinin 2 ($NK_2$) receptors are grown in Dulbecco's minimal essential medium supplemented with 10% fetal calf serum, 0.1 mM non-essential amino acids, 2 mM glutamine, 100 units/ml of penicillin and streptomycin, and 0.8 mg of G418/ml at 37° C. in a humidified atmosphere containing 5% $CO_2$.

Cells are detached from T-175 flasks with a sterile solution containing 5 mM EDTA in phosphate buffered saline. Cells are harvested by centrifugation and washed in RPMI media at 40° C. for 5 minutes. The pellet is resuspended inTris-HCl (pH7.4) containing 1 uM phosphoramidon and 4 ug/ml of chymostatin at a cell density of $30 \times 10^6$ cells/ml. The suspension is then homogenized in a Brinkman Polytron (setting 5) for 30–45 seconds. The homogenate is centrifuged at 800×g for 5 min at 4° C. to collect unbroken cells and nuclei. The supematant is centrifuged in a Sorvall RC5C at 19,000 rpm (44,00×g) for 30 min at 4° C. The pellet is resuspended, an aliquot is removed for a protein determination (BCA) and washed again. The resulting pellet is stored at −80° C.

To assay receptor binding, 50 μl of [$^3$H]-Substance P (9-Sar, 11-Met [02]) (specific activity 41 Ci/mmol) (Dupont-NEN) (0.8 nM for the NK- 1 assay) or [$^3$H]-Neurokinin A (specific activity 114 CV mmole) (Zenca) (1.0 nM for the NK-2 assay) is added to tubes containing buffer (50 mM Tris-HCl (pH 7.4) with 1 mM $MnCl_2$ and 0.2% Bovine Serum Albumin) and either DMSO or test compound. Binding is initiated by the addition of 100 μl of membrane (10–20 μg) containing the human NK-1 or NK-2 receptor in a final volume of 200 μl. After 40 minutes at room temperature, the reaction is stopped by rapid filtration onto Whatman GF/C filters which have been presoaked in 0.3% polyethylenimine. Filters are washed 2 times with 3 ml of 50 mM Tris-HCl (pH7.4). Filters are added to 6 mls of Ready-Safe liquid scintillation cocktail and quantified by liquid scintillation spectrometry in a LKB 1219 RackBeta counter. Non-specific binding is determined by the addition of either 1 μM of CP-99994 ($NK_1$) or 1μM SR-48968 ($NK_2$) (both synthesized by the chemistry department of Schering-Plough Research Institute). $IC_{50}$ values are determined from competition binding curves and Ki values are determined according to Cheng and Prusoff using the experimentally determined value of 0.8 nM for the $NK_1$ receptor and 2.4 nM for the $NK_2$ receptor.

For all of the compounds of the invention, the $NK_1$ binding is in a range of about 0–100% inhibition at 1 μM concentration. For all of the compounds of the invention, the $NK_2$ binding is in a range of about 0–100% inhibition at 1 μM concentration. It should be understood that while the NK binding for certain compounds of the invention is as low as 0% at 1 μM concentration, that at higher concentrations these compounds are expected to have NK binding inhibition activity.

Representative values for racemic compounds except specifically defined enantiomers of the invention are as follows:

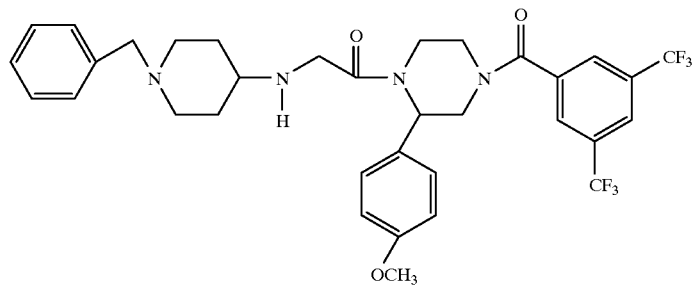
has a $K_i$ for $NK_1$ binding, of 2.5 nM; and a $K_i$ for $NK_2$ binding of 48 nM.
has a $K_i$ for $NK_1$ binding, of 0.9 nM; and a $K_i$ for $NK_2$ binding of >66 nM.
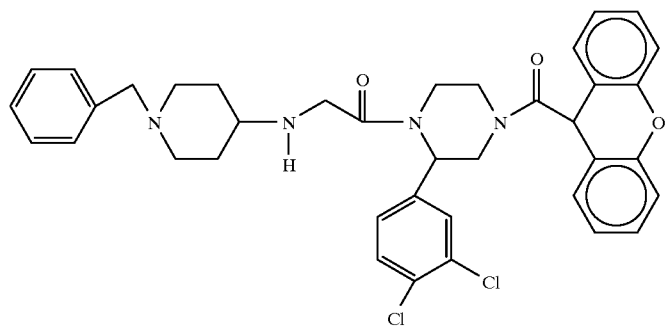
has a $K_i$ for $NK_1$ binding, of 117 nM; and a $K_i$ for $NK_2$ binding of 187 nM.
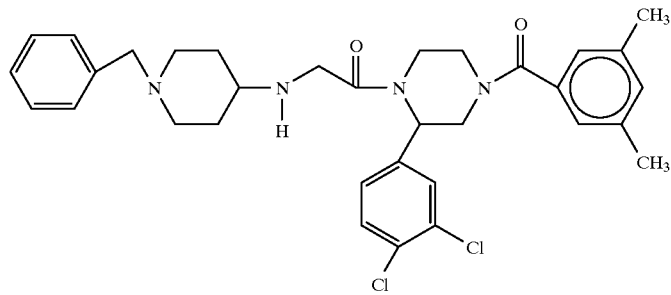
has a $K_i$ for $NK_1$ binding, of 1.6 nM; and a $K_i$ for $NK_2$ binding of 4.3 nM.
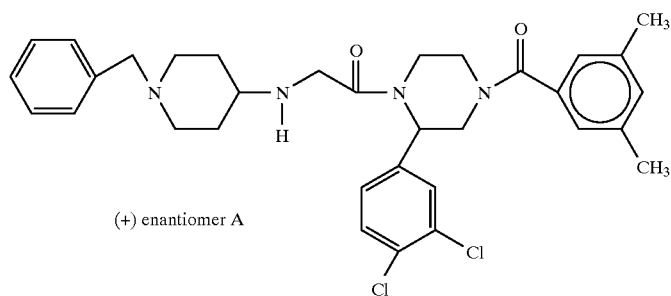
(+) enantiomer A

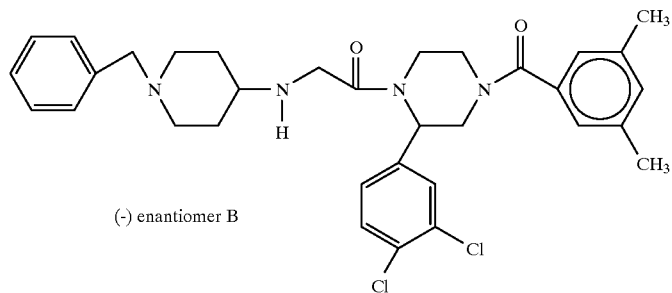

(-) enantiomer B has a $K_i$ for $NK_1$ binding, of 24 nM; and a $K_i$ for $NK_2$ binding of 3.4 nM.

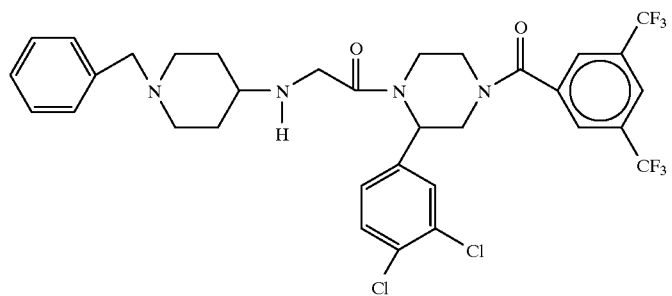

has a $K_i$ for $NK_1$ binding, of 4.9 nM; a Ki for $NK_2$ binding of 11.4 nM; and a Ki for $NK_3$ binding of 433 nM.

$NK_3$ activity is determined by a radioligand receptor binding assay as described in the literature, i.e. Molecular Pharmacology, 1995, 48, 711–716, which is hereby incorporated by reference.

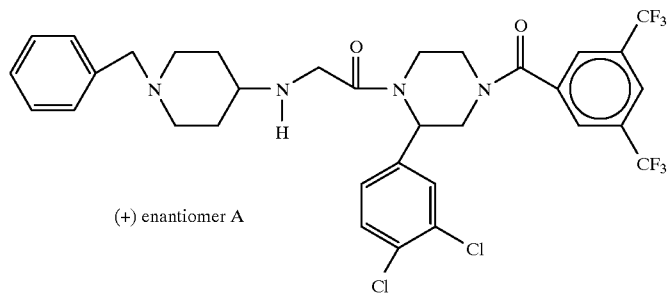

(+) enantiomer A has a $K_i$ for $NK_1$ binding, of 2.2 nM; and a $K_i$ for $NK_2$ binding of 355 nM.

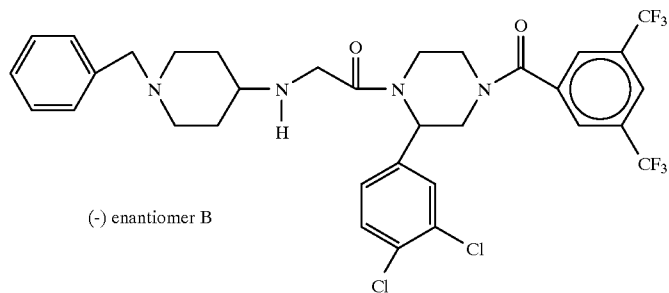
(-) enantiomer B
has a $K_i$ for $NK_1$ binding, of 48 nM; and a $K_i$ for $NK_2$ binding of 8.3 nM.
has a $K_i$ for $NK_1$ binding, of 74 nM; and for $NK_2$ binding a 7% inhibition at 1 μM.
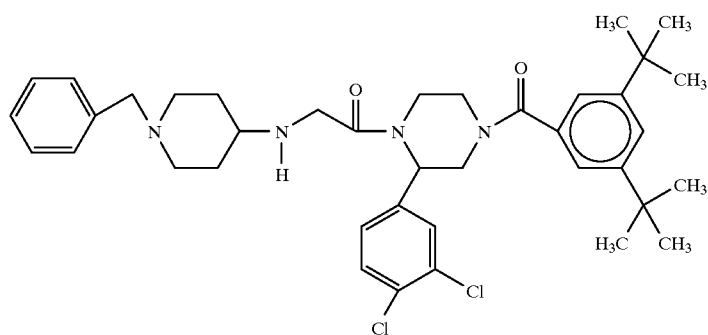
has a $K_i$ for $NK_1$ binding, of 63 nM; and a $K_i$ for $NK_2$ binding of 68 nM.
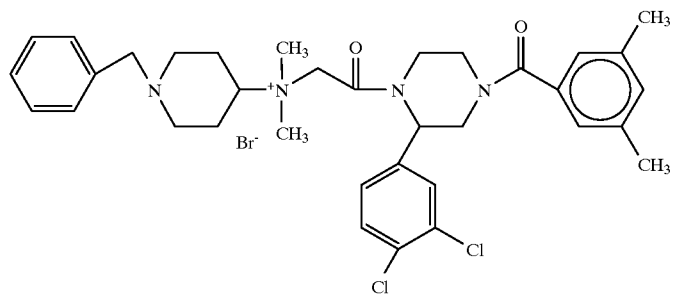
has a $K_i$ for $NK_1$ binding, of 0.58 nM; and a $K_i$ for $NK_2$ binding of 93 nM.
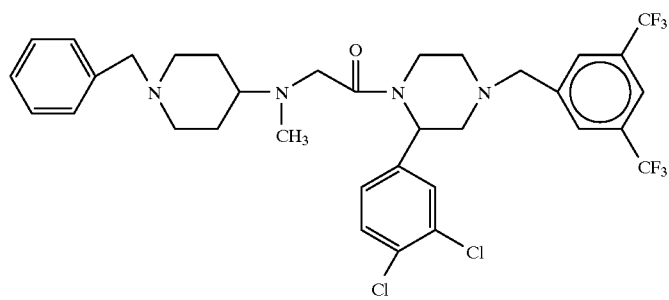

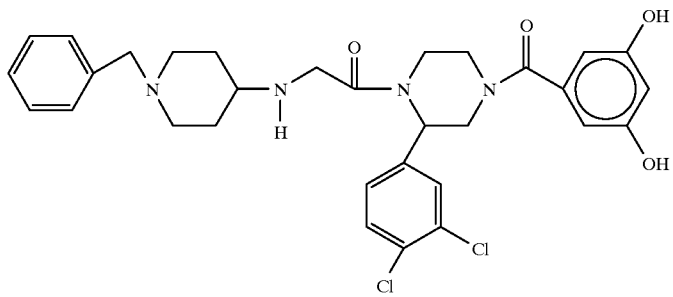

has for NK₁ binding, a 14% inhibition at 1 μM; and for NK₂ binding a 22% inhibition at 1 μM.

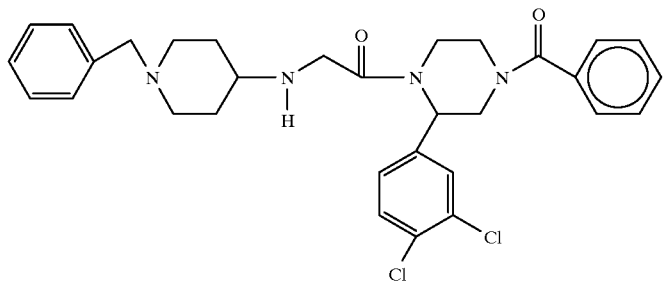

has a $K_i$ for NK₁ binding, of 93 nM; and a $K_i$ for NK₂ binding of 3.4 nM.

The $K_i$ of a compound is that concentration at which the compound caused 50% inhibition of either NK₁ or NK₂. For those compounds of the invention having higher than 50% inhibition of NK₁, $K_i$'s for NK₁ were determined. The $K_i$'s for NK₁ for such compounds fell within a range of about 0.1 nM to about 1 μM.

For those compounds of the invention having higher than 50% inhibition of NK₂, $K_i$'s for NK₂ were determined. The $K_i$'s for NK₂ for such compounds fell within a range of about 0.1 nM to about 1 μM.

Compounds of formula I exhibit NK₁ and NK₂ antagonist activity to varying degrees, i.e., certain compounds have strong NK₁ antagonist activity, but weaker NK₂ antagonist activity. Others are strong NK₂ antagonists, but weaker NK₁ antagonists. Certain compounds have both strong NK₁ and NK₂ antagonist activities. Some compounds can also be NK₃ antagonists.

Many compounds of formula I have an asymmetric center and therefore exist as a pair of enantiomers. In such cases, one enantiomer can have different biological activity than the other. For example, one enantiomer can have strong NK₁ activity and weak NK₂ activity while the other enantiomer has weak NK₁ activity and strong NK₂ activity.

Certain compounds of formula I have been found to be antagonists of both NK₁ and NK₂ receptors, and are therefore useful in treating conditions caused or aggravated by the activity of NK₁ and NK₂ receptors.

The present invention also relates to a pharmaceutical composition comprising a compound of formula I and a pharmaceutically acceptable carrier. Compounds of this invention can be administered in conventional oral dosage forms such as capsules, tablets, powders, cachets, suspensions or solutions, or in injectable dosage forms such as solutions, suspensions, or powders for reconstitution. The pharmaceutical compositions can be prepared with conventional excipients and additives, using well known formulation techniques. Pharmaceutically acceptable excipients and additives include nontoxic and chemically compatible fillers, binders, disintegrants, buffers, preservatives, antioxidants, lubricants, flavorings, thickeners, coloring agents, emulsifiers and the like.

The daily dose of a compound of formula I for treating asthma, cough, bronchospasm, inflammatory disease, migraine, nociception and gastrointestinal disorders is about 0.1 mg to about 20 mg/kg of body weight per day, preferably about 0.5 to about 15 mg/kg, more preferably 0.5 to about 5 mg/kg. For an average body weight of 70 kg, the dosage range is therefore from about 1 to about 1500 mg of drug per day, preferably about 50 to about 100 mg, given in a single dose or 2–4 divided doses. The exact dose, however is determined by the attending clinician, and is dependent on the potency of the compound administered, the age, weight, condition and response of the patient.

The invention disclosed herein is exemplified by the following examples, which should not be construed to limit the scope of the disclosure. Alternative mechanistic pathways and analogous structures within the scope of the invention will be apparent to those skilled in the art.

EXAMPLE 1

Preparation of (+/−)-1-[[3,5-bis(trifluoromethyl)phenyl]methyl]-3-phenylpiperazine, dihydrochloride salt, quarter hydrate.

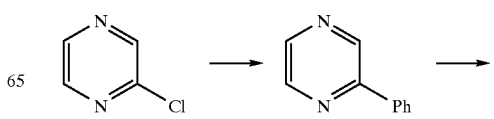

-continued

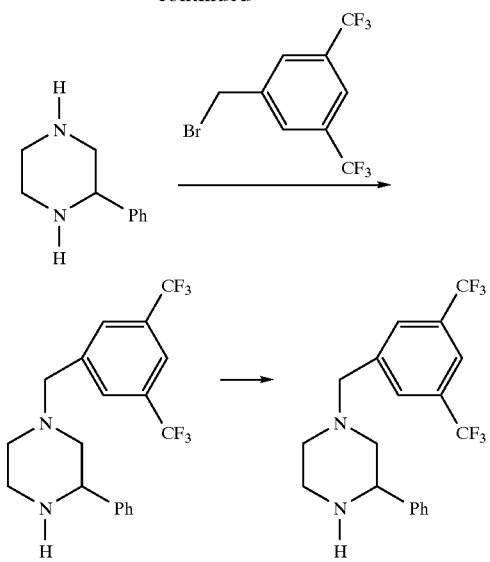

Chloropyrazine (20.68 gram, 177 mmol) and [1,2-bis (diphenylphosphino)ethane]nickel(II) chloride (41.08 gram, 77.8 mmol) in dry THF (1.5 liter) were mixed and stirred for 80 minutes in a flask (cooled with a water bath) under nitrogen. A solution of phenylmagnesium bromide (3M in $Et_2O$) (103 ml, 309 mmol) was added slowly through a dropping funnel into the cooled brick-red slurry at room temperature under nitrogen over 3.5 hours. After stirring at room temperature overnight, TLC showed that the reaction was complete. 3 N HCl (100 ml) was added slowly through a dropping funnel under nitrogen and the mixture was stirred for one hour. The THF layer was separated from the aqueous layer. The aqueous layer was adjusted to pH 12 with 6 N NaOH and extracted with EtOAc (100 ml, 3x). The organic fractions (THF and EtOAc) were combined and dried over $MgSO_4$, filtered and concentrated to give a solid. The product was purified by flash chromatography on 300 g of flash grade silica gel in 2.5% $EtOAc/CH_2Cl_2$ to give 10.79 gram (69 mmol, 39%) of 2-phenylpyrazine, m.p. 69–70° C.; FAB mass $[M+1]^+157$;

Found, C, 76.55; H, 5.22; N, 17.71. Calcd. for $C_{10}H_8N_2$, C, 76.90; H, 5.16; N, 19.93.

To a solution of 2-phenylpyrazine (11.64 gram, 74.53 mmol) in acetic acid (58.2 ml) was added palladium acetate $Pd(OAc)_2$ (2.33 gram, 9.94 mmol). The mixture was hydrogenated at 50 psi for four hours. After the reaction was complete, the catalyst was filtered off and rinsed with a small portion of acetic acid. The filtrate was concentrated under house vacuum to give a brown-black solid which was suspended in deionized water (300 ml) and adjusted to pH 13 with 20% NaOH solution. The product was extracted from aqueous solution with EtOAc (200 ml, 3x), dried over $MgSO_4$, filtered and evaporated to dryness to give 2-phenylpiperazine (7.2 gram). An additional 1.6 g of 2-phenylpiperazine was obtained by evaporating the aqueous fraction to a solid and triturating the solid with $CH_2Cl_2$. Total yield of 2-phenyl-piperazine was 73%. The crude material was crystallized from EtOAc and hexane for characterization, m.p. 86–88° C.; FAB mass $[M+1]^+163$;

Found, C, 74.04; H, 8.66; N, 17.15. Calcd. for $C_{10}H_{14}N_2$, C, 74.04; H, 8.69; N, 17.26.

To a solution of 2-phenylpiperazine (4.0 gram, 24.65 mmol) in dry $CH_2Cl_2$ (200 ml) at −78° C. under nitrogen was added $Et_3N$ (5.15 ml, 36.97 mmol) followed by the dropwise addition of a $CH_2Cl_2$ solution(46.60 ml) of bis (trifluoromethyl)benzyl bromide (4.66 ml, 24.65 mmol). The flask was kept at −78° C. then it was gradually warmed to room temperature overnight. After TLC showed that the reaction was complete, the material was washed with brine (150 ml, 2x), dried over $MgSO_4$, filtered, and evaporated under vacuum to yield a tan solid. The crude product was purified by flash silica gel chromatography (150 g), eluting with 2.5% $MsOH/CH_2Cl_2$ to give (+,−) 1-[[3,5-bis (trifluoromethyl)phenyl]methyl]-3-phenylpiperazine (6.96 gram, 17.92 mmol, 72.7%) as an oil. A portion of this oil (0.5 gram, 1.287 mmol)) was converted to its hydrochloride salt by dissolving the oil in $CH_2Cl_2$ (20 ml) and treating with 2.3 M HCl-EtOH (1.3 ml, 2.99 mmol). After stirring at room temperature for 10 minutes, all solvents were removed under high vacuum and the residue was dried overnight, m.p. 229–233° C.; FAB mass $[M+1]^+389$;

Found, C, 48.83; H, 4.28; N, 5.87; Cl, 14.77; F, 24.03. Calcd. for $C_{19}H_{18}N_2F_6 \cdot 2HCl \cdot 0.25 H_2O$, C, 48.99; H, 4.43; N, 6.01; Cl, 15.22; F, 24.47.

EXAMPLE 2

Preparation of (+,−)-4-[[3,5-bis(trifluoromethyl)phenyl] methyl]-2-phenyl-1-[[[1-(phenylmethyl)-4-piperidinyl] amino]acetyl]piperazine, trihydrochloride salt, dihydrate.

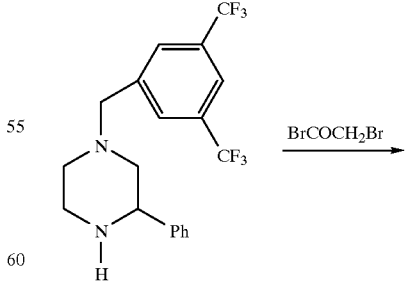

-continued

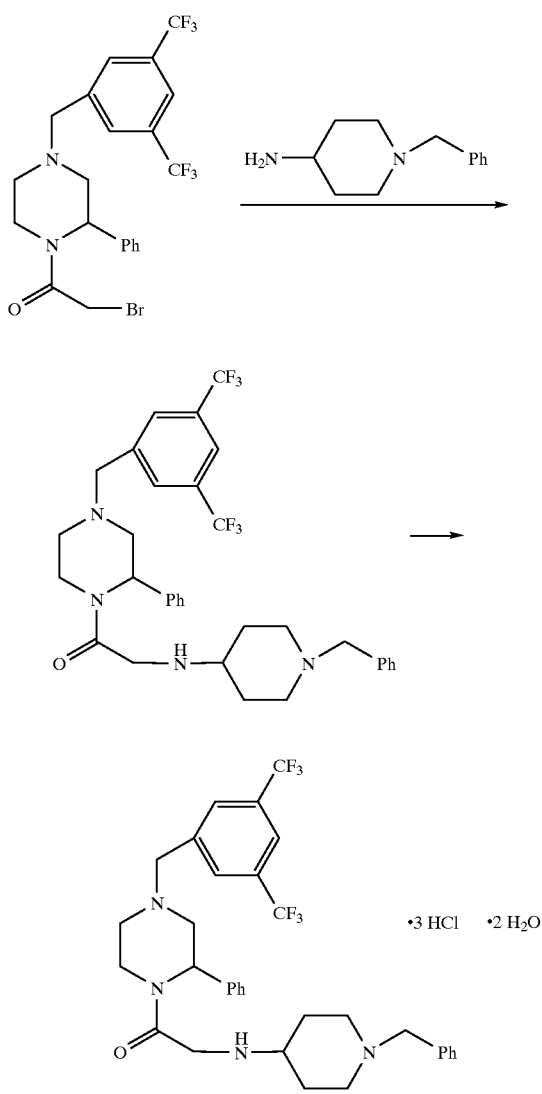

To a solution of (+,−) 1-[[3,5-bis(trifluoromethyl)phenyl]methyl]-3-phenylpiperazine (0.76 gram, 1.975 mmol) in dry CH$_2$Cl$_2$ (15.2 ml) at −78° C. was added Et$_3$N (0.286 ml, 2.055 mmol) followed by the dropwise addition of bromoacetyl bromide (0.179 ml, 2.055 mmol). After stirring at −78° C. for 4 hours, the reaction was diluted with CH$_2$Cl$_2$ (200 ml), washed with brine (100 ml, 2×) and dried over MgSO$_4$. After filtration, the solvent was removed to give a light yellow solid which was used without further purification. FAB mass [M+1]$^+$509.2 ($^{79}$Br).

The product from the previous reaction (1.067 gram, 2.096 mmol) was dissolved in dry CH$_2$Cl$_2$ (10.67 ml) and cooled to −78° C. under nitrogen. To this cooled solution were added 4-amino-1-benzylpiperidine (0.44 ml, 2.11 mmol) and diisopropylethylamine (0.402 ml, 2.3 mmol). The reaction was gradually warmed to room temperature overnight under nitrogen. After completion, CH$_2$Cl$_2$ (300 ml) was added and the organic layer was washed with brine (100 ml, 2×), dried over MgSO$_4$ and filtered. The filtrate was evaporated under vacuum to give a crude oil which was purified by flash chromatography on flash grade silica gel (100 g), eluting with 2.5% NH$_3$-MeOH-2.5% EtOH/CH$_2$Cl$_2$ to give a light yellow oil (0.76 g, 1,229 mmol, 59%). A portion of the oil (0.27 gram, 0.436 mmol) was converted to its hydrochloride salt by dissolving in CH$_2$Cl$_2$ (13.5 ml) and treating with 2.3 M HCl-EtOH (0.938 ml, 2.182 mmol). After stirring at room temperature for 40 minutes, solvent was evaporated and the residue was vacuum dried overnight, m.p. 199–202° C.; FAB mass [M+1]$^+$619.5;

Found, C, 51.73; H, 5.98; N, 7.18; Cl, 13.69; F, 14.75. Calcd. for C$_{33}$H$_{36}$N$_4$OF$_6$.3 HCl.2 H$_2$O, C, 51.87 H, 5.67; N, 7.33; Cl, 13.92; F, 14.91.

EXAMPLE 3

By a process analogous to that described in Example 2, the following compound was prepared by using (1S,4S,)-benzyl-2,5-diazobicyclo[2.2.1] heptane dihydrobromide in place of 4-amino-1-benzylpiperidine.

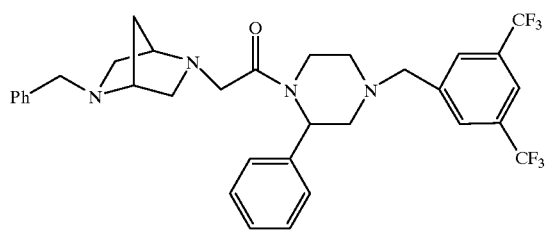

| free form | m.p. | High Res. Mass |
|---|---|---|
|  | 45–47° C. | Cal'd 617.2715 |
|  |  | Found 617.2731 |

EXAMPLE 4

Preparation of (+,−)-4-[[3,5-bis(trifluoromethyl)phenyl]methyl]-2-phenyl-N-[1-(phenylmethyl)-4-piperidinyl]-1-piperazineethanamine, tetrahydrochloride salt, monohydrate.

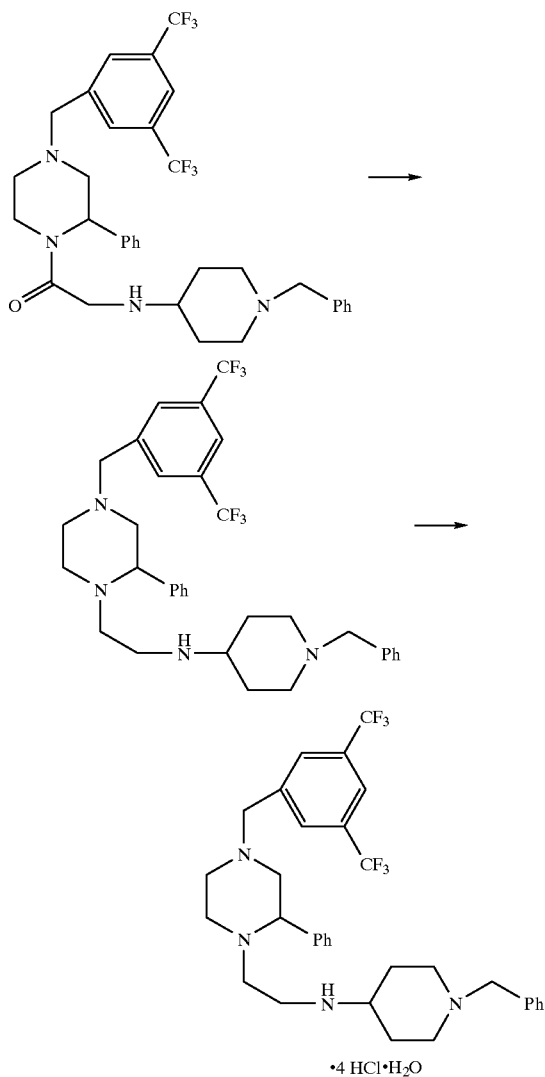

To a solution of (+,−)-4-[[3,5-bis(trifluoromethyl)phenyl]methyl]-2-phenyl-1-[[[1-(phenylmethyl)-4-piperidinyl]amino]acetyl]piperazine (0.48 g, 0.776 mmol) in THF (12 ml) was added 10 M $BH_3 \cdot S(CH_3)_2$ (0.388 ml, 3.88 mmol). The mixture was heated in an oil bath at 80° C. under nitrogen overnight. After completion, excess $BH_3$ was decomposed by dropwise addition of MeOH to the cooled solution under nitrogen. MeOH was evaporated and the residue was redissolved in EtOH (14.4 ml). $K_2CO_3$ (0.235 gram, 1.707 mmol) was added and the mixture was refluxed at 80° C. for five hours. After TLC showed that the reaction was complete, the solid was filtered off and the filtrate was evaporated under vacuum. The residue was redissolved in EtOAc (300 ml), washed with brine (100 ml) and dried over $MgSO_4$. It was filtered and evaporated under vacuum to give an oil which was purified by flash chromatography on flash grade silica gel (80 g), eluting with 3% $NH_3$-MeOH/$CH_2Cl_2$ to give the desired material as an oil (0.373 gram, 0.615 mmol, 79%). A portion of the oil (0.36 gram) was converted to its hydrochloride salt by dissolving in dry $CH_2Cl_2$ (18 ml), followed by the addition of 2.3 M HCl-EtOH (1.3 ml). Solvents were removed after stirring at room temperature for 0.5 hour and the residue was vacuum dried, m.p. 238–241° C.; FAB mass $[M+1]^+ 605.6$;

Found, C, 51.96; H, 5.83; N, 7.01; Cl, 14.52; F, 18.21. Calcd. for $C_{33}H_{38}N_4F_6 \cdot 4$ HCl$\cdot H_2O$, C, 51.57; H, 5.77; N, 7.29, Cl, 14.83; F, 18.45.

EXAMPLE 5

Preparation of 2-(3,4-dichlorophenyl)piperazine

METHOD 1

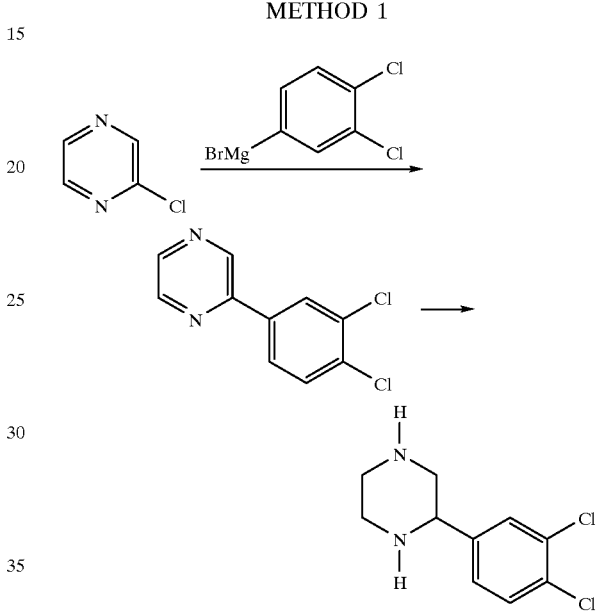

2-(3,4-Dichlorophenyl)pyrazine was prepared according to the analogous method described in Example 1. m.p. 118–119° C.; FAB mass $[M+1]^{+35}$ Cl 225.

To a solution of 2-(3,4-dichlorophenyl)pyrazine (10 g, 44.43 mmol) in dry THF (150 ml) was added slowly a solution of DIBAL-H (1 M in THF, 444.3 ml) through a dropping funnel at 10° C. under $N_2$. The color of solution turned into red wine at the end of addition. The solution was gradually warmed up to room temperature overnight. After completion (checked by TLC) the reaction was quenched slowly by the addition of saturated $Na_2SO_4$ solution until no more $H_2$ evolved. White precipitate was formed after stirring for 1.0 h. The precipitate was filtered off, rinsed with THF, dried over $MgSO_4$ and evaporated to dryness. The crude material (10 g) was purified by flash chromatography on 300 g of flash grade silica gel in 7.5% $NH_3$.MeOH/$CH_2Cl_2$ to give 4.11 g (17.77 mmol, 40%) of 2-(3,4-dichloro-phenyl)piperazine. m.p. 74–76° C.; FAB mass $[M+1]^{+35}$ Cl 231.

METHOD 2

2-(3,4-Dichlorophenyl)pyrazine was also synthesized according to the method published in J.Med.Chem. 9, 191, 1966.

General method for the synthesis of 2-aryl-piperazine derivatives.

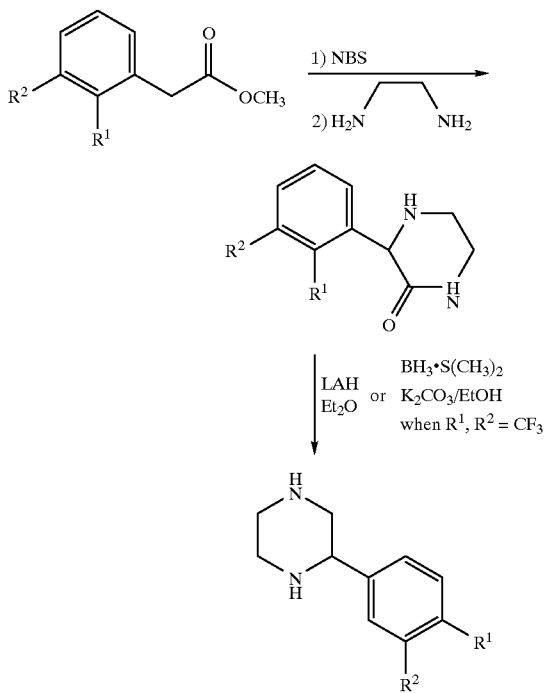

R¹ = Cl, H or other substituents i.e. OCH₃, CF₃, Br, I, F, etc.
R² = Cl, H or other substituents i.e. OCH₃, CF₃, Br, I, F, etc.

Resolution of 2-(3,4-dichlorophenyl)-piperazine.

Step 1

Treat a solution of piperazine (10.6 g, 45.8 mmol) in methanol (130 mL) with two equivalents of N-acetyl-L-leucine (15.9 g, 91.5 mmol) and heat until all of the material dissolves. Add EtOAc (660 mL) to this solution and let sit at ambient temperature overnight. Decant the solvent phase from the precipitated salt and concentrate in vacuo to obtain 18.5 g of salt with the piperazine enriched 3.0:1.0 of enantiomer A to B. Concentrate the precipitated salt to give 12.3 g of a colorless solid with the piperazine enriched 1.0:7.1 of enantiomer A to B.

Step 2

Dissolve the precipitated salt from step 1 in 0.5 N NaOH (400 mL) and extract with $CH_2Cl_2$ (4×150 mL). Combined organic layers, dry ($MgSO_4$) and concentrate to give 3.8 g piperazine free base. Recrystallize the free base two times in hexane (100 and 70 mL) to give 2.5 g of piperazine (98% ee of enantiomer B) as colorless crystals.

Step 3

Recrystallize the salt from the solvent phase in step 1 with 350 mL of EtOAc:methanol (5:1) to give 15.3 g of salt from the solvent phase. Recrystallized this salt with 250 mL of EtOAc:methanol (5:1) to give 9.9 g of salt from the solvent phase that is 5.5:1.0 enriched with piperazine A to B. Add the salt to 0.5 N NaOH (250 mL) and extract with $CH_2Cl_2$ (3×100 mL). Combine organic layers, dry ($MgSO_4$) and concentrate to give 2.8 g of crude free base. Recrystallize from hexane (65 mL) to give 1.0 g of piperazine (98% ee of enantiomer A).

Analytical procedure for measuring piperazine enantiomeric purity.

The enantiomeric purity of the piperazine is measured by chiral HPLC analysis of the di-tert-butoxycarbonyl piperazine derivative. The di-tert-butoxycarbonyl derivative is prepared by adding a small piperazine sample (free base or salt)(~0.2 mg) to di-tert-butyl dicarbonate (~1 mg) and methanol (0.5 mL) and heating at 80° C. for 1 hour. If the piperazine sample is a salt, triethylamine (20 µL) is also added. The derivative is analyzed by HPLC using a Chiral-Pak AD column eluting with 95:5 hexane-isopropyl alcohol.

EXAMPLE 6

Preparation of (+,−)-4-[[3,5-bis(trifluoromethyl)phenyl]methyl]-2-(3,4-dichlorophenyl)-1-[[[1-(phenylmethyl)-4-piperidinyl]amino]acetyl]-piperazine.

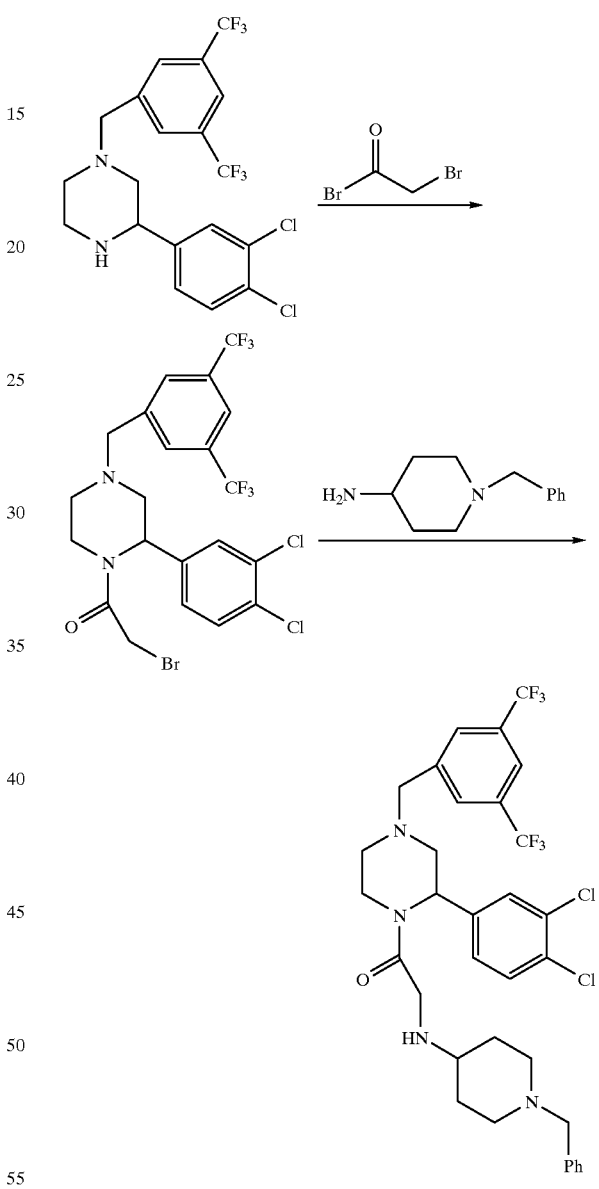

By a procedure analogous to the procedure described in the first part of example 2, using (+,−)-1-[[3,5-bis(trifluoromethyl)phenyl]methyl]-3-(3,4-dichlorophenyl) piperazine (Examples 1 and 5) in place of (+,−)-1-[[3,5-bis-(trifluoromethyl)phenyl]methyl]-3-phenylpiperazine, the bromo-acetyl derivative was obtained in 78% from its starting material as a solid, m.p. 146–148° C.; FAB mass $[M+1]^{+35}Cl$ 577.579.

By a procedure analogous to the procedure described in the second part of Example 2, the title compound was obtained as a solid (48%) after purification by flash chromatography on flash grade silica gel (70 g), eluting with 4% MeOH/CH$_2$Cl$_2$, m.p. 53–55° C.; FAB mass [M+1]$^{+35}$Cl 687;

Found, C, 56.98; H, 4.72; N, 8.13; Cl, 10.67; F, 16.30. Calcd. for C$_{33}$H$_{34}$N$_4$Cl$_2$F$_6$O.0.25 H$_2$O, C, 57.27; H, 5.03; N, 8.10; Cl, 10.25; F, 16.47.

EXAMPLE 7

By a procedure analogous to the procedure described in Example 2, but using (+,−)-1-[[3,5-bis(trifluoromethyl) phenyl]methyl]-3-(3,4-dichlorophenyl)piperazine in place of (+,−)-1-[[3,5-bis(trifluoromethyl)-phenyl]methyl]-3-phenylpiperazine, and employing (1S,4S)-2-benzyl-2,5-diazabicyclo[2.2.1]heptane dihydrobromide, in place of 4-amino-1-benzyl-piperidine, the following compound was prepared.

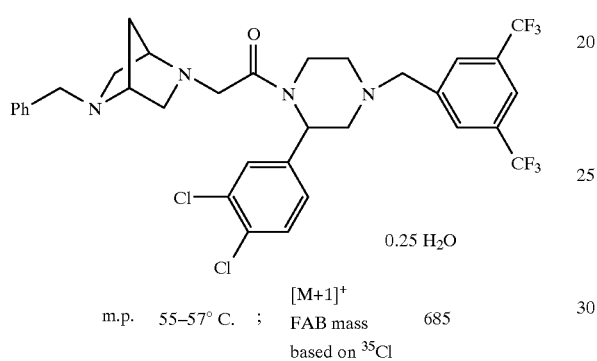

m.p. 55–57° C.; [M+1]$^+$ FAB mass 685 based on $^{35}$Cl 0.25 H$_2$O

EXAMPLE 8

Preparation of (+,−)-4-[[3,5-bis(trifluoromethyl)phenyl] acetyl]-2-phenyl-1-[[[1-(phenylmethyl)-4-piperidinyl] amino]acetyl]piperazine.

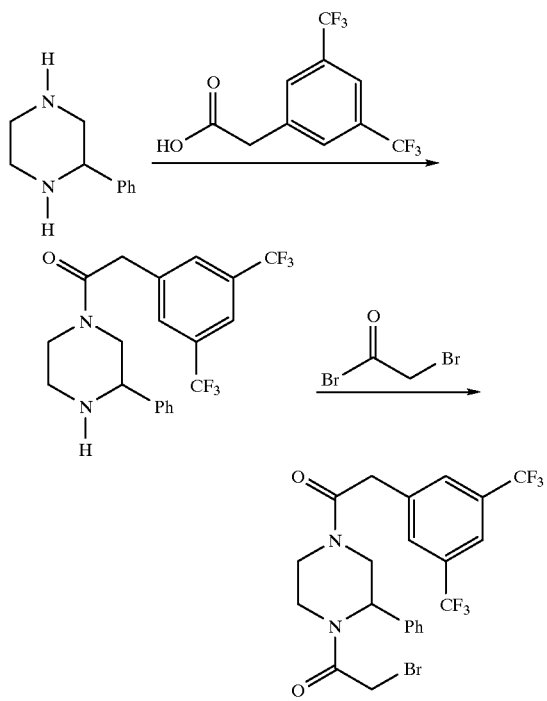

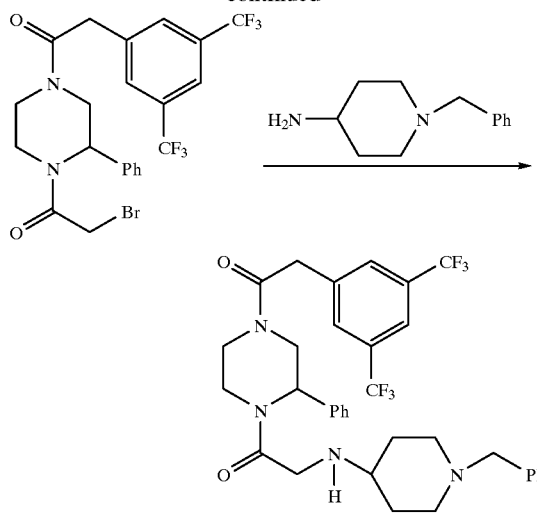

To cooled CH$_2$Cl$_2$ (127 ml) containing 2-phenyl-piperazine (Example 1, 1.0 gram, 6.164 mmol), 3,5-bis (trifluoromethyl)phenylacetic acid (1.797 g, 6.472 mmol), and N-hydroxybenzotriazole monohydrate (HOBT) (0.874 g, 6.472 mmol) at −20° C. were added Et$_3$N (0.9 ml, 6.472 mmol) and N,N-dimethylaminopropylethylcarbodimide (DEC) under nitrogen. The reaction was kept at −20° C. for an hour and gradually warmed to RT overnight. After stirring 20 hours, the reaction was complete and CH$_2$Cl$_2$ (200 ml) was added. The organic solution was washed with 5% NaHCO$_3$ (100 ml) and brine (100 ml, 3×), dried over MgSO$_4$, filtered and concentrated under vacuum to give 2.5 g of crude product. The product was purified by flash chromatography on flash grade silica gel (120 g), eluting with 3% NH$_3$-MeOH/CH$_2$Cl$_2$ to give a gummy solid (2.08 g, 4.996 mmol, 81%). A portion of this solid (1.0 g) was crystallized from hexane and characterized to yield a solid, m.p. 80–82° C.; FAB mass [M+1]$^{1+}$417.2;

Calcd. for C$_{20}$H$_{18}$ON$_2$F$_6$, C, 57.69; H, 4.36; N, 6.73; F, 27.38.

Found, C, 57.91; H, 4.55; N, 6.69; F, 27.61.

To a solution of the above compound (1.11 g, 2.642 mmol) in dry CH$_2$Cl$_2$ (22.2 ml) at −78° C. was added diisopropylethylamine (0.483 ml, 2.774 mmol) followed by the dropwise addition of bromoacetyl bromide (0.246 ml, 2.774 mmol). After stirring at −78° C. for 7 hours under nitrogen, additional diisopropylethylamine (0.51 ml, 2.9 mmol) and 4-amino-1-benzylpiperidine (0.605 ml, 2.9 mmol) were added at −78° C. The reaction was gradually warmed to RT overnight. After the reaction was complete, the reaction was diluted with CH$_2$Cl$_2$ (150 ml), washed with brine (50 ml, 3×) and dried over MgSO$_4$. After filtration, the solvent was removed under vacuum to give a light yellow solid which was purified by flash chromatography on flash grade silica gel (150 g), eluting with 5% NH$_3$-MeOH/CH$_2$Cl$_2$ to give the title compound as a white solid (0.94, g, 1.453 mmol, 55%), m.p.49–52° C.; FAB mass [M+1]$^+$647.3;

Calcd. for C$_{34}$H$_{36}$O$_2$N$_4$F$_6$, C, 63.15; H, 5.16; N, 8.66; F, 17.62. Found, C, 62.73; H, 5.77; N, 8.56; F, 17.68.

EXAMPLE 9

Preparation of (+,−)-4-[2-[3,5-bis(trifluoromethyl)phenyl] ethyl]-2-phenyl-N-[1-(phenylmethyl)-4-piperidinyl]-1-piperazineethanamine, four hydrochloride salt, hemihydrate.

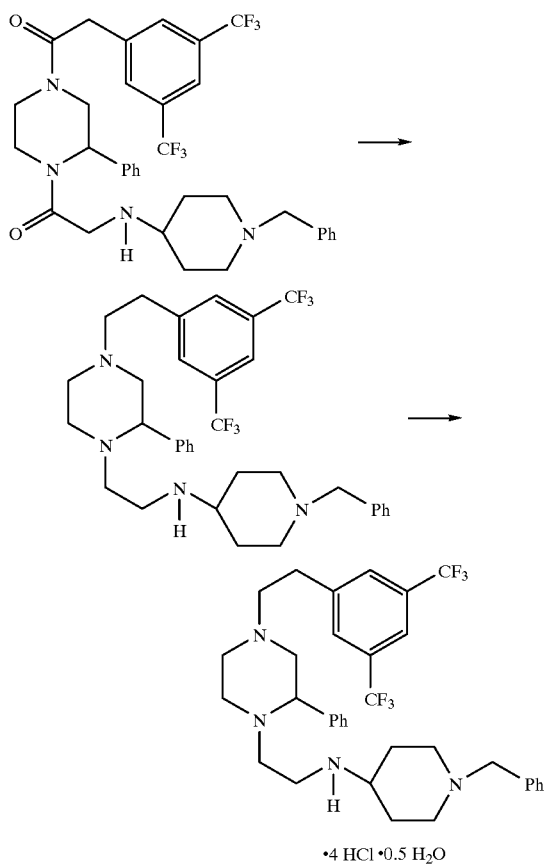

·4 HCl ·0.5 H₂O

To a solution of the product from Example 8 (0.463 gram, 0.72 mmol) in dry THF (21.6 ml) was added a 10 M solution of BH$_3$.S(CH$_3$)$_2$ (0.716 ml, 7.16 mmol) at RT under nitrogen. The solution was heated at 80° C. under nitrogen for 24 hours. After cooling to RT, MeOH (5 ml) was added slowly to decompose excess BH$_3$.S(CH$_3$)$_2$. All solvents were removed under vacuum and the residue was redissolved in absolute EtOH (14.1 ml), followed by the addition of K$_2$CO$_3$ (0.22 g, 1.58 mmol). The mixture was heated at 80° C. for 6.5 hours under nitrogen. After cooling K2CO3 was filtered and EtOH was removed to give a residue which was redissolved in EtOAc (150 ml) and washed with brine (50 ml, 2×). It was dried over MgSO$_4$, filtered, and evaporated under vacuum to give a solid (0.42 g) which was purified by flash chromatography on flash grade silica gel (80 g), eluting with 4% NH$_3$-MeOH/CH$_2$Cl$_2$ to give a white solid (0.14 g, 0.227 mmol, 49%).

The above material (0.14 g, 0.227 mmol) was treated with CH$_2$Cl$_2$ (6.8 ml) and 2.3M HCl-EtOH (0.592 ml, 1.362 mmol). After stirring at RT for 10 minutes, the solution was evaporated under high vacuum to give a white solid, m.p. 182–190° C.; High Res. MS [M+1]$^+$; Calcd. for C$_{34}$H$_{41}$N$_4$F$_6$, 619.3235, Found, 619.3222.

Calcd. for C$_{34}$H$_{40}$N$_4$F$_6$.4HCl.0.5 H$_2$O, C, 52.79; H, 5.86; N, 7.24, F, 14.73; Cl, 18.33. Found, C, 52.58; H, 6.10; N, 7.21; F, 14.77; Cl, 16.71.

EXAMPLE 10
Preparation of (+,–)-2-phenyl-1-[[[(1-phenylmethyl)-4-piperidinyl]amino]acetyl]-4-[(3,4,5-trimethoxylphenyl) acetyl]piperazine, hemihydrate.

By a procedure analogous to the procedure described in Example 8, using 3,4,5-trimethoxyphenylacetic acid in place of 3,5-bis(trifluoromethyl)phenylacetic acid, the title compound was prepared as a solid, m.p. 53–56° C., High Res. MS:[M+1]+Calcd. for C$_{35}$H$_{45}$N$_4$O$_5$ 601.3390; Found, 601.3393.

Calcd. for C$_{35}$H$_{44}$N$_4$O$_5$.0.5 H$_2$O, C, 68.94; H, 7.43; N, 9.19. Found, C,69.21; H,7.53; N, 9.22.

EXAMPLE 11
Preparation of (+,–)-2-phenyl-N-[1-(phenylmethyl)-4-piperidinyl]-4-[2-(3,4,5-trimethoxyphenyl)ethyl]-1-piperazineethanamine, four hydrochloride salt, monohydrate.

By essentially the same process as described in Example 9, using the product from Example 10 in place of the product from Example 8, the title compound was prepared as a solid, m.p. 167° C. (wet, no sharp melting point); High Res. MS: [M+1]$^+$ Calcd. for C$_{35}$H$_{49}$N$_4$O$_3$, 573.3805, Found, 573.3810.

Calcd. for C$_{35}$H$_{48}$N$_4$O$_3$. 4 HCl.H$_2$O, C, 57.07; H, 7.39; N, 7.61; Cl, 19.25. Found, C, 57.16; H, 7.88; N, 7.64, Cl, 18.71.

EXAMPLE 12
Preparation of (+/–)-4-[2-[3,5-bis(trifluoromethyl)phenyl) ethyl]-2-phenyl-1-[[[1-(phenylmethyl)-4-piperidinyl] amino]acetyl]piperazine, trihydrochloride salt.

By a process analogous to the reduction process described in the first part of Example 9, using (+,–)-[[3,5-bis-(trifluoromethyl)phenyl]acetyl]-3-phenylpiperazine (described in the first part of Ex. 8) as a starting material, (+,–)-4-[2-[bis(trifluoromethyl)-phenyl]ethyl]-2-phenyl piperazine was prepared as a solid after purification by flash chromatography, m.p. 193–195° C., FAB mass [M+1]$^+$ 403.3. This material (0.38 g, 0.94 mmol) was converted to its bromoacetyl derivative according to the same procedure as described in the second step of Example 8. After reaction was complete, the material was alkylated with 4-amino-1-benzylpiperidine without isolation, using the same procedure as described in the third step of Example 16. The title compound was obtained as a solid by flash chromatography, then converted to its HCl salt by treatment with HCl/MeOH solution. m.p. 214–216° C., High Res. MS: [M+1]$^+$ Calcd. for C$_{34}$H$_{39}$N$_4$OF$_6$, 633.3028; Found, 633.3034.

EXAMPLE 13
Preparation of (+,–)-2-phenyl-1-[[[(1-phenylmethyl)-4-piperidinyl]amino]acetyl]-4-[2-(3,4,5-trimethoxyphenyl) ethyl]piperazine.

By a reduction process analogous to that described in the first part of Example 9, using (+,–)-3-phenyl-1-[(3,4,5-trimethoxyphenyl)acetyl]piperazine as a starting material, the reduced product, (+,–)-2-phenyl-4-[[2-(3,4,5-trimethoxy)phenyl]ethyl]piperazine was prepared as a solid after purification by flash chromatography, m.p. 160–162° C., FAB mass [M+1]$^+$357.4. This material (0.53 g, 1.48 mmol) was converted to its bromoacetyl derivative according to the same procedure as described in the second step of Example 8. After reaction is complete, the bromoacetyl derivative is alkylated in situ with 4-amino-1-benzylpiperidine, using the same procedure as described in the third step of Example 8.

The title compound can be obtained and purified by flash chromatography.

EXAMPLE 14
Preparation of (+,–)-[3,5-bis(trifluoromethyl)benzoyl]-3-(3, 4-dichlorophenyl)piperazine

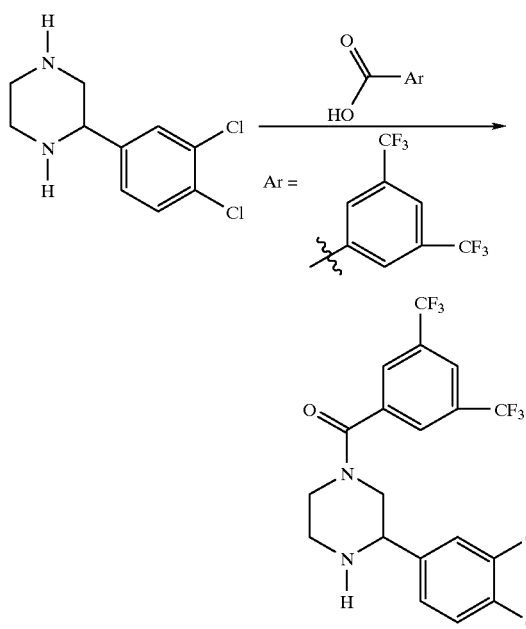

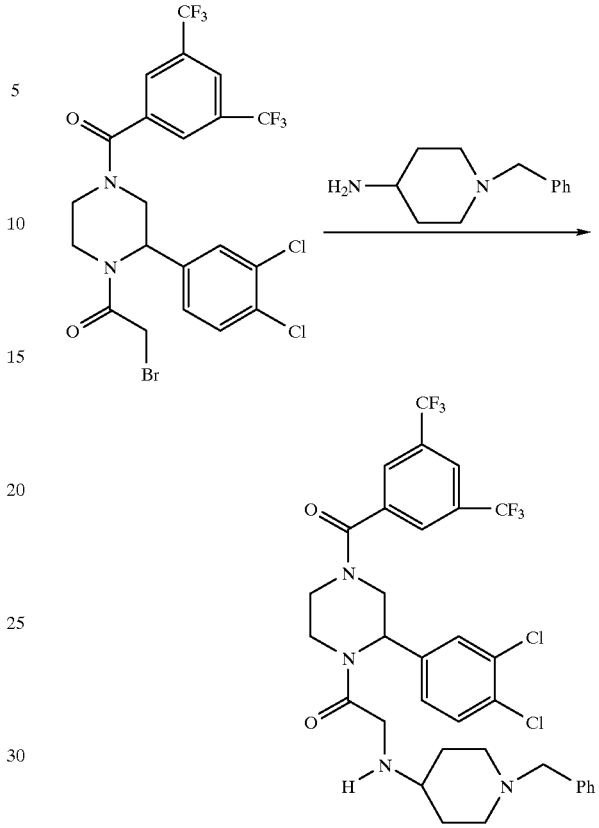

To a cooled solution of $CH_2Cl_2$ (103 ml) containing 2-(3,4-dichlorophenyl)piperazine (1.15 gram, 5.0 mmol), 3,5-bis-(trifluoromethyl)benzoic acid (1.34 g, 5.09 mmol), and N-hydroxybenzotriazole monohydrate (0.688 g, 5.09 mmol) at $-20°$ C. were added $Et_3N$ (0.711 ml, 5.09 mmol) and N,N-dimethylaminopropyl-ethylcarbodimide (DEC) (0.967 g, 5.09 mmol) under nitrogen. The reaction was kept at $-20°$ C. for an hour and gradually warmed to RT overnight. After stirring 20 hours, the reaction was complete and $CH_2Cl_2$ (200 ml) was added. The organic solution was washed with 5% $NaHCO_3$ (80 ml) and brine (80 ml, 2x), dried over $MgSO_4$, filtered and concentrated under vacuum to give 2.1 g of crude product. The product was purified by flash chromatography on flash grade silica gel (120 g), eluting with 2% $NH_3$-MeOH/$CH_2Cl_2$ to give a foam solid (1.25 g, 2.65 mmol, 53%). m.p. 50–53° C.; FAB mass $[M+1]^{+35}$ Cl 470.9;

Calcd. for $C_{19}H_{14}ON_2F_6Cl_2$, C, 48.42; H, 2.99; N, 5.94; F, 24.19; Cl, 15.05.

Found, C, 48.57; H, 2.90; N, 5.94; F, 23.90; Cl, 15.03.

EXAMPLE 15

Preparation of (+,−)-4-[3,5-bis(trifluoromethyl)benzoyl]-2-(3,4-dichlorophenyl)-1-[[[1-(phenylmethyl)-4-piperidinyl]amino]acetyl]piperazine

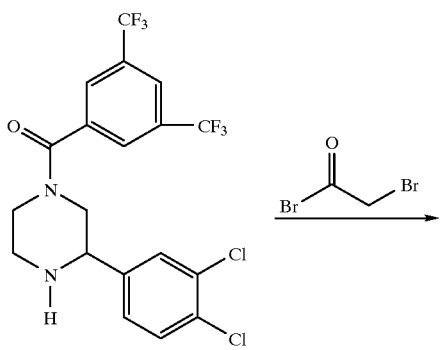

To a solution of (+,−)-[3,5-bis(trifluoromethyl)benzoyl]-3-(3,4-dichlorophenyl)piperazine (0.6 g, 1.274 mmol) in dry $CH_2Cl_2$ (12.0 ml) at $-78°$ C. was added diisopropylethylamine (0.266 ml, 1.53 mmol) followed by the dropwise addition of bromoacetyl bromide (0.124 ml, 1.40 mmol). After stirring at $-78°$ C. for 3.5 hours under nitrogen, additional diisopropylethylamine (0.234 ml, 1.342 mmol) and 4-amino-1-benzylpiperidine (0.279 ml, 1.342 mmol) were added at $-78°$ C. The reaction was gradually warmed to RT overnight. After the reaction was complete, the reaction was diluted with $CH_2Cl_2$ (200 ml), washed with brine (80 ml, 3x) and dried over $MgSO_4$. After filtration, the solvent was removed under vacuum to give a light yellow solid which was purified by flash chromatography on flash grade silica gel (150 g), eluting with 5% $NH_3$-MeOH/$CH_2Cl_2$ to give the title compound as a white solid (0.55 g, 1.274 mmol, 62%), m.p.66–69° C.; FAB mass $[M+1]^{+35}Cl$ 701.

Calcd. for $C_{33}H_{32}O_2N_4F_6Cl_2$, C, 56.50; H, 4.60; N, 7.99; F, 16.25, Cl, 10.11. Found, C, 56.57; H, 4.66; N, 7.94; F, 16.07, Cl, 9.90.

EXAMPLE 16

By employing methods analogous to those described in Example 14 and Example 15, using appropriate amino reagents, and using parallel synthesis methods, the following compound was obtained.

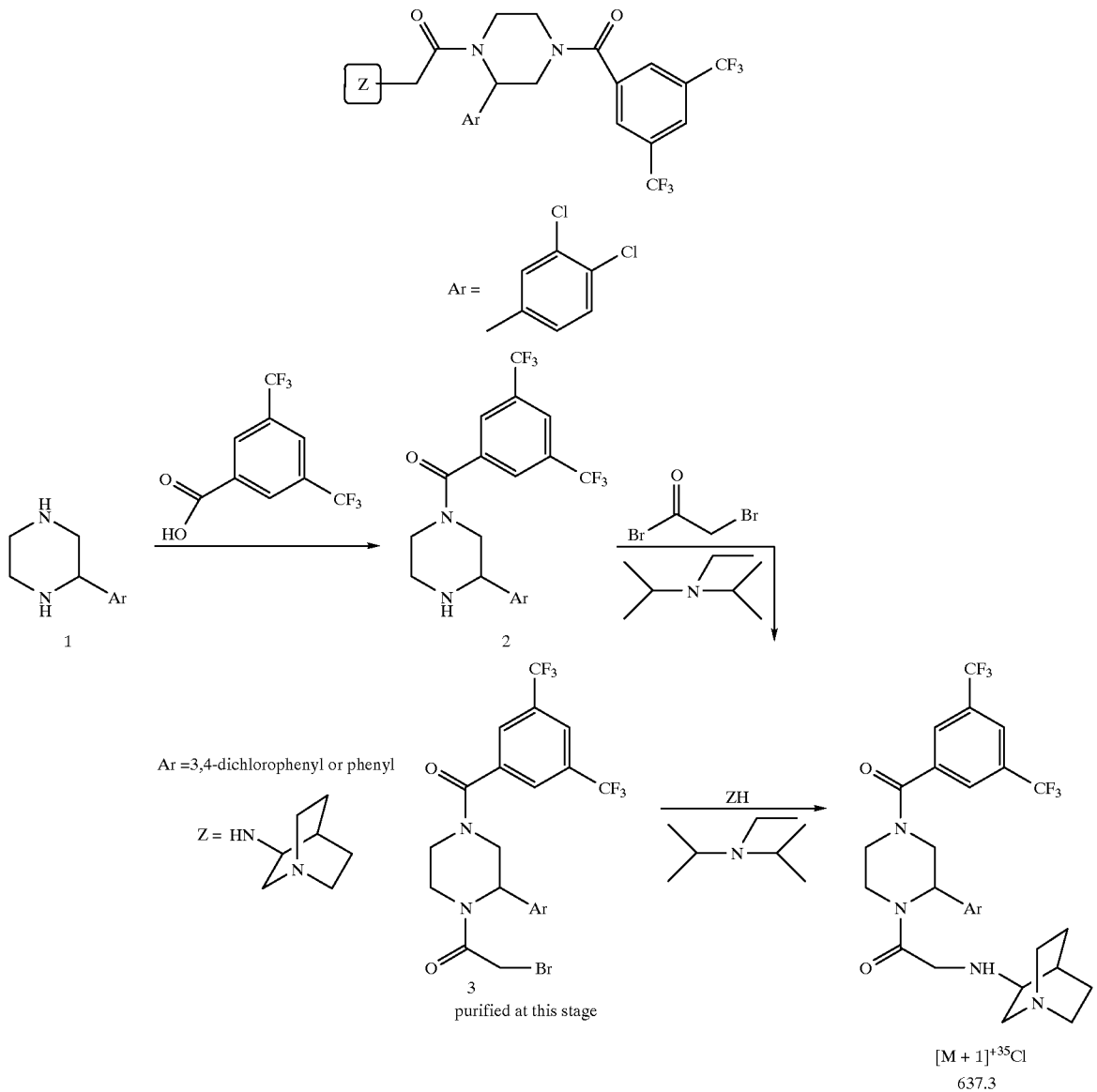
EXAMPLE 17
Preparation of (+)-4-[3,5-bis(trifluoromethyl)benzoyl]-2-(3,4-dichlorophenyl)-1-[[[1-(phenylmethyl)-4-piperidinyl]amino]acetyl]piperazine dihydrochloride dihydrate
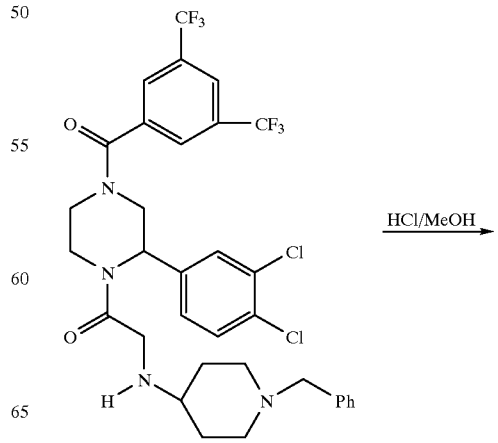

121

-continued

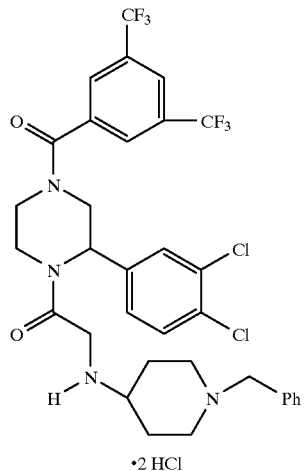

·2 HCl

The compound from Example 15 (100 mg) was separated on a Chiral Pak AD column (5×50 cm), eluting with hexane:isopropanol (80:20). The first fraction was evaporated to give 37 mg of enantiomer A which was converted to its hydrochloride salt by dissolving in MeOH and treating with three equivalents of anhydrous HCl/MeOH for 20 minutes. After the solvent was evaporated a white solid was obtained: m.p. 205–220° C.; $[\alpha]_D^{25.1}$=+21.1 (MeOH); FAB mass $[M+1]^{+35}Cl$ 701.

Calcd. for $C_{33}H_{32}O_2N_4F_6Cl_2 \cdot 2$ HCl.2 $H_2O$, C, 48.90; H, 4.73; N, 6.91; F, 14.06, Cl, 17.49. Found: C, 49.34 H, 4.84; N, 6.82. High Resolution Mass: Calc. for $[M+1]^+$ $C_{33}H_{33}O_2N_4F_6Cl_2$ 701.1885, Found: 701.1879.

EXAMPLE 18

Preparation of (−)-4-[3,5-bis(trifluoromethyl)benzoyl]-2-(3,4-dichlorophenyl)-1-[[[1-(phenylmethyl)-4-piperidinyl]amino]acetyl]piperazine dihydrochloride dihydrate.

The compound from Example 15 (100 mg) was separated on a Chiral Pak AD column (5×50 cm), eluting with hexane:isopropanol (80:20). The second fraction was evaporated to give 45 mg of enantiomer B which was converted to its hydrochloride salt by dissolving in MeOH and treating with three equivalents of anhydrous HCl/MeOH for 20 minutes. After the solvent was evaporated a white solid was obtained: m.p. greater than 258° C.; $[\alpha]_D^{25.1}$=−18.5 (MeOH), FAB mass $[M+1]^{+35}Cl$ 701.

Calcd. for $C_{33}H_{32}O_2N_4F_6Cl_2 \cdot 2$ HCl.2 $H_2O$, C, 48.90; H, 4.73; N, 6.91; F, 14.06, Cl, 17.49. Found: C, 48.88; H, 4.83; N, 6.71. High Resolution Mass: Calc. for $[M+1]^+$ $C_{33}H_{33}O_2N_4F_6Cl_2$ 701.1885, Found: 701.1885.

EXAMPLE 19

Preparation of (+,−)-2-(3,4-dichlorophenyl)-1-[[[1-(phenylmethyl)-4-piperidinyl]amino]acetyl]-4-(3,4,5-trimethoxybenzoyl)piperazine By employing methods analogous to those described in Example 14 and Example 15, and using 3,4,5-trimethoxybenzoic acid in place of 3,5-bis-(trifluoromethyl) benzoic acid in the coupling reaction, the title compound was obtained in 60% yield, m.p.67–70° C.; FAB mass $[M+1]^{+35}Cl$ 655.

Calcd. for $C_{34}H_{40}O_5N_4Cl_2$, C, 62.29; H, 6.15; N, 8.54; Cl, 10.81. Found, C, 61.87; H, 6.15; N, 8.46; Cl, 10.62.

EXAMPLE 20

Preparation of (+,−)-2-(3,4-dichlorophenyl)-4-[3-(1-methylethoxy)benzoyl]1-[[[1-(phenylmethyl)-4-piperidinyl]amino]acetyl]piperazine, hemihydrate

122

By employing methods analogous to those described in Example 14 and Example 15, and using 3-(1-methylethoxy) benzoic acid in place of 3,5-bis-(trifluoromethyl)benzoic acid in the coupling reaction, the title compound was obtained in 49.5% yield, m.p.58–61° C.; FAB mass $[M+1]^{+35}$ Cl 623.3.

Calcd. for $C_{34}H_{40}O_3N_4Cl_2 \cdot 0.5$ $H_2O$, C, 64.55; H, 6.53; N, 8.86; Cl, 11.20. Found, C, 64.55; H, 6.64; N, 8.92; Cl, 11.26.

EXAMPLE 21

Preparation of (+,−)-2-(3,4-dichlorophenyl)-4-[2-methoxybenzoyl]-1-[[[1-(phenylmethyl)-4-piperidinyl] amino]acetyl]piperazine By employing methods analogous to those described in Example 14 and Example 15, and using 2-methoxybenzoic acid in place of 3,5-bis-(trifluoromethyl)benzoic acid in the coupling reaction, the title compound was obtained in 42.0% yield, m.p.71–73° C. FAB mass $[M+1]^{+35}Cl$ 595.2.

EXAMPLE 22

Preparation of (+,−)-4-[3,5-bis(trifluoromethyl)benzoyl]-2-(3,4-dichlorophenyl)-1-[[5-(phenylmethyl)-2,5-diazabicyclo[2.2.1]heptan-2-yl]acetyl]piperazine By employing methods analogous to those described in Example 14 and Example 15, and using 5-phenylmethyl-2,5-diazabicyclo[2.2.1.]heptane in place of 1-amino-4-benzylpiperidine as the nucleophile, the title compound was obtained in 75% yield, m.p.75–77° C. FAB mass $[M+1]^{+35}$ Cl 699.2;

Calcd. for $C_{33}H_{30}O_2N_4F_6Cl_2$, C, 56.66; H, 4.32; N, 8.01; Cl, 10.14; F, 16.30.

Found, C, 56.55; H, 4.41; N, 7.95; Cl, 9.93; F, 16.53.

EXAMPLE 23

Preparation of (+,−)-4-[[3,5-bis(trifluoromethyl)phenyl] acetyl]-2-phenyl-1-[[[1-(phenylmethyl)-4-piperidinyl] amino]acetyl]piperazine.

By employing methods analogous to those described in Example 14 and Example 15, using 2-phenylpiperazine in place of 2-(3,4-dichloro-phenyl)piperazine and 3,5-bis (trifluoromethyl)phenylacetic acid in place of 3,5-bis (trifluoromethyl)benzoic acid in the coupling reaction, the title compound was obtained in 55% yield, m.p. 49–52° C.; FAB mass $[M+1]^+$647.3;

Calcd. for $C_{34}H_{36}O_2N_4F_6$, C, 63.15; H, 5.61; N, 8.66; F, 17.62.

Found, C, 62.73; H, 5.77; N, 8.59; F, 17.68.

EXAMPLE 24

Preparation of (+,−)-2-phenyl-1-[[[(1-phenylmethyl)-4-piperidinyl]amino]acetyl]-4-[(3,4,5-trimethoxylphenyl) acetyl]piperazine, hemihydrate.

By employing methods analogous to those described in Example 14 and Example 15, and using 2-phenylpiperazine in place of 2-(3,4-dichlorophenyl)-piperazine and 3,4,5-trimethoxyphenylacetic acid in place of 3,5-bis (trifluoromethyl)benzoic acid, the title compound was prepared as a solid, m.p. 53–56° C., High Res. MS:$[M+1]^+$ Calcd. for $C_{35}H_{45}N_4O_5$, 601.3390; Found, 601.3393.

Calcd. for $C_{35}H_{44}N_4O_5 \cdot 0.5$ $H_2O$, C, 68.94; H, 7.43; N, 9.19.

Found, C, 69.21; H, 7.53; N, 9.22.

EXAMPLE 25

Preparation of (+,−)-4-[3,5-bis(trifluoromethyl)benzoyl]-2-phenyl-1-[[[1-(phenylmethyl)-4-piperidinyl]amino]acetyl] piperazine By employing methods analogous to those described in Example 14 and Example 15, and using 2-phenylpiperazine in place of 2-(3,4-dichlorophenyl)-piperazine, the title compound was prepared with 71% yield as a solid: m.p. 65–67° C., FAB MS [M+1]$^{+35}$Cl 633.4

Calcd. for $C_{33}H_{34}N_4O_2F_6 \cdot 0.25\ H_2O$, C, 62.16; H, 5.46; N, 8.80; F, 17.89.

Found, C, 62.00; H, 5.65; N, 8.78; F, 18.08.

EXAMPLE 26

Preparation of (+,−)-4-[3,5-dimethylbenzoyl]-2-(3,4-dichlorophenyl)-1-[[[1-(phenylmethyl)-4-piperidinyl]amino]acetyl]piperazine

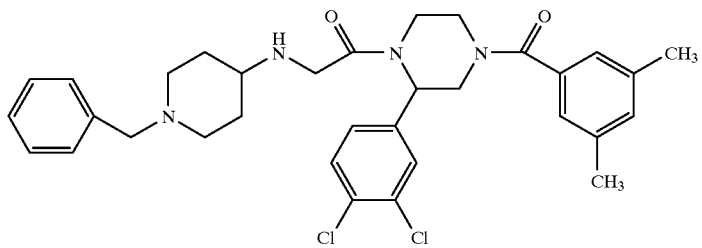

By employing methods analogous to those described in Example 14 and Example 15, and using 3,5-dimethylbenzoic acid in place of 3,5-bis(trifluoromethyl)-benzoic acid, the title compound was prepared as a solid, m.p.69–70° C.; FAB mass [M+1]$^{+35}$Cl 593.1.

Calcd. for $C_{33}H_{38}N_4O_2Cl_2$: C, 66.77; H, 6.45; N, 9.44; Cl, 11.94.

Found: C, 66.64; H, 6.74; N, 9.48; Cl, 11.89.

This racemic compound was resolved into Enantiomers A and B by the analogous methods described in Example 17 and Example 18.

Enantiomer A m.p. 64–66° C. $[\alpha]_D^{25}$=+26.3 (MeOH) FAB mass [M+1]$^{+35}$Cl 593.3;

Enantiomer B m.p. 64–66° C. $[\alpha]_D^{25}$=34.8 (MeOH) FAB mass [M+1]$^{+35}$Cl 593.3;

EXAMPLE 27

By employing methods analogous to those described in Example 14, Example 15, Example 16, and Example 26, using appropriate amino reagents, the following compounds were obtained.

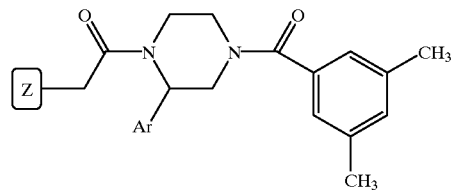

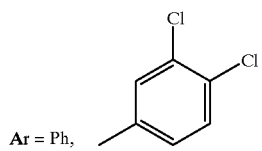

Ar = Ph,

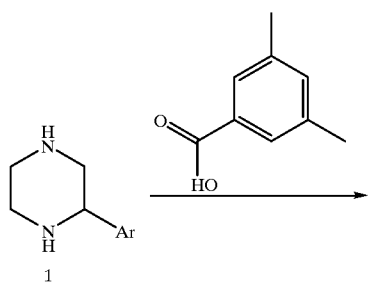

1

-continued
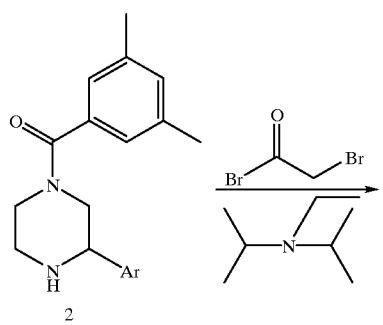
2
Ar = 3,4-dichlorophenyl or phenyl
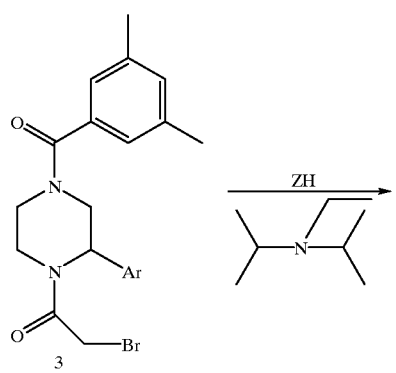
3
purified at this stage
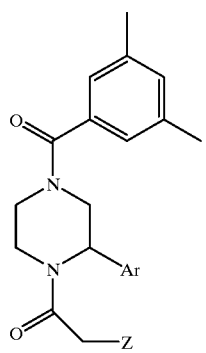
| | FAB MASS [M + 1]+ 35Cl | M.P. ° C. |
|---|---|---|
| 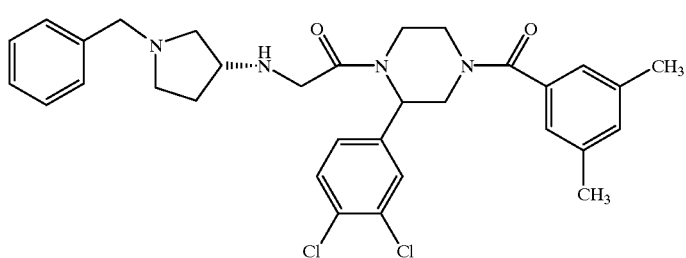 | 579.3 | 60–62 |

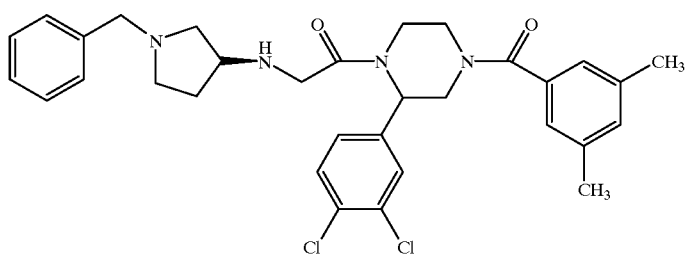
579.3   60–62
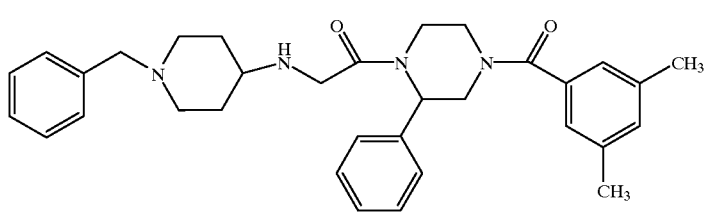
High Res. Mass
Calc'd 525.3299
Found 525.3230
EXAMPLE 28
Preparation of (+,−)-2-(3,4-dichlorophenyl)-4-(3,5-dimethylbenzoyl)-1-[[[1-(2-furanylmethyl)-4-piperldinyl)amino]acetyl]]piperazine
General method of synthesis
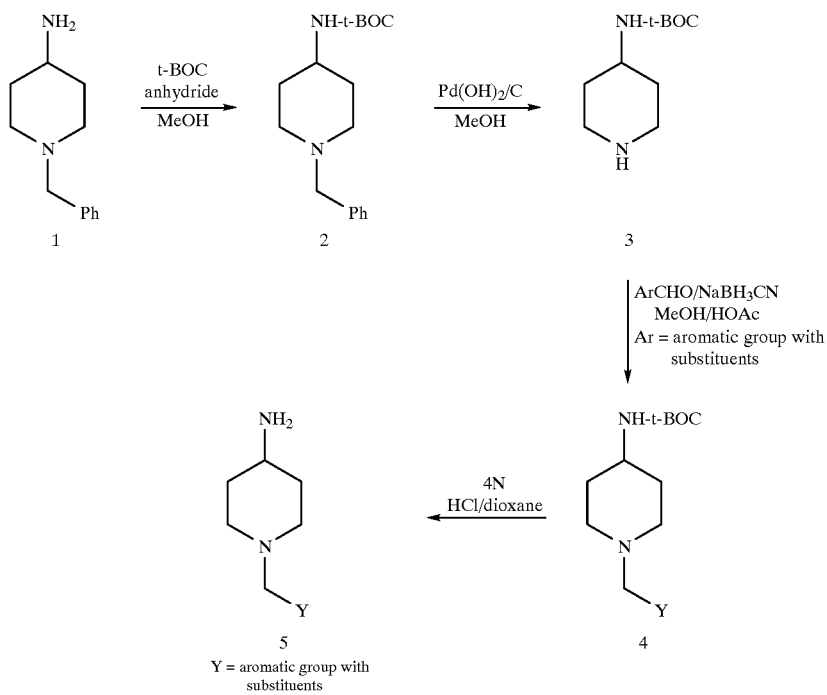

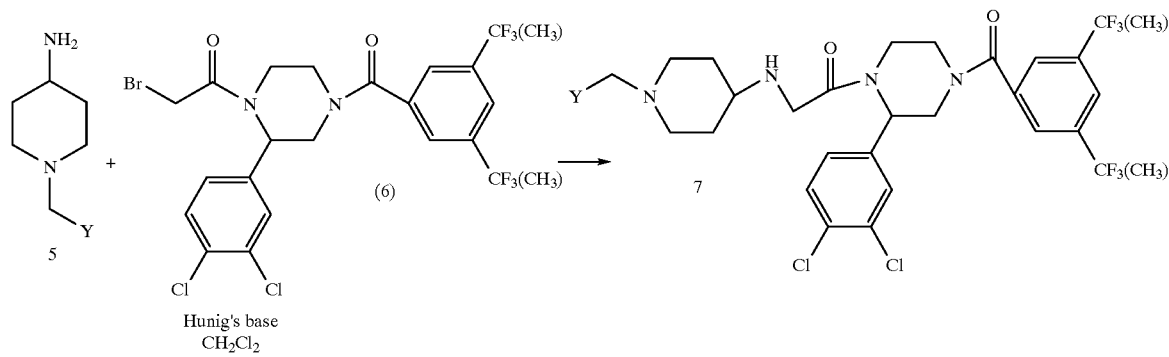

To a solution of 4-amino-1-benzylpiperidine (9.5, 50 mmol) in methanol (150 ml) at −10° C. was added a solution of di-t-butyldicarbonate (10.9 g, 50 mmol) in methanol (60 ml). The mixture was gradually warmed to room temperatures overnight. After the reaction was complete, solvent was removed to give a white solid (2) FAB MASS [M+1]$^{+35}$Cl 291.3

Compound (2) (11.6 g, 40 mmol) was dissolved in methanol (140 ml). To this solution was added Pd(OH)$_2$(20%) on carbon (2.4 g) and the mixture was hydrogenolyzed at 47 pounds per square inch. After the reaction was complete, the catalyst was filtered. The filtrate was evaporated to give a white solid of compound 3 (8 g, 40 mmol).

A mixture of compound 3 (0.7 g, 35 mmole) and 2-furaldehyde in MeOH (10 ml) was stirred at RT for 10 min. NaBH$_3$CN (0.5 g, 8 mmol) and acetic acid (1 ml) were added later. The mixture was stirred at RT overnight under an atmosphere of nitrogen. After the reaction was complete, CH$_2$Cl$_2$ (50 ml) was added and the mixture was washed with saturated NaHCO$_3$ solution (30 ml) and brine (30 ml 2×). The organic layer was evaporated after drying over MgSO$_4$ to give a crude tan solid 4 (Y is 2-furanylmethyl) which was used without purification. Compound 4 was dissolved in dry CH$_2$Cl$_2$ (2 ml) and treated with 4N HCl/dioxane (5 ml) solution. Solvents and excess HCl were evaporated after stirring the reaction at RT for 2 hours. It gave compound 5 as an off-white solid (0.65 g) as HCl salt.

Compound 5 was converted in situ to the free base with Hünig's base then reacted with the bromoacetyl key intermediate (6) in the above scheme to give the title compound analogous to the method described in Example 15.

m.p. 65–67° C.; FAB mass [M+1]$^{+35}$Cl 583.

EXAMPLE 29

By procedures analogous to the methods described in Example 28 and Example 15, the following compounds were obtained.

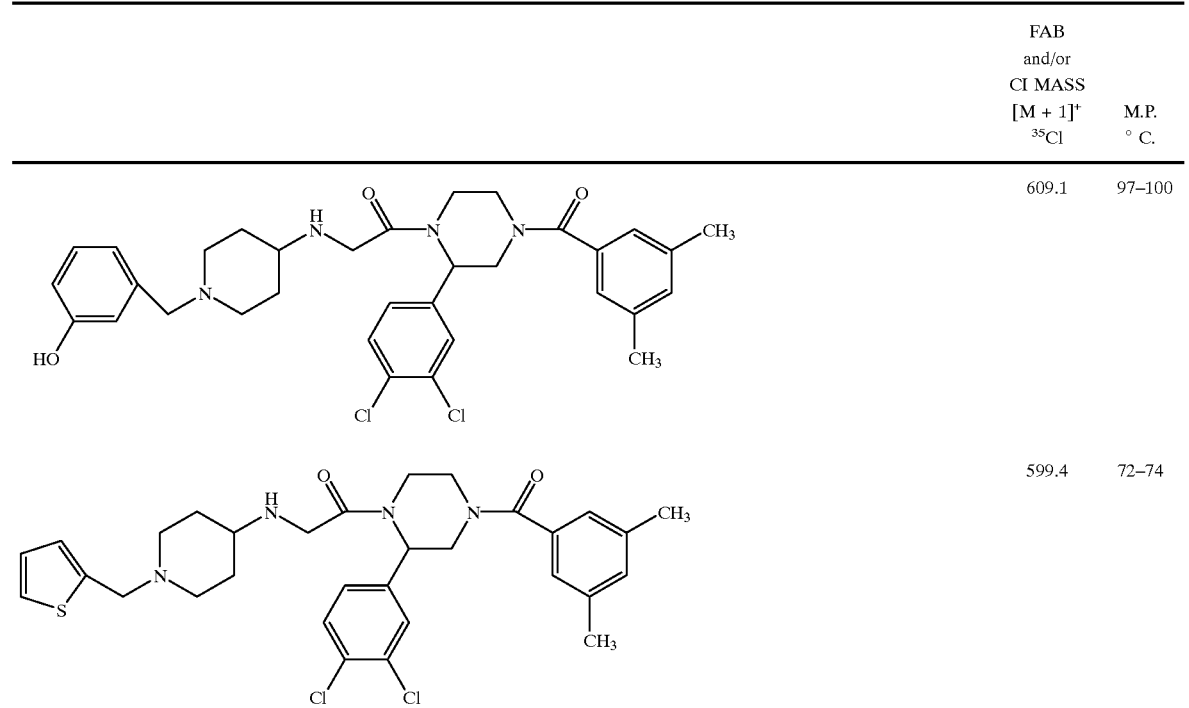

| | FAB and/or CI MASS [M + 1]$^+$ $^{35}$Cl | M.P. ° C. |
|---|---|---|
| (structure 1) | 609.1 | 97–100 |
| (structure 2) | 599.4 | 72–74 |

| Structure | FAB and/or CI MASS [M + 1]+ $^{35}$Cl | M.P. ° C. |
|---|---|---|
| (thiophene-CH2-piperidine-NH-CH2-CO-piperazine[2-(3,4-diClC6H3)]-CO-3,5-(CH3)2C6H3) | 599.4 | 68–70 |
| (furan-3-CH2-piperidine-NH-CH2-CO-piperazine[2-(3,4-diClC6H3)]-CO-3,5-(CH3)2C6H3) | 583.1 | 64–66 |
| (furan-2-CH2-piperidine-NH-CH2-CO-piperazine[2-(3,4-diClC6H3)]-CO-3,5-(CH3)2C6H3) | 583.1 | 65–67 |
| (imidazole-CH2-piperidine-NH-CH2-CO-piperazine[2-(3,4-diClC6H3)]-CO-3,5-(CH3)2C6H3) | 583.1 | 105–110 |
| (pyrrole-CH2-piperidine-NH-CH2-CO-piperazine[2-(3,4-diClC6H3)]-CO-3,5-(CH3)2C6H3) | 582.1 | 83–88 |

EXAMPLE 30

Preparation of (+,−)-1-[[[1-[[[1,1'-biphenyl]-4-yl]methyl]-4-piperldinyl]amino]acetyl]-2-(3,4-dichlorophenyl)-4-(3,5-dimethylbenzoyl)piperazine By methods analogous to those described in Example 28, compound (3) (0.6 g, 3 mmol) from Example 28, was mixed with 4-(chloromethyl)biphenyl (0.61 g, 3 mmol) (Y=C$_6$H$_5$—C$_6$H$_5$), Hünig's base (0.43 g, 3 mole) in CH$_2$Cl$_2$ (10 ml) and stirred at RT for two days. After completion, the reaction mixture was diluted with CH$_2$Cl$_2$ (50 ml) and washed with brine (30 ml, 2×). The CH$_2$Cl$_2$ layer was dried over MgSO$_4$, filtered, and concentrated to give a white solid (1 g). The crude product was purified on flash grade silica gel, eluting with 2% NH$_4$OH-MeOH/CH$_2$Cl$_2$ system to give compound 4 (Y=C$_6$H$_5$—C$_6$H$_5$) as in Example 39 as a white solid (0.7 g, 64%).

The next reaction leading to the synthesis of the title compound was analogous to the last step of Example 28 as described above. FAB Mass [M+1]$^{+35}$Cl 669; m.p. 87–89° C.

EXAMPLE 31

By procedures analogous to the methods described in Examples 16, 28, and 30, the following compounds were obtained.

| Structure | FAB and/or CI MASS [M + 1]+ 35Cl | M.P. ° C. |
|---|---|---|
| (4-Cl-benzyl-piperidine)-NH-CH2-C(O)-piperazine[2-(3,4-diCl-phenyl)]-C(O)-(3,5-diCF3-phenyl) | 735.1 | 71–73 |
| (3,4-diCl-benzyl-piperidine)-NH-CH2-C(O)-piperazine[2-(3,4-diCl-phenyl)]-C(O)-(3,5-diCF3-phenyl) | 770.9 | 73–75 |
| (3-Cl-benzyl-piperidine)-NH-CH2-C(O)-piperazine[2-(3,4-diCl-phenyl)]-C(O)-(3,5-diCH3-phenyl) | 627.2 | 68–70 |
| (4-F-benzyl-piperidine)-NH-CH2-C(O)-piperazine[2-(3,4-diCl-phenyl)]-C(O)-(3,5-diCF3-phenyl) | 719.0 | 70–72 |
| (3,4-diF-benzyl-piperidine)-NH-CH2-C(O)-piperazine[2-(3,4-diCl-phenyl)]-C(O)-(3,5-diCF3-phenyl) | 737.1 | 71–73 |

-continued
| | FAB and/or CI MASS $[M + 1]^+$ $^{35}Cl$ | M.P. °C. |
|---|---|---|
| 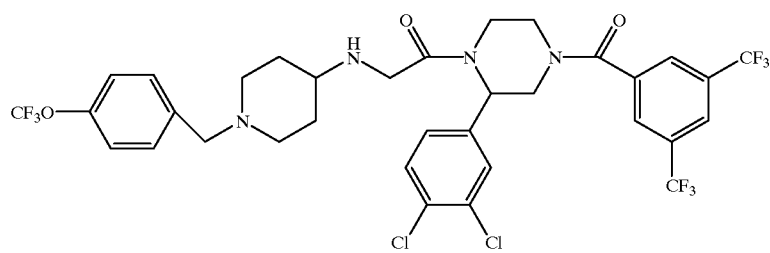 | 785.0 | 70–72 |
| 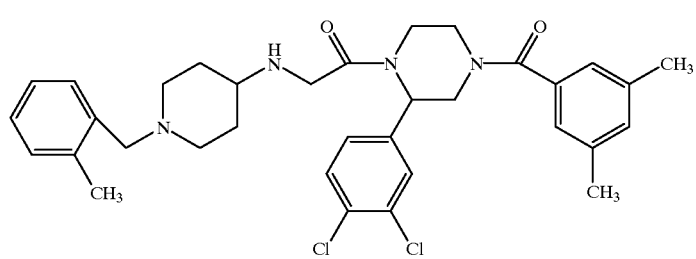 | 607.2 | 73–75 |
| 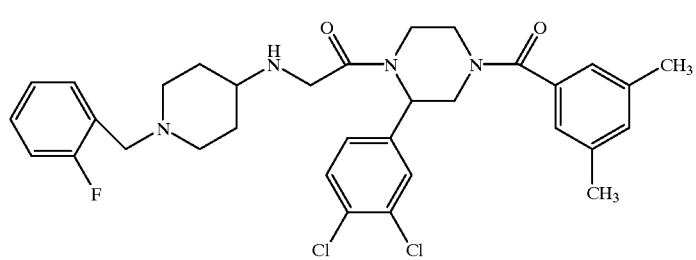 | 611.0 | 67–69 |
| 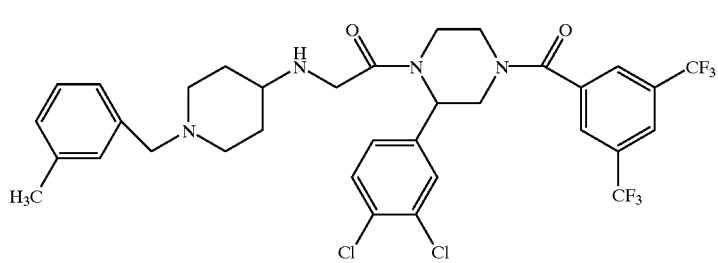 | 715.0 | 69–71 |
| 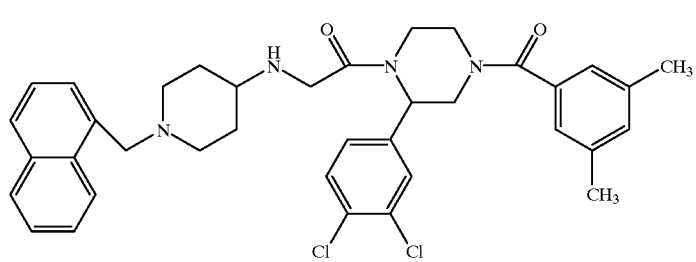 | 643.2 | 89–91 |

-continued
| | FAB and/or CI MASS [M + 1]+ 35Cl | M.P. ° C. |
|---|---|---|
| 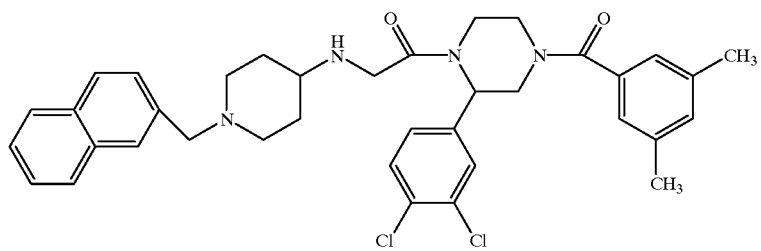 | 643 | 83–85 |
| 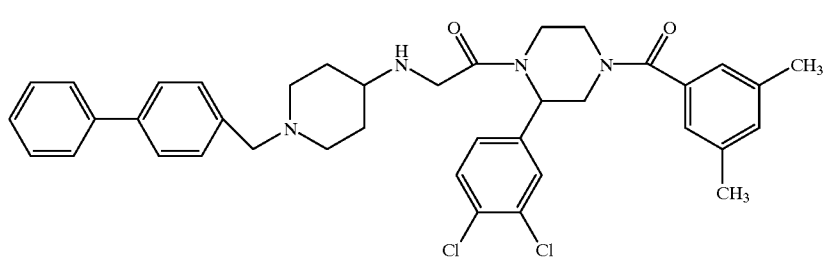 | 669.0 | 87–89 |
| 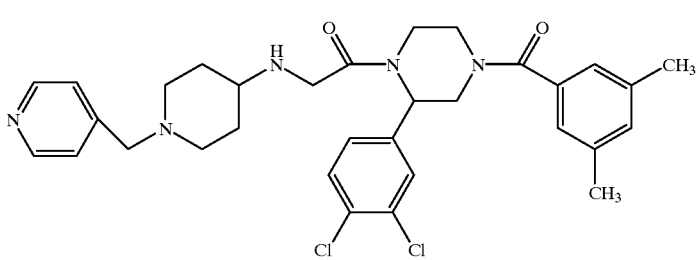 | 594.2 | 75–76 |
| 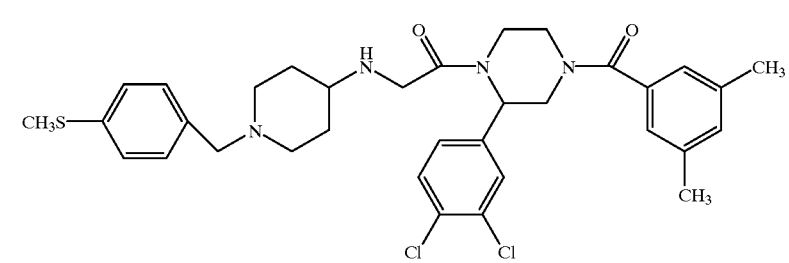 | 639 | 72–74 |
| 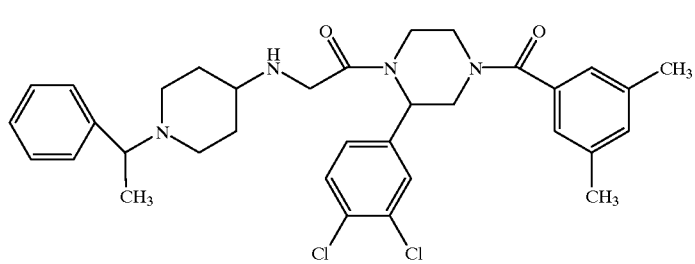 | 607.1 | 72–74 |

| | FAB and/or CI MASS $[M + 1]^+$ $^{35}Cl$ | M.P. °C. |
|---|---|---|
| (structure) | 607.1 | 61–63 |
| (structure) | 651.0 | 79–81 |
EXAMPLE 32
Preparation of (+,−)-2-(3,4-dichlorophenyl)-4-[(4-fluoro-1-naphthalenyl)carbonyl]-1-[[[1-(phenylmethyl)-4-piperidinyl]amino]acetyl]piperazine
GENERAL METHODS
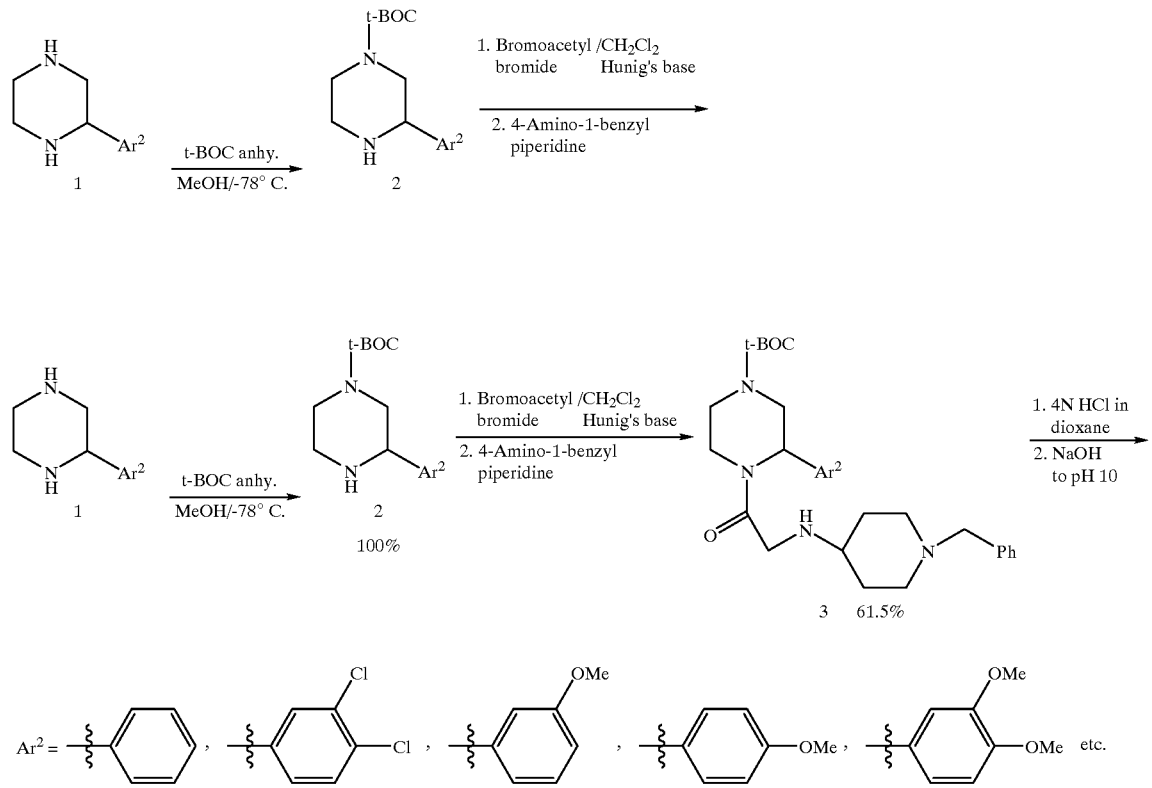

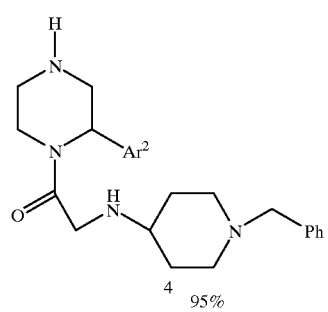
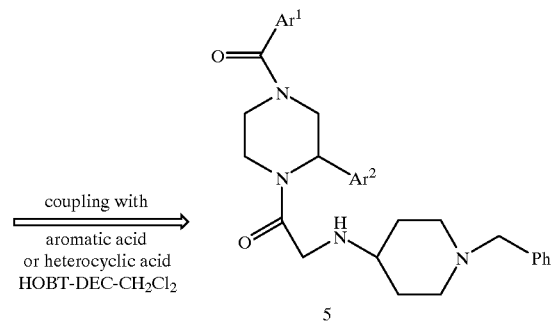

coupling with
aromatic acid
or heterocyclic acid
HOBT-DEC-CH$_2$Cl$_2$ 4  95%

5

To a cooled solution of 2-(3,4-dichlorophenyl)piperazine (1; Ar$^2$=3,4-dichlorophenyl) (20 g, 86.53 mmol) in MeOH (900 ml) at −78° C. was added dropwise a solution of t-BOC anhydride (19.47 g, 86.53 mmol) in MeOH (263 ml) over 3 h period under N$_2$. The solution was gradually warmed up to RT overnight. After reaction was complete, the solvent was evaporated and the residue was dried under high vacuum overnight to give 2 as a white solid. (28 g) (Ar$^2$=3,4-dichlorophenyl) FAB Mass [M+1]$^{+35}$ Cl 331.2.

To a cooled solution of compound 2 (23.8 g, 71.85 mmol) in CH$_2$Cl$_2$ (500 ml) at −78° C. was added a solution of bromoacetylbromide (6.88 ml, 79.04 mmol) in CH$_2$Cl$_2$ (10 ml) through a dropping funnel under N$_2$ over a 10 min. period. After stirring at −78° C. for 3 h, TLC showed that the reaction was complete. To this cooled solution were added Hünig's base (13.76 ml, 79 mmol) and 4-amino-1-benzylpiperidine (29.30 ml, 143.7 mmol). It was kept at −78° C. for one hour then gradually warmed up to RT overnight. After completion, CH$_2$Cl$_2$ (200 ml) was added and washed with brine (200 ml, 3×), dried over MgSO$_4$, filtered and concentrated to give a light brown residue of compound 3 (46 g) (Ar2=3,4-dichlorophenyl). Compound 3 was purified by flash chromatography on 400 g of flash grade silica gel, eluting with 3.5% NH$_3$-MeOH/CH$_2$Cl$_2$ to give 24.8 g (44.2 mmol, 61.5%) of pure compound 3 (Ar$^2$=3,4-dichlorophenyl). FAB mass [M+1]$^{+35}$Cl 561.3.

To a solution of compound 3 (Ar$^2$=3,4-dichlorophenyl) (16 g, 28.49 mmol) in CH$_2$Cl$_2$ (142.5 ml) at 0° C. was added 4N HCl-dioxane solution (71.24 ml, 284.9 mmol) through a dropping funnel. The reaction was gradually warmed up to RT and stirred for 4 h. After completion, the solvents were evaporated to give a light yellow solid which was dissolved in H$_2$O (400 ml) and brought to pH 10 with 1 N NaOH. The product was extracted from basic aqueous solution with CH$_2$Cl$_2$(200 ml, 4×), dried over MgSO$_4$, filtered and concentrated to give compound 4 (Ar$^2$=3,4-dichlorophenyl) as a light yellow solid (12.5 g, 27.09 mmol, 95%). FAB Mass [M+1]$^{+35}$ Cl 461.1 Compound 4 was the key intermediate which was used to couple with various aromatic acid for the synthesis of many target compounds.

To a solution of compound 4 (Ar$^2$=3,4-dichlorophenyl) (200 mg, 0.433 mmol) in CH$_2$Cl$_2$ (5 ml) were sequentially added 4-fluoro-1-naphthoic acid (84 mg, 0.433 mmol), HOBT (58.5 mg, 0.434 mmol), Et$_3$N (63.4 ml, 0.455 mmol) and DEC (85 mg, 0.434 mmol) at RT. The reaction was stirred at RT under N$_2$ overnight. After completion, the reaction was diluted with EtOAc (150 ml) and washed with brine (50 ml, 3×), dried over MgSO$_4$, filtered and concentrated to give a crude product 5 (Ar$^2$=3,4-dichlorophenyl, Ar$^1$=4-fluoro-1-naphthyl) which was purified by flash chromatography (50 g flash grade silica gel), eluting with 4% sat'd NH$_3$-MeOH in CH$_2$Cl$_2$ to give the title compound (0.21 g, 0.331 mmol, 76.5%). Fab Mass [M+1]$^{+35}$ Cl 633.2; m.p. 78–81° C.

EXAMPLE 33

The following compounds were prepared according to the procedures in Example 32. The key intermediate compound 4 in Example 32 (Ar$^2$=3,4-dichlorophenyl) was coupled with the appropriate aromatic acid to obtain the target compounds. Those compounds without melting points were prepared via parallel synthesis.

| | FAB and/or CI MASS [M + 1]$^+$ $^{35}$Cl | m.p. ° C. |
|---|---|---|
| 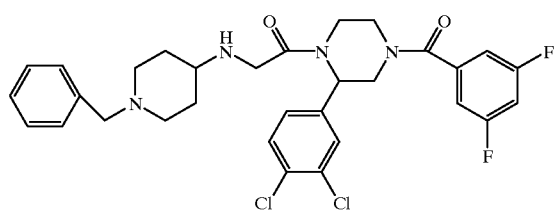 | 601 | 68–70 |

-continued

| Structure | FAB and/or CI MASS [M + 1]+ 35Cl | m.p. °C. |
|---|---|---|
| (1-benzylpiperidin-4-yl)-NH-CH2-C(O)-N-piperazine(2-(3,4-dichlorophenyl))-N'-C(O)-(3,5-dichlorophenyl) | 633/635 (M + 1)+ for (4 × 35Cl)/ (3 × 35Cl + 1 × 37Cl) | 66–69 |
| (1-benzylpiperidin-4-yl)-NH-CH2-C(O)-N-piperazine(2-(3,4-dichlorophenyl))-N'-C(O)-(3-iodophenyl) | 691 | 76–78 |
| (1-benzylpiperidin-4-yl)-NH-CH2-C(O)-N-piperazine(2-(3,4-dichlorophenyl))-N'-C(O)-(4-CF3-phenyl) | 633 | |
| (1-benzylpiperidin-4-yl)-NH-CH2-C(O)-N-piperazine(2-(3,4-dichlorophenyl))-N'-C(O)-(3,4-dimethoxyphenyl) | 625 | 73–75 |
| (1-benzylpiperidin-4-yl)-NH-CH2-C(O)-N-piperazine(2-(3,4-dichlorophenyl))-N'-C(O)-(3,5-dibromophenyl) | 723 | 81–83 |
| (1-benzylpiperidin-4-yl)-NH-CH2-C(O)-N-piperazine(2-(3,4-dichlorophenyl))-N'-C(O)-(2,3,5-triiodophenyl) | 943 | 108–110 |

-continued
| | FAB and/or CI MASS [M + 1]+ 35Cl | m.p. ° C. |
|---|---|---|
| 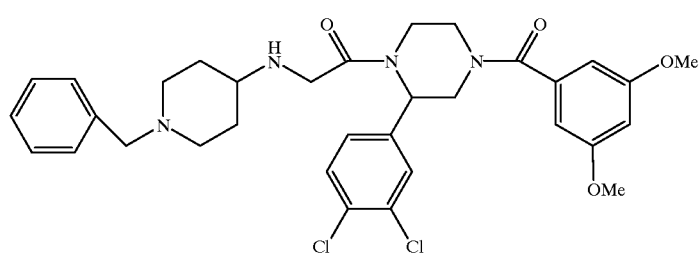 | 625 | 66–68 |
| 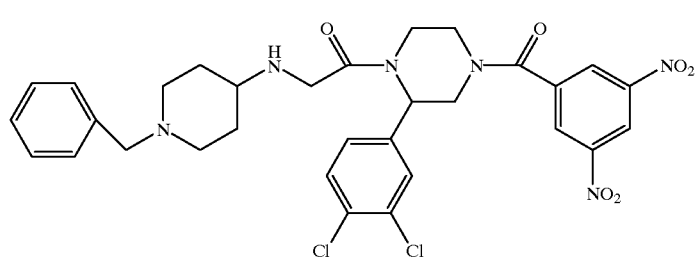 | 655.0 | |
| 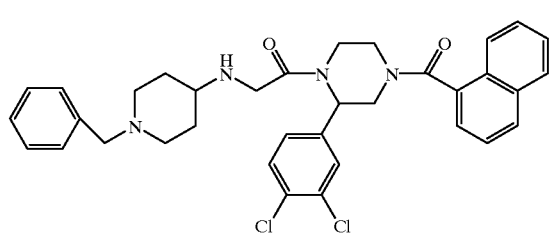 | 615 | 87–89 |
| 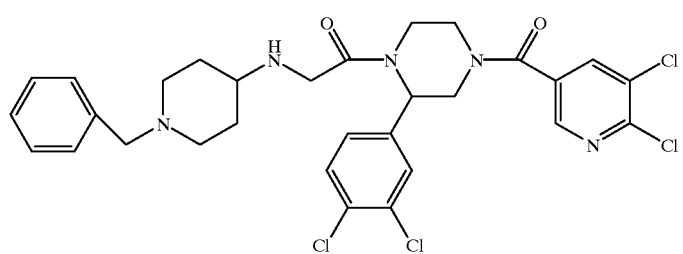 | 634/636.1 (M + 1)+ for (4 × 35Cl)/ (3 × 35Cl + 1 × 37Cl) | 76–80 |
| 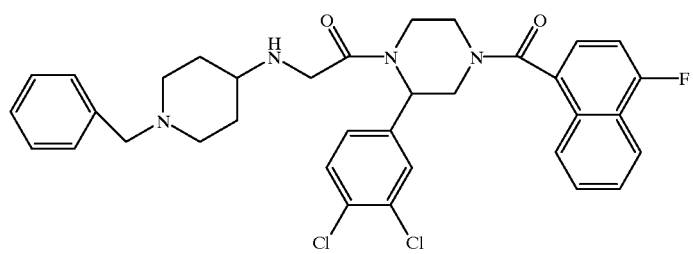 | 633.2 | 78–81 |

| | FAB and/or CI MASS [M + 1]+ 35Cl | m.p. ° C. |
|---|---|---|
| 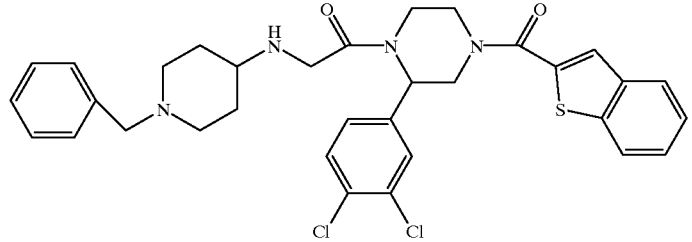 | 621.2 | 70–73 |
| 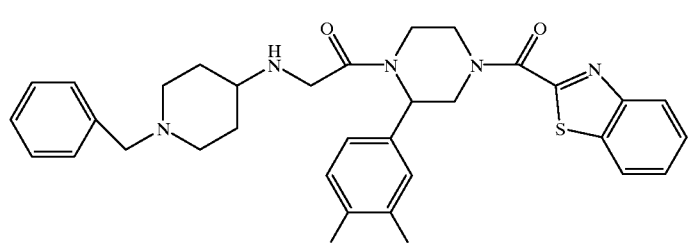 | 622.18 | 62–65 |
| 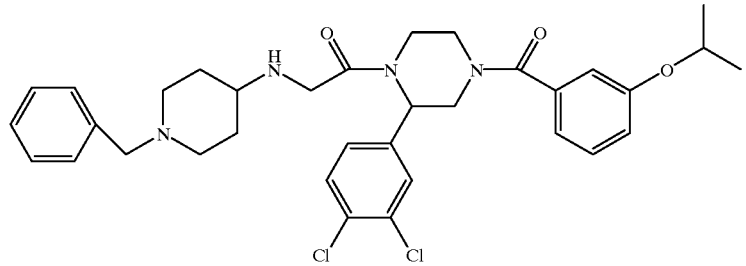 | 623.3 | 58–61 |
| 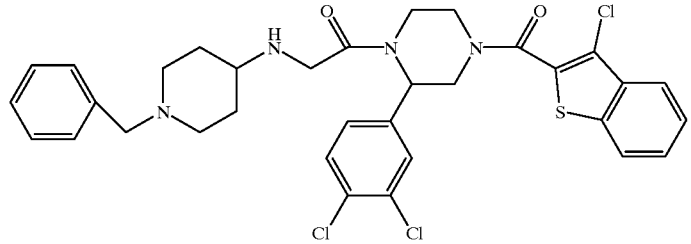 | 655.0 | |
| 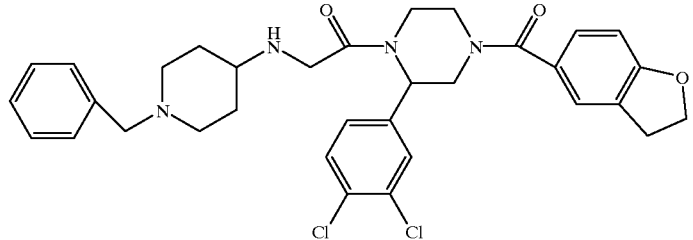 | 607 | |

| | FAB and/or CI MASS [M + 1]+ 35Cl | m.p. ° C. |
|---|---|---|
| 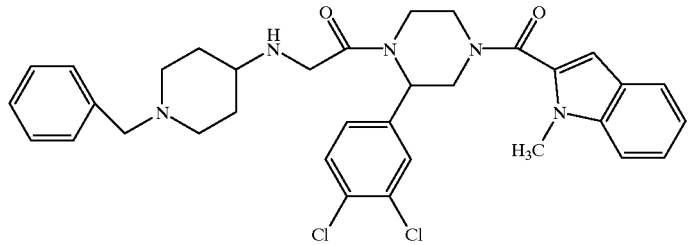 | 618 | |
| 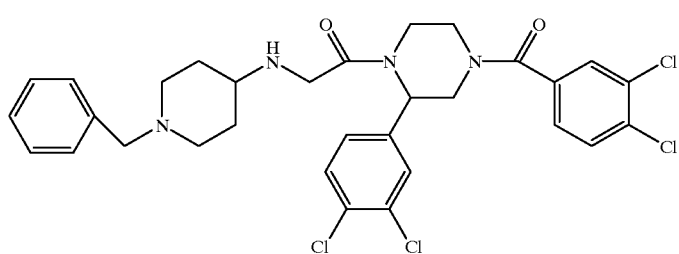 | 633/635 (M + 1)+ for (4 × 35Cl)/ (3 × 35Cl + 1 × 37Cl) | |
| 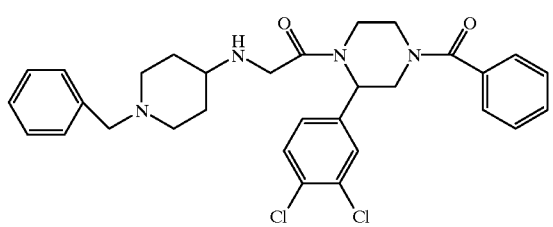 | 565 | |
| 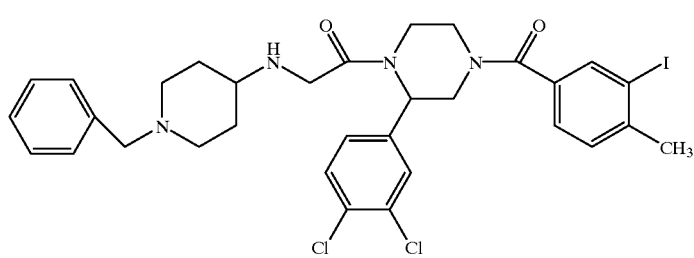 | 705 | |
| 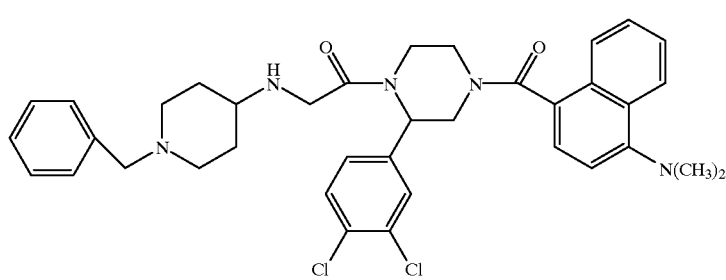 | 658 | |

| | FAB and/or CI MASS [M + 1]+ 35Cl | m.p. ° C. |
|---|---|---|
| (structure) | 614 | |
| (structure) | 634/636 (M + 1)+ for (4 × 35Cl)/ (3 × 35Cl + 1 × 37Cl) | |
| (structure) | 655.1 | 70–73 |

EXAMPLE 34

The following compounds were prepared according to the procedures in Example 32. The key intermediate compound 4 in Example 32 (Ar²=phenyl) was prepared first then coupled with the appropriate aromatic acid as described in Example 32 to obtain the target compounds. Those compounds without melting points were made by parallel synthesis.

| | FAB and/or CI MASS [M + 1]+ 35Cl | m.p. ° C. |
|---|---|---|
| (structure) | 565.2 | |
| (structure) | 525.1 | |

-continued
| | FAB and/or CI MASS [M + 1]+ 35Cl | m.p. °C. |
|---|---|---|
| | 623.1 | |
| | 633.4 | |
| | 623.1 | |
| | 565.3 | |
EXAMPLE 35
Preparation of (+,−)-4-(3,5-dimethylbenzoyl)-1-[[[1-(phenylmethyl)-4-piperidinyl]amino]acetyl]-2-[4-(trifluoromethyl)phenyl]piperazine,1.2 hydrate
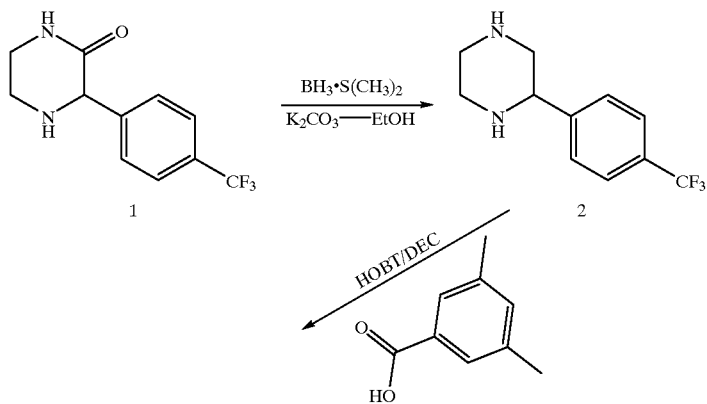

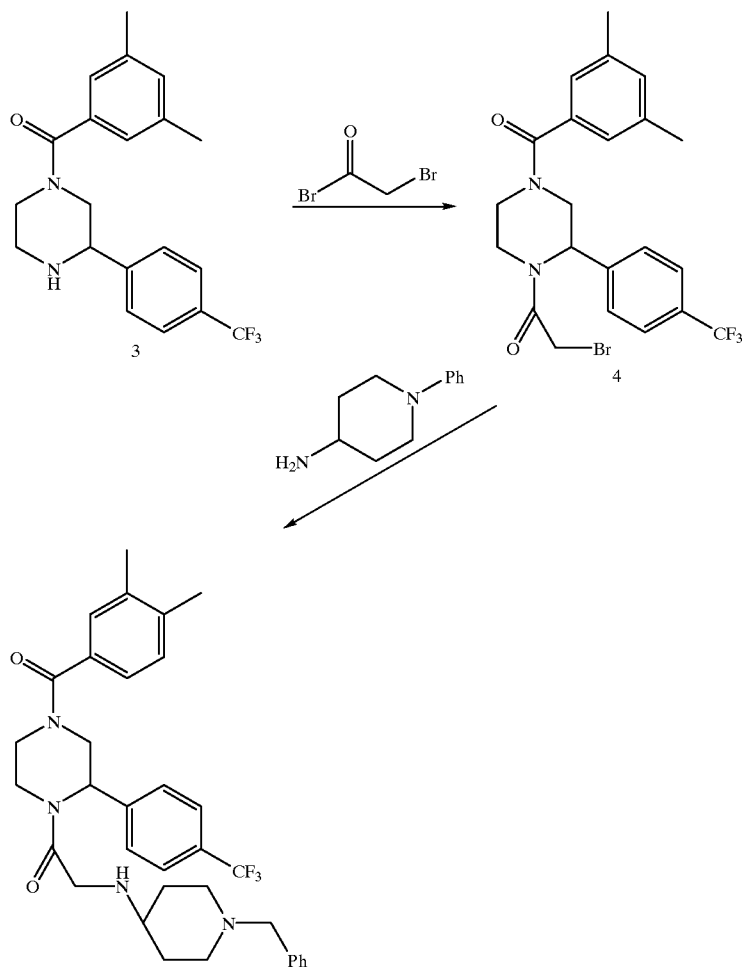

3-(4-Trifluoromethylphenyl)-2-piperazinone (1) was prepared according to the procedures published in J.Med.Chem. 9, 191, 1966. To a solution of compound 1 (0.65 g, 2.66 mmol) in anhydrous THF (22 ml) was added dropwise 10 M $BH_3 \cdot S(CH_3)_2$ (0.798 ml) at RT. The mixture was refluxed for 22 hr. The mixture was cooled in an ice-water bath and quenched with MeOH (5 ml). The solvent was evaporated and the residue was dissolved in absolute EtOH (30 ml). To this solution was added anhydrous $K_2CO_3$ (0.8 g) and the mixture was refluxed for 1 h then stirred at RT for 1 h, filtered and concentrated to give an orange solid which was purified by flash chromatography using flash grade silica gel (24 g), eluting with 2.5%–4% of saturated $NH_3$/MeOH in $CH_2Cl_2$ to give compound 2 (0.143 g, 23.4%). Compound 2 was carried on the next three steps in the above diagram according to the procedures described in Example 14 and Example 15 for the preparation of the title compound. FAB Mass $[M+1]^{+35}Cl$ 593.1.

EXAMPLE 36

The following compounds were prepared according to the procedures described in Example 5 (Method 2), Example 14, and Example 15 by using appropriate reagents.

| | FAB and/or CI MASS $[M + 1]^+$ $^{35}Cl$ | M.P.° |
|---|---|---|
| | 663 | 183–185 |

-continued

| | FAB and/or CI MASS [M + 1]⁺ ³⁵Cl | M.P.° |
|---|---|---|
| 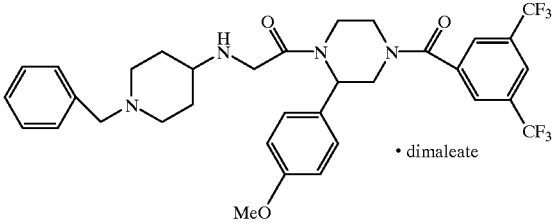 • dimaleate | 663 | 195–197 |
| 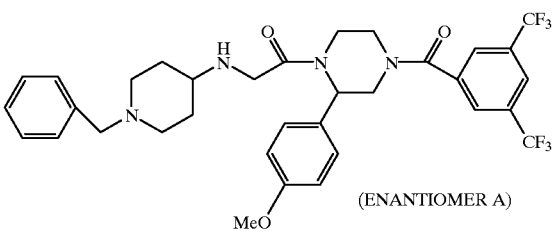 (ENANTIOMER A) | 663.2782 High Resolution Mass | glassy |
| 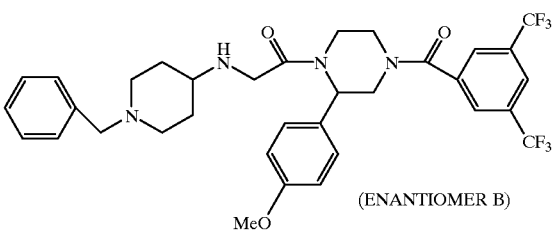 (ENANTIOMER B) | 663.2782 High Resolution Mass | glassy |
| 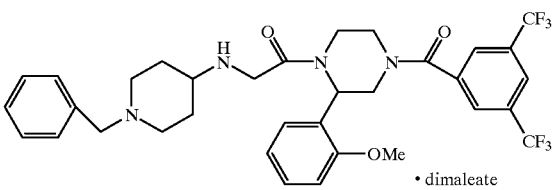 • dimaleate | 663 | 168–170 |
| 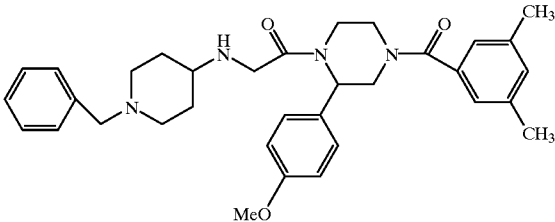 | 555 | 68–71 |

EXAMPLE 37

Preparation of (+,−)-4-[3,5-bis(trifluoromethyl)benzoyl]-2-(3-hydroxyphenyl)-1-[[[1-(phenylmethyl)-4-piperidinyl]amino]acetyl]piperazine, dimaleate, hemihydrate To a stirred solution of (+,−)-4-[3,5-bis(trifluoromethyl)benzoyl]-2-(3-methoxyphenyl)-1-[[[1-(phenylmethyl)-4-piperidinyl]amino]acetyl]-piperazine, dimaleate (1 g, 1.51 mmol) in anhydrous 1,2-dichloroethane (50 ml) at 0° C. was added a 1 M solution of $BBr_3 \cdot S(CH_3)_2$ in $CH_2Cl_2$ (15 ml). The mixture was stirred at 0° C.-RT for 1 h then gradually heated to 80° C. and maintained at 80° C. for 1 h. After cooling, the solution was poured into ice-water and basified with $NH_4OH$. The product was extracted from aqueous solution with $CH_2Cl_2$(100 ml, 3×) and combined. The organic extract was washed with brine, dried ($MgSO_4$), filtered and concentrated to give a solid (0.92 g) which was purified by flash silica chromatography, eluting with MeOH-$CH_2Cl_2$-28% $NH_4OH$ (90:10:0.2) to yield 0.62 g of the desired compound as a syrup. FAB Mass [M+1]⁺³⁵ Cl 649.4

To a solution of this syrup (0.61 g, 0.94 mmol) in EtOAc (10 ml) was added a solution of maleic acid (0.218 g, 1.88 mmol) in EtOAc (20 ml). The precipitate was collected and recrystallized from MeOH-EtOAc to give the title compound as a white solid (0.58 g). FAB Mass [M+1]⁺³⁵ Cl 649.3; m.p. 186–187° C. Calcd for $C_{33}H_{34}F_6N_4O_3 \cdot 2 (C_4H_4O_4) \cdot 0.5 H_2O$: C, 55.34; H, 4.87; N 6.30. Found: C, 55.18; H, 5.14; N, 6.35.

EXAMPLE 38
Preparation of (+,−)-4-[3,5-bis(trifluoromethyl)benzoyl-2-(4-hydroxyphenyl)-1-[[[1-(phenylmethyl)-4-piperidinyl]amino]acetyl]piperazine, dimaleate, hemihydrate Following the same procedure described in Example 37 using (+,−)-4-[3,5-bis(trifluoromethyl)benzoyl]-2-(4-methoxyphenyl)-1-[[[1-(phenylmethyl)-4-piperidinyl]amino]acetyl]piperazine, dimaleate as starting material, the title compound was obtained as a white solid dimaleate salt. FAB Mass [M+1]$^{+35}$Cl 649.3; m.p. 175–178° C.

EXAMPLE 39
Preparation of 2-(R,S)-(3,4-dichlorophenyl)-4-(3,5-dimethylbenzoyl)-1-[3-hydroxy-1-oxo-2(S)-[[1-(phenylmethyl)-4-piperidinyl]amino]propyl]piperazine, hemihydrate To a solution of 2-(R,S)-(3,4-dichlorophenyl)-4-(3,5-dimethylbenzoyl)piperazine (1.0 g, 2.753 mmol) in CH$_2$Cl$_2$ (10 ml) were added bis(2-oxo-3-oxazolidinyl)phosphinic chloride (0.72 g, 2.753 mmol) and Hünig's base (0.48 ml, 2.753 mmol). The mixture was stirred at RT for 4 days. The reaction was diluted with CH$_2$Cl$_2$ (200 ml), washed with brine (80 ml, 3×), dried (MgSO$_4$), filtered and evaporated to dryness to give 2.3 g crude product. The crude material was purified by silica flash chromatography, eluting with 2% sat'd NH$_3$/MeOH in CH$_2$Cl$_2$ to give (0.21 g, 0.38 mmol 14%) of compound 2 in Example 39. The tBOC protecting group of compound 2 was removed by treatment with CF$_3$COOH in CH$_2$Cl$_2$ overnight to give compound 3.

To a solution of compound 3 (180 mg, 0.32 mmol) in MeOH (3.2 ml) at RT was added 1-benzyl-4-piperidone (60 μl, 0.32 mmol). After stirring at RT for 1 h, NaBH$_3$CN (26 mg, 0.47 mmol) and acetic acid (32 μl) were added. The mixture was stirred at RT overnignt. The reaction was stopped by addition of H$_2$O (100 ml) and adjusted to pH 11 with 1 N NaOH. The product was extracted from the aqueous layer with CH$_2$Cl$_2$ (50 ml, 3×) and combined, dried (MgSO$_4$), filtered and evaporated to dryness. The crude material was purified by silica flash chromatography, eluting with 4% sat'd NH$_3$-MeOH/CH$_2$Cl$_2$ to give the title compound as a white solid. FAB Mass[M+1]$^{+35}$Cl 623; m.p.69–72° C.

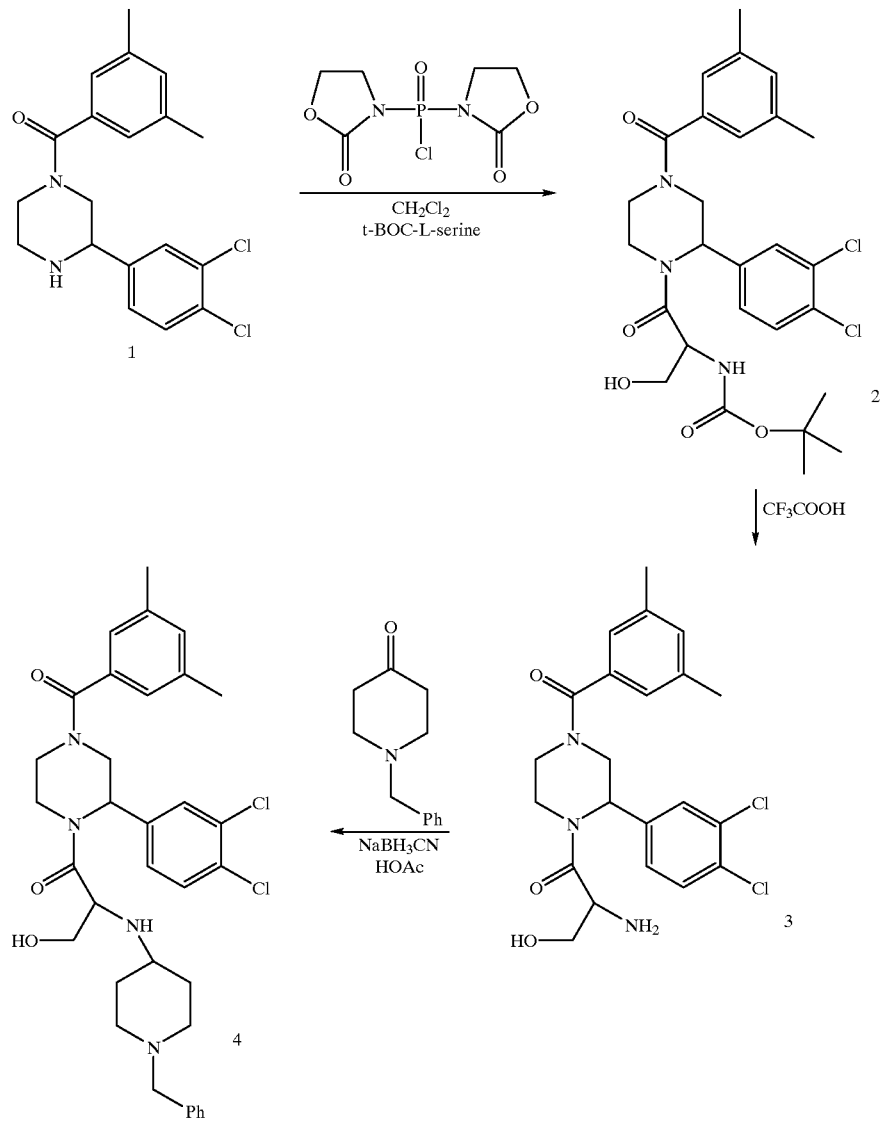

EXAMPLE 40
Preparation of 2-(R,S)-(3,4-dichlorophenyl)-4-(3,5-dimethylbenzoyl)-1-[4-methyl-1-oxo-2(R,S)-[[1-(phenylmethyl)-4-piperidinyl]amino]pentyl]piperazine By employing the methods described in Example 39 using (D, L)-isoleucine in place of L-serine, the title compound was obtained as a white solid. FAB Mass [M+1]$^{+35}$Cl 649.1; m.p. 68–71° C.

EXAMPLE 41
Preparation of (+,−)-N-[2-[2-(3,4-dichlorophenyl)-4-(3,5-dimethylbenzoyl)-1-(piperazinyl]-2-oxo-ethyl]-N-[1-phenylmethyl)-4-piperidinyl]acetamide, hemihydrate To a solution of (+,−)-2-(3,4-dichlorophenyl)-4-(3,5-dimethylbenzoyl)-1-[[[(phenylmethyl)-4-piperidinyl]amino]acetyl]piperazine (Example 26) (0.26 g, 0.43 mmol) in anhydrous CH$_2$Cl$_2$ (2.5 ml) at −78° C. were added Hünig's base (0.1 ml, 0.57 mmol), and acetyl chloride (32 ml, 0.45 mmol). The mixture was gradually warmed to RT overnight under N$_2$. The reaction was quenched with saturated NaCl solution and extracted with CH$_2$Cl$_2$ twice, combined and washed with brine twice. The organic layer was dried over MgSO$_4$, filtered and concentrated to give a solid which was purified by flash silica chromatography, eluting with 4% sat'd NH$_3$/MeOH in CH$_2$Cl$_2$ to give a white solid 0.22 g (0.35 mmol, 79%). FAB Mass [M+1]$^{+35}$Cl 635.2; m.p.99–102° C.

EXAMPLE 42
Preparation of (+,−)-2-(3,4-dichlorophenyl)-4-(3,5-dimethylbenzoyl)-1-[[υ2-hydroxyethyl][1-(phenylmethyl)-4-piperidinyl]amino]acetyl]piperazine, hemihydrate To a mixture of 4-amino-1-benzylpiperidine (2.13 g, 11.2 mmol) and 2-bromoethanol (0.15 g, 4.08 mmol) in anhydrous CH$_2$Cl$_2$ (20 ml) was added Hünig's base (2.6 ml, 5.7 mmol). The solution was refluxed for 24 hours. After evaporating off CH$_2$Cl$_2$, the crude material was purified by silica flash chromatography to afford 2-[[1-(phenylmethyl)-4-piperidinyl]amino]ethanol (0.88 g, 3.8 mmol) with 92% yield. FAB Mass [M+1]$^{+35}$Cl 235.

By employing an analogous method to that described in Example 15, using β-hydroxyethyl-4-amino-1-benzylpiperidine in place of 4-amino-1-benzylpiperidine, the title compound was obtained as a white solid after silica flash chromatography. FAB Mass [M+1]$^{+35}$Cl 637; m.p. 70–73° C.

EXAMPLE 43
Preparation of (+,−)-N-[2-[2-(3,4-dichlorophenyl)-4-(3,5-dimethylbenzoyl)-1-piperazinyl]-2-oxoethyl]-N,N-dimethylamino-1-(phenylmethyl)-4-piperidinaminium bromide, dimethanolate To a solution of 4-amino-1-benzylpiperidine (1.47 g, 7.7 mmol) in CF$_3$CH$_2$OH (14 ml) were added molecular sieve 4 Å (5 g), and paraformaldehyde (0.51 g, 17 mmol). After stirring at RT for 1 h, NaCNBH$_3$ (2.5 g, 39.8 mmol) was added and stirred for 16 h at RT. The reaction was stopped by addition of H$_2$O and the product was extracted with (4:1) (Et$_2$O:CH$_2$Cl$_2$). Organic fractions were combined and washed with brine (2x), dried over MgSO$_4$, filtered and concentrated to give a crude material which was purified by silica flash chromatography to afford 4-dimethylamino-1-benzylpiperidine (80% yield). FAB Mass [M+1]$^{+35}$Cl 219.

By employing an analogous method to that described in Example 15, using N,N-dimethyl-4-amino-1-benzylpiperidine in place of 4-amino-1-benzylpiperidine, the title compound was obtained as a white solid after silica flash chromatography. FAB Mass [M+1]$^{+35}$Cl 621.2.

EXAMPLE 44
Preparation of (+,−)-2-(3,4-dichlorophenyl)-4-(3,5-dimethylbenzoyl)-1-[[methyl[1-(phenylmethyl)-4-piperidinyl]amino]acetyl]piperazine To a solution of 1-benzyl-4-piperidone (1.9 g, 10 mmol) in MeOH (10 ml) were added methylamine (8 ml, 16 mmol) and 3 Å molecular sieves. After stirring at RT for 1 h, the reaction was cooled in an ice-bath and 4 N HCl in dioxane (2.5 ml, 10 mmole) and NaCNBH$_3$ (1.2 g, 20 mmol) were added. The reaction was stirred at RT overnight. After the reaction was complete, H$_2$O was added the pH was adjusted to 10 with 50% NaOH solution. The product was extracted with EtOAc (100 ml, 3x) from aqueous solution and combined. The combined organic solution was washed with brine, dried over MgSO$_4$, filtered and concentrated to give an oil which was purified by silica flash chromatography, eluting with 8% saturated NH$_3$/MeOH in CH$_2$Cl$_2$ to give 4-methylamino-1-benzyl piperidine (1.77 g, 8.66 mmol, 86%). FAB Mass [M+1]$^{+35}$Cl 205.

By employing an analogous method to that described in Example 15, using 4-methylamino-1-benzylpiperidine in place of 4-amino-1-benzylpiperidine, the title compound was obtained as a white solid after silica flash chromatography. FAB Mass [M+1]$^{+35}$Cl 607.

EXAMPLE 45
Preparation of (+,−)-2-(3,4-dichlorophenyl)-4-(3,5-dimethylbenzoyl)-2-methyl-1-[[[1-(phenylmethyl)-4-piperidinyl]amino]acetyl]piperazine, 0.6 methanol A solution of 3,4-dichlorophenylacetic acid (5.126 g, 25 mmol) in THF was added dropwise over 15 min to a cooled solution of 1.0 M Li(TMS)$_2$/THF (55 ml, 55 mmol) at −78° C. under N$_2$. The reaction mixture was stirred in a water-ice bath for 2 h then cooled to −78° C. and MeI (12 ml) was added. The mixture was gradually warmed to RT. After reaction was complete, the precipitate was filtered off and rinsed with THF. The precipitate was dissolved in H$_2$O and acidified to about pH 2.0 then extracted with EtOAc (100 ml, 3x). The extracts were combined, dried (MgSO$_4$), filtered and concentrated to give 91% yield of 1-(3,4-dichlorophenyl)propionic acid (4.984 g, 22.7 mmol) as an oil. FAB Mass[M+1]$^{+35}$ Cl 219.

1-(3,4-dichlorophenyl)propionic acid (20.23 g, 99.1 mmol) was dissolved in MeOH (200 ml). To this solution was added conc. H$_2$SO$_4$ (2 ml) and the solution refluxed for 1 h. After cooling, the solution was basified with NaHCO$_3$ and extracted with CH$_2$Cl$_2$. Following by regular work-up, methyl 1-(3,4-dichlorophenyl)propionate was obtained as an oil.

By employing an analogous method as described in J. Med.Chem. 9, 191, 1966, methyl 1-bromo-1-(3,4-dichlorophenyl)propionate was obtained by bromination of methyl 1-(3,4-dichlorophenyl)propionate with NBS/CCl$_4$.

A mixture of methyl 1-bromo-1-(3,4-dichlorophenyl) propionate (3.39 g, 10.9 mmol) and ethylenediamine (7 ml) was stirred at RT for 3.5 hours. After reaction was complete, brine (100 ml) was added and the product was extracted from the aqueous layer with CH$_2$Cl$_2$ (50 ml, 2x). The combined organic extracts were washed with brine, dried over MgSO$_4$, filtered and concentrated to give a 95% yield of 3-(3,4-dichlorophenyl)-3-methyl-2-piperazinone which was reduced with LiAlH$_4$/Et$_2$O at 40° C. to 2-methyl-2-(3,4-dichlorophenyl)-1-piperidine as described in J. Med. Chem. 9, 191, 1966.

The title compound was prepared according to the analogous methods described in Examples 14 and 15. FAB Mass [M+1]+35 Cl 607.2; m.p.58–61° C.

EXAMPLE 46
Preparation of (+,−)-2-(3,4-dichlorophenyl)-4-(4-fluoro-1-naphthalenylcarbonyl)-2-methyl-1-[[[1-(phenylmethyl)-4-piperidinyl]amino]acetyl]piperazine By employing analogous methods described in Example 14, Example 15 and Example 45, the title compound was obtained as a white solid. FAB Mass [M+1]$^{+35}$Cl 647.2; m.p.93–96° C.

EXAMPLE 47

Preparation of (+,−)-4-[3,5-dimethylbenzoyl]-4-hydroxymethyl-2-(3,4-dichlorophenyl)-1-[[[1-(phenylmethyl)-4-piperidinyl]amino]acetyl]piperazine

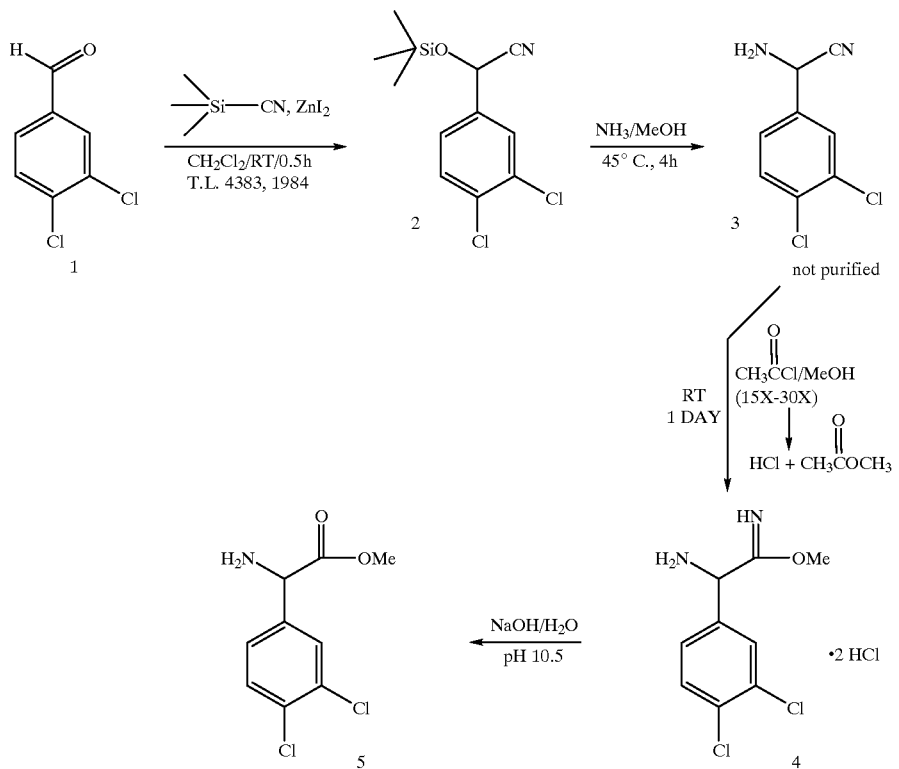

α-Amino-(3,4-dichlorophenyl)-acetonitrile (3) was prepared according to the procedure in Tetrahedron Letters 4383, 1984. Compound (3) was reacted with HCl/MeOH solution which was generated from acetyl chloride in MeOH to give compound (4). The methyl α-amino-(3,4-dichlorobenzene) acetate (5) was obtained by hydrolysis of (4) at pH 10.5. FAB Mass [M+1]$^{+35}$Cl 243.1.

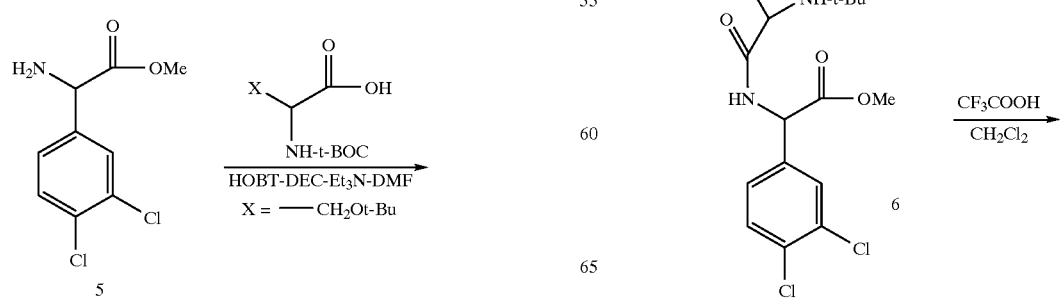

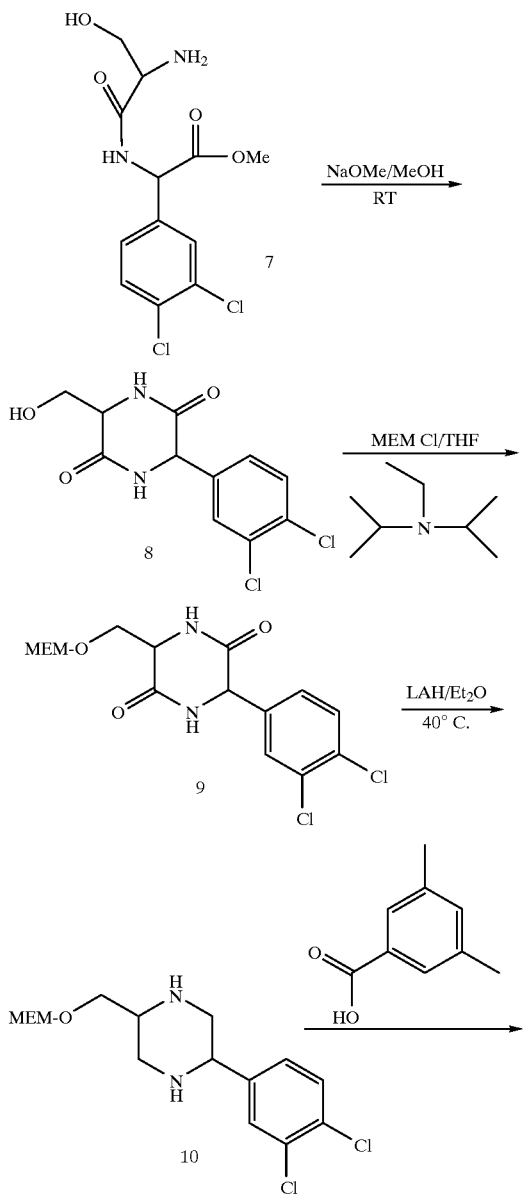

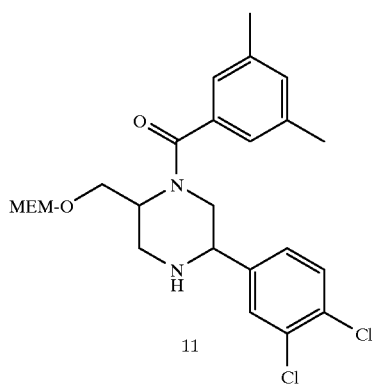

Methyl α-amino-(3,4-dichlorobenzene) acetate (5) was coupled with O-t-Bu-N-t-BOC-L-serine to give compound (6) which was deprotected with $CF_3COOH$ to give compound (7), FAB Mass $[M+1]^{+35}Cl$ 321. Compound (7) was cyclized by treatment with 25% NaOMe/MeOH solution in MeOH to give compound (8), FAB Mass $[M+1]^{+35}Cl$ 289.

Compound (8) was reacted with 2-methoxyethoxymethyl chloride (MEMCl) in THF in the presence of Hünig's base to give compound (9) which is reduced with LAH to afford compound (10). Compound (10) is coupled with 3,5-dimethylbenzoic acid according to the procedure described in Example 14 to give compound 11. By employing analogous procedures described in Example 15, the title compound is obtained as follows.

167 168

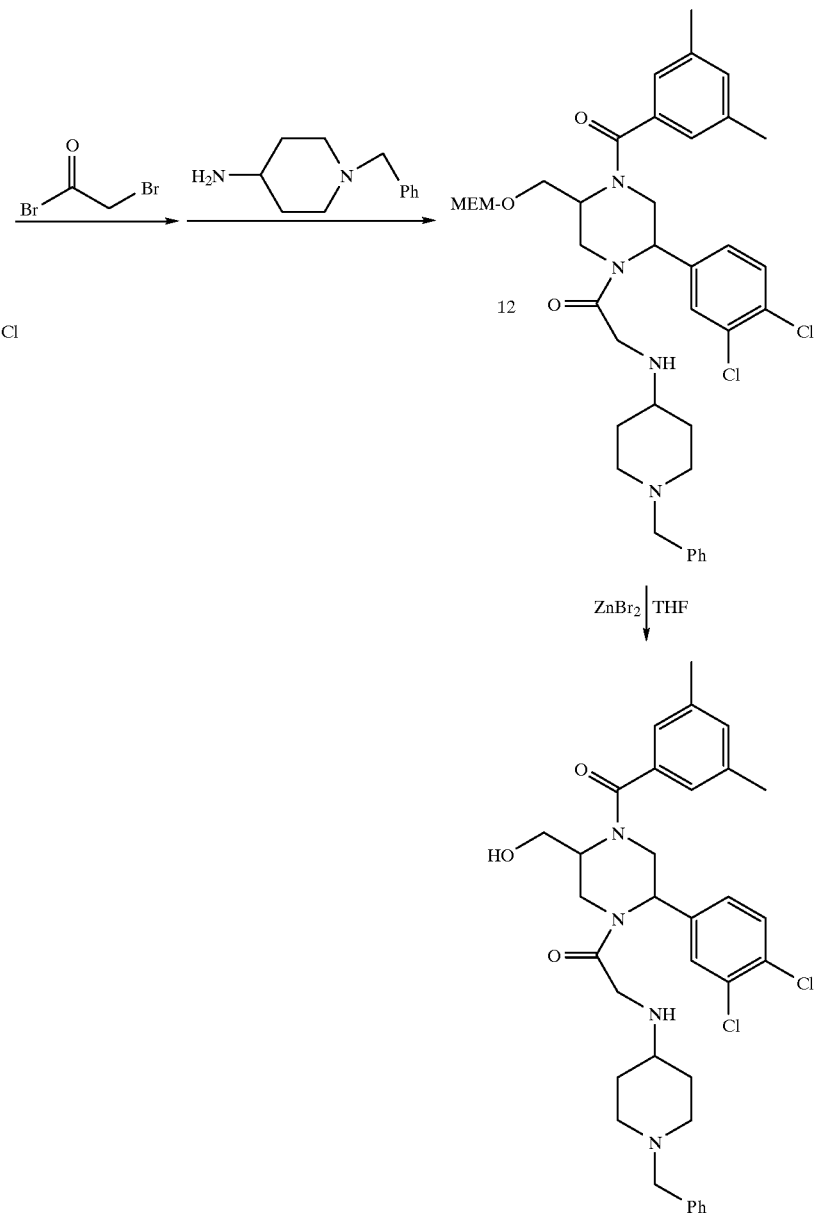

EXAMPLE 48

Preparation of (+,−)-1-[3,5-bis(trifluoromethyl)benzoyl]-2-(3,4-dichlorophenyl)-4-[[[1-(phenylmethyl)-4-piperidinyl]amino]acetyl]piperazine, dimaleate, monohydrate 1,1-Dimethylethyl-3-(3,4-dichlorophenyl)-1-piperazinecarboxylate (compound 2 in Example 32) was coupled with 3,5-dimethylbenzoic acid as described in Example 14. The t-BOC group was removed with trifluoroacetic acid. By analogous methods as described in Example 15, the title compound was obtained as a white solid, FAB Mass $[M+1]^{+35}Cl$ 701; m.p. 170–172° C.

EXAMPLE 49

Preparation of (+,−)-2-(3,4-dichlorophenyl)-4-(3,5-dimethylbenzoyl)-1-[[[1-[1-oxo-2-phenyl)ethyl]-4-piperidinyl]amino]acetyl]piperazine

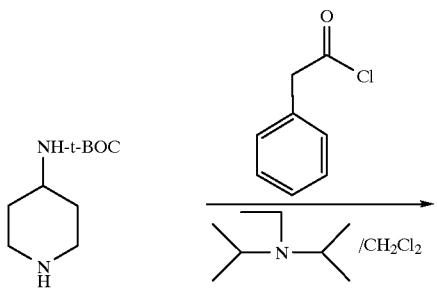
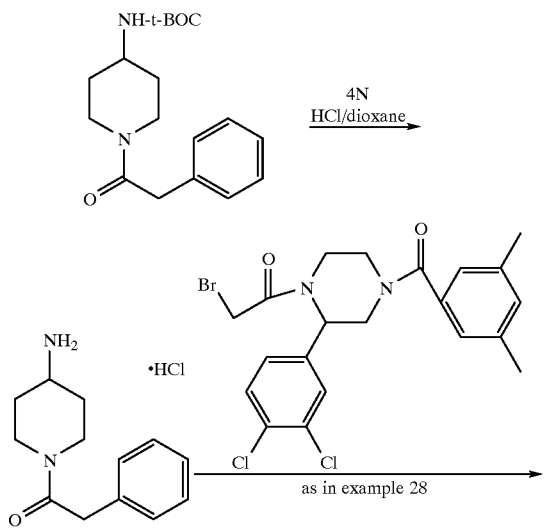
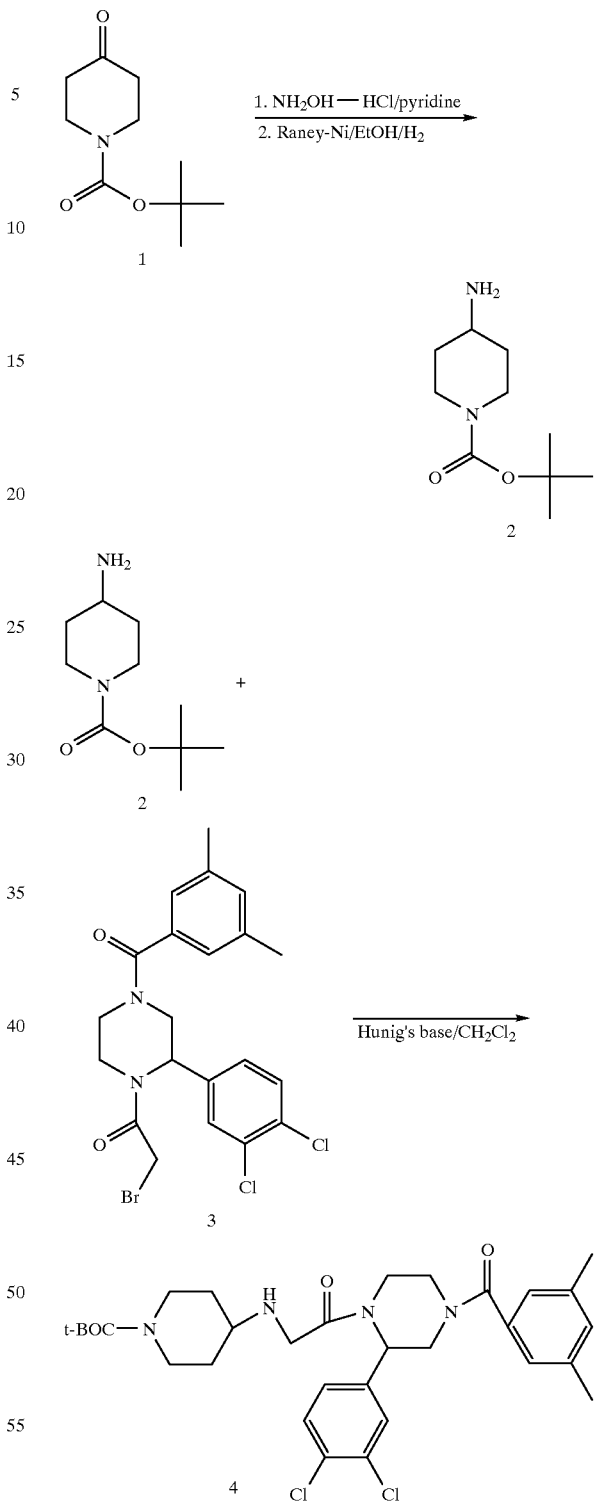

By methods analogous to those described in Example 28, compound (3) (0.69, 3 mmol) from Example 28, was mixed with phenylacetyl chloride (0.46 g, 3 mmol) and Hünig's base (0.43 g, 3.3 mole) in $CH_2Cl_2$ (10 ml) at −5° C. and gradually warmed to RT overnight. After completion, the reaction was diluted with $CH_2Cl_2$ (50 ml) and washed with brine (30 ml, 3×). The $CH_2Cl_2$ layer was dried over $MgSO_4$, filtered, and concentrated to give a white solid (0.81 g). This crude material was dissolved in dry $CH_2Cl_2$ (3 ml) and 4 N HCl-dioxane (6 ml) was added. After stirring at RT for 2 h, solvents were evaporated to dryness to give a white solid (0.8 g) of 4-amino-1-(1-oxo-2-phenylethyl)piperidine as a HCl salt. FAB Mass [M+1]219.

The next reaction leading to the synthesis of the title compound is analogous to the method described in Example 28. FAB Mass $[M+1]^+$ $^{35}Cl$ 621.1; m.p.87–89° C.

EXAMPLE 50

Preparation of (+,−)-1,1-dmethylethyl 4-[[2-[2-(3,4-dichlorophenyl)-1-(,3,5-dimethylbenzoyl)-1-piperazinyl]-2-oxoethyl]amino]-1-piperidinecarboxylate To a solution of N-t-butoxycarbonyl-4-piperidone (15 g, 75.3 mmol) in pyridine (50 ml) was added hydroxyamine-.HCl (5.23 g, 75.3 mmol). The mixture was heated in an oil bath at 65° C. for one hour. After cooling, pyridine was removed under reduced pressure and dried under high vacuum overnight to give a solid. To this solid was added water (100 ml) and sonicated. The precipitate was filtered and washed with water then dried under high vacuum to give oxime derivative of compound 1 (10.5 g, 65%). FAB Mass [M+1]⁺215.3. The oxime compound (10 g, 46.67 mmol) was dissolved in absolute EtOH (100 ml) and followed by the addition of Raney Ni (29 g, washed with abs. EtOH). The mixture was hydrogenated in a Parr shaker at 50 psi overnight. After reaction was complete, Raney Ni was filtered off (caution of fire) and filtrate was concentrated to give compound 2 (9.2 g, 46 mmol, 98% yield) as an oil which was solidified under high vacuum drying. FAB Mass [M+1]⁺ 201.3.

To a solution of bromoacetyl derivative (3.0 g, 6.2 mmol) (prepared in Example 27, compound 3) in CH$_2$Cl$_2$ (62 ml) at −10° C. was added Hünig's base (1.2 ml, 6.82 mmol) and compound 2 (2.48 g, 12.39 mmol). The solution was gradually warmed to RT overnight. After reaction was complete, CH$_2$Cl$_2$ (300 ml) was added and washed with brine (100 ml, 3×), dried over MgSO$_4$, filtered. The filtrate was evaporated to dryness to give a light yellow solid which was purified by flash chromatography on flash grade silica gel (200 g), eluting with 5% NH$_4$OH/MeOH (1:9)/CH$_2$Cl$_2$ to give 71% yield of the title compound as a white solid (2.66 g, 4.4 mmol), m.p. 78–81° C.; FAB Mass [M+1]⁺³⁵Cl 603.1; Calcd. for C$_{31}$H$_{40}$N$_4$O$_4$Cl$_2$, C, 61.69; H, 6.68; N, 9.28; Cl, 11.74. Found: C, 61.33; H, 6.94; N, 9.17; Cl, 11.27.

EXAMPLE 52

Preparation of (+,−)-2-(3,4-dichlorophenyl)-4-[3,5-dimethylbenzoyl]-1-1(4-piperidinylamino)acetyl]piperazine, dihydrochloride

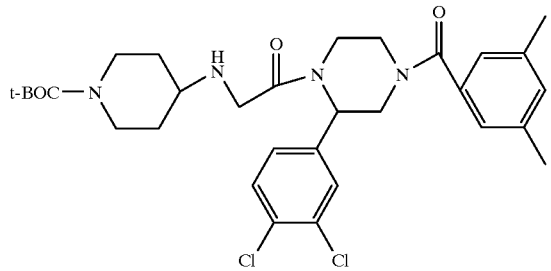
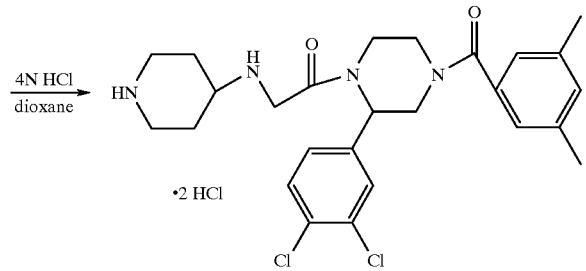

To a solution of (+,−)-1,1-dimethylethyl 4-[[2-[2-(3,4-dichlorophenyl)-1-(,3,5-dimethylbenzoyl)-1-piperazinyl]-2-oxoethyl]amino]-1-piperidinecarboxylate (Example 50) (2.5 g, 4.14 mmol) in CH$_2$Cl$_2$ (20 ml) at 0° C. was added 4N HCl (10.35 ml, 41.4 mmol). The mixture was stirred at 0° C. then gradually warmed to RT in 3 hours. After reaction was complete, excess HCl and solvent were evaporated to give a pale yellow solid which was used without further purification. FAB Mass [M+1]⁺³⁵Cl 503.1.

EXAMPLE 53

Preparation of (−)-2-(3,4-dichlorophenyl)-4-[3,5-dimethylbenzoyl]-1-[(4-piperidinylamino)acetyl]piperazine, dihydrochloride By employing method analogous to that described in Example 52 using compound obtained from example 51, the title compound was obtained as a pale yellow solid, FAB Mass [M+1]⁺³⁵Cl 503.2.

EXAMPLE 54

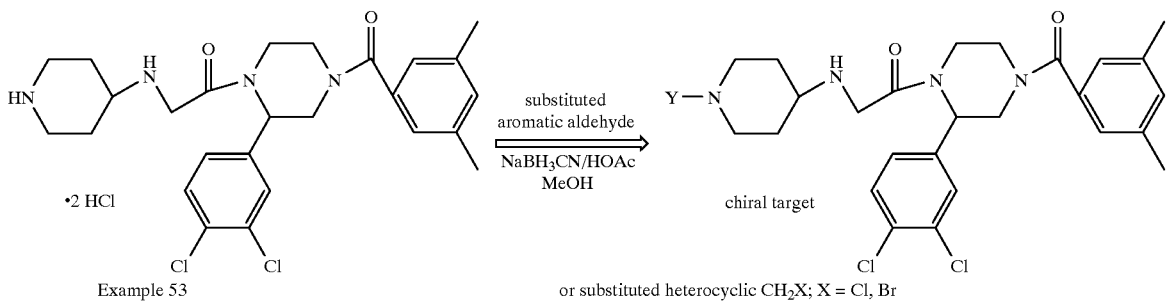

EXAMPLE 51

Preparation of (−)-1,1-dimethylethyl 4-[[2-[2-(3,4-dichlorophenyl)-1-(,3,5-dimethylbenzoyl)-1-piperazinyl]-2-oxoethyl]amino]-1-piperidinecarboxylate By employing methods analogous to those described in Example 50 using chiral bromoacetyl intermediate 3 which was prepared according to the scheme of example 27, and using enantiomer A of 2-(3,4-dichlorophenyl)piperazine (resolved in example 5) as the starting material, the title compound was obtained as a white solid, m.p.72–75° C.; FAB Mass [M+1]⁺³⁵Cl 603.2; [α]$_D^{22}$=−32.8 (MeOH).

A series of Y derivatives of (−)-2-(3,4-dichlorophenyl)-4-[3,5-dimethyltbenzoyl]-1-[(4-piperidinyl-amino)acetyl]piperazine, dihydrochloride (Example 53) were prepared by parallel synthesis according to the reductive amination method described in Example 28 using appropriate aldehyde or by halide displacement reaction described in Example 30, using halide reagents as shown above. Representative compounds made by the above routes are shown below.

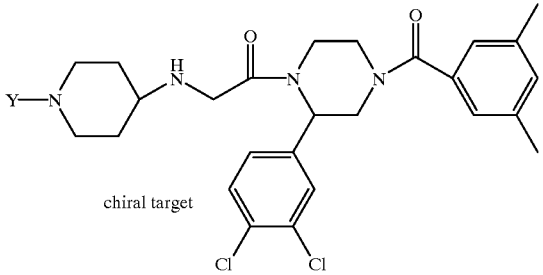
chiral target
| Y | FAB MASS [M+ 1]+ 35Cl | Y | FAB MASS [M+ 1]+ 35Cl |
|---|---|---|---|
| 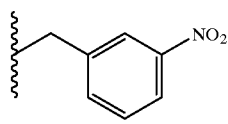 | 638.2 | 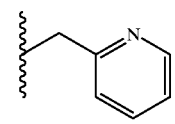 | 594.2 |
| 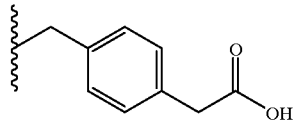 | 651.2 | 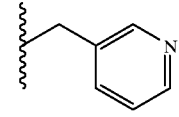 | 594.2 |
| 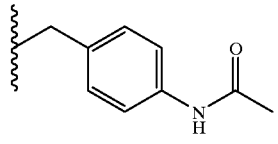 | 650.2 | 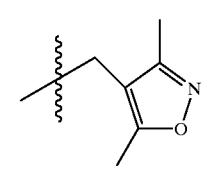 | 612.2 |
| 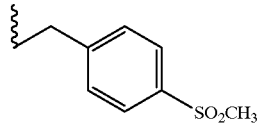 | 671.2 | 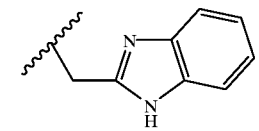 | 633.2 |
| 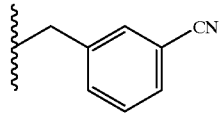 | 618.1 | 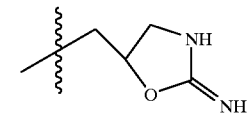 | 601.1 |
| 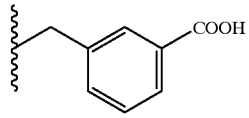 | 637.2 | 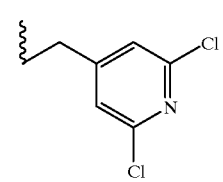 | 662.0 |
| 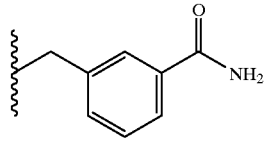 | 636.2 | 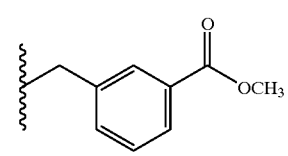 | 651.1 |

-continued
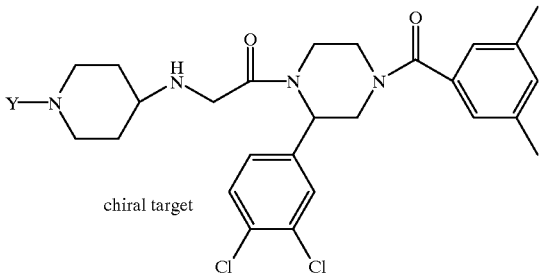
chiral target
| Y | FAB MASS [M+ 1]+ 35Cl | Y | FAB MASS [M+ 1]+ 35Cl |
|---|---|---|---|
| 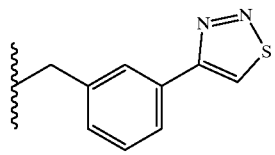 | 677.2 | 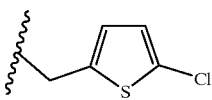 | 633.1 |
| 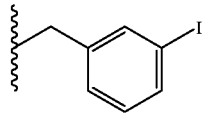 | 673.9 | 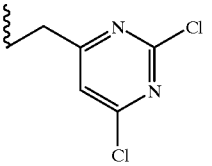 | 663 |
| 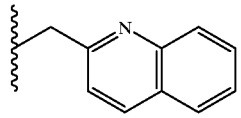 | 644.2 | | |
| 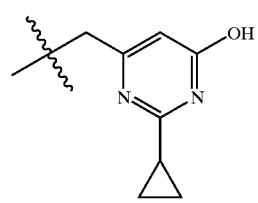 | 651.1 | 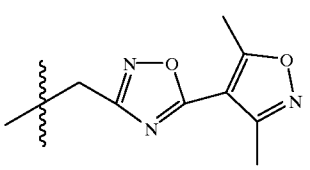 | 680.1 |
| 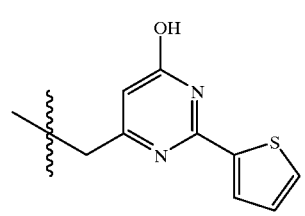 | 693.1 | 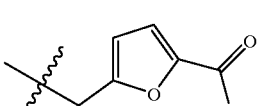 | 641.1 |
| 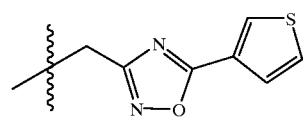 | 667.1 | 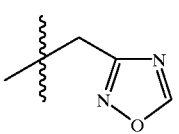 | 585.1 |

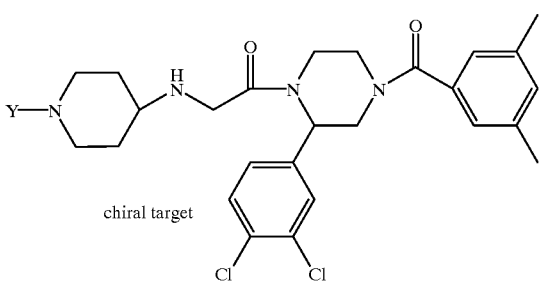

| Y | FAB MASS [M+ 1]+ 35Cl | Y | FAB MASS [M+ 1]+ 35Cl |
|---|---|---|---|
| 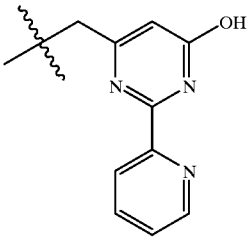 | 688.1 | 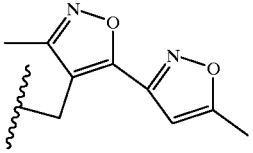 | 679.1 |

EXAMPLE 55

Preparation of (+,−)-1-benzoyl-4-[[2-[2-(3,4-dichlorophenyl)-4-(3,5-dimethylbenzoyl)-1-piperazinyl]-2-oxoethyl]amino]piperidine

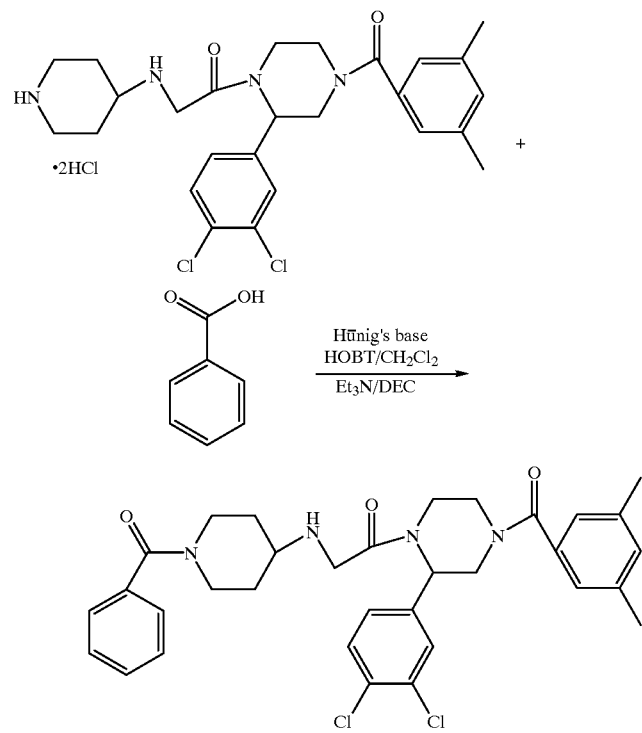

To a solution of compound obtained from Example 52 (0.23 g, 0.4 mmol) in CH$_2$Cl$_2$ (5 ml) was added Hünig's base (0.13 g, 1.0 mmol) to neutralize HCl salt. It was followed by the addition of benzoic acid (49 mg, 0.4 mmol), HOBT (54 mg, 0.4 mmol), Et$_3$N (40 mg, 0.4 mmol) and DEC (77 mg, 0.4 mmol) at 0° C. The solution was gradually warmed to RT and stirred overnight. After reaction was complete, the solution was diluted with CH$_2$Cl$_2$ (50 ml) and washed with saturated NaHCO$_3$ solution (30 ml, 2×) and brine (20 ml, 3×). The organic layer was dried over MgSO$_4$, filtered and concentrated to give a crude material as an oil. Product was purified by silica chromatography on flash grade silica (50 g), eluting with 5% NH$_4$OH/MeOH (1:9)/CH$_2$Cl$_2$ to give the title compound as a white solid (0.18 g), m.p. 94–96° C.; FAB Mass [M+1]$^{+35}$Cl 607.3.

EXAMPLE 56

Preparation of (+,−)-2-(3,4-dichlorophenyl)-4-(3,5-dimethylbenzoyl)-1-[[[1-(2-oxo-2-phenylethyl)-4-piperidinyl]amino]acetyl]piperazine

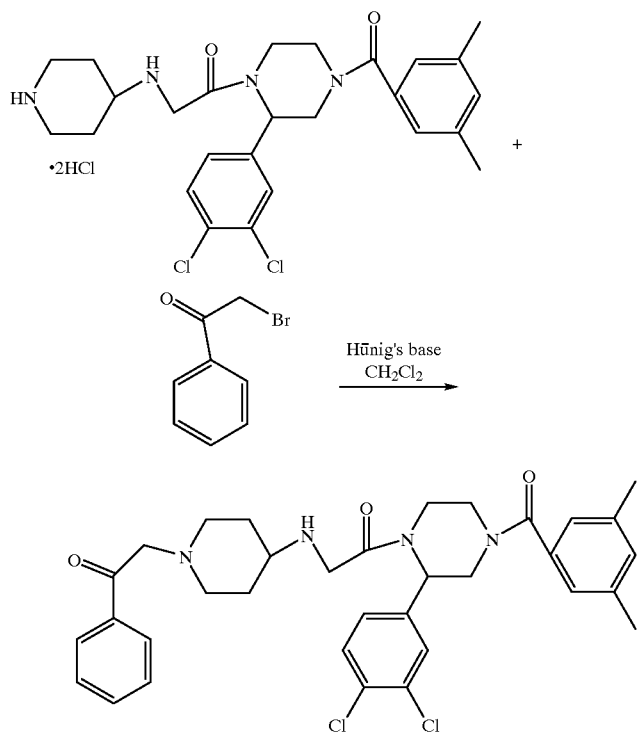

To a solution of compound obtained from Example 52 (0.23 g, 0.4 mmol) in CH$_2$Cl$_2$ (5 ml) were added Hünig's base (0.21 g, 1.6 mmol) and bromoacetophenone (80 mg, 0.4 mmol) at RT. The mixture was stirred at RT overnight under N$_2$. After reaction was complete, it was worked up and purified according to the methods described in Example 55 to give the title compound as a solid, m.p. 69–71° C.; FAB Mass [M+1]$^{+35}$ Cl 621.3.

EXAMPLE 57

Preparation of (+,−)-2-(3,4-dichlorophenyl)-4-(3,5-dimethylbenzoyl)-1-[[[1-(3-phenylpropyl)-4-piperidinyl]amino]acetyl]piperazine

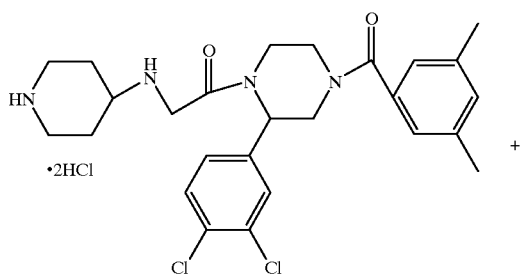

-continued

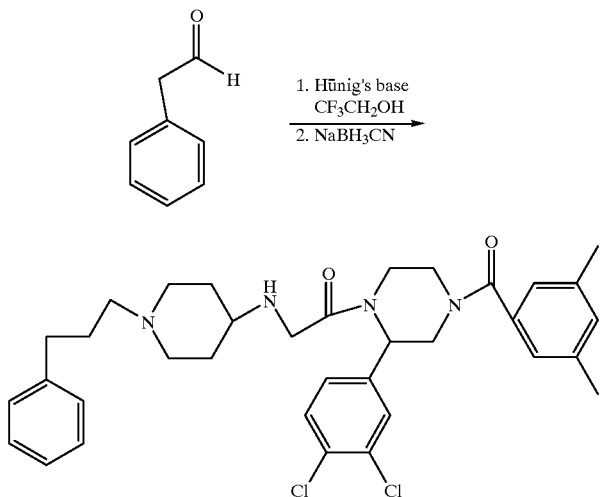

To a solution of compound obtained from Example 52 (0.4 g, 0.7 mmol) in CF$_3$CH$_2$OH (5 ml) was added Hünig's base (0.21 g, 1.6 mmol) at 0° C. After stirring at 0° C. for 10 min, hydrocinnamaldehyde (94 mg, 0.7 mmol) was added. The reaction was stirred at 0° C. for additional 2.5 h, and NaBH$_3$CN (100 mg, 1.6 mmol) was added. The mixture was stirred at 0° C. and gradually warmed to RT overnight. After reaction was complete, it was worked up and purified as described in Example 55 to give the title compound as a white solid, m.p. 52–54° C.; FAB Mass [M+1]+35 Cl 621.3.

EXAMPLE 58

Preparation of 2-(3,4-dichlorophenyl)-4-[3,5-dimethylbenzoyl]-1-[[[3-methyl-1-(phenylmethyl)-4-piperidinyl]amino]acetyl]piperazine diastereomers

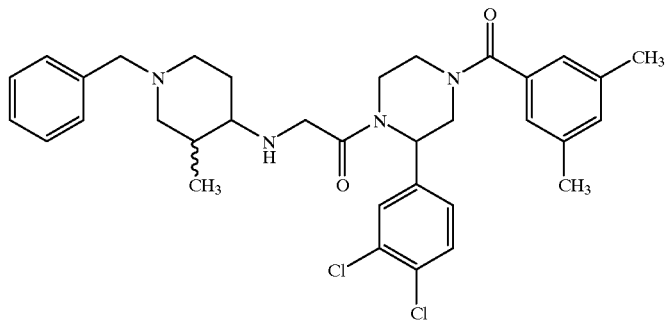

Step 1

To a solution of BOC glycine (0.979 g, 5.59 mmol) and Et$_3$N (0.85 mL, 6.1 mmol) in CH$_2$Cl$_2$ (10 mL) was added BOP-Cl reagent (2.46 g, 5.57 mmol). After stirring for 15 min, (+,−)-(3,5-dimethybenzoyl)-3-(3,4-dichlorophenyl) piperazine (1.83 g, (5.03 mmol) was added. After 5 h, the reaction mixture was added to 0.2 N HCl (100 mL) and extracted with CH$_2$Cl$_2$ (3×60 mL). The combined organic layers were washed with brine, dried with MgSO$_4$ and concentrated. The crude material was purified by flash chromatography on silica gel eluting with 50:1 to 30:1 CH$_2$Cl$_2$-MeOH to give 2.15 g of product as a white foam (4.1 mmol, 82%).

Step 2

The product from step 1 (1.32 g, 2.5 mmol) was treated with HCl saturated MeOH (15 mL) for 2.5 h and concentrated. The resulting powder was dissolved in CH$_2$Cl$_2$, washed with sat. NaHCO$_3$, dried with MgSO$_4$ and concentrated to give the amino product as the free base.

Step 3

To a −78° C. solution of LDA (10.79 mmol) in THF (30 mL) was added 1-benzyl-4-piperidone (2.0 mL, 10.8 mmol). The reaction mixture was warmed to 0° C. for 20 min and then cooled back to −78° C. Methyl iodide (0.67 mL, 10.8 mmol) was added to the enolate solution and stirred at 0° C. for 2 h then warmed to room temp overnight. The reaction mixture was quenched with sat. NH$_4$Cl and concentrated. The residue was suspended in H$_2$O and extracted with CH$_2$Cl$_2$. The combined organic layers was dried with MgSO$_4$, concentrated. The product was purified by flash chromatography on silica gel elution with 1:1 hexane-EtOAc to give the desired product as a yellow oil (0.65 g, 30%).

Step 4

2 (34 mg, 0.17 mmol) was stirred in titanium isopropoxide (45 mg, 0.16 mmol) for 1.5 h. To the mixture was added ethanol (1.0 mL) and NaCNBH$_3$ (5.4 mg, 8.6 mmol) and stirred overnight. The reaction mixture was filtered and washed with EtOAc. The filtrate was washed with H$_2$O and brine, dried with MgSO$_4$ and concentrated. The residue was chromatographed on silica gel eluting with 5% NH$_3$ sat. MeOH in CH$_2$Cl$_2$ to give both diastereomers.

Diastereomer A (15 mg) HRMS (FAB, M+H$^+$): m/e calc'd for $[C_{34}H_{41}N_4Cl_2O_2]^+$ 607.2607; found 607.2603.

Diastereomer B (17 mg) HRMS (FAB, M+H$^+$): m/e calc'd for $[C_{34}H_{41}N_4Cl_2O_2]^+$ 607.2607; found 607.2597.

EXAMPLE 59

Preparation of 2-(3,4-dichlorophenyl)-4-[3,5-dimethylbenzoyl]1-[[[1-(phenylmethyl)-3-piperidinyl]amino]acetyl]piperazine

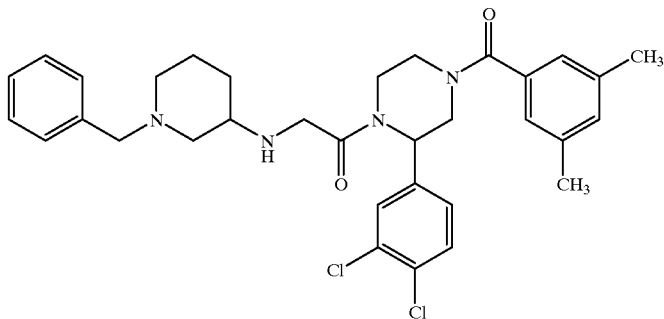

By procedure analogous to the method described in Example 58 step 4, the title compound was prepared as a solid foam. HRMS (FAB, M+H$^+$): m/e calc'd for $[C_{33}H_{39}N_4Cl_2O_2]^+$ 593.2450; found 593.2458.

What is claimed is:

1. A compound of the formula:

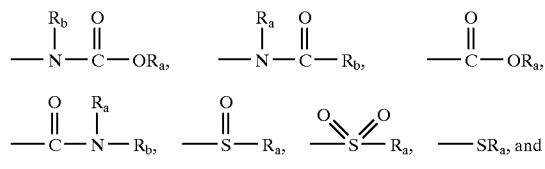

wherein:

u is 0 to 2;

y is 1 to 3;

with the proviso that no more than one $R_c$ is other than H in the

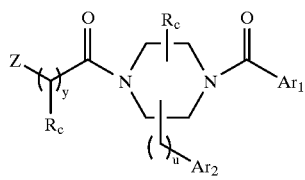

moiety;

$R_c$ is independently selected from the group consisting of H, $C_1$–$C_6$ alkyl, hydroxy($C_1$–$C_6$)alkyl, carboxy($C_1$–$C_6$) alkyl and $H_2NC(O)$-($C_1C_6$)alkyl;

$R_1$ and $R_2$ are independently selected from the group consisting of H, $C_1$–$C_6$ alkyl, $CF_3$, $C_2F_5$, Cl, Br, I, F, $NO_2$, $OR_a$, CN, $NR_aR_b$,

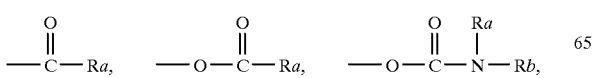

-continued

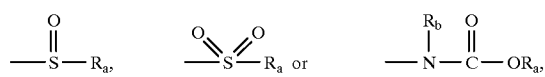

-continued

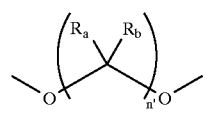

and where $R_a$ is not H in

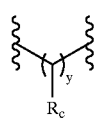

or when $R_1$ and $R_2$ are on adjacent carbons on a ring, they can form wherein n' is 1 or 2;

$R_3$ is independently selected from the group consisting of H, $C_1$–$C_6$ alkyl, $CF_3$, $C_2F_5$, Cl, Br, I, or F, $OR_a$, $OCF_3$ and phenyl;

$R_a$ and $R_b$ are independently selected from the group consisting of H, $C_1$–$C_6$ alkyl, phenyl, benzyl, allyl,

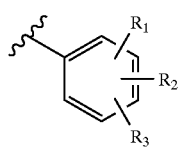 and 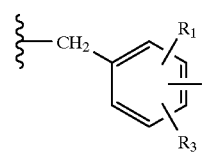

or $R_a$ and $R_b$ together are $C_2$–$C_6$ alkylene and are attached to the same nitrogen, so that $R_a$ and $R_b$, together with the nitrogen to which they are attached, join to form a 4 to 7 membered ring;

$Ar_1$ is

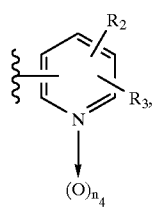

wherein $n_4$ is 0 or 1,

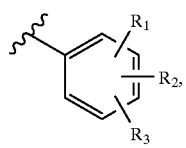, 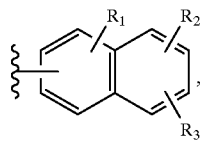

quinolyl, benzothienyl, benzothiazolyl, indolyl or 2,3-dihydrobenzofuranyl;

$Ar_2$ is

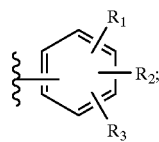

Z is

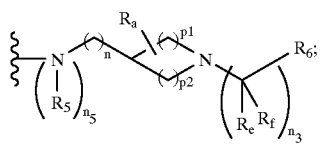

$p_1$ and $p_2$ are independently 1 or 2, provided that $p_1$ and $p_2$ together are 3 or 4;

n is 0 to 2;

$n_3$ is 0 to 4;

$n_5$ is 1 or 2;

when $n_5$ is 1, $R_5$ is H, OH, $C_1$–$C_6$ alkyl, hydroxy($C_1$–$C_6$) alkyl or —C(O)—$R_a$; and when $n_5$ is 2, each $R_5$ is independently selected from the group consisting of $C_1$–$C_6$ alkyl and the two $R_5$ groups and the nitrogen to which they are attached form a quaternary salt with a bromine atom;

$R_e$ and $R_f$ are independently selected from the group consisting of H, $C_1$–$C_6$ alkyl, allyl,

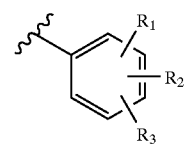 and 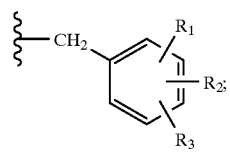

$R_6$ is H, $C_1$–$C_6$ alkyl, $C_3$–$C_6$ cycloalkyl,

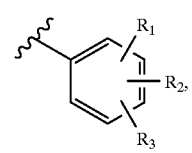, 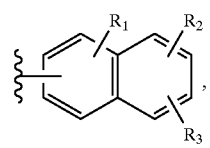,

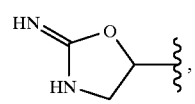, heteroaryl or substituted heteroaryl, wherein heteroaryl is selected from the group consisting of imidazolyl, oxadiazolyl, thiadiazolyl, thiazolyl, thienyl, pyrrolyl, furyl, pyridyl, isoxazolyl, tetrazolyl, benzimidazolyl, pyrimidyl and quinolyl; and wherein substituted heteroaryl are heteroaryl rings substituted with $R_1$; $R_2$ and $R_3$;

or a pharmaceutically acceptable salt thereof.

2. A compound according to claim 1 of the formula

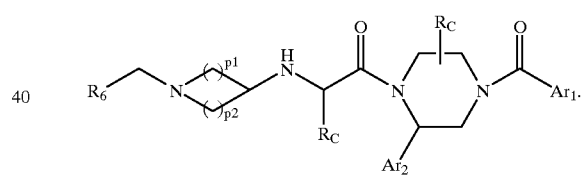

I'

3. A compound according to claim 2 wherein each $R_c$ is H, $p_1$ and $p_2$ are 2, $Ar_1$ and $Ar_2$ are both

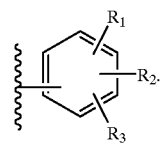

4. A compound according to claim 2 wherein $R_6$ is

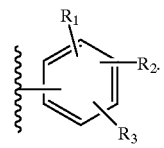

5. A compound selected from the group consisting of

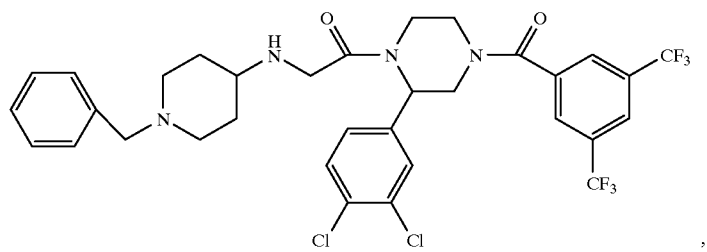,
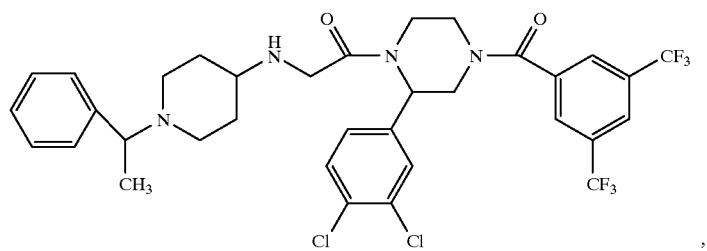,
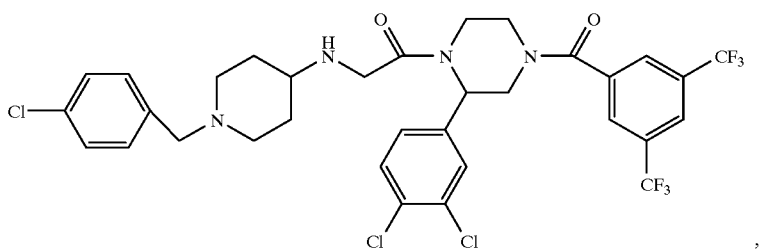,
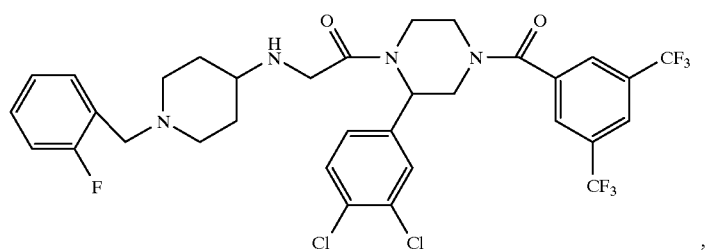,
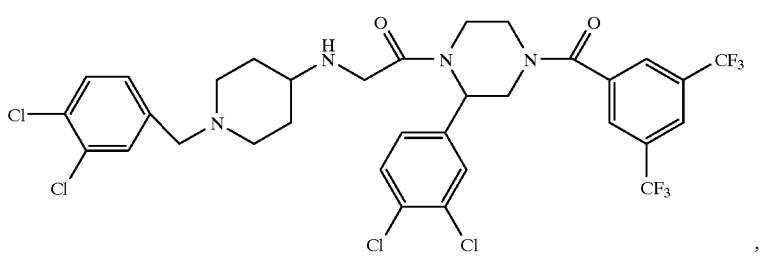,
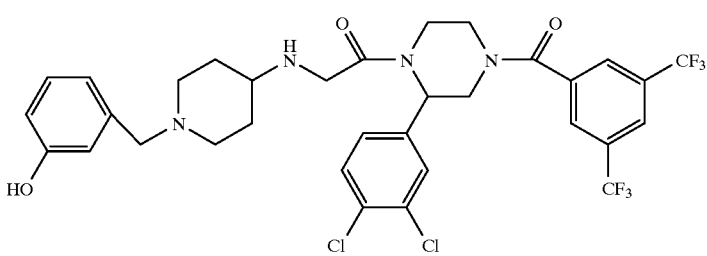,

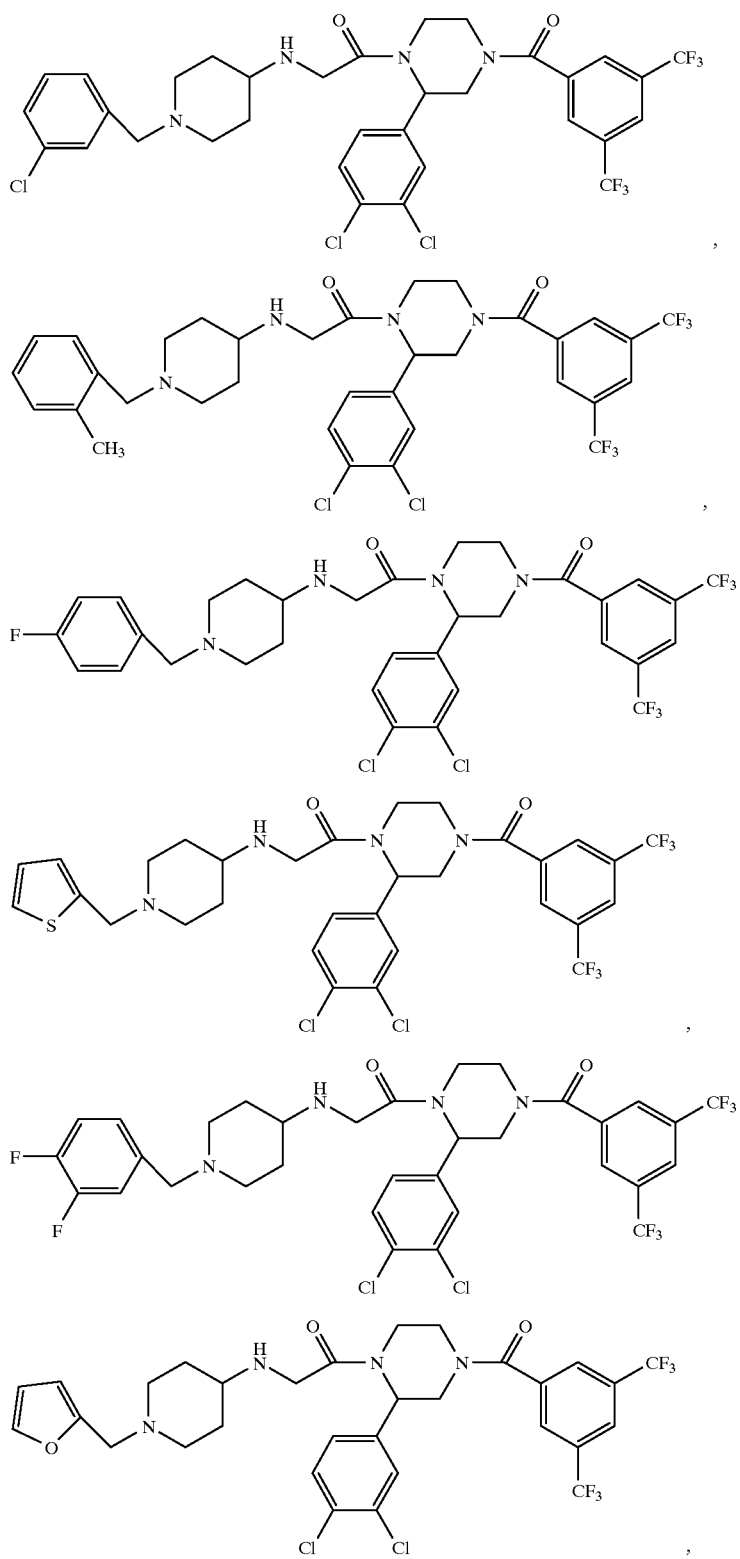

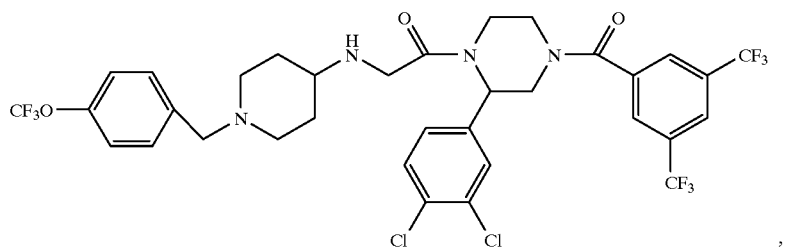
,
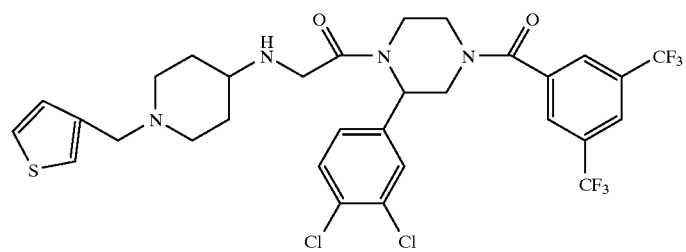
,
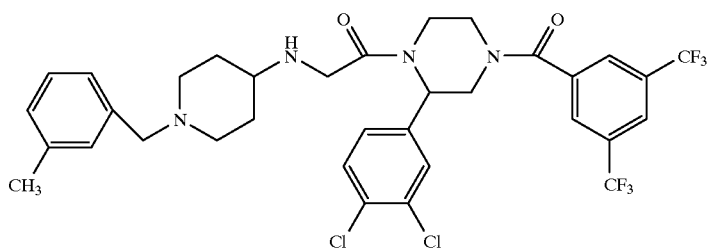
,
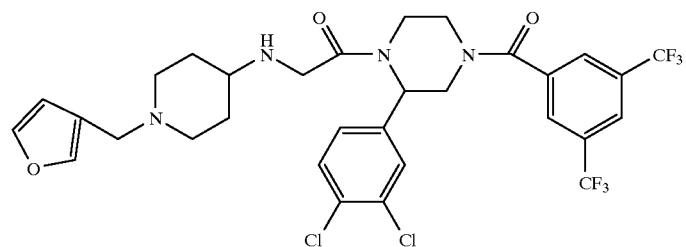
,
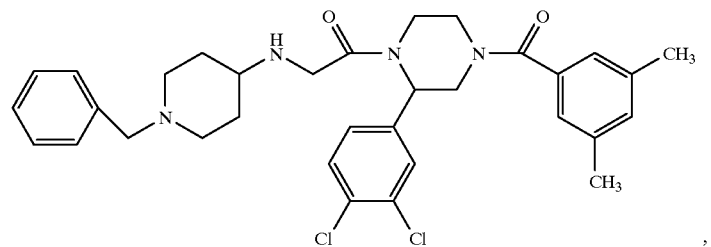
,
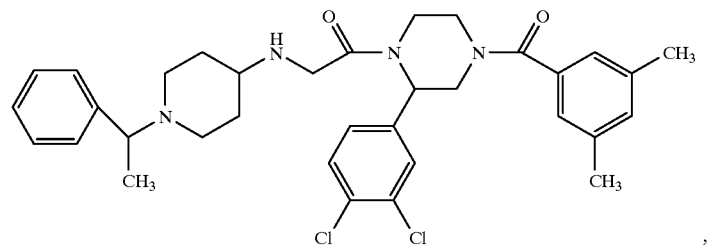
,

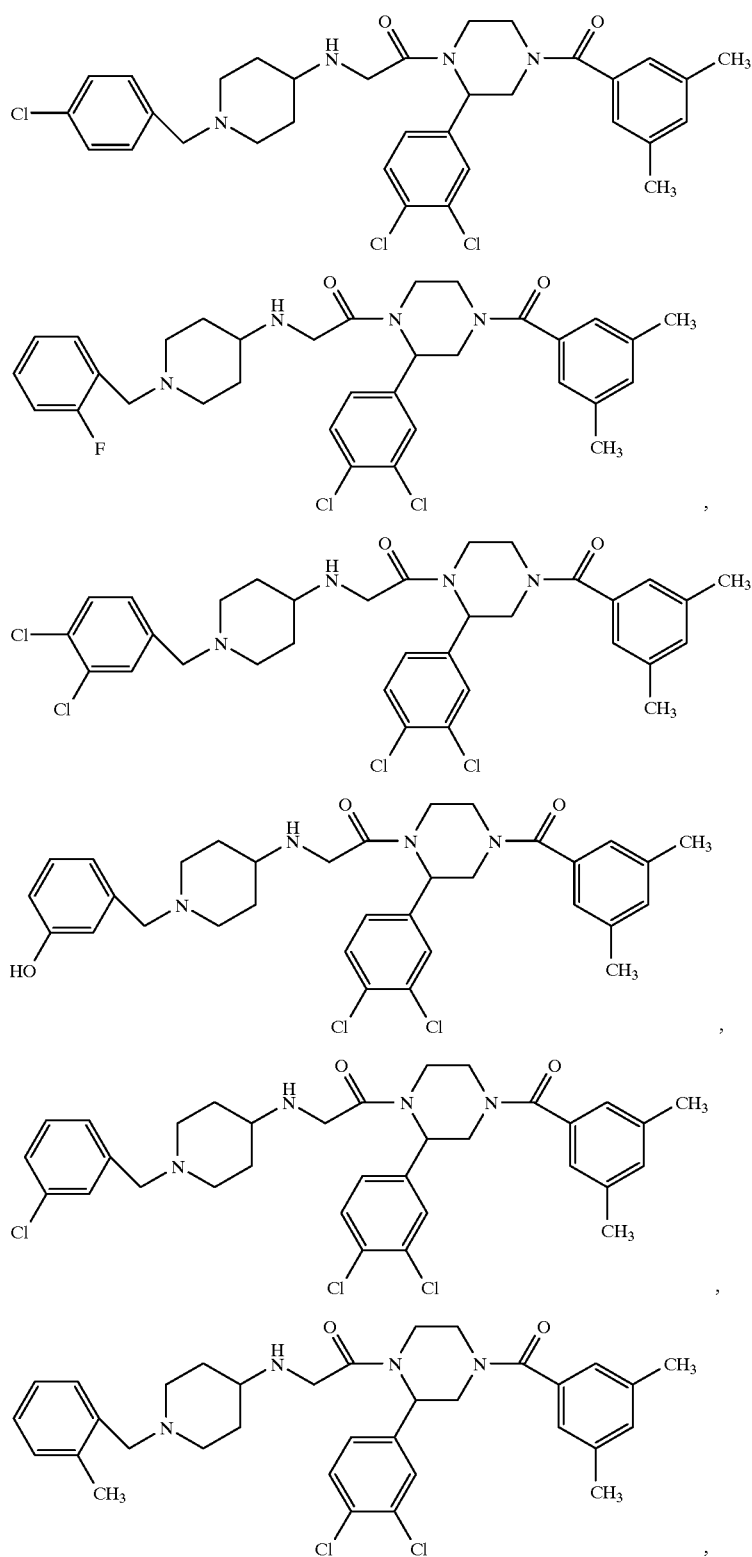

-continued
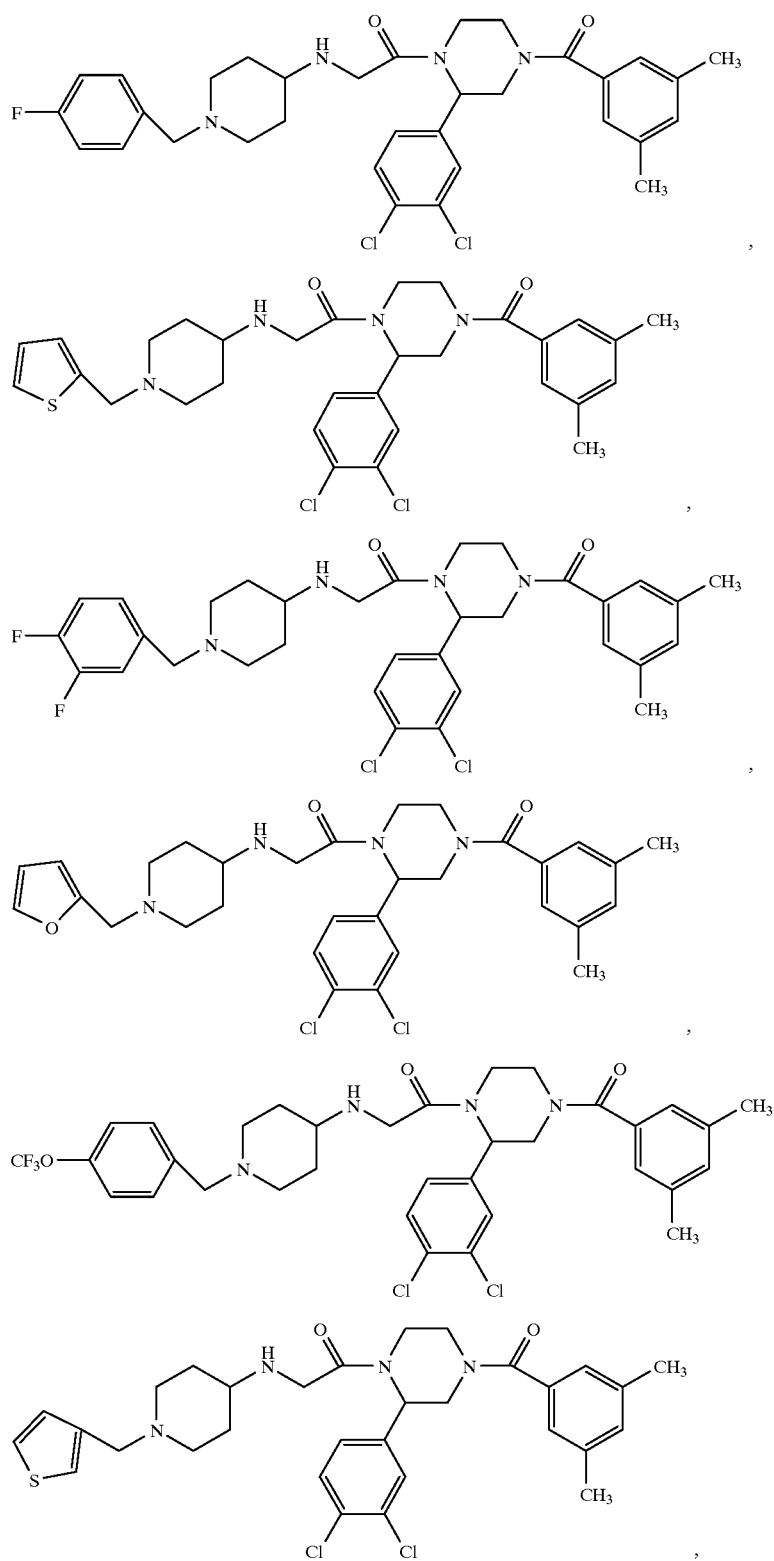

-continued
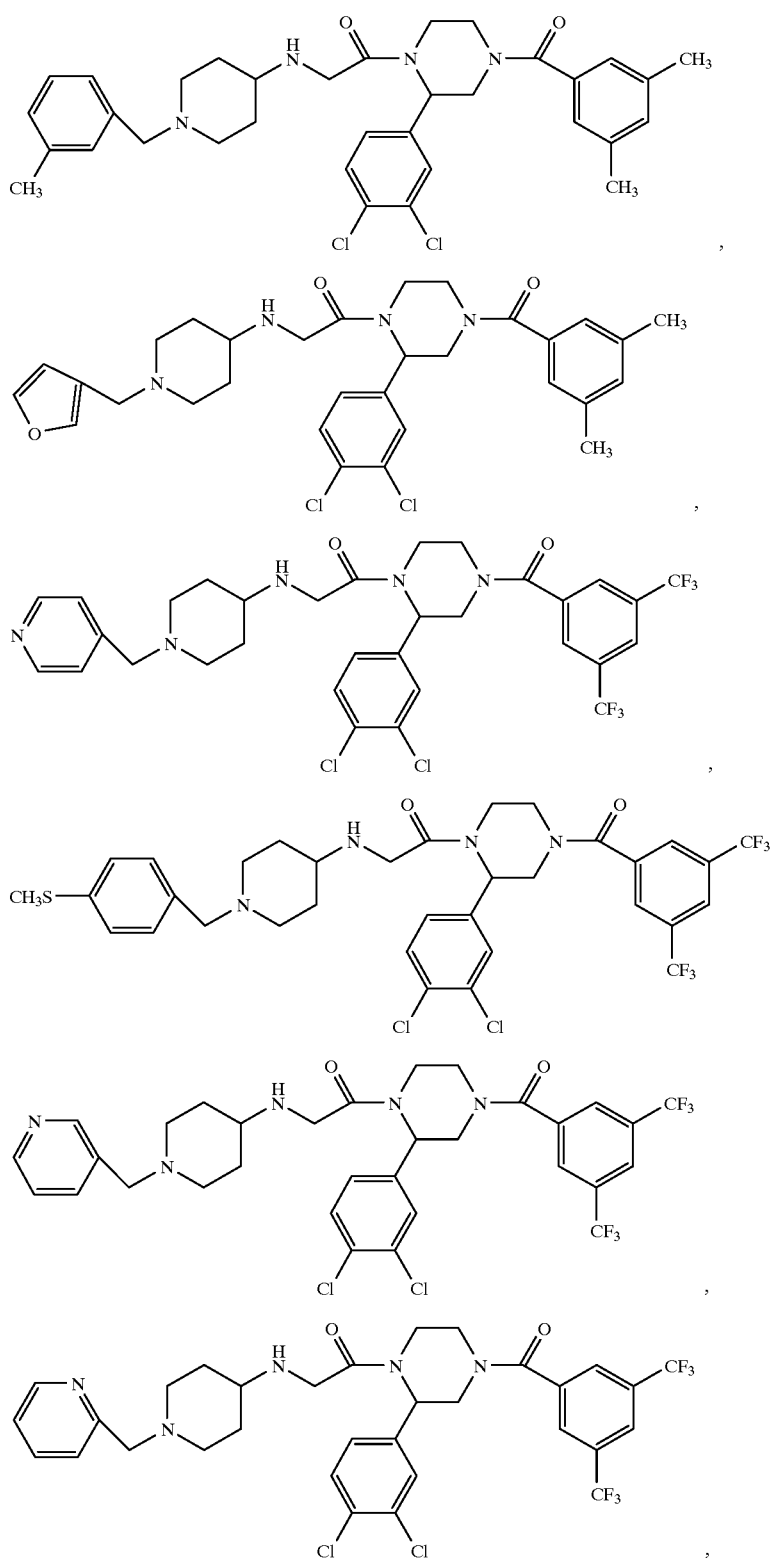

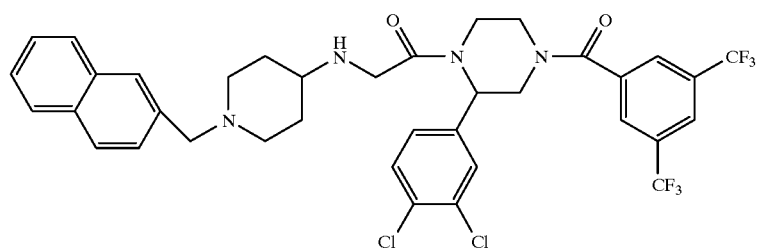
,
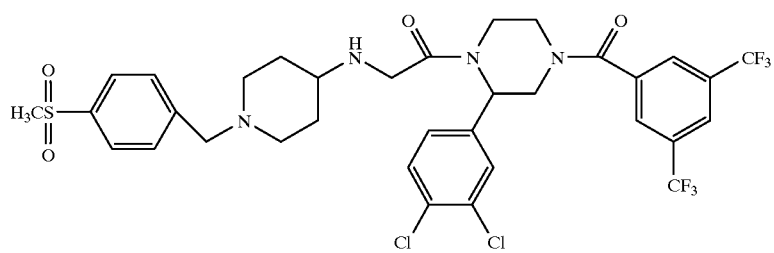
,
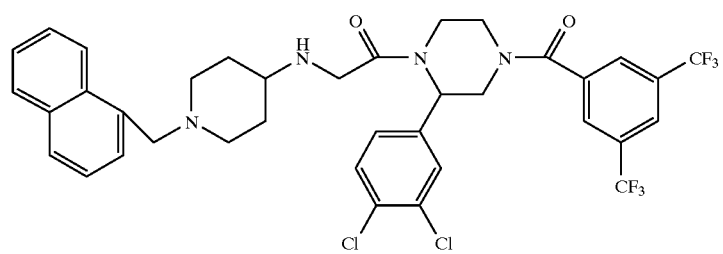
,
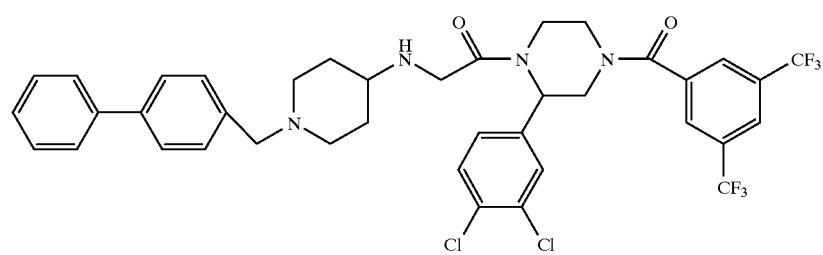
,
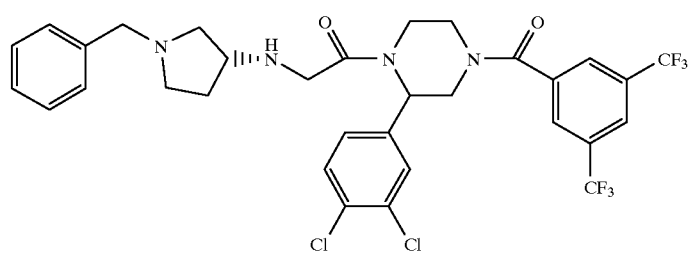
,
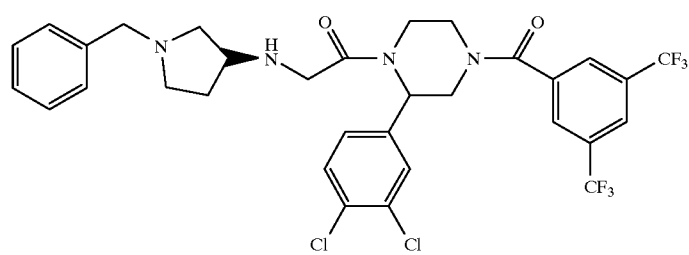
, -continued
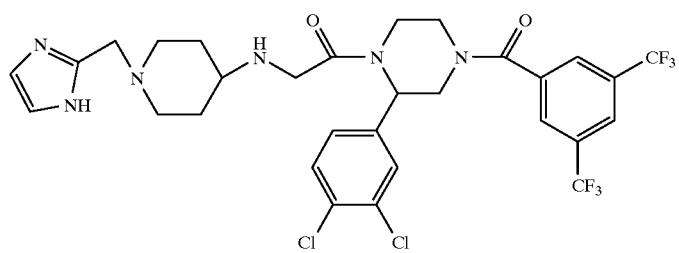
,
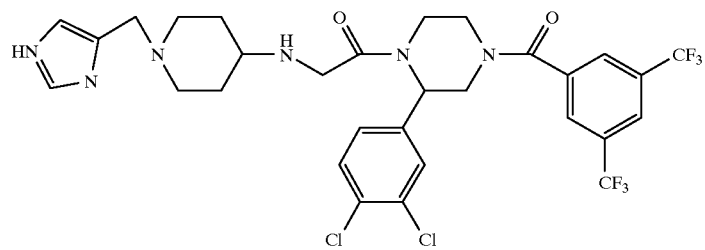
,
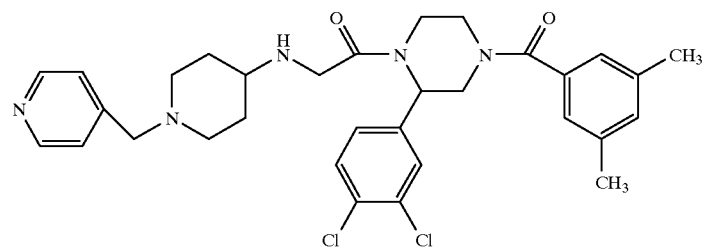
,
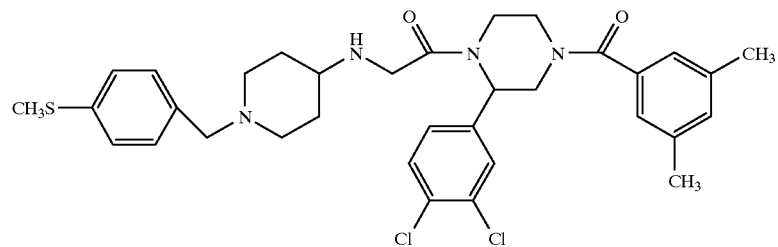
,
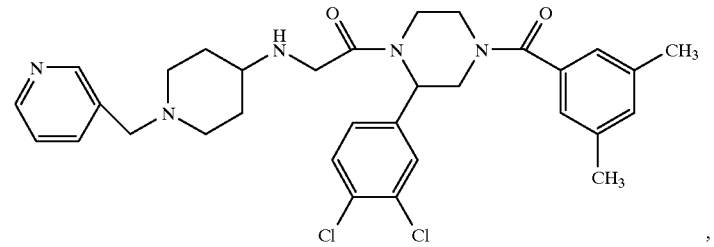
,
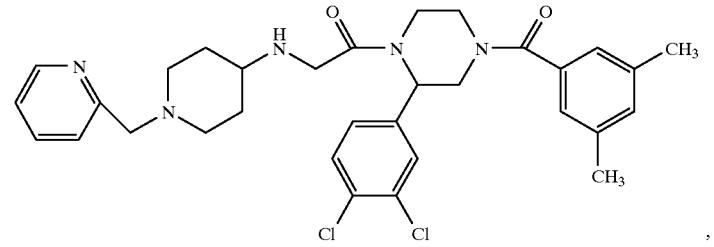
, -continued
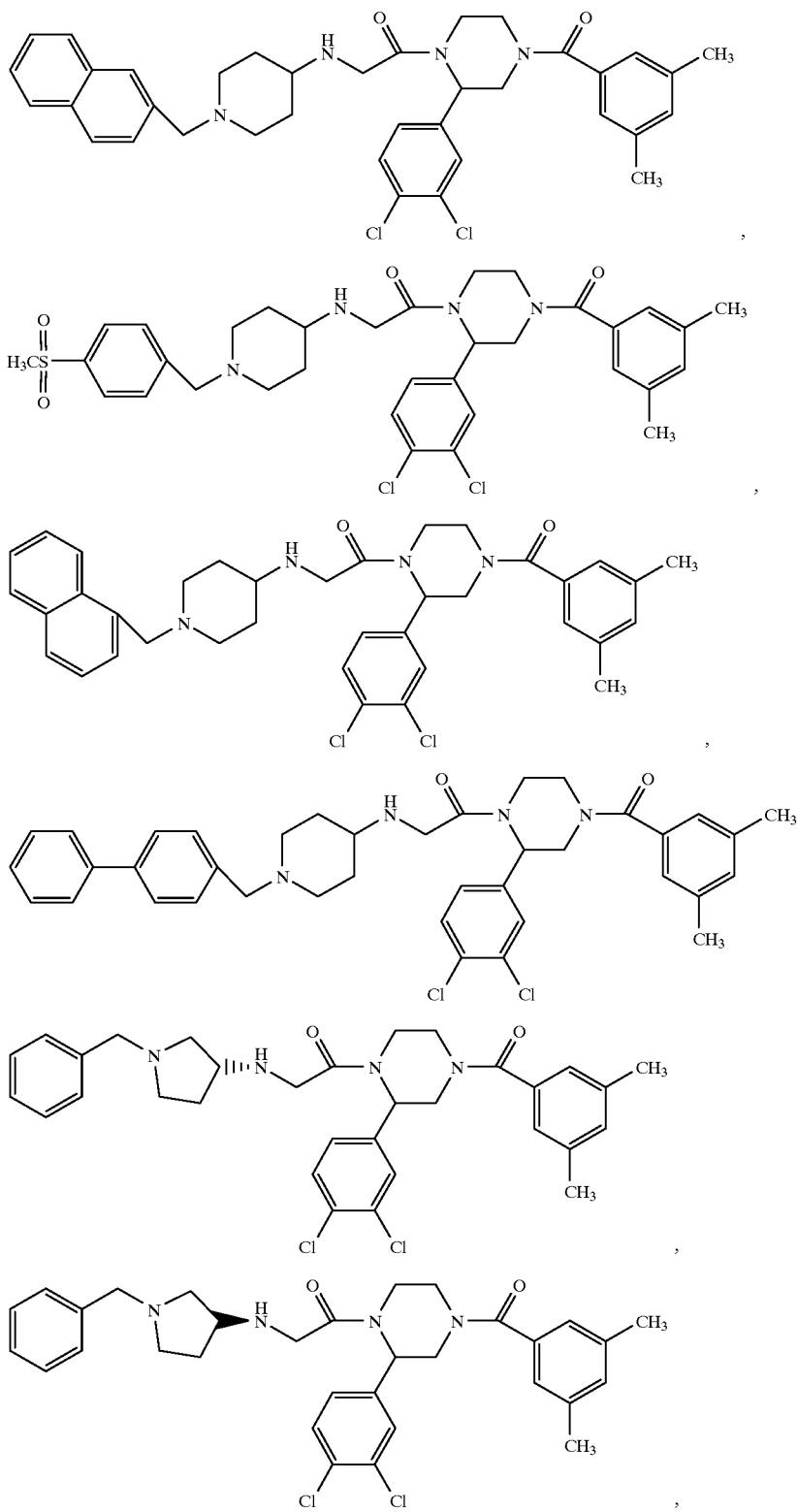

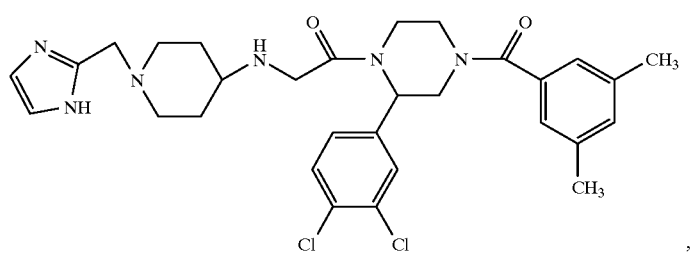,
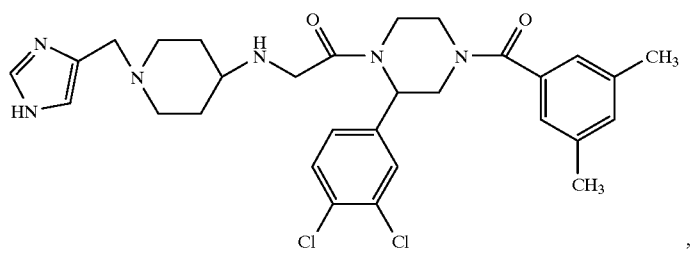,
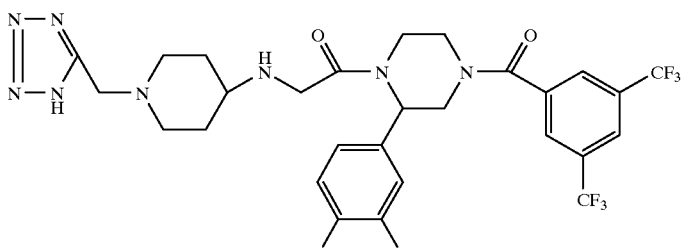,
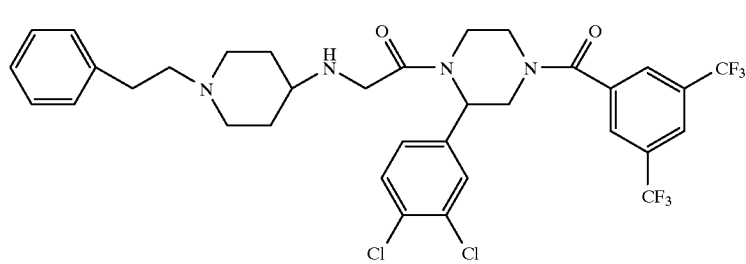,
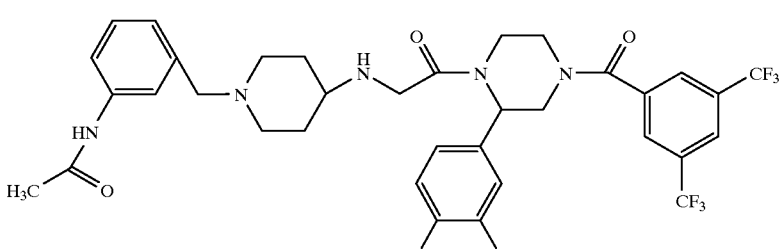,
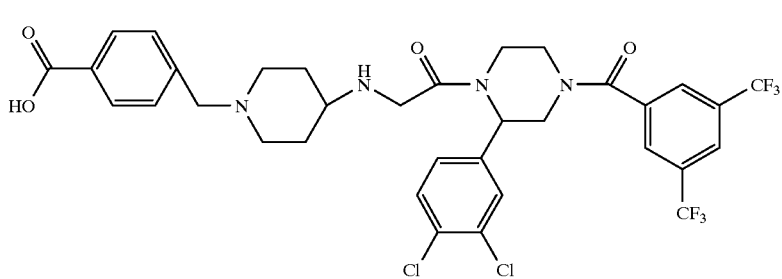,

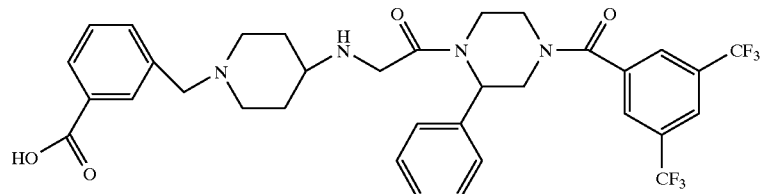,
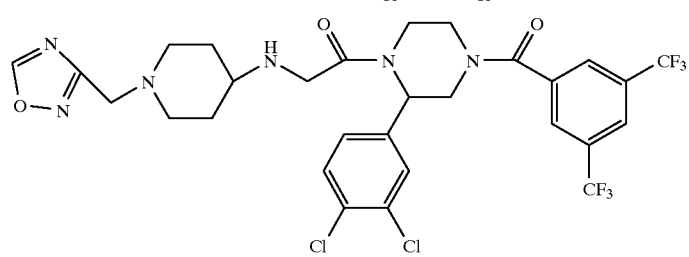,
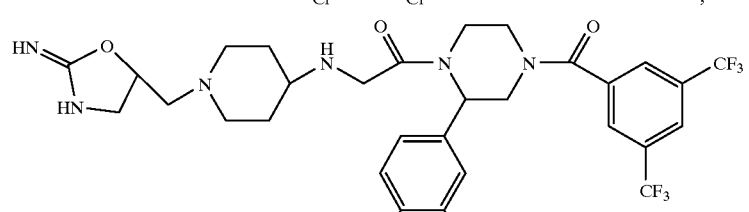,
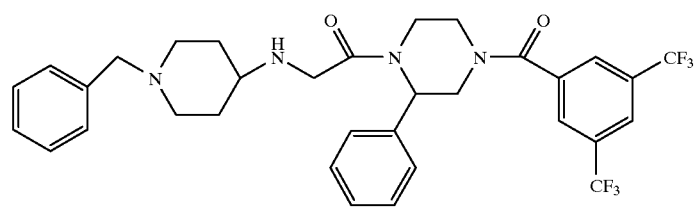,
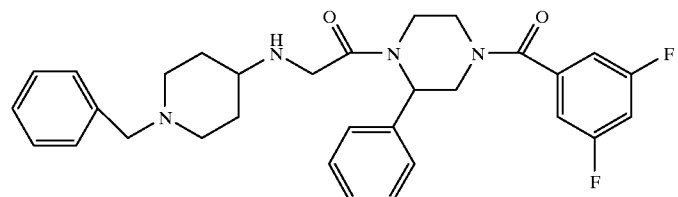,
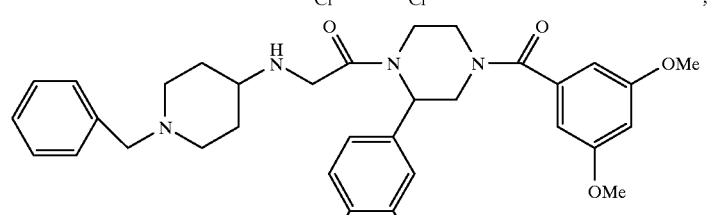,
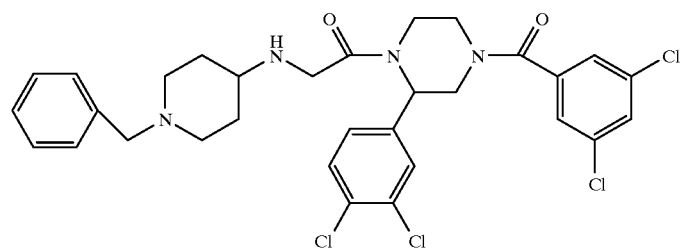,

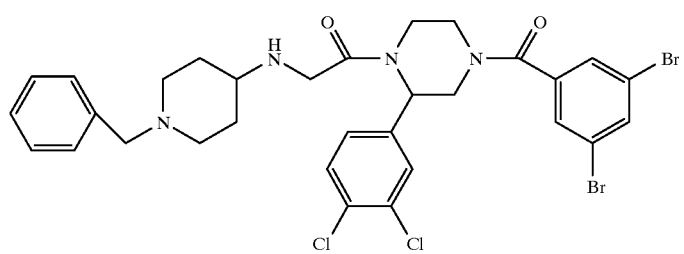
,
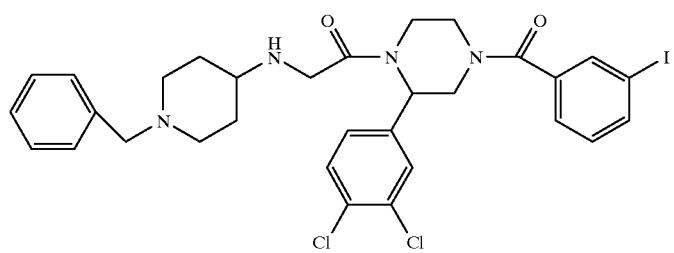
,
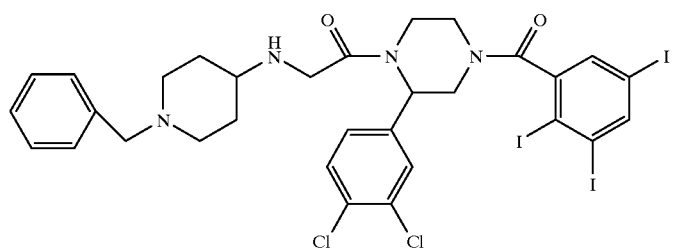
,
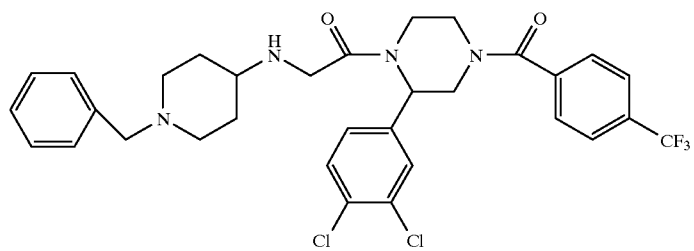
,
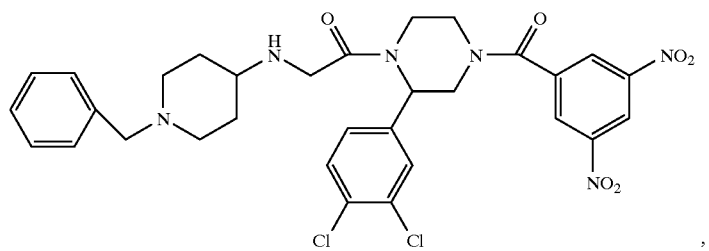
,
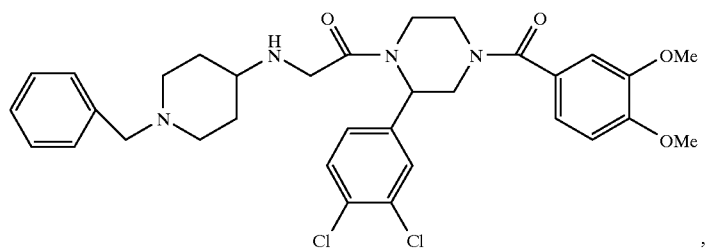
,

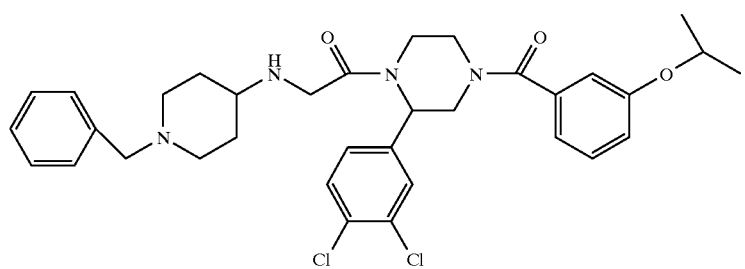,
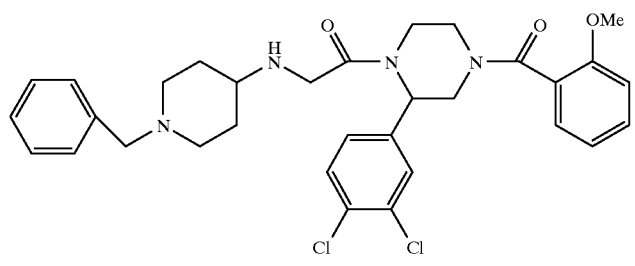,
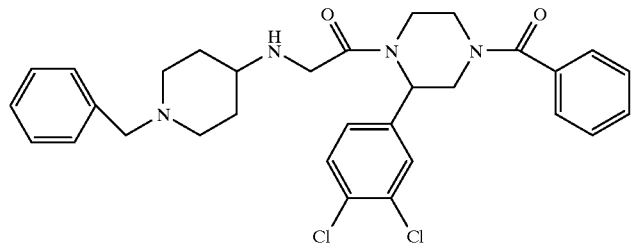,
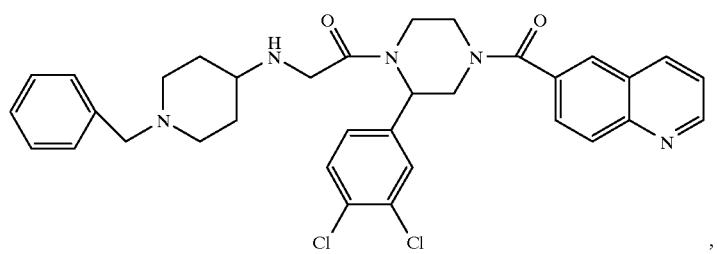,
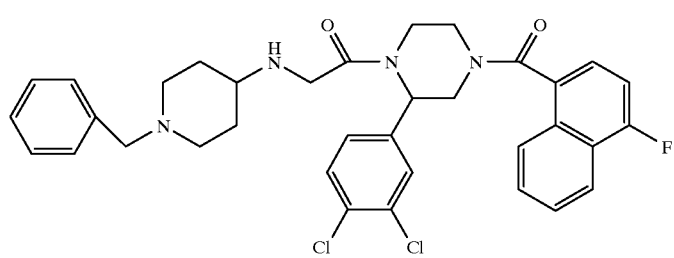,
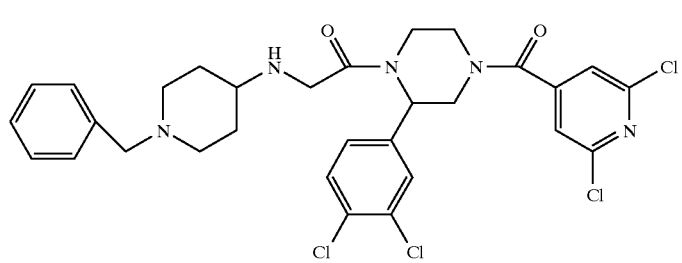,

-continued
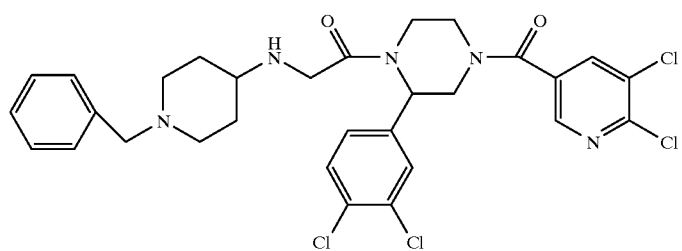
,
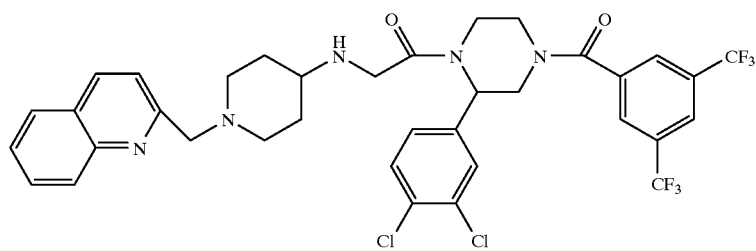
,
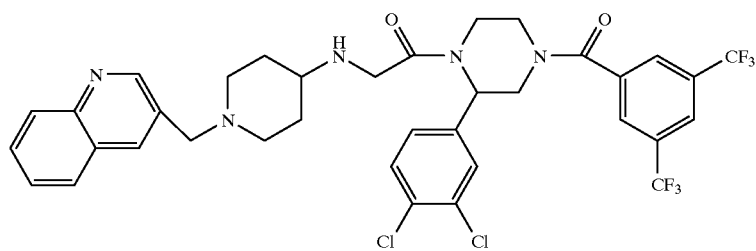
,
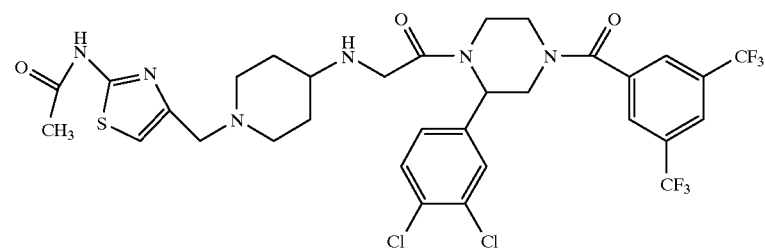
,
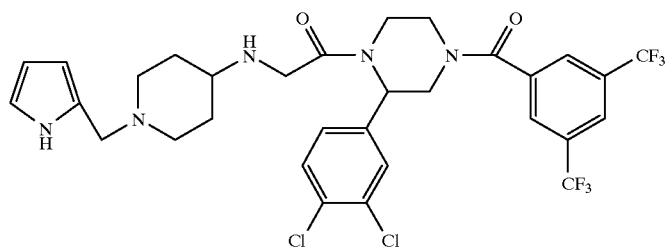
,
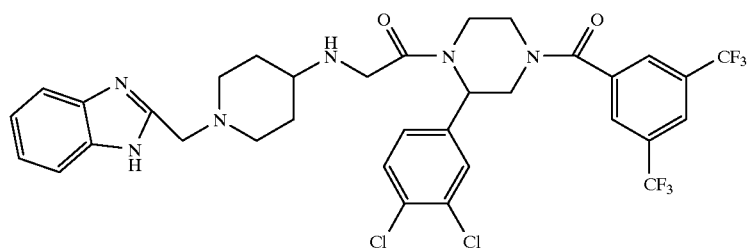
,

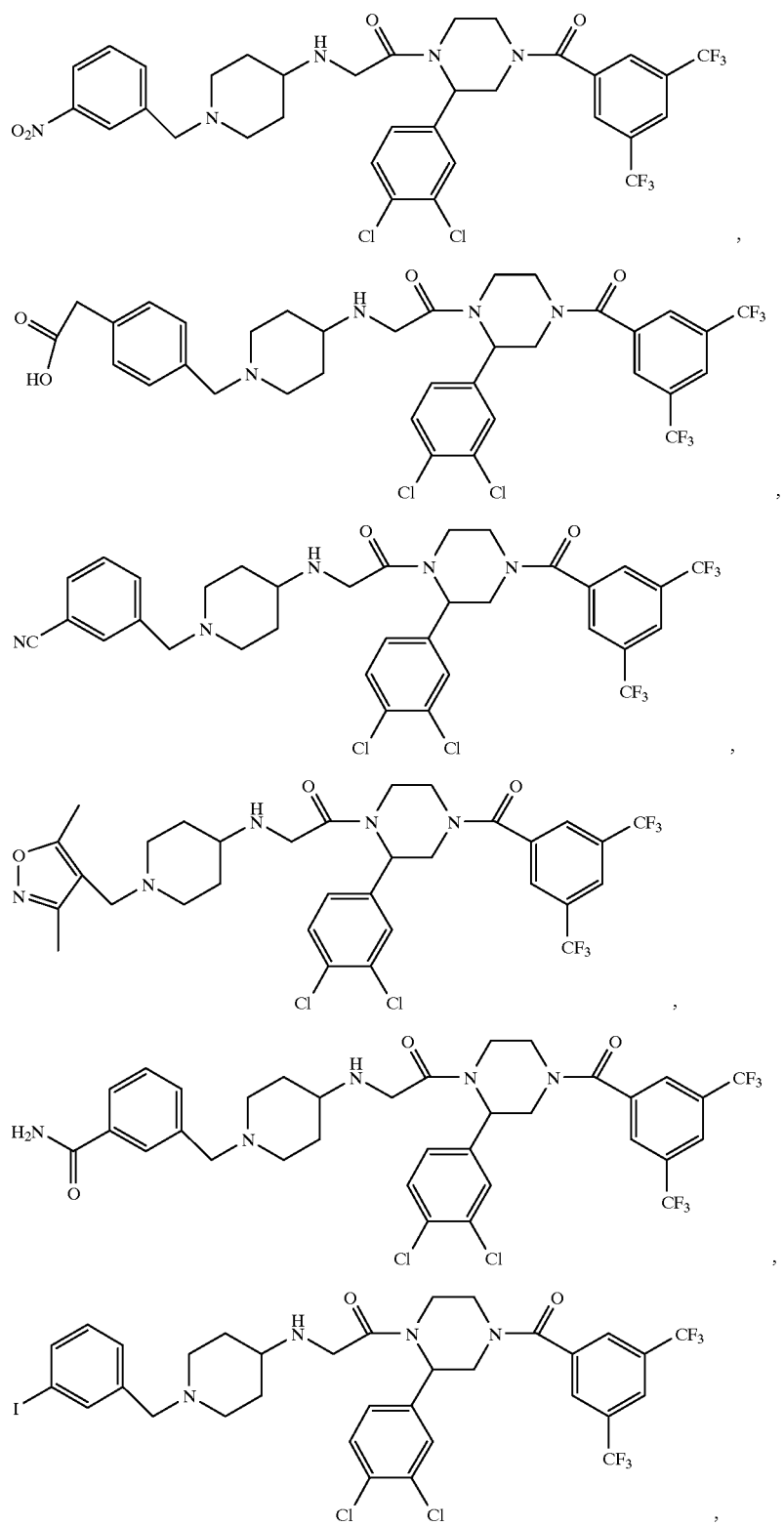

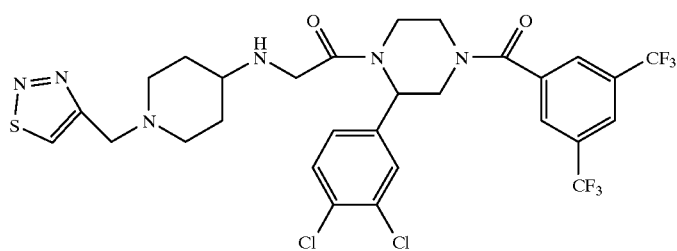
,
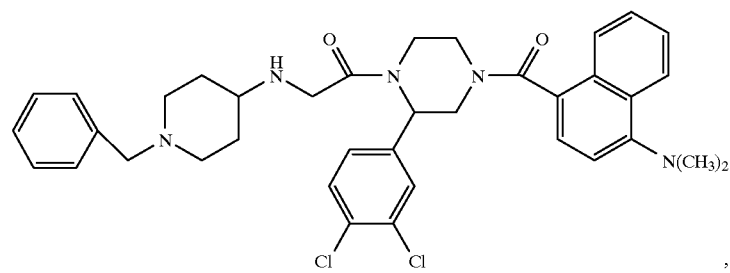
,
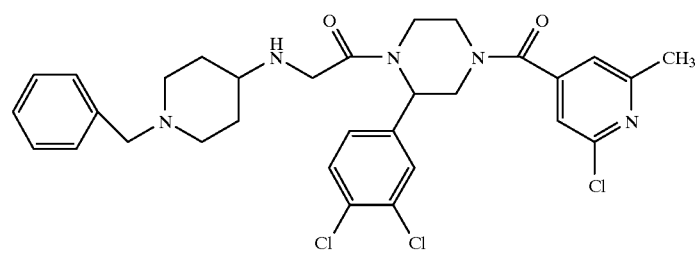
,
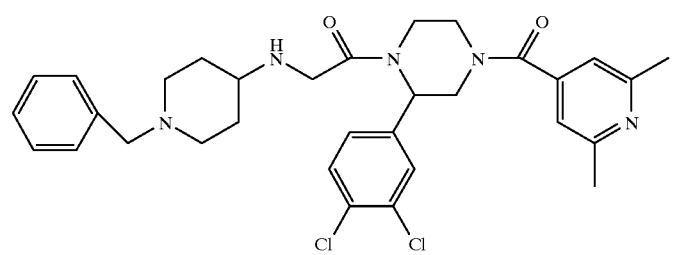
,
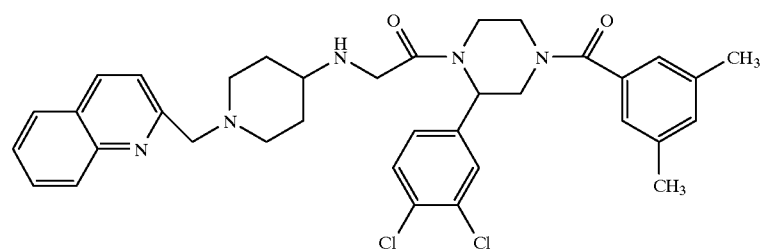
,
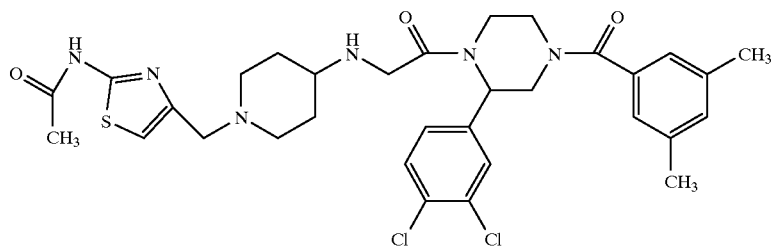
,

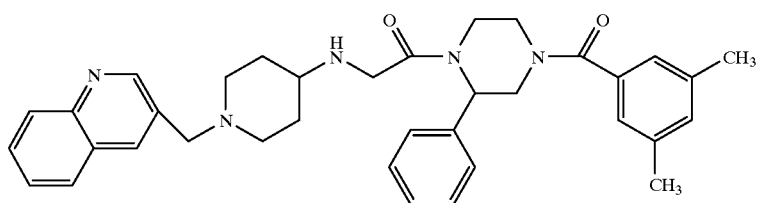
,
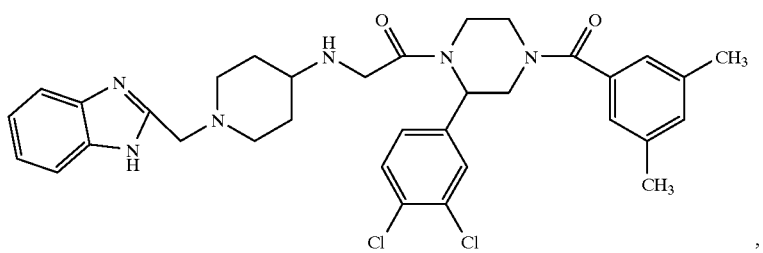
,
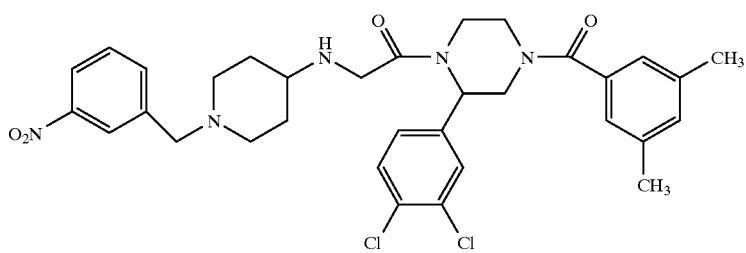
,
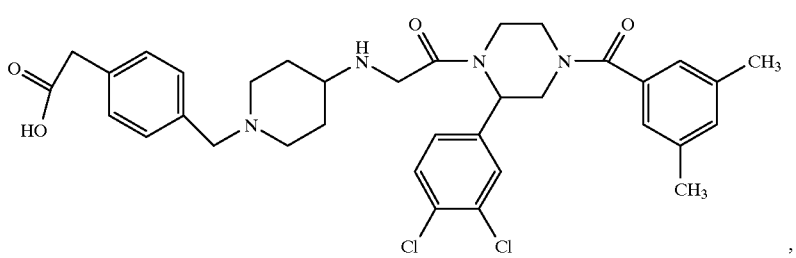
,
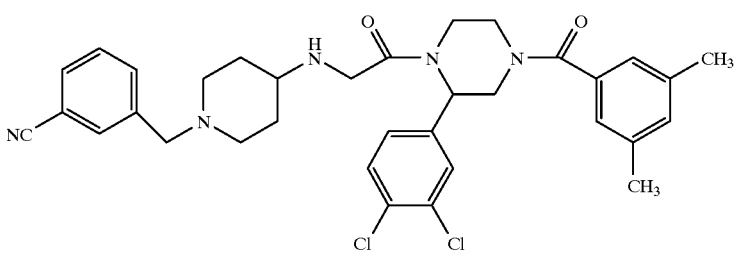
,
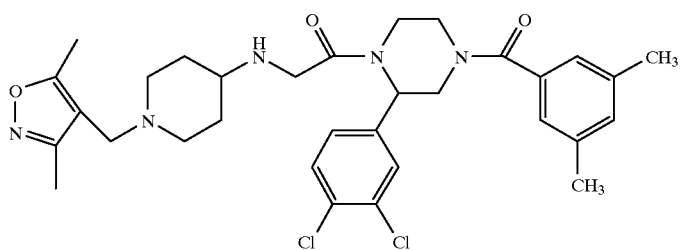
, -continued
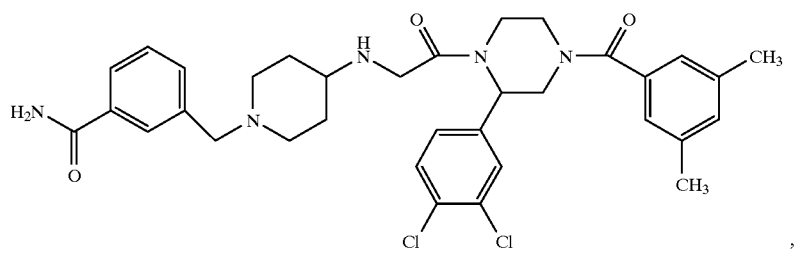
,
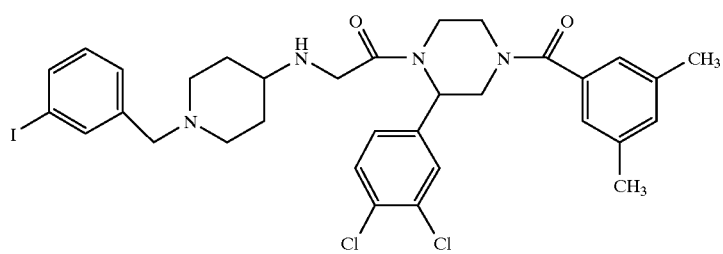
,
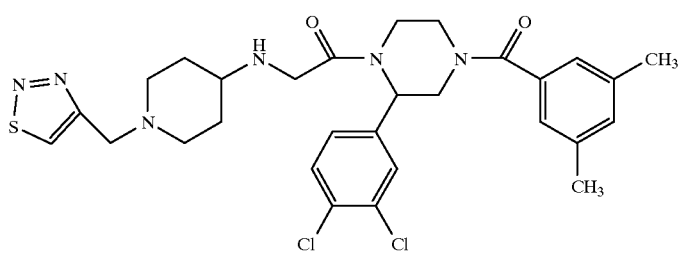
,
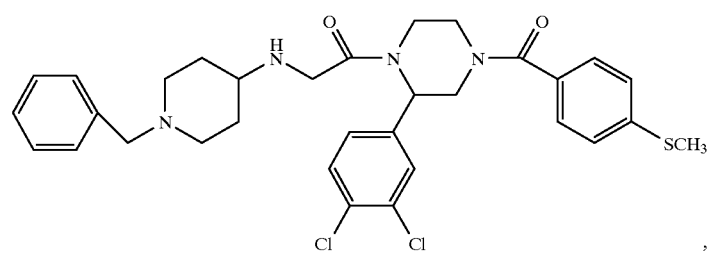
,
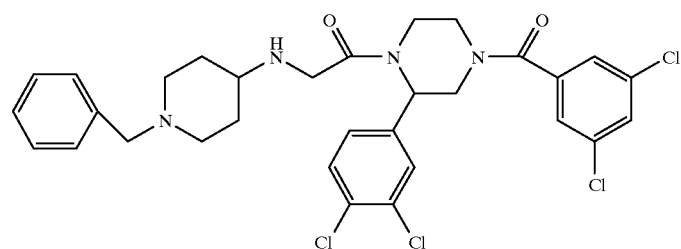
,
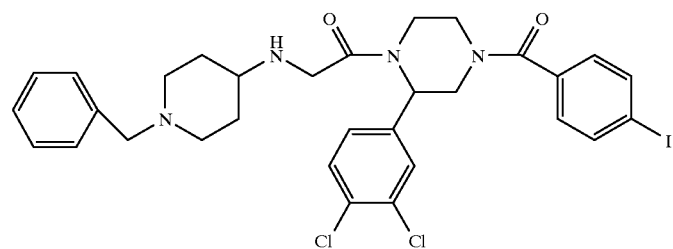
, -continued
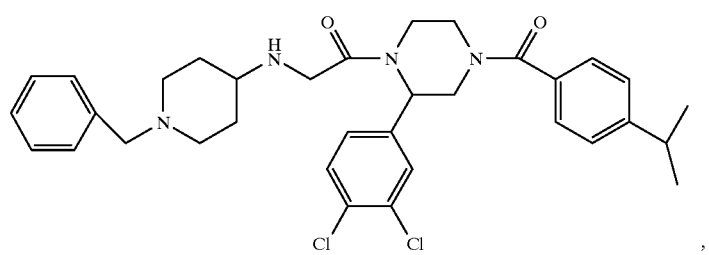,
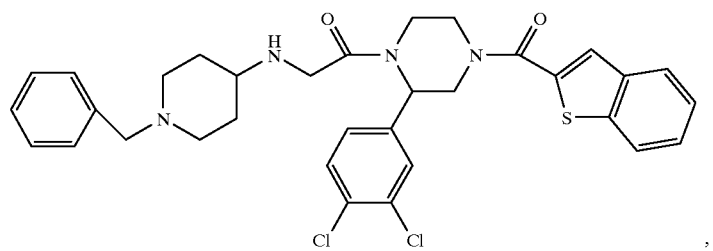,
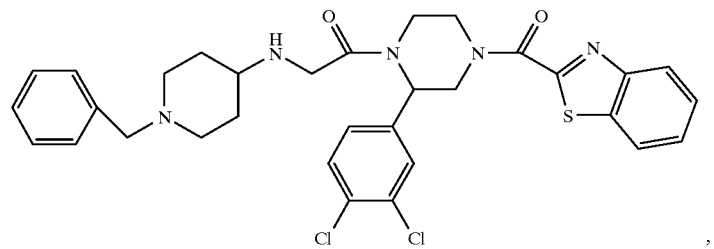,
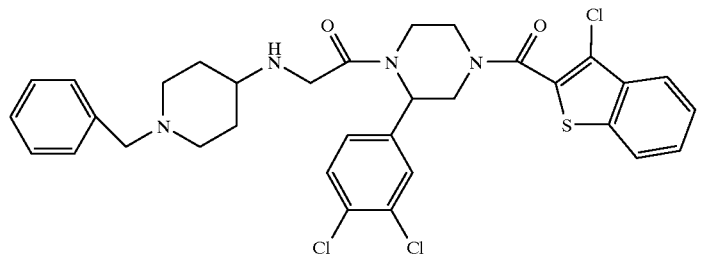,
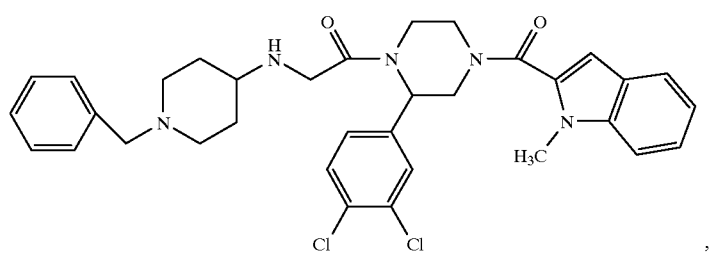,
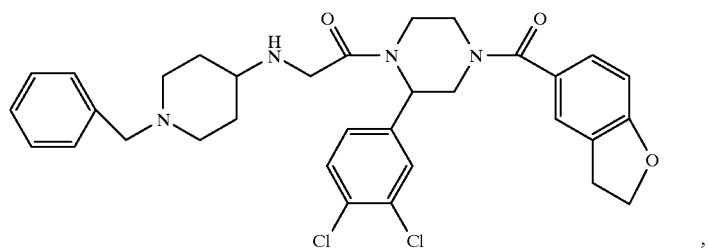,

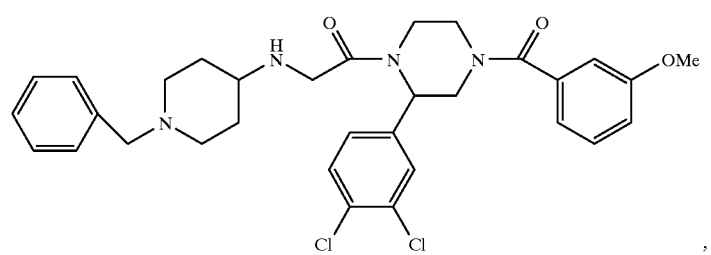,
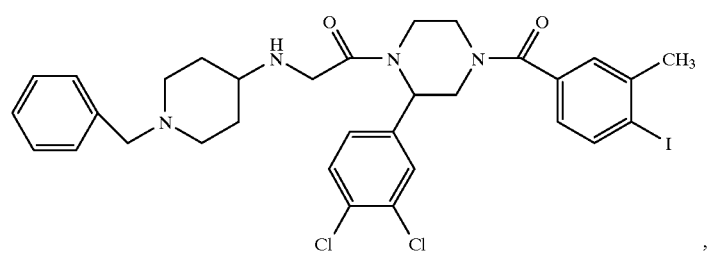,
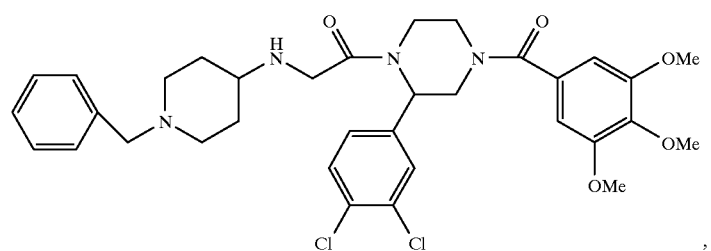,
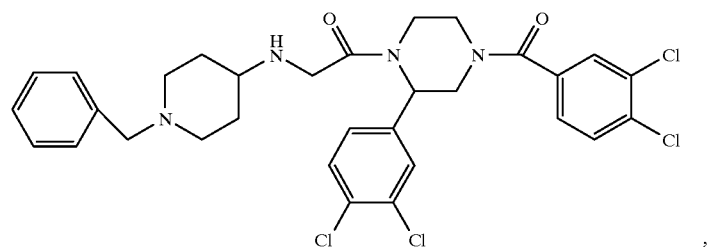,
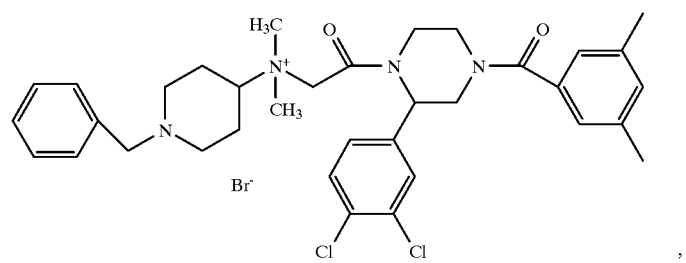,
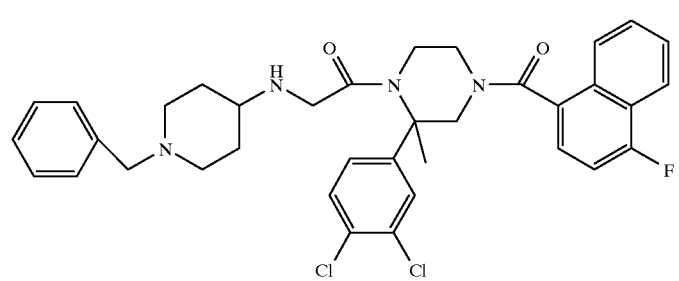,

-continued
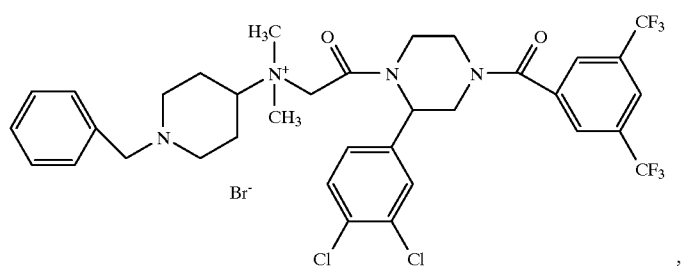
,
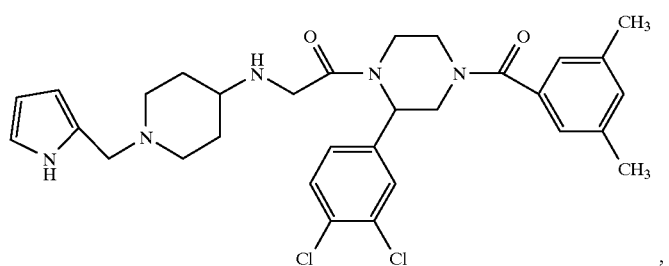
,
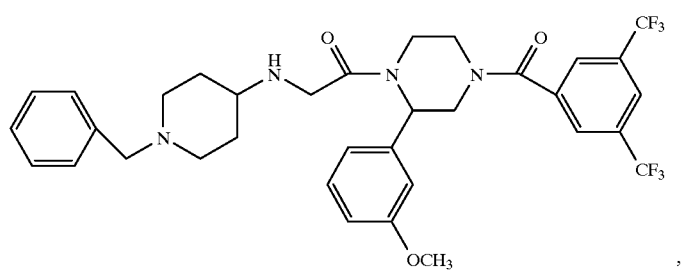
,
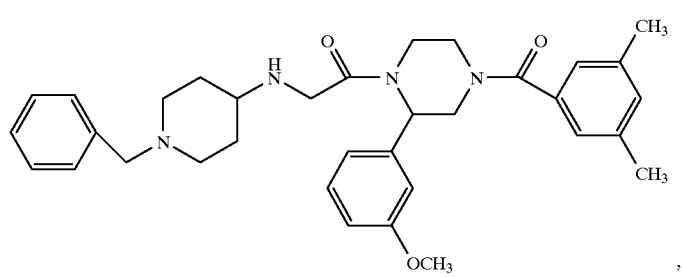
,
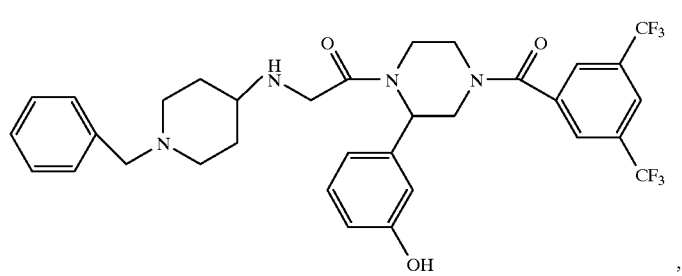
,
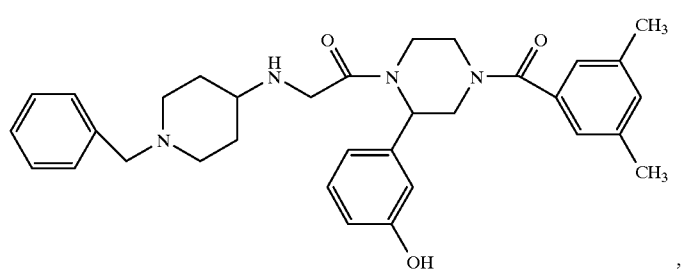
,

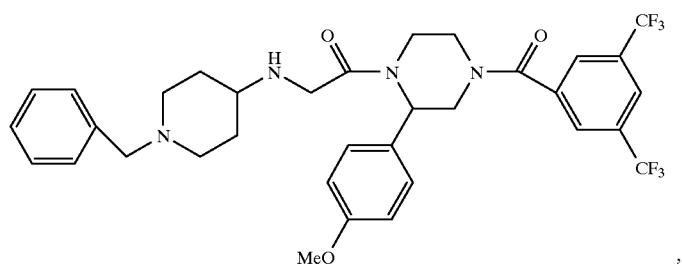,
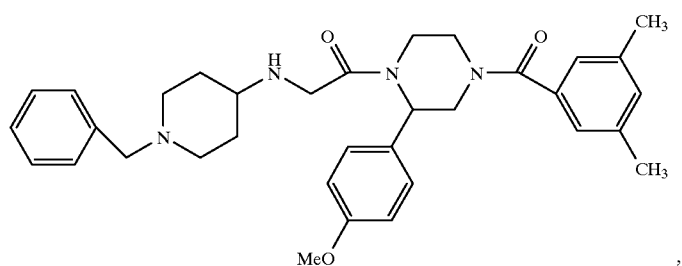,
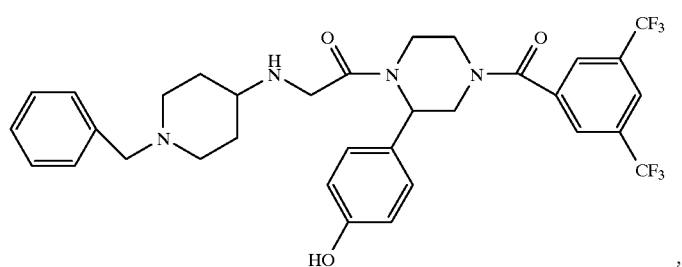,
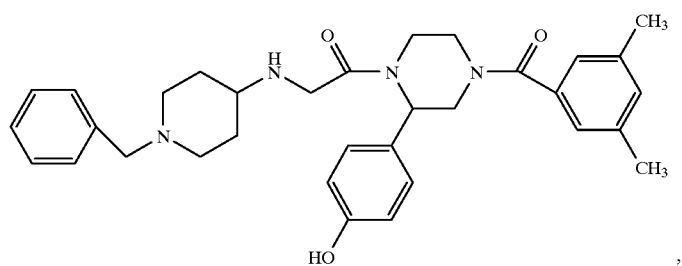,
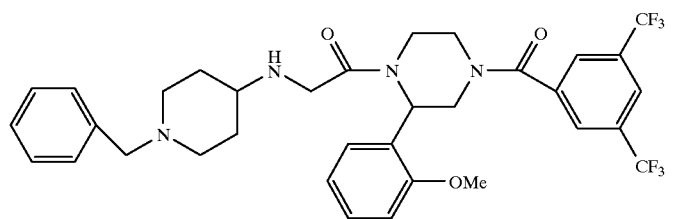,
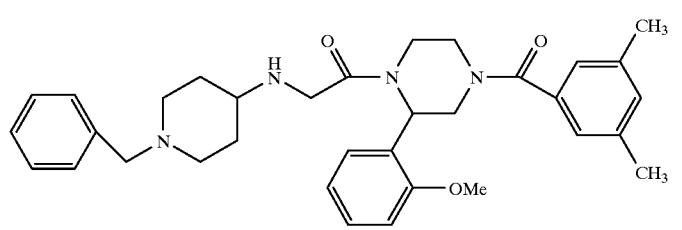,

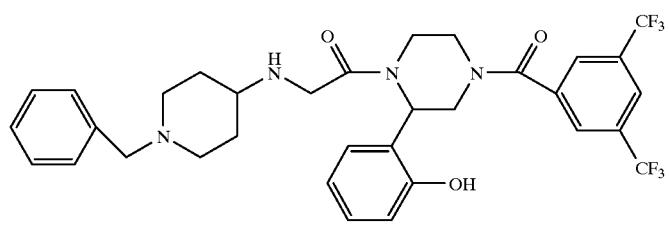
,
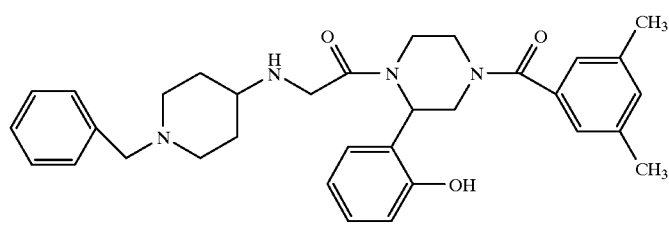
,
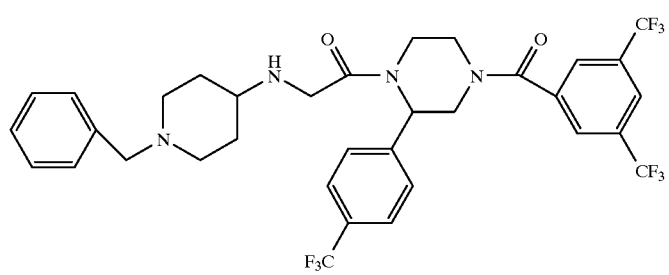
,
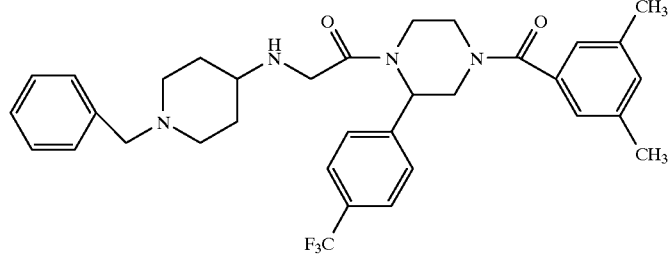
,
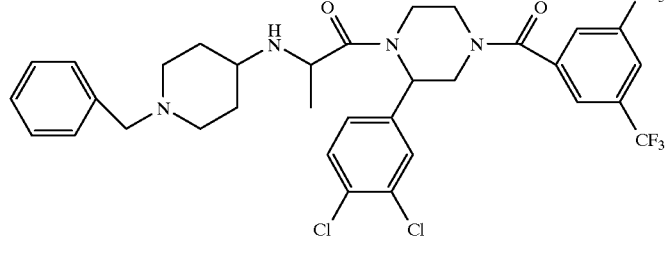
,
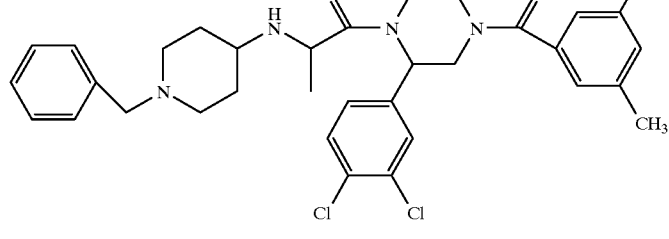
,

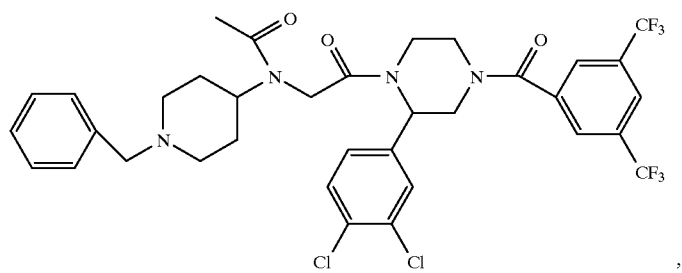,
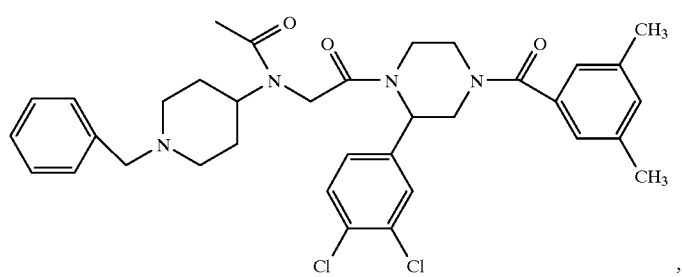,
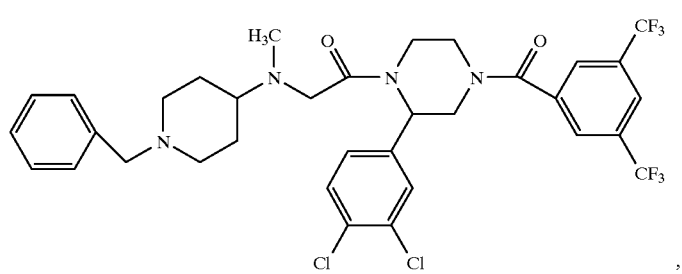,
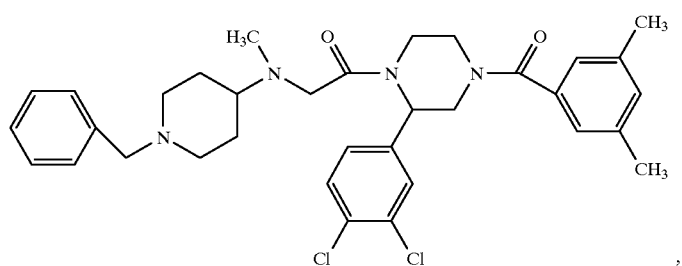,
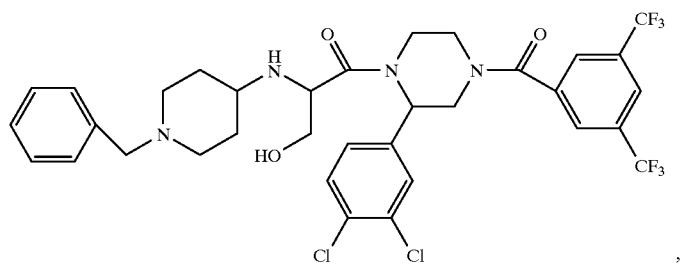,
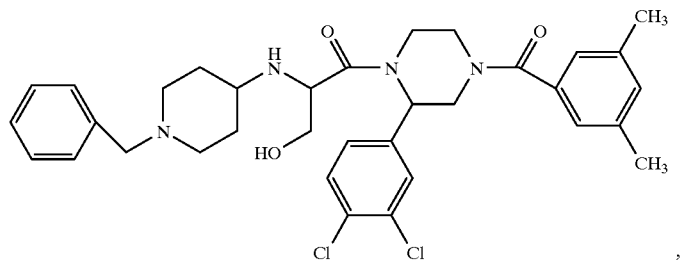,

-continued
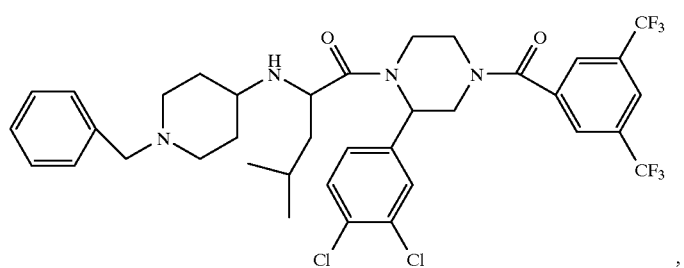
,
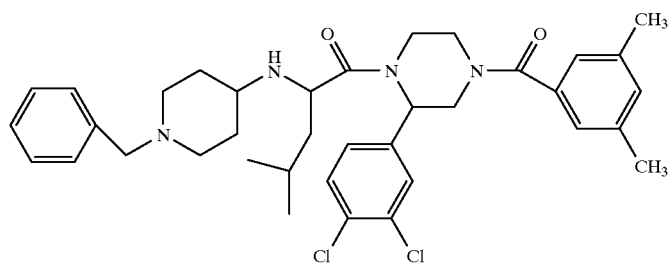
,
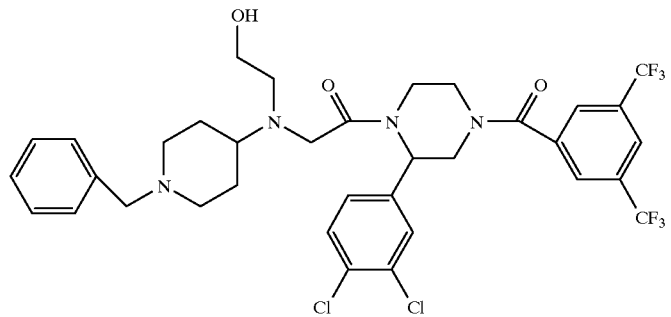
,
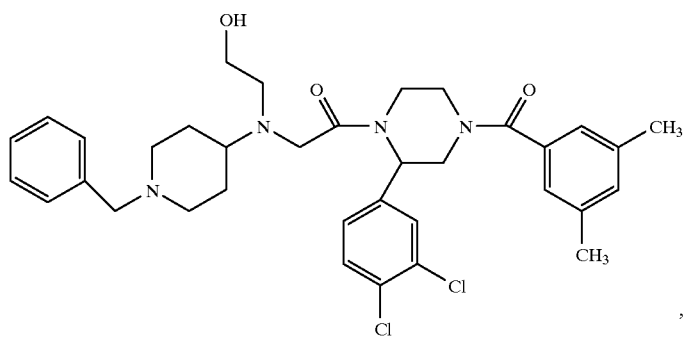
,
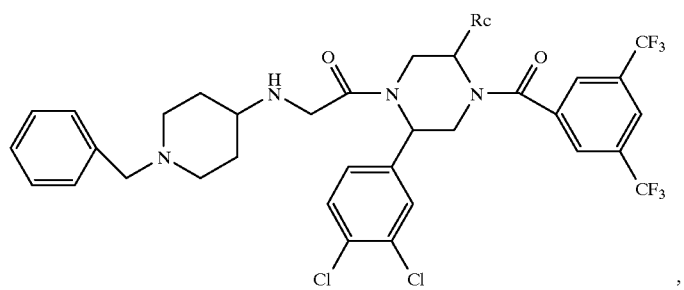
,
Rc = CH$_3$, isobutyl, —(CH$_2$)$_{n1}$—COOH,
—(CH$_2$)$_{n1}$—OH, —(CH$_2$)$_{n1}$—CONH$_2$,
n$_1$ = 1–6

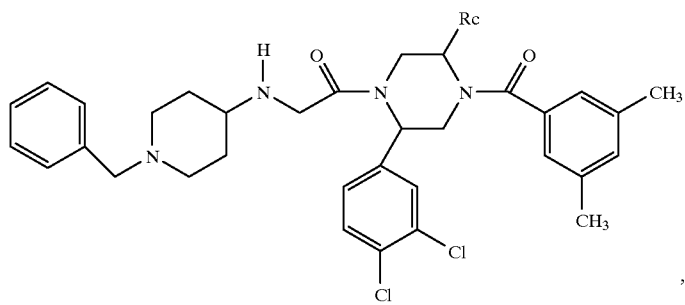
Rc = CH₃, isobutyl, —(CH₂)n1—COOH,
—(CH₂)n1—OH, —(CH₂)n1—CONH₂,
n₁ = 1–6
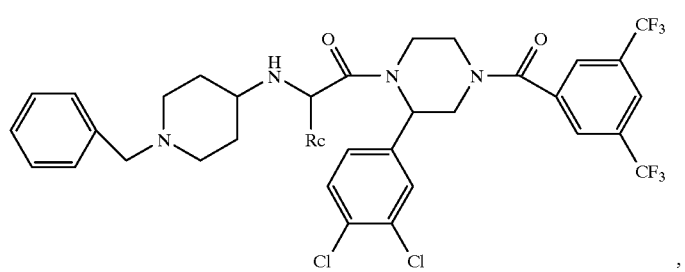
Rc = —(CH₂)n2—OH, —(CH₂)n1—COOH,
—(CH₂)n1—COOH
n₁ = 1–6, n₂ = 2–6
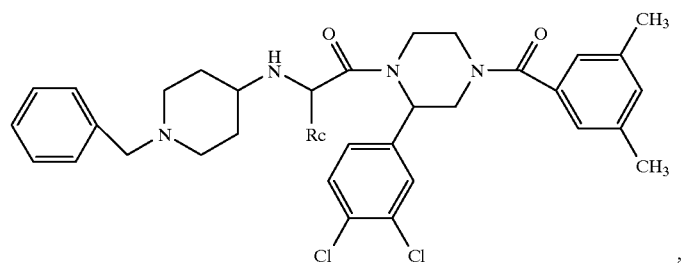
Rc = —(CH₂)n2—OH, —(CH₂)n1—COOH,
—(CH₂)n1—COOH
n₁ = 1–6, n₂ = 2–6
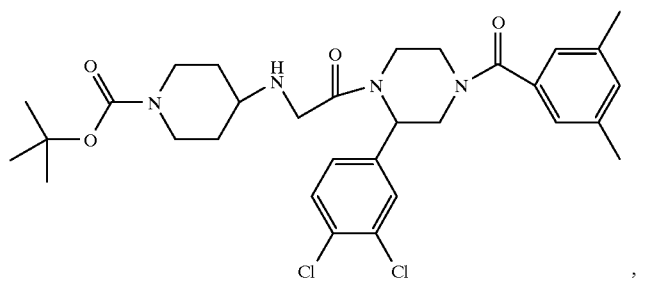
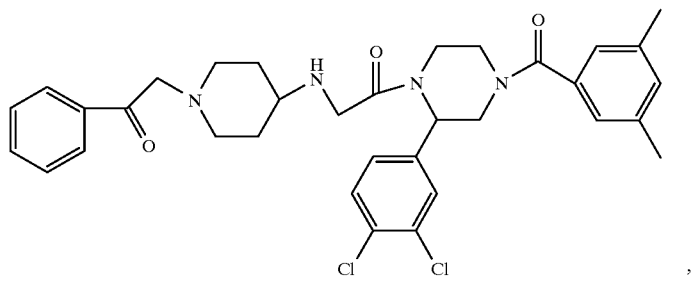

-continued

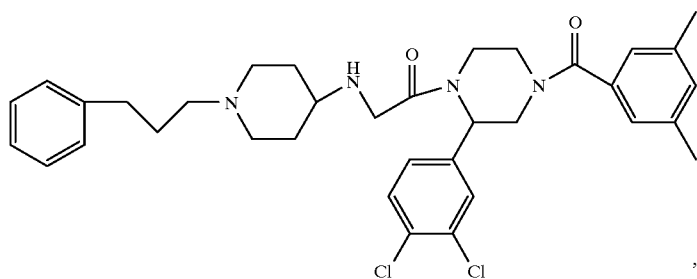

,

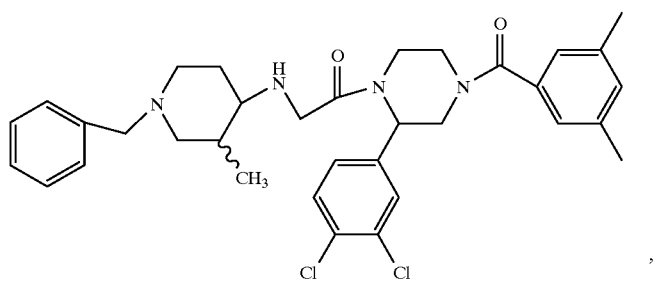

,

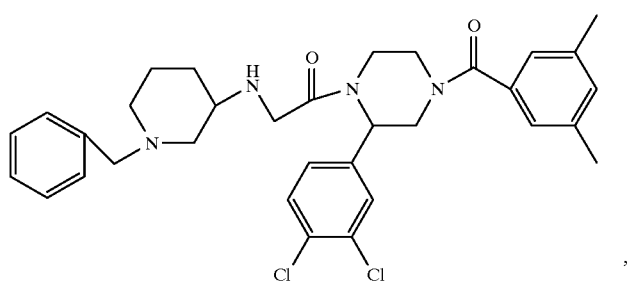

,

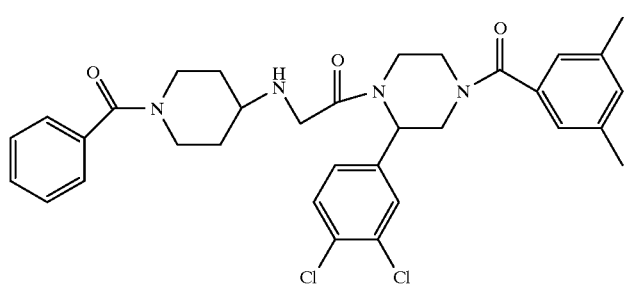

or a pharmaceutically acceptable salt thereof.

6. A composition comprising a neurokinin antagonistic effective amount of a compound according to claim 1 and a pharmaceutically acceptable carrier material.

7. A method for treating asthma, bronchospasm, allergies, anxiety, coughing or pain, which comprises administering a therapeutically effective amount of a compound according to claim 1 to a mammal in need of such treatment.

* * * * *